United States Patent
Kania et al.

(10) Patent No.: US 11,926,642 B2
(45) Date of Patent: Mar. 12, 2024

(54) COMPOUNDS AND METHODS FOR THE TREATMENT OF COVID-19

(71) Applicant: Pfizer Inc., New York, NY (US)

(72) Inventors: Robert Steven Kania, Del Mar, CA (US); Padmavani Bezawada, Vernon Hills, IL (US); Emma Louise Hawking, Deal (GB); Rohit Jaini, Chicago, IL (US); Samir Kulkarni, East Lyme, CT (US); Matthew Nathan O'Brien Laramy, Evanston, IL (US); Jonathan Richard Lillis, Ramsgate (GB); Suman Luthra, Westford, MA (US); Dafydd Rhys Owen, Concord, MA (US); Klimentina Dimitrova Pencheva, Ramsgate (GB); Anil Mahadeo Rane, Mystic, CT (US); Matthew Forrest Sammons, Quincy, MA (US); Bradley Paul Sullivan, Gurnee, IL (US); Andrew John Thiel, Gurnee, IL (US); Martyn David Ticehurst, Wingham (GB); Jamison Bryce Tuttle, Marblehead, MA (US); Robert Louis Hoffman, San Diego, CA (US)

(73) Assignee: Pfizer inc., New York, NY (US)

(*) Notice: Subject to any disclaimer, the term of this patent is extended or adjusted under 35 U.S.C. 154(b) by 431 days.

(21) Appl. No.: 17/365,213

(22) Filed: Jul. 1, 2021

(65) Prior Publication Data
US 2022/0017548 A1    Jan. 20, 2022

Related U.S. Application Data

(63) Continuation of application No. 17/221,676, filed on Apr. 2, 2021, now abandoned.

(60) Provisional application No. 63/163,635, filed on Mar. 19, 2021, provisional application No. 63/114,289, filed on Nov. 16, 2020, provisional application No. 63/073,145, filed on Sep. 1, 2020, provisional application No. 63/065,658, filed on Aug. 14, 2020, provisional application No. 63/061,628, filed on Aug. 5, 2020, provisional application No. 63/038,454, filed on Jun. 12, 2020, provisional application No. 63/005,407, filed on Apr. 5, 2020.

(51) Int. Cl.
*C07F 9/572* (2006.01)
*A61P 31/14* (2006.01)

(52) U.S. Cl.
CPC ............ *C07F 9/5728* (2013.01); *A61P 31/14* (2018.01); *C07B 2200/13* (2013.01)

(58) Field of Classification Search
CPC .................................................. C07F 9/3826
See application file for complete search history.

(56) References Cited

FOREIGN PATENT DOCUMENTS

| EA | 201200096 | 8/2012 |
|---|---|---|
| WO | 2005049070 | 6/2005 |
| WO | WO 2005113580 | 12/2005 |
| WO | WO 2006061714 | 6/2006 |
| WO | 2011005646 | 1/2011 |
| WO | 2018085476 | 5/2018 |

OTHER PUBLICATIONS

Fleisher et al, Review Improved oral drug delivery: solubility limitations overcome by the use of prodrugs, 1996, Advanced Drug Delivery Reviews, vol. 19, p. 115-130. (Year: 1996).*
Rayaprolu et al, Excipients in parenteral formulations: selection considerations and effective utilization with small molecules and biologics, 2018, Drug Development and Industrial Pharmacy, vol. 44, No. 10, p. 1565-1571. (Year: 2018).*
Berge et al, Pharmaceutical Salts, 1977, Journal of Pharmaceutical Sciences, vol. 66, No. 1, p. 1-19. (Year: 1977).*
Boras, Britton, et al., "Discovery of Novel Inhibitor of Coronavirus 3CL Protease for the Potential Treatment of COVID-19", Feb. 12, 2021, pp. 1-67, https://www.biorxiv.org/content/10.1101/2020.09.12.293498v3.full.pdf, XP05580340.
Fayed, Marwa A.A., et al., "Structure- and Ligand-Based in silico Studies towards the Repurposing of Marion Bioactive Compounds to Target SARS-CoV-2", Arabian Journal of Chemistry, Feb. 25, 2021, 103092, 14 pages, 14(4).

(Continued)

*Primary Examiner* — Samantha L Shterengarts
*Assistant Examiner* — Karen Cheng
(74) *Attorney, Agent, or Firm* — John A. Wichtowski

(57) ABSTRACT

The invention relates to compounds of formula I

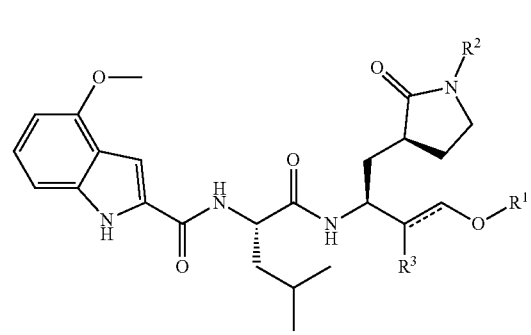

wherein $R^1$, $R^2$ and - - - - - are as defined herein, pharmaceutical compositions comprising the compounds and methods of treating COVID-19 in a patient by administering therapeutically effective amounts of the compounds and methods of inhibiting or preventing replication of SARS-CoV-2 with the compounds.

19 Claims, 28 Drawing Sheets

Specification includes a Sequence Listing.

(56) References Cited

OTHER PUBLICATIONS

Hoffman, Robert L., et al., "Discovery of Ketone-Bsed Covalent Inhibitors of Coronavirus 3CL Proteases for the Potential Therapeutic Treatment of COVID-19", Journal of Medicinal Chemistry, Oct. 15, 2020, pp. 12725-12747, 63(21).
International Patent Application PCT/IB2021/052741, Search Report and Written Opinion, filed Apr. 1, 2021, dated Jun. 28, 2021, 24 pages.
Jornada, Daniela H., et al., "The Prodrug Approach: A Successful Tool for Improving Drug Solubility", Molecules, Dec. 29, 2015, pp. 1-31, 21(1).
Berenbaum, M.C., "What is synergy?", Pharmacological Reviews, Jun. 1, 1989, pp. 93-141, 41(2).
Bliss, C.I., "The toxicity of Poisons Applied Jointly1", Annals of Applied Biology, 1939, pp. 585-615, vol. 26.
Fehr, A.R., et al., "Coronaviruses: An Overview of Their Replication and Pathogenesis", Methods of Molecules Biology, 2015, Chapter 1, pp. 1-23, vol. 1282.
Loewe, S., "The problem of synergism and antagonism of combined drugs", Arzneimittelforschung, Jun. 1953, pp. 285-290, 3(6).
Taiwan Patent Application No. 110112267, Search Report dated Aug. 4, 2022, 2 pages.
Xu, Zhijian, et al., "Nelfinavir was predicted to be a potential inhibitor of 2019-nCov main protease by an integrative approach combining homology modelling, molecular docking and binding free energy calculation", BioRxiv Posted Jan. 28, 2020, pp. 1-20.
Zieburh, John, et al., "Virus-encoded proteinases and proteolytic processing in th Nidovirales", Journal General Virology, 2000, pp. 853-873, 81(4).
Xu, J.; Zhao, S.; Teng, T.; Abdalla, A.E.; Zhu, W.; Xie, L.; Wang, Y.; Guo, X.; Systematic Comparison of Two Animal-to-Human Transmitted Human Coronaviruses: SARS-CoV-2 and SARS-CoV; Viruses 2020, 12, 244; doi:10.3390/v12020244.
Lu, R. et al. "Genomic characterisation and epidemiology of 2019 novel coronavirus: implications for virus origins and receptor binding", The Lancet, 2020, pp. 565-574, 395(10224).
Lu, J. et. al., "On the origin and continuing evolution of SARS-CoV-2", National Science Review, 2020, pp. 1012-1023, 7(6).
Wan, Y. et al., "Receptor Recognition by the Novel Coronavirus from Wuhan: an Analysis Based on Decade-Long Structural Studies of SARS Coronavirus", Journal of Virology, Mar. 17, 2020, pp. e00127-20, 94(7).
Zhang, L.; Lin, D.; Sun, X.; Rox, K.; Hilgenfeld, R.; X-ray Structure of Main Protease of the Novel Coronavirus SARS-CoV-2 Enables Design of a-Ketoamide Inhibitors; bioRxiv preprint doi: https://doi.org/10.1101/2020.02.17.952879.
Hoffman, R., et al., "The Design of Reversible and Irreversible Classes of SARS 3CL Protease Inhibitors", 238th ACS National Meeting, Washington, D.C., Division fo Medicinal Chemistry, Aug. 16, 2009, 29 pages.
ClinicalTrials.gov , "First-in-human Study to Evaluate Safety, Tolerability, and Pharmacokinetics Following Single Ascending and Multiple Ascending Doses of PF-07304814 in Hospitalized Participants With COVID-19", ClinicalTrials.gov Identifier: NCT04535167, 10 pages, last posted Jun. 24, 2021.
International Patent Application No. PCT/IB2021/051768, filed Mar. 3, 2021, Specification and Drawings.
International Patent Application No. PCT/IB2021/052738, filed Apr. 1, 2021, Specification, Drawings, and Sequence Listing.
International Patent Application No. PCT/IB2021/052689, filed Mar. 31, 2021, Specification, Drawings, and Sequence Listing.
International Patent Application No. PCT/IB2021/056093, filed Jul. 7, 2021. Specification and Sequence Listing.
U.S. Appl. No. 17/221,676, filed Apr. 2, 2021.
ClinicalTrials.gov , "Single Ascending Dose Study of Intravenous Infusion of PF-07304814 in Healthy Adult Participants", ClinicalTrials.gov Identifier: NCT04627532, 8 pages, last posted Jan. 6, 2021.
Pfizer Press Release, "Pfizer Investor Day Features Significant Number of Pipeline Advances for COVID-19 Programs and Across Numberous Therapeutic Areas", Sep. 15, 2021—1:45 pm, 9 pages.
Boras, Britton, et al., "Discovery of a Novel Inhibitor of Coronavirus 3CL Protease as a Clinical Candidate for the Potential Treatment of COVID-19: Short Title: Novel 3CL Protease Inhibitors for COVID-19", Sep. 13, 2020, bioRxiv Preprint doi: https://doi.org/10.1101/2020.09.12.293498, 32 pages.
Vrsies, Maren, et al., "A comparative analysis of SARS-CoV-2 antivirals in human airway models characterizes 3CLPro inhibitor PF-00835231 as a potential new treatment for COVID-19", Feb. 19, 2021, bioRxiv Preprint doi: https://doi.org/10.1101/2020.08.28.272880, 57 pages.

\* cited by examiner

COMPOUNDS AND METHODS FOR THE TREATMENT OF COVID-19

CROSS REFERENCE TO PRIOR APPLICATIONS

This application is a CONTINUATION of application Ser. No. 17/221,676, filed Apr. 2, 2021 which claims the benefit of U.S. Provisional Application Ser. No. 63/163,635, filed Mar. 19, 2021, and U.S. Provisional Application Ser. No. 63/114,289, filed Nov. 16, 2020, and U.S. Provisional Application Ser. No. 63/073,145, filed Sep. 1, 2020, and U.S. Provisional Application Ser. No. 63/065,658, filed Aug. 14, 2020, and U.S. Provisional Application Ser. No. 63/061,628, filed Aug. 5, 2020, and U.S. Provisional Application Ser. No. 63/038,454, filed Jun. 12, 2020, and U.S. Provisional Application Ser. No. 63/005,407, filed Apr. 5, 2020 under 35 USC 119(e), the disclosures of which are hereby incorporated in their entirety.

SEQUENCE LISTING

This application contains a Sequence Listing submitted as an electronic text file named "PC072623B-SeqListing.txt", having a size in bytes of 7,000, and created on Aug. 10, 2021. The information contained in this electronic file is hereby incorporated by reference in its entirety. No new matter has been added.

BACKGROUND OF THE INVENTION

The invention relates to compounds and methods of inhibiting viral replication activity comprising contacting a SARS-Cov-2-related 3C-like ("3CL") proteinase with a therapeutically effective amount of a SARS-Cov-2-related 3C-like protease inhibitor. The invention also relates to methods of treating Coronavirus Disease 2019 ("COVID-19") in a patient by administering a therapeutically effective amount of a SARS-Cov-2-related 3C-like protease inhibitor to a patient in need thereof. The invention further relates to methods of treating COVID-19 in a patient, the method comprising administering a pharmaceutical composition comprising a therapeutically effective amount of the SARS-Cov-2-related 3C-like protease inhibitor to a patient in need thereof.

A worldwide outbreak of Coronavirus Disease 2019 ("COVID-19") has been associated with exposures originating in late 2019 in Wuhan, Hubei Province, China. By early April 2020 the outbreak of COVID-19 has evolved into a global pandemic with over one million people having been confirmed as infected and resulting in over 50,000 deaths and by March 2021 there have been over 1.5 million deaths globally. The causative agent for COVID-19 has been identified as a novel coronavirus which has been named Severe Acute Respiratory Syndrome Corona Virus 2 ("SARS-CoV-2"). The genome sequence of SARS-CoV-2 has been sequenced from isolates obtained from nine patients in Wuhan, China and has been found to be of the subgenus Sarbecovirus of the genus Betacoronovirus. Lu, R. et al. The Lancet, Jan. 29, 2020; http://doi.org/10.1016/S0140-6736 (20). The sequence of SARS-CoV-2 was found to have 88% homology with two bat-derived SARS-like coronaviruses, bat-SL-CoVZC45 and bat-SL-CoVZXC21 which were collected in 2018 in Zhoushan, eastern China. SARS-CoV-2 was also found to share about 79% homology with Severe Acute Respiratory Syndrome Corona Virus ("SARS-CoV"), the causative agent of the SARS outbreak in 2002-2003, and about 50% homology with Middle East Respiratory Syndrome Coronavirus ("MERS-CoV"), the causative agent of a respiratory viral outbreak originating in the Middle East in 2012. Based on a recent analysis of 103 sequenced genomes of SARS-CoV-2 it has been proposed that SARS-CoV-2 can be divided into two major types (L and S types) with the S type being ancestral and the L type having evolved from the S-type. Lu, J.; Cui, J. et al. On the origin and continuing evolution of SARS-CoV-2; http://doi.org/10.1093/nsr/nwaa036. The S and L types can be clearly defined by just two tightly linked SNPs at positions 8,782 (orf1ab:T8517C, synonymous) and 28,144 (ORF8: C251T, S84L). In the 103 genomes analyzed approximately 70% were of the L-type and approximately 30% were of the S-type. It is unclear if the evolution of the L-type from the S-type occurred in humans or through a zoonotic intermediate but it appears that the L-type is more aggressive than the S-type and human interference in attempting to contain the outbreak may have shifted the relative abundance of the L and S types soon after the SARS-CoV-2 outbreak began. The discovery of the proposed S- and L-subtypes of SARS-CoV-2 raises the possibility that an individual could potentially be infected sequentially with the individual subtypes or be infected with both subtypes at the same time. In view of this evolving threat there is an acute need in the art for an effective treatment for COVID-19 and for methods of inhibiting replication of the SARS-CoV-2 coronavirus.

Recent evidence clearly shows that the newly emerged coronavirus SARS-CoV-2, the causative agent of COVID-19 (Centers for Disease Control, CDC) has acquired the ability of human to human transmission leading to community spread of the virus. The sequence of the SARS-CoV-2 receptor binding domain ("RBD"), including its receptor-binding motif (RBM) that directly contacts the angiotensin 2 receptor, ACE2, is similar to the RBD and RBM of SARS-CoV, strongly suggesting that SARS-CoV-2 uses ACE2 as its receptor. Yushun Wan, Y.; Shang, J.; Graham, R.; 2, Baric, R. S.; Li, F.; Receptor recognition by novel coronavirus from Wuhan: An analysis based on decade-long structural studies of SARS; J. Virol. 2020; doi:10.1128/JVI.00127-20. Several critical residues in SARS-CoV-2 RBM (particularly $Gln^{493}$) provide favorable interactions with human ACE2, consistent with SARS-CoV-2's capacity for human cell infection. Several other critical residues in SARS-CoV-2's RBM (particularly $Asn^{501}$) are compatible with, but not ideal for, binding human ACE2, suggesting that SARS-CoV-2 uses ACE2 binding in some capacity for human-to-human transmission.

Coronavirus replication and transcription function is encoded by the so-called "replicase" gene (Ziebuhr, J., Snijder, E. J., and Gorbaleya, A. E.; Virus-encoded proteinases and proteolytic processing in Nidovirales. J. Gen. Virol. 2000, 81, 853-879; and Fehr, A. R.; Perlman, S.; Coronaviruses: An Overview of Their Replication and Pathogenesis Methods Mol Biol. 2015; 1282: 1-23. doi: 10.1007/978-1-4939-2438-7_1), which consists of two overlapping polyproteins that are extensively processed by viral proteases. The C-proximal region is processed at eleven conserved interdomain junctions by the coronavirus main or "3C-like" protease (Ziebuhr, Snijder, Gorbaleya, 2000 and Fehr, Perlman et al., 2015). The name "3C-like" protease derives from certain similarities between the coronavirus enzyme and the well-known picornavirus 3C proteases. These include substrate preferences, use of cysteine as an active site nucleophile in catalysis, and similarities in their putative overall polypeptide folds. The SARS-CoV-2 3CL protease sequence (Accession No. YP_009725301.1) has been found to share 96.08% homology when compared with the SARS-CoV 3CL protease (Accession No. YP_009725301.1) Xu, J.; Zhao, S.; Teng, T.; Abdalla, A. E.; Zhu, W.; Xie, L.; Wang, Y.; Guo, X.; Systematic Comparison of Two Animal-to-Human Transmitted Human Coronaviruses: SARS-CoV-2 and SARS-CoV; Viruses 2020, 12, 244; doi:10.3390/v12020244. Very recently Hilgenfeld and colleagues published a high-resolution X-ray structure of the SARS-CoV-2 coronavirus main protease (3CL) Zhang, L.; Lin, D.; Sun, X.; Rox, K.; Hilgenfeld, R.; X-ray Structure of Main Protease of the Novel Coronavirus SARS-CoV-2 Enables Design of α-Ketoamide Inhibitors; bioRxiv preprint doi: https://doi.org/10.1101/2020.02.17.952879. The structure indicates that there are differences when comparing the 3CL proteases of SARS-CoV-2 and SARS-CoV. In the SARS-CoV but not in the SARS-CoV-2 3CL protease dimer, there is a polar interaction between the two domains III involving a 2.60-Å hydrogen bond between the side-chain hydroxyl groups of residue Thr$^{285}$ of each protomer, and supported by a hydrophobic contact between the side-chain of Ile$^{286}$ and Thr$^{285}$ Cγ$_2$. In the SARS-CoV-2 3CL, the threonine is replaced by alanine, and the isoleucine by leucine when compared with the same residues in the SARS-CoV 3CL. The Thr285Ala replacement observed in the SARS-CoV-2 3CL protease allows the two domains III to approach each other somewhat closer (the distance between the Cα atoms of residues 285 in molecules A and B is 6.77 Å in SARS-CoV 3CL protease and 5.21 Å in SARS-CoV-2 3CL protease and the distance between the centers of mass of the two domains III shrinks from 33.4 Å to 32.1 Å). In the active site of SARS-CoV-2 3CL Cys$^{145}$ and His$^{41}$ form a catalytic dyad which when taken together with a with a buried water molecule that is hydrogen bonded to His$^{41}$ can be considered to constitute a catalytic triad of the SARS-CoV-2 3CL protease. In view of the ongoing SARS-CoV-2 spread which has caused the current worldwide COVID-19 outbreak it is desirable to have new methods of inhibiting SARS-CoV-2 viral replication and of treating COVID-19 in patients.

SUMMARY OF THE INVENTION

The present invention provides novel compounds which act in inhibiting or preventing SARS-Cov-2 viral replication and thus are useful in the treatment of COVID-19. The present invention also provides pharmaceutical compositions comprising the compounds and methods of treating COVID-19 and inhibiting SARS-Cov-2 viral replication by administering the compounds of the invention or pharmaceutical compositions comprising the compounds of the invention.

A first embodiment of a first aspect of the present invention is a compound of Formula I

I

Wherein ------ is absent or a bond; R$^1$ is selected from the group consisting of —CH(R$^{4a}$)—OC(O)R$^4$, —C(O)OR$^4$, —CH(R$^{4a}$)—OC(O)OR$^4$, —P(O)(OR$^5$)$_2$, —P(O)(C$_1$-C$_6$alkyl)(OR$^5$) and —C(O)N(R$^6$)$_2$; R$^2$ is selected from the group consisting of hydrogen, —C(O)R$^7$, —CO$_2$R$^7$ and —C$_1$-C$_6$alkyl-OC(O)OR$^7$, and when R$^2$ is —C(O)R$^7$, —CO$_2$R$^7$ or —C$_1$-C$_6$alkyl-OC(O)OR$^7$, then R$^1$ is selected from the group consisting of hydrogen, —CH(R$^{4a}$)—OC(O)R$^4$, —C(O)OR$^4$, —CH(R$^{4a}$)—OC(O)OR$^4$, —P(O)(OR$^5$)$_2$, —P(O)(C$_1$-C$_6$alkyl)(OR$^5$) and —C(O)N(R$^6$)$_2$; R$^3$ is oxo when ------ is absent or when ------ is a bond R$^3$ taken together with R$^1$ and the oxygen to which R$^1$ is attached are —OC(O)O—; R$^4$ and R$^7$ are each independently selected from the group consisting of C$_1$-C$_6$alkyl unsubstituted or substituted with one to three R$^8$, C$_3$-C$_7$cycloalkyl unsubstituted or substituted with one to three R$^8$, C$_5$-C$_{12}$bicycloalkyl unsubstituted or substituted with one to three R$^8$, four to seven membered heterocycloalkyl comprising one to three heteroatoms selected independently from N, O and S and which is unsubstituted or substituted with one to three R$^8$, C$_6$-C$_{10}$aryl unsubstituted or substituted with one to three R$^8$, and a five to ten membered heteroaryl comprising one to four heteroatoms selected independently from N, O and S and which is unsubstituted or substituted with one to three R$^8$; R$^{4a}$ is hydrogen or C$_1$-C$_6$alkyl, R$^5$ at each occurrence is independently hydrogen or C$_1$-C$_6$alkyl, or both R$^5$ groups taken together are a C$_2$-C$_4$alkylene which is optionally substituted with phenyl; R$^6$ at each occurrence is independently selected from hydrogen and C$_1$-C$_6$alkyl which is unsubstituted or substituted with one to three R$^8$; or both R$^6$ groups taken together with the nitrogen to which they are attached are a four- to seven-membered heterocycloalkyl optionally comprising an additional one to three heteroatoms independently selected from N, O and S, wherein said heterocycloalkyl is unsubstituted or substituted with one to three R$^8$; and R$^8$ at each occurrence is independently selected from halo, hydroxy, cyano, C$_1$-C$_3$alkyl, C$_1$-C$_3$alkoxy, C$_1$-C$_3$alkoxyC$_1$-C$_3$alkyl, C$_3$-C$_6$cycloalkyl, C$_3$-C$_6$cycloalkoxy, di(C$_1$-C$_3$alkyl)amino, (C$_1$-C$_3$alkyl)amino, amino, di(C$_1$-C$_3$alkyl)amino-C$_1$-C$_3$alkyl, (C$_1$-C$_3$alkyl)amino-C$_1$-C$_3$alkyl, amino-C$_1$-C$_3$alkyl and four to seven membered heterocycloalkyl comprising one to three heteroatoms selected independently from N, O and S, or a pharmaceutically acceptable salt thereof.

A second embodiment of a first aspect of the present invention is the compound of the first embodiment of the first aspect of Formula Ia Ia

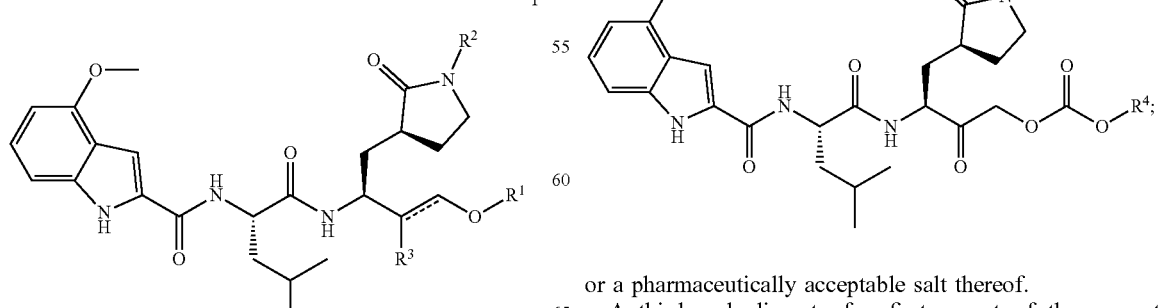

or a pharmaceutically acceptable salt thereof.

A third embodiment of a first aspect of the present invention is the compound of the second embodiment of the first aspect wherein R$^2$ is selected from the group consisting of hydrogen, —C(O)OCH₃, —C(O)OC(CH₃)₃, —CH(CH₃)OC(O)OCH₃, and —CH₂OC(O)OCH₃, and R⁴ is selected from the group consisting of methyl, ethyl, isopropyl and t-butyl; or a pharmaceutically acceptable salt thereof. A fourth embodiment of a first aspect of the present invention is the compound of the third embodiment of the first aspect wherein $R^2$ is hydrogen; or a pharmaceutically acceptable salt thereof. A fifth embodiment of a first aspect of the present invention is the compound of the third embodiment of the first aspect selected from the group consisting of: (3S)-3-({N-[(4-methoxy-1H-indol-2-yl)carbonyl]-L-leucyl}amino)-2-oxo-4-[(3S)-2-oxopyrrolidin-3-yl]butyl methyl carbonate; (3S)-3-({N-[(4-methoxy-1H-indol-2-yl)carbonyl]-L-leucyl}amino)-2-oxo-4-[(3S)-2-oxopyrrolidin-3-yl]butyl propan-2-yl carbonate; (3S)-4-[(3S)-1-acetyl-2-oxopyrrolidin-3-yl]-3-({N-[(4-methoxy-1H-indol-2-yl)carbonyl]-L-leucyl}amino)-2-oxobutyl methyl carbonate; (3S)-4-[(3S)-1-{(1S)-1-[(methoxycarbonyl)oxy]ethyl}-2-oxopyrrolidin-3-yl]-3-({N-[(4-methoxy-1H-indol-2-yl)carbonyl]-L-leucyl}amino)-2-oxobutyl methyl carbonate; ethyl (3S)-3-({N-[(4-methoxy-1H-indol-2-yl)carbonyl]-L-leucyl}amino)-2-oxo-4-[(3S)-2-oxopyrrolidin-3-yl]butyl carbonate; methyl (3S)-3-[(2S)-4-[(methoxycarbonyl)oxy]-2-({N-[(4-methoxy-1H-indol-2-yl)carbonyl]-L-leucyl}amino)-3-oxobutyl]-2-oxopyrrolidine-1-carboxylate; tert-butyl (3S)-3-({N-[(4-methoxy-1H-indol-2-yl)carbonyl]-L-leucyl}amino)-2-oxo-4-[(3S)-2-oxopyrrolidin-3-yl]butyl carbonate; and tert-butyl (3S)-3-[(2S)-4-[(tert-butoxycarbonyl)oxy]-2-({N-[(4-methoxy-1H-indol-2-yl)carbonyl]-L-leucyl}amino)-3-oxobutyl]-2-oxopyrrolidine-1-carboxylate; or a pharmaceutically acceptable salt thereof.

A sixth embodiment of a first aspect of the present invention is the compound of the first embodiment of the first aspect of Formula Ib

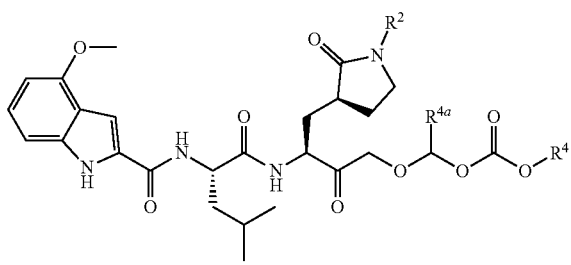

Ib or a pharmaceutically acceptable salt thereof.

A seventh embodiment of a first aspect of the present invention is the compound of the sixth embodiment of the first aspect wherein $R^2$ is selected from the group consisting of hydrogen, —C(O)CH₃, —CO₂CH₃, —CH₂OC(O)OCH₃ and —CH(CH₃)OC(O)OCH₃, R⁴ is selected from the group consisting of methyl, ethyl, isopropyl and t-butyl; and $R^{4a}$ is selected from the group consisting of hydrogen, methyl and ethyl; or a pharmaceutically acceptable salt thereof.

An eighth embodiment of the first aspect of the present invention is the compound of the sixth embodiment of the first aspect selected from the group consisting of (1R)-1-({(3S)-3-({N-[(4-methoxy-1H-indol-2-yl)carbonyl]-L-leucyl}amino)-2-oxo-4-[(3S)-2-oxopyrrolididn-3-yl]butyl}oxy)ethyl methyl carbonate; (1R)-1-({(3S)-3-({N-[(4-methoxy-1H-indol-2-yl)carbonyl]-L-leucyl}amino)-2-oxo-4-[(3S)-2-oxopyrrolidin-3-yl]butyl}oxy)ethyl propan-2-yl carbonate; (1R)-1-({(3S)-3-({N-[(4-methoxy-1H-indol-2-yl)carbonyl]-L-leucyl}amino)-2-oxo-4-[(3S)-2-oxopyrrolidin-3-yl]butyl}oxy)propyl methyl carbonate; (1R)-1-({(3S)-3-({N-[(4-methoxy-1H-indol-2-yl)carbonyl]-L-leucyl}amino)-2-oxo-4-[(3S)-2-oxopyrrolidin-3-yl]butyl}oxy)propyl propan-2-yl carbonate; ({(3S)-3-({N-[(4-methoxy-1H-indol-2-yl)carbonyl]-L-leucyl}amino)-2-oxo-4-[(3S)-2-oxopyrrolidin-3-yl]butyl}oxy)methyl methyl carbonate; ({(3S)-3-({N-[(4-methoxy-1H-indol-2-yl)carbonyl]-L-leucyl}amino)-2-oxo-4-[(3S)-2-oxopyrrolidin-3-yl]butyl}oxy)methyl propan-2-yl carbonate; ethyl (1R)-1-({(3S)-3-({N-[(4-methoxy-1H-indol-2-yl)carbonyl]-L-leucyl}amino)-2-oxo-4-[(3S)-2-oxopyrrolidin-3-yl]butyl}oxy)ethyl carbonate; ethyl (1R)-1-({(3S)-3-({N-[(4-m ethoxy-1H-indol-2-yl)carbonyl]-L-leucyl}amino)-2-oxo-4-[(3S)-2-oxopyrrolidin-3-yl]butyl}oxy)propyl carbonate; ethyl ({(3S)-3-({N-[(4-methoxy-1H-indol-2-yl)carbonyl]-L-leucyl}amino)-2-oxo-4-[(3S)-2-oxopyrrolidin-3-yl]butyl}oxy)methyl carbonate; methyl (3S)-3-[(2S)-4-{[(methoxycarbonyl)oxy]methoxy}-2-({N-[(4-methoxy-1H-indol-2-yl)carbonyl]-L-leucyl}amino)-3-oxobutyl]-2-oxopyrrolidine-1-carboxylate; tert-butyl (1R)-1-({(3S)-3-({N-[(4-methoxy-1H-indol-2-yl)carbonyl]-L-leucyl}amino)-2-oxo-4-[(3S)-2-oxopyrrolidin-3-yl]butyl}oxy)ethyl carbonate; tert-butyl (1R)-1-({(3S)-3-({N-[(4-methoxy-1H-indol-2-yl)carbonyl]-L-leucyl}amino)-2-oxo-4-[(3S)-2-oxopyrrolidin-3-yl]butyl}oxy)propyl carbonate; tert-butyl ({(3S)-3-({N-[(4-methoxy-1H-indol-2-yl)carbonyl]-L-leucyl}amino)-2-oxo-4[(3S)-2-oxopyrrolidin-3-yl]butyl}oxy)methyl carbonate; {(3S)-3-[(2S)-4-{[(methoxycarbonyl)oxy]methoxy}-2-({N-[(4-methoxy-1H-indol-2-yl)carbonyl]-L-leucyl}amino)-3-oxobutyl]-2-oxopyrrolidin-1-yl}methyl methyl carbonate; {[(3S)-4-[(3S)-1-acetyl-2-oxopyrrolidin-3-yl]-3-({N-[(4-methoxy-1H-indol-2-yl)carbonyl]-L-leucyl}amino)-2-oxobutyl]oxy}methyl methyl carbonate; and {[(3S)-4-[(3S)-1-{(1R)-1-[(methoxycarbonyl)oxy]ethyl}-2-oxopyrrolidin-3-yl]-3-({N-[(4-methoxy-1H-indol-2-yl)carbonyl]-L-leucyl}amino)-2-oxobutyl]oxy}methyl methyl carbonate; or a pharmaceutically acceptable salt thereof.

A ninth embodiment of a first aspect of the present invention is the compound of the first embodiment of the first aspect of the formula Ic

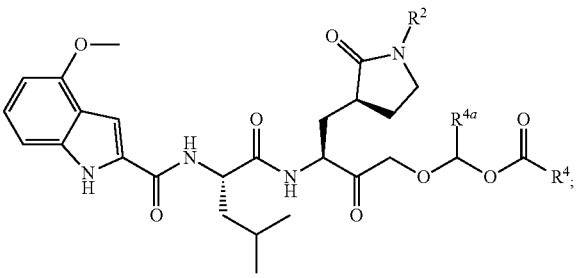

Ic or a pharmaceutically acceptable salt thereof.

A tenth embodiment of a first aspect of the present invention is the compound of the ninth embodiment of the first aspect wherein $R^2$ is selected from the group consisting of hydrogen, —C(O)CH₃, —CO₂CH₃, —CH₂OC(O)OCH₃ and —CH(CH₃)OC(O)OCH₃, R⁴ is selected from the group consisting of 1-amino-2-methylpropyl, (dimethylamino)methyl, ethyl, isopropyl, t-butyl and 2,6-dimethylphenyl; and $R^{4a}$ is selected from the group consisting of hydrogen, methyl and ethyl; or a pharmaceutically acceptable salt thereof.

An eleventh embodiment of the first aspect of the present invention is the compound of the ninth embodiment of the first aspect selected from the group consisting of (1R)-1-({(3S)-3-({N-[(4-methoxy-1H-indol-2-yl)carbonyl]-L-leucyl}amino)-2-oxo-4-[(3S)-2-oxopyrrolidin-3-yl]butyl}oxy) ethyl 2,2-dimethylpropanoate; (1S)-1-({(3S)-3-({N-[(4-methoxy-1H-indol-2-yl)carbonyl]-L-leucyl}amino)-2-oxo-4-[(3S)-2-oxopyrrolidin-3-yl]butyl}oxy)ethyl 2-methylpropanoate; (1S)-1-({(3S)-3-({N-[(4-methoxy-1H-indol-2-yl)carbonyl]-L-leucyl}amino)-2-oxo-4[(3S)-2-oxopyrrolidin-3-yl]butyl}oxy)ethyl propanoate; (1 S)-1-({(3S)-3-({N-[(4-methoxy-1H-indol-2-yl)carbonyl]-L-leucyl}amino)-2-oxo-4-[(3S)-2-oxopyrrolidin-3-yl]butyl}oxy)propyl 2,2-dimethylpropanoate; (1S)-1-({(3S)-3-({N-[(4-methoxy-1H-indol-2-yl)carbonyl]-L-leucyl}amino)-2-oxo-4-[(3S)-2-oxopyrrolidin-3-yl]butyl}oxy)propyl 2,2-dimethylpropanoate; (1S)-1-({(3S)-3-({N-[(4-methoxy-1H-indol-2-yl)carbonyl]-L-leucyl}amino)-2-oxo-4-[(3S)-2-oxopyrrolidin-3-yl]butyl}oxy)propyl 2-methylpropanoate; (1S)-1-({(3S)-3-({N-[(4-methoxy-1H-indol-2-yl)carbonyl]-L-leucyl}amino)-2-oxo-4-[(3S)-2-oxopyrrolidin-3-yl]butyl}oxy)propyl propanoate; ({(3S)-3-({N-[(4-methoxy-1H-indol-2-yl)carbonyl]-L-leucyl}amino)-2-oxo-4-[(3S)-2-oxopyrrolidin-3-yl]butyl}oxy)methyl 2,2-dimethylpropanoate; ({(3S)-3-({N-[(4-methoxy-1H-indol-2-yl)carbonyl]-L-leucyl}amino)-2-oxo-4-[(3S)-2-oxopyrrolidin-3-yl]butyl}oxy)methyl 2,6-dimethylbenzoate; ({(3S)-3-({N-[(4-methoxy-1H-indol-2-yl)carbonyl]-L-leucyl}amino)-2-oxo-4-[(3S)-2-oxopyrrolidin-3-yl]butyl}oxy)methyl 2-methylpropanoate; ({(3S)-3-({N-[(4-methoxy-1H-indol-2-yl)carbonyl]-L-leucyl}amino)-2-oxo-4-[(3S)-2-oxopyrrolidin-3-yl]butyl}oxy)methyl D-valinate; ({(3S)-3-({N-[(4-methoxy-1H-indol-2-yl)carbonyl]-L-leucyl}amino)-2-oxo-4-[(3S)-2-oxopyrrolidin-3-yl]butyl}oxy)methyl N,N-dimethylglycinate; ({(3S)-3-({N-[(4-methoxy-1H-indol-2-yl)carbonyl]-L-leucyl}amino)-2-oxo-4-[(3S)-2-oxopyrrolidin-3-yl]butyl}oxy)methyl propanoate; methyl (3S)-3-{(2S)-2-({N-[(4-methoxy-1H-indol-2-yl)carbonyl]-L-leucyl}amino)-3-oxo-4-[(propanoyloxy)methoxy]butyl}-2-oxopyrrolidine-1-carboxylate; {[(3S)-4-[(3S)-1-acetyl-2-oxopyrrolidin-3-yl]-3-({N-[(4-methoxy-1H-indol-2-yl)carbonyl]-L-leucyl}amino)-2-oxobutyl]oxy}methyl propanoate; and {[(3S)-4-[(3S)-1-{(1S)-1-[(methoxycarbonyl)oxy]ethyl}-2-oxopyrrolidin-3-yl]-3-({N-[(4-methoxy-1H-indol-2-yl)carbonyl]-L-leucyl}amino)-2-oxobutyl]oxy} methyl propanoate; or a pharmaceutically acceptable salt thereof.

A twelfth embodiment of a first aspect of the present invention is the compound of the first embodiment of the first aspect of formula Id

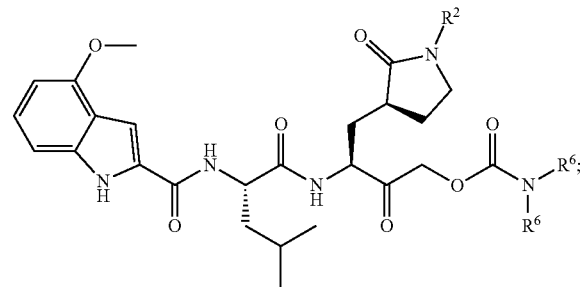

Id or a pharmaceutically acceptable salt thereof.

A thirteenth embodiment of a first aspect of the present invention is the compound of claim 12 wherein $R^2$ is selected from the group consisting of hydrogen, —C(O)CH$_3$, —CO$_2$CH$_3$, —CH$_2$OC(O)OCH$_3$ and —CH(CH$_3$)OC(O)OCH$_3$, each $R^6$ is independently selected from hydrogen, methyl, (dimethylamino)methyl, (dimethylamino)ethyl; or both $R^6$ groups taken together with the nitrogen to which they are attached are a piperidine ring which is unsubstituted or substituted with a piperidinyl; or a pharmaceutically acceptable salt thereof.

A fourteenth embodiment of a first aspect of the present invention is the compound of the thirteenth embodiment of the first aspect which is selected from the group consisting of (3S)-3-({N-[(4-methoxy-1H-indol-2-yl)carbonyl]-L-leucyl}amino)-2-oxo-4-[(3S)-2-oxopyrrolidin-3-yl]butyl 1,4'-bipiperidine-1'-carboxylate; (3S)-3-({N-[(4-methoxy-1H-indol-2-yl)carbonyl]-L-leucyl}amino)-2-oxo-4-[(3S)-2-oxopyrrolidin-3-yl]butyl [2-(dimethylamino)ethyl]carbamate; (3S)-3-({N-[(4-methoxy-1H-indol-2-yl)carbonyl]-L-leucyl}amino)-2-oxo-4-[(3S)-2-oxopyrrolidin-3-yl]butyl [2-(dimethylamino)ethyl] methylcarbamate; (3S)-3-({N-[(4-methoxy-1H-indol-2-yl)carbonyl]-L-leucyl}amino)-2-oxo-4-[(3S)-2-oxopyrrolidin-3-yl]butyl piperidine-1-carboxylate; (3S)-4-[(3S)-1-(methoxycarbonyl)-2-oxopyrrolidin-3-yl]-3-({N-[(4-methoxy-1H-indol-2-yl)carbonyl]-L-leucyl}amino)-2-oxobutyl piperidine-1-carboxylate; (3S)-4-[(3S)-1-acetyl-2-oxopyrrolidin-3-yl]-3-({N-[(4-methoxy-1H-indol-2-yl)carbonyl]-L-leucyl}amino)-2-oxobutyl piperidine-1-carboxylate; and (3S)-4-[(3S)-1-{(1S)-1-[(methoxycarbonyl)oxy]ethyl}-2-oxopyrrolidin-3-yl]-3-({N-[(4-methoxy-1H-indol-2-yl)carbonyl]-L-leucyl}amino)-2-oxobutyl piperidine-1-carboxylate; or a pharmaceutically acceptable salt thereof.

A fifteenth embodiment of a first aspect of the present invention is the compound of claim 1 of the formula Ie

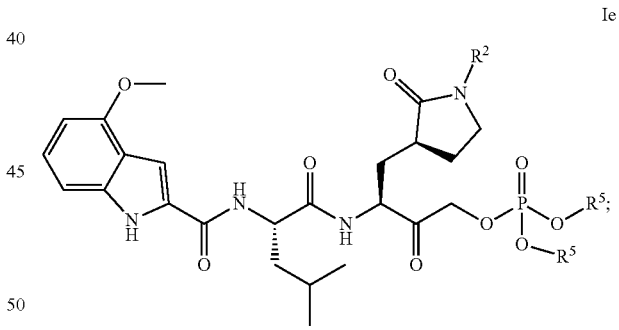

Ie or a pharmaceutically acceptable salt thereof.

A sixteenth embodiment of a first aspect of the present invention is the compound of the fifteenth embodiment of the first aspect wherein $R^2$ is selected from the group consisting of hydrogen, —C(O)CH$_3$, —CO$_2$CH$_3$, —CH$_2$OC(O)OCH$_3$ and —CH(CH$_3$)OC(O)OCH$_3$, and $R^5$ at each occurrence is independently selected from the group consisting of hydrogen, methyl, ethyl, isopropyl and t-butyl; or both $R^5$ groups taken together are —CH(Phenyl)CH$_2$CH$_2$—; or a pharmaceutically acceptable salt thereof.

A seventeenth embodiment of a first aspect of the present invention is the compound of the fifteenth embodiment of the first aspect selected from the group consisting of (1S)-1-{(3S)-3-[(2S)-4-[(dimethoxyphosphoryl)oxy]-2-({N-[(4-methoxy-1H-indol-2-yl)carbonyl]-L-leucyl}amino)-3- oxobutyl]-2-oxopyrrolidin-1-yl}ethyl methyl carbonate; (3S)-3-({N-[(4-methoxy-1H-indol-2-yl)carbonyl]-L-leucyl}amino)-2-oxo-4-[(3S)-2-oxopyrrolidin-3-yl]butyl dihydrogen phosphate; (3S)-3-({N-[(4-methoxy-1H-indol-2-yl)carbonyl]-L-leucyl}amino)-2-oxo-4-[(3S)-2-oxopyrrolidin-3-yl]butyl dimethyl phosphate; (3S)-3-({N-[(4-methoxy-1H-indol-2-yl)carbonyl]-L-leucyl}amino)-2-oxo-4-[(3S)-2-oxopyrrolidin-3-yl]butyl dipropan-2-yl phosphate; (3S)-4-[(3S)-1-acetyl-2-oxopyrrolidin-3-yl]-3-({N-[(4-methoxy-1H-indol-2-yl)carbonyl]-L-leucyl}amino)-2-oxobutyl dimethyl phosphate; 4-methoxy-N-[(2S)-4-methyl-1-({(2S)-4-[(2-oxido-4-phenyl-1,3,2-dioxa phosphinan-2-yl)oxy]-3-oxo-1-[(3S)-2-oxopyrrolidin-3-yl]butan-2-yl}amino)-1-oxopentan-2-yl]-1H-indole-2-carboxamide; diethyl (3S)-3-({N-[(4-methoxy-1H-indol-2-yl)carbonyl]-L-leucyl} amino)-2-oxo-4-[(3S)-2-oxopyrrolidin-3-yl]butyl phosphate; and methyl (3S)-3-[(2S)-4-[(dimethoxyphosphoryl)oxy]-2-({N-[(4-methoxy-1H-indol-2-yl)carbonyl]-L-leucyl} amino)-3-oxobutyl]-2-oxopyrrolidine-1-carboxylate; or a pharmaceutically acceptable salt thereof.

An eighteenth embodiment of a first aspect of the present invention is the compound of the first embodiment of the first aspect wherein $R^1$ is —P(O)($C_1$-$C_6$alkyl)($OR^5$), or a pharmaceutically acceptable salt thereof. A nineteenth embodiment of a first aspect of the present invention is the compound of the eighteenth embodiment of the first aspect which is (3S)-3-({N-[(4-methoxy-1H-indol-2-yl)carbonyl]-L-leucyl}amino)-2-oxo-4-[(3S)-2-oxopyrrolidin-3-yl]butyl methyl methylphosphonate; or a pharmaceutically acceptable salt thereof.

A twentieth embodiment of a first aspect of the present invention is the compound of the first embodiment of the first aspect of formula If

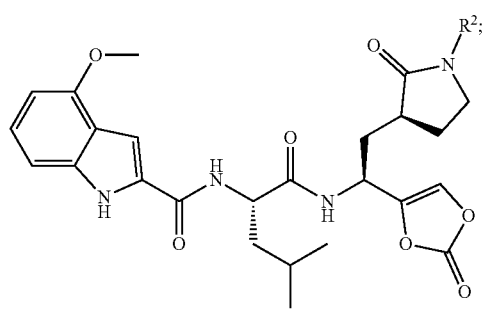

or a pharmaceutically acceptable salt thereof.

A twenty first embodiment of a first aspect of the present invention is the compound of the twentieth embodiment of the first aspect wherein $R^2$ is selected from the group consisting of hydrogen, —C(O)$CH_3$, —$CO_2CH_3$, —$CH_2$OC(O)$OCH_3$ and —CH($CH_3$)OC(O)$OCH_3$, or a pharmaceutically acceptable salt thereof.

A twenty second embodiment of a first aspect of the present invention is the compound of the twentieth embodiment of the first aspect selected from the group consisting of (1S)-1-{(3S)-3-[(2S)-2-({N-[(4-methoxy-1H-indol-2-yl)carbonyl]-L-leucyl}amino)-2-(2-oxo-1,3-dioxol-4-yl)ethyl]-2-oxopyrrolidin-1-yl}ethyl methyl carbonate; 4-methoxy-N-[(2S)-4-methyl-1-oxo-1-({(1S)-1-(2-oxo-1,3-dioxol-4-yl)-2-[(3S)-2-oxopyrrolidin-3-yl]ethyl}amino)pentan-2-yl]-1H-indole-2-carboxamide; N-[(2S)-1-{[(1S)-2-[(3S)-1-acetyl-2-oxopyrrolidin-3-yl]-1-(2-oxo-1,3-dioxol-4-yl)ethyl]amino}-4-methyl-1-oxopentan-2-yl]-4-methoxy-1H-indole-2-carboxamide; and methyl (3S)-3-[(2S)-2-({N-[(4-methoxy-1H-indol-2-yl)carbonyl]-L-leucyl}amino)-2-(2-oxo-1,3-dioxol-4-yl)ethyl]-2-oxopyrrolidine-1-carboxylate; or a pharmaceutically acceptable salt thereof.

A twenty third embodiment of a first aspect of the present invention is a compound of formula Ig

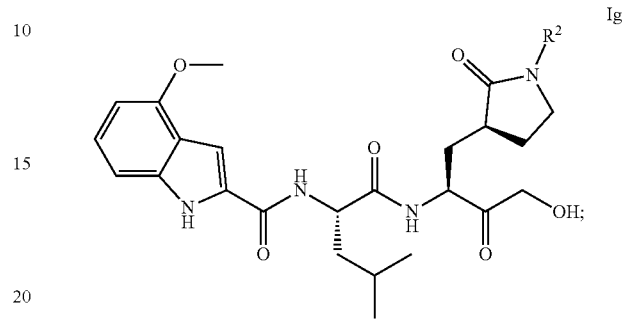

wherein $R^2$ is selected from the group consisting of —C(O)$R^7$, —$CO_2R^7$ and —$C_1$-$C_6$alkyl-OC(O)$OR^7$, or a pharmaceutically acceptable salt thereof.

A twenty fourth embodiment of a first aspect of the present invention is the compound of the twenty third embodiment of the first aspect selected from the group consisting of (1S)-1-{(3S)-3-[(2S)-4-hydroxy-2-({N-[(4-methoxy-1H-indol-2-yl)carbonyl]-L-leucyl}amino)-3-oxobutyl]-2-oxopyrrolidin-1-yl}ethyl methyl carbonate; N-[(2S)-1-({(2S)-1-[(3S)-1-acetyl-2-oxopyrrolidin-3-yl]-4-hydroxy-3-oxobutan-2-yl}amino)-4-methyl-1-oxopentan-2-yl]-4-methoxy-1H-indole-2-carboxamide; methyl (3S)-3-[(2S)-4-hydroxy-2-({N-[(4-methoxy-1H-indol-2-yl)carbonyl]-L-leucyl}amino)-3-oxobutyl]-2-oxopyrrolidine-1-carboxylate; and {(3S)-3-[(2S)-4-hydroxy-2-({N-[(4-methoxy-1H-indol-2-yl)carbonyl]-L-leucyl}amino)-3-oxobutyl]-2-oxopyrrolidin-1-yl}methyl methyl carbonate; or a pharmaceutically acceptable salt thereof.

A first embodiment of a second aspect of the present invention is a pharmaceutical composition comprising a therapeutically effective amount of a compound of any one of the first through twenty fourth embodiments of the first aspect or a pharmaceutically acceptable salt thereof together with a pharmaceutically acceptable carrier. A second embodiment of a second aspect of the present invention is the pharmaceutical composition of the first embodiment of the second aspect wherein the composition is in the form of an oral dosage form. A third embodiment of a second aspect of the present invention is the pharmaceutical composition of the first embodiment of the second aspect wherein the composition is in an intranasal dosage form or inhalation dosage form. A fourth embodiment of a second aspect of the present invention is the pharmaceutical composition of the first embodiment of the second aspect further comprising an additional therapeutic agent. A fifth embodiment of a second aspect of the present invention is the pharmaceutical composition of the fourth embodiment of the second aspect wherein the pharmaceutical composition further comprises one or more of chloroquine, hydroxychloroquine, azithromycin and remdesivir.

Another embodiment of the present invention is a method of treating COVID-19 in a patient, the method comprising administering a therapeutically effective amount of a compound of any one of the first through twenty fourth embodiments of the first aspect or a pharmaceutically acceptable salt thereof to a patient in need thereof.

Another embodiment of the present invention is a method of treating COVID-19 in a patient, the method comprising administering a pharmaceutical composition of any one of the first through fifth embodiments of the second aspect of the invention to a patient in need thereof.

Another embodiment of the invention is a method of inhibiting or preventing SARS-CoV-2 viral replication comprising contacting the SARS-CoV-2 coronavirus 3CL protease with a therapeutically effective amount of a compound of any one of first through twenty fourth embodiments of the first aspect or a pharmaceutically acceptable salt thereof or a pharmaceutically acceptable salt thereof or a metabolite of the compound or pharmaceutically acceptable salt.

Another embodiment of the present invention is a method of inhibiting or preventing SARS-CoV-2 viral replication in a patient the method comprising administering to the patient in need of inhibition of or prevention of SARS-CoV-2 viral replication a therapeutically effective amount of a compound of any one of first through twenty fourth embodiments of the first aspect or a pharmaceutically acceptable salt thereof.

Another embodiment of the invention is the use of a compound of any one of first through twenty fourth embodiments of the first aspect or a pharmaceutically acceptable salt thereof for the treatment of COVID-19. Another embodiment of the invention is the use of a compound of any one first through twenty fourth embodiments of the first aspect or a pharmaceutically acceptable salt thereof for the preparation of a medicament that is useful for the treatment of COVID-19.

Another embodiment of the present invention is method of treating COVID-19 in a patient, the method comprising administering a therapeutically effective amount of (3S)-3-({N-[(4-methoxy-1H-indol-2-yl)carbonyl]-L-leucyl}amino)-2-oxo-4-[(3S)-2-oxopyrrolidin-3-yl]butyl dihydrogen phosphate or a pharmaceutically acceptable salt thereof to a patient in need thereof.

Yet another embodiment of the present invention is the immediately preceding embodiment further comprising administering one or more additional therapeutic agents to a patient in need thereof.

Yet another embodiment of the present invention is the immediately preceding embodiment wherein the additional therapeutic agents are selected from remdesivir and azithromycin.

The following embodiments of the invention, E1-E49 are particularly preferred embodiments of the invention.

E1 is a compound of Formula I wherein
- - - - - - is absent or a bond;
$R^1$ is selected from the group consisting of —CH($R^{4a}$)—OC(O)$R^4$, —C(O)O$R^4$, —CH($R^{4a}$)—OC(O)O$R^4$, —P(O)(O$R^5$)$_2$, —P(O)($C_1$-$C_6$alkyl)(O$R^5$) and —C(O)N($R^6$)$_2$;
$R^2$ is selected from the group consisting of hydrogen, —C(O)$R^7$, —CO$_2R^7$ and —$C_1$-$C_6$alkyl-OC(O)O$R^7$;
and when $R^2$ is —C(O)$R^7$, —CO$_2R^7$ or —$C_1$-$C_6$alkyl-OC(O)O$R^7$, then $R^1$ is selected from the group consisting of hydrogen, —CH($R^{4a}$)—OC(O)$R^4$, —C(O)O$R^4$, —CH($R^{4a}$)—OC(O)O$R^4$, —P(O)(O$R^5$)$_2$, —P(O)($C_1$-$C_6$alkyl)(O$R^5$) and —C(O)N($R^6$)$_2$;
$R^3$ is oxo when - - - - - is absent or when - - - - - is a bond $R^3$ taken together with $R^1$ and the oxygen to which $R^1$ is attached are —OC(O)O—;
$R^4$ and $R^7$ are each independently selected from the group consisting of $C_1$-$C_6$alkyl unsubstituted or substituted with one to three $R^8$, $C_3$-$C_7$cycloalkyl unsubstituted or substituted with one to three $R^8$, $C_5$-$C_{12}$bicycloalkyl unsubstituted or substituted with one to three $R^8$, four to seven membered heterocycloalkyl comprising one to three heteroatoms selected independently from N, O and S and which is unsubstituted or substituted with one to three $R^8$, $C_6$-$C_{10}$aryl unsubstituted or substituted with one to three $R^8$, and a five to ten membered heteroaryl comprising one to four heteroatoms selected independently from N, O and S and which is unsubstituted or substituted with one to three $R^8$;
$R^{4a}$ is hydrogen or $C_1$-$C_6$alkyl;
$R^5$ at each occurrence is independently hydrogen or $C_1$-$C_6$alkyl, or both $R^5$ groups taken together are a $C_2$-$C_4$alkylene which is optionally substituted with phenyl;
$R^6$ at each occurrence is independently selected from hydrogen and $C_1$-$C_6$alkyl which is unsubstituted or substituted with one to three $R^8$;
or both $R^6$ groups taken together with the nitrogen to which they are attached are a four- to seven-membered heterocycloalkyl optionally comprising an additional one to three heteroatoms independently selected from N, O and S, wherein said heterocycloalkyl is unsubstituted or substituted with one to three $R^8$; and
$R^8$ at each occurrence is independently selected from halo, hydroxy, cyano, $C_1$-$C_3$alkoxy, $C_1$-$C_3$alkoxy$C_1$-$C_3$alkyl, $C_3$-$C_6$cycloalkyl, $C_3$-$C_6$cycloalkoxy, di($C_1$-$C_3$alkyl)amino, ($C_1$-$C_3$alkyl)amino, amino, di($C_1$-$C_3$alkyl)amino-$C_1$-$C_3$alkyl, ($C_1$-$C_3$alkyl)amino-$C_1$-$C_3$alkyl, amino-$C_1$-$C_3$alkyl and four to seven membered heterocycloalkyl comprising one to three heteroatoms selected independently from N, O and S;
or a pharmaceutically acceptable salt, solvate or hydrate thereof.

E2 is the compound of E1 of the formula Ie

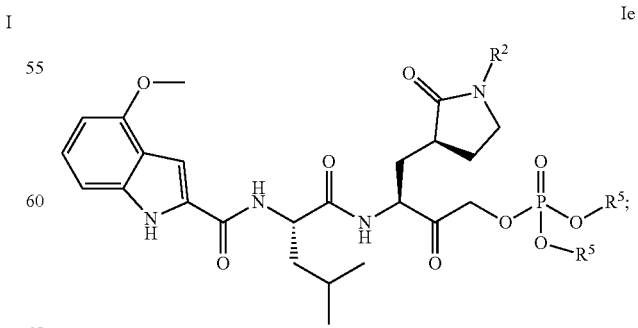

or a pharmaceutically acceptable salt, solvate or hydrate thereof.

E3 is the compound of claim E2 wherein $R^2$ is selected from the group consisting of hydrogen, —C(O)CH$_3$, —CO$_2$CH$_3$, —CH$_2$OC(O)OCH$_3$ and —CH(CH$_3$)OC(O)OCH$_3$, and $R^5$ at each occurrence is independently selected from the group consisting of hydrogen, methyl, ethyl, isopropyl and t-butyl; or both $R^5$ groups taken together are —CH(Phenyl)CH$_2$CH$_2$—, or a pharmaceutically acceptable salt, solvate or hydrate thereof.

E3 is the compound of E2 selected from the group consisting of (1S)-1-{(3S)-3-[(2S)-4-[(dimethoxyphosphoryl)oxy]-2-({N-[(4-methoxy-1H-indol-2-yl)carbonyl]-L-leucyl}amino)-3-oxobutyl]-2-oxopyrrolidin-1-yl}ethyl methyl carbonate; (3S)-3-({N-[(4-methoxy-1H-indol-2-yl)carbonyl]-L-leucyl}amino)-2-oxo-4-[(3S)-2-oxopyrrolidin-3-yl]butyl dihydrogen phosphate; (3S)-3-({N-[(4-methoxy-1H-indol-2-yl)carbonyl]-L-leucyl}amino)-2-oxo-4-[(3S)-2-oxopyrrolidin-3-yl]butyl dimethyl phosphate; (3S)-3-({N-[(4-methoxy-1H-indol-2-yl)carbonyl]-L-leucyl}amino)-2-oxo-4-[(3S)-2-oxopyrrolidin-3-yl]butyl dipropan-2-yl phosphate; (3S)-4-[(3S)-1-acetyl-2-oxopyrrolidin-3-yl]-3-({N-[(4-methoxy-1H-indol-2-yl)carbonyl]-L-leucyl}amino)-2-oxobutyl dimethyl phosphate; 4-methoxy-N-[(2S)-4-methyl-1-({(2S)-4-[(2-oxido-4-phenyl-1,3,2-dioxa phosphinan-2-yl)oxy]-3-oxo-1-[(3S)-2-oxopyrrolidin-3-yl]butan-2-yl}amino)-1-oxopentan-2-yl]-1H-indole-2-carboxamide; diethyl (3S)-3-({N-[(4-methoxy-1H-indol-2-yl)carbonyl]-L-leucyl}amino)-2-oxo-4-[(3S)-2-oxopyrrolidin-3-yl]butyl phosphate; and methyl (3S)-3-[(2S)-4-[(dimethoxyphosphoryl)oxy]-2-({N-[(4-methoxy-1H-indol-2-yl)carbonyl]-L-leucyl}amino)-3-oxobutyl]-2-oxopyrrolidine-1-carboxylate; or a pharmaceutically acceptable salt, solvate or hydrate thereof.

E5 is the compound of E4 which is (3S)-3-({N-[(4-methoxy-1H-indol-2-yl)carbonyl]-L-leucyl}amino)-2-oxo-4-[(3S)-2-oxopyrrolidin-3-yl]butyl dihydrogen phosphate; or a pharmaceutically acceptable salt, solvate or hydrate thereof.

E6 is the compound of E5 which is in the form of a hydrate.

E7 is the compound of E6 which is a crystalline (3S)-3-({N-[(4-methoxy-1H-indol-2-yl)carbonyl]-L-leucyl}amino)-2-oxo-4-[(3S)-2-oxopyrrolidin-3-yl]butyl dihydrogen phosphate hydrate.

E8 is the compound of claim E7 which is crystalline (3S)-3-({N-[(4-methoxy-1H-indol-2-yl)carbonyl]-L-leucyl}amino)-2-oxo-4-[(3S)-2-oxopyrrolidin-3-yl]butyl dihydrogen phosphate Form 1 hydrate having one or more characteristics selected from the group consisting of a powder X-ray diffraction pattern, a $^{13}$C solid state NMR spectrum and a Raman spectrum; wherein the powder X-ray diffraction pattern characteristic is selected from
a) a powder X-ray diffraction pattern comprising peaks at 4.1±0.2 and 7.2±0.2 degrees 2-Theta;
b) a powder X-ray diffraction pattern comprising peaks at 4.1±0.2, 7.2±0.2 and 10.4±0.2 degrees 2-Theta; and
c) a powder X-ray diffraction pattern comprising peaks at 4.1±0.2, 7.2±0.2, 10.4±0.2 and 14.5±0.2 degrees 2-Theta;
wherein the $^{13}$C solid state NMR spectrum characteristic is selected from
a) $^{13}$C solid state NMR spectrum comprising peaks at 21.7, 153.8 and 172.2 ppm; each peak±0.2 ppm;
b) a $^{13}$C solid state NMR spectrum comprising peaks at 21.7, 153.8, 172.2 and 118.6 ppm; each peak±0.2 ppm;
c) a $^{13}$C solid state NMR spectrum comprising peaks at 21.7, 153.8, 172.2, 118.6 and 57.8 ppm; each peak±0.2 ppm; and wherein the Raman spectrum characteristic is selected from
a) a Raman spectrum comprising Raman peaks at 1271, 1421 and 1217 cm$^{-1}$, each peak±2 cm$^{-1}$,
b) a Raman spectrum comprising Raman peaks at 1271, 1421, 1217 and 1640 cm$^{-1}$; each peak±2 cm$^{-1}$, and
c) a Raman spectrum comprising Raman peaks at 1271, 1421, 1217, 1640 and 3074 cm$^{-1}$; each peak±2 cm$^{-1}$.

E9 is the compound of E5 which is in the form of a methyl ethyl ketone solvate.

E10 is the compound of E9 which is a crystalline (3S)-3-({N-[(4-methoxy-1H-indol-2-yl)carbonyl]-L-leucyl}amino)-2-oxo-4-[(3S)-2-oxopyrrolidin-3-yl]butyl dihydrogen phosphate, methyl ethyl ketone solvate.

E11 is the compound of E10 which is crystalline (3S)-3-({N-[(4-methoxy-1H-indol-2-yl)carbonyl]-L-leucyl}amino)-2-oxo-4-[(3S)-2-oxopyrrolidin-3-yl]butyl dihydrogen phosphate, methyl ethyl ketone solvate having one or more characteristics selected from the group consisting of a powder X-ray diffraction pattern, a $^{13}$C NMR spectrum and a Raman spectrum;
wherein the powder X-ray diffraction pattern characteristic is selected from
a) a powder X-ray diffraction pattern comprising peaks at 7.7±0.2, 8.1±0.2 and 23.1±0.2 degrees 2-Theta;
b) a powder X-ray diffraction pattern comprising peaks at 7.7±0.2, 8.1±0.2, 23.1±0.2 and 17.0±0.2 degrees 2-Theta; and
c) a powder X-ray diffraction pattern comprising peaks at 7.7±0.2, 8.1±0.2, 23.1±0.2, 17.0±0.2 and 25.8±0.2 degrees 2-Theta;
wherein the $^{13}$C solid state NMR spectrum characteristic is selected from
a) a $^{13}$C solid state NMR spectrum comprising peaks at 7.2, 206.4 and 215.8 ppm; each ±0.2 ppm;
b) a $^{13}$C solid state NMR spectrum comprising peaks at 7.2, 206.4, 215.8 and 42.2 ppm; each ±0.2 ppm; and
c) a $^{13}$C solid state NMR spectrum comprising peaks at 7.2, 206.4, 215.8, 42.2 and 101.2 ppm; each ±0.2 ppm; and wherein the Raman spectrum characteristic is selected from
a) a Raman spectrum comprising peaks at 1511, 1644 and 3081 cm$^{-1}$; each ±2 cm$^{-1}$;
b) a Raman spectrum comprising peaks at 1511, 1644, 3081 and 1265 cm$^{-1}$; each ±2 cm$^{-1}$; and
c) a Raman spectrum comprising peaks at 1511, 1644, 3081, 1265 and 446 cm$^{-1}$; each ±2 cm$^{-1}$.

E12 is the compound of E5 which is in the form of a dimethylsulfoxide solvate.

E13 is the compound of E12 which is crystalline (3S)-3-({N-[(4-methoxy-1H-indol-2-yl)carbonyl]-L-leucyl}amino)-2-oxo-4-[(3S)-2-oxopyrrolidin-3-yl]butyl dihydrogen phosphate, dimethylsulfoxide solvate.

E14 is the compound of E13 which is crystalline (3S)-3-({N-[(4-methoxy-1H-indol-2-yl)carbonyl]-L-leucyl}amino)-2-oxo-4-[(3S)-2-oxopyrrolidin-3-yl]butyl dihydrogen phosphate, dimethylsulfoxide solvate having one or more characteristics selected from the group consisting of a powder X-ray diffraction pattern, a $^{13}$C solid state NMR spectrum and a Raman spectrum;
wherein the powder X-ray diffraction pattern characteristic is selected from a) a powder X-ray diffraction pattern comprising peaks at 7.4±0.2, 14.8±0.2 and 26.2±0.2 degrees 2-Theta;
b) a powder X-ray diffraction pattern comprising peaks at 7.4±0.2, 14.8±0.2, 26.2±0.2 and 10.8±0.2 degrees 2-Theta; and
c) a powder X-ray diffraction pattern comprising peaks at 7.4±0.2, 14.8±0.2, 26.2±0.2, 10.8±0.2 and 22.3±0.2 degrees 2-Theta;
wherein the $^{13}$C solid state NMR spectrum characteristic is selected from
a) a $^{13}$C solid state NMR spectrum comprising peaks at 173.4±0.2, 210.7±0.2 and 26.2±0.2 ppm;
b) a $^{13}$C solid state NMR spectrum comprising peaks at 173.4±0.2, 210.7±0.2, 26.2±0.2 and 22.8±0.2 ppm; and
c) a $^{13}$C solid state NMR spectrum comprising peaks at 173.4±0.2, 210.7±0.2, 26.2±0.2, 22.8±0.2 and 25.5±0.2 ppm; and
wherein the Raman spectrum characteristic is
a) a Raman spectrum comprising peaks at 1717±2 and 675±2 cm$^{-1}$.

E15 is the compound of claim E5 which is in the form of a dimethylsulfoxide solvate hydrate.

E16 is the compound of E15 which is crystalline (3S)-3-({N-[(4-methoxy-1H-indol-2-yl)carbonyl]-L-leucyl}amino)-2-oxo-4-[(3S)-2-oxopyrrolidin-3-yl]butyl dihydrogen phosphate, dimethylsulfoxide solvate hydrate.

E17 is the compound of E13 which is crystalline (3S)-3-({N-[(4-methoxy-1H-indol-2-yl)carbonyl]-L-leucyl}amino)-2-oxo-4-[(3S)-2-oxopyrrolidin-3-yl]butyl dihydrogen phosphate, dimethylsulfoxide solvate hydrate having a powder X-ray diffraction pattern characteristic;
wherein the X-ray powder diffraction pattern characteristic is selected from
a) a powder X-ray diffraction pattern comprising peaks at 14.5±0.2, 25.6±0.2 and 26.6±0.2 degrees 2-Theta;
b) a powder X-ray diffraction pattern comprising peaks at 14.5±0.2, 25.6±0.2, 26.6±0.2 and 21.9±0.2 degrees 2-Theta; and
c) a powder X-ray diffraction pattern comprising peaks at 14.5±0.2, 25.6±0.2, 26.6±0.2, 21.9±0.2, 17.8±0.2 degrees 2-Theta.

E18 is the compound of E5 which is (3S)-3-({N-[(4-methoxy-1H-indol-2-yl)carbonyl]-L-leucyl}amino)-2-oxo-4-[(3S)-2-oxopyrrolidin-3-yl]butyl dihydrogen phosphate.

E19 is the compound of E18 which is amorphous (3S)-3-({N-[(4-methoxy-1H-indol-2-yl)carbonyl]-L-leucyl}amino)-2-oxo-4-[(3S)-2-oxopyrrolidin-3-yl]butyl dihydrogen phosphate.

E20 is the compound of E19 which is amorphous (3S)-3-({N-[(4-methoxy-1H-indol-2-yl)carbonyl]-L-leucyl}amino)-2-oxo-4-[(3S)-2-oxopyrrolidin-3-yl] butyl dihydrogen phosphate having one or more characteristics selected from the group consisting of a $^{13}$C solid state NMR spectrum and a combination of a $^{13}$C solid state NMR spectrum and a $^{31}$P solid state NMR spectrum;
wherein the $^{13}$C solid state NMR spectrum characteristic is selected from
a) a $^{13}$C solid state NMR spectrum comprising peaks at 175.0±0.4, 204±1.5 and 181.8±0.4 ppm;
b) a $^{13}$C solid state NMR spectrum comprising peaks at 175.0±0.4, 204±1.5, 181.8±0.4 and 54.8±0.2 ppm; and
c) a $^{13}$C solid state NMR spectrum comprising peaks at 175.0±0.4, 204±1.5, 181.8±0.4, 54.8±0.2 and 162.9±0.2 ppm; and
the combination of a $^{13}$C solid state NMR spectrum and a $^{31}$P solid state NMR spectrum is a $^{13}$C solid state NMR spectrum comprising peaks at 175.0±0.4 and 204±1.5 and a $^{31}$P solid state NMR spectrum with a peak at −0.8±0.2 ppm.

E21 is the compound of E5 which is (3S)-3-({N-[(4-methoxy-1H-indol-2-yl)carbonyl]-L-leucyl}amino)-2-oxo-4-[(3S)-2-oxopyrrolidin-3-yl]butyl dihydrogen phosphate, sodium salt.

E22 is the compound of E21 which is amorphous (3S)-3-({N-[(4-methoxy-1H-indol-2-yl)carbonyl]-L-leucyl}amino)-2-oxo-4-[(3S)-2-oxopyrrolidin-3-yl]butyl dihydrogen phosphate, sodium salt.

E23 is the compound of claim E22 which is amorphous (3S)-3-({N-[(4-methoxy-1H-indol-2-yl)carbonyl]-L-leucyl}amino)-2-oxo-4-[(3S)-2-oxopyrrolidin-3-yl]butyl dihydrogen phosphate sodium salt having one or more characteristics selected from the group consisting of a $^{13}$C solid state NMR spectrum and a combination of a $^{13}$C solid state NMR spectrum and a $^{31}$P solid state NMR spectrum;
wherein the $^{13}$C solid state NMR spectrum characteristic is selected from
a) a $^{13}$C solid state NMR spectrum comprising peaks at 126.0±0.4 ppm, 181.0±0.4 ppm and 208.0±1.5 ppm;
b) a $^{13}$C solid state NMR spectrum comprising peaks at 126.0±0.4 ppm, 181.0±0.4 ppm, 208.0±1.5 ppm and 174.1±0.4 ppm 175.0±0.4 ppm; and
c) a $^{13}$C solid state NMR spectrum comprising peaks at 126.0±0.4 ppm, 181.0±0.4 ppm, 208.0±1.5 ppm, 174.1±0.4 ppm and 163.1±0.2 ppm; and the combination of a $^{13}$C solid state NMR spectrum and a $^{31}$P solid state NMR spectrum is a $^{13}$C solid state NMR spectrum comprising peaks at 126.0±0.4 ppm, 181.0±0.4 ppm and a $^{31}$P solid state NMR spectrum with a peak at 1.9±0.2 ppm.

E24 is a pharmaceutical composition comprising a therapeutically effective amount of (3S)-3-({N-[(4-methoxy-1H-indol-2-yl)carbonyl]-L-leucyl}amino)-2-oxo-4-[(3S)-2-oxopyrrolidin-3-yl]butyl dihydrogen phosphate, or a pharmaceutically acceptable salt, solvate or hydrate thereof according to any one of claims E5 to E23 together with a pharmaceutically acceptable carrier.

E25 is the pharmaceutical composition of E24 wherein the pharmaceutical composition further comprises a buffering agent.

E26 is the pharmaceutical composition of E25 wherein:
a) the pharmaceutically acceptable salt is selected from the group consisting of benzathine, calcium, choline, diethylamine, diolamine, magnesium, meglumine, lysine, piperazine, potassium, tris(hydroxymethyl)aminomethane and sodium;
b) the molar ratio of the salt counterion to the (3S)-3-({N-[(4-methoxy-1H-indol-2-yl)carbonyl]-L-leucyl}amino)-2-oxo-4-[(3S)-2-oxopyrrolidin-3-yl]butyl dihydrogen phosphate in the pharmaceutically acceptable salt is approximately 0.5:1 to approximately 3:1; and
c) the buffering agent is selected from the group consisting of phosphoric acid, citric acid, maleic acid, tartaric acid, lactic acid and acetic acid.

E27 is the pharmaceutical composition of E26 wherein:
a) the pharmaceutically acceptable salt is sodium;
b) the molar ratio of the sodium counterion to the (3S)-3-({N-[(4-methoxy-1H-indol-2-yl)carbonyl]-L-leucyl}amino)-2-oxo-4-[(3S)-2-oxopyrrolidin-3-yl]butyl dihydrogen phosphate in the pharmaceutically acceptable salt is approximately 0.5:1 to approximately 2:1;
c) the buffering agent is citric acid; and d) the molar ratio of (3S)-3-({N-[(4-methoxy-1H-indol-2-yl)carbonyl]-L-leucyl}amino)-2-oxo-4-[(3S)-2-oxopyrrolidin-3-yl]butyl dihydrogen phosphate to citric acid is approximately 2:1 to approximately 10:1.

E28 is the pharmaceutical composition of any one of E25 to E27 wherein the composition is in the form of a powder or lyophile wherein the solution pH of the reconstituted formulation is in the range of 2 to 6.

E29 is the pharmaceutical composition of E28 wherein the solution pH of the reconstituted formulation is in the range of 3 to 5.

E30 is the pharmaceutical composition of any one of E24 to E29 wherein the pharmaceutical composition further comprises one or more stabilizing agents.

E31 is the pharmaceutical composition of E30 wherein the one or more stabilizing agents are selected from the group consisting of dextrans, sucrose, lactose, trehalose, mannitol, sorbitol, glucose, raffinose, glycine, histidine, polyvinyl pyrrolidones, and polyethylene glycols.

E32 is the pharmaceutical composition of E30 wherein the one or more stabilizing agents are selected from the group consisting of polyethylene glycol 300, polyethylene glycol 400 and polyethylene glycol 3350.

E33 is the pharmaceutical composition of E32 wherein the total amount of the one or more stabilizing agents is up to approximately 15% w/w of the formulation.

E34 is the pharmaceutical composition of any one of claims E24 to E33 wherein the pharmaceutical composition further comprises one or more solubilizing agents.

E35 is the pharmaceutical composition of E34 wherein the solubilizing agent is selected from the group consisting of polysorbate 20, polyethoxylated castor oil, polyethylene glycol (15)-hydroxystearate, hydroxypropyl-beta-cyclodextrin, sulfobutylether-beta cyclodextrin, gamma cyclodextrin, and polysorbate 80.

E36 is the pharmaceutical composition of E35 wherein the solubilizing agent is polysorbate 80 and the buffering agent is citric acid.

E37 is the pharmaceutical composition of E32 wherein the composition is a powder or lyophile which, when reconstituted with water for injection, 0.9% saline or 5% w/v provides an aqueous solution wherein the concentration of (3S)-3-({N-[(4-methoxy-1H-indol-2-yl)carbonyl]-L-leucyl}amino)-2-oxo-4-[(3S)-2-oxopyrrolidin-3-yl]butyl dihydrogen phosphate or a pharmaceutically acceptable salt thereof is about 1 mg/mL to about 200 mg/mL.

E38 is the pharmaceutical composition of E37 wherein the solution pH of the formulation after reconstitution is in the range of about 3 to about 5.

E39 is the pharmaceutical composition of E38, which after reconstitution has a polysorbate 80 concentration is up to approximately 5% w/w.

E40 is the pharmaceutical composition of E37 wherein the pharmaceutical powder or lyophile has a water content of less than about 1%.

E41 is the pharmaceutical composition of any one of E24 to E40 which is an aqueous solution suitable for parenteral administration or is reconstituted with water for injection, 0.9% saline or 5% w/v dextrose to form an aqueous solution suitable for parenteral administration.

E42 is a method of treating a coronavirus infection in a patient, the method comprising administering a therapeutically effective amount of (3S)-3-({N-[(4-methoxy-1H-indol-2-yl)carbonyl]-L-leucyl}amino)-2-oxo-4-[(3S)-2-oxopyrrolidin-3-yl]butyl dihydrogen phosphate; or a pharmaceutically acceptable salt, solvate or hydrate thereof according to any one of E5 to E23 to a patient in need thereof.

E43 is the method of E42 wherein the coronavirus infection is COVID-19.

E44 is the method of E43 wherein about 0.1 g to about 5 g of (3S)-3-({N-[(4-methoxy-1H-indol-2-yl)carbonyl]-L-leucyl}amino)-2-oxo-4-[(3S)-2-oxopyrrolidin-3-yl]butyl dihydrogen phosphate; or a pharmaceutically acceptable salt, solvate or hydrate thereof is administered daily.

E45 is the method of E44 wherein about 0.1 to about 1 g (3S)-3-({N-[(4-methoxy-1H-indol-2-yl)carbonyl]-L-leucyl}amino)-2-oxo-4-[(3S)-2-oxopyrrolidin-3-yl]butyl dihydrogen phosphate; or a pharmaceutically acceptable salt, solvate or hydrate thereof is intravenously administered daily.

E46 is a method of treating COVID-19 in a patient, the method comprising administering a pharmaceutical composition according to E41 to a patient in need of treatment thereof.

E47 is the method of any one of E42 to E46 wherein one or more additional therapeutic agents are administered to the patient.

E48 is the method of E47 wherein the one or more additional therapeutic agent is selected from the group consisting of remdesivir, galidesivir, favilavir/avifavir, mulnupiravir (MK-4482/EIDD 2801), AT-527, AT-301, BLD-2660, favipiravir, camostat, SLV213 emtrictabine/tenofivir, clevudine, dalcetrapib, boceprevir, ABX464, dexamethasone, hydrocortisone, convalescent plasma, gelsolin (Rhu-p65N), monoclonal antibodies, regdanvimab (Regkirova), ravulizumab (Ultomiris), VIR-7831/VIR-7832, BRII-196/BRII-198, COVI-AMG/COVIDROPS (STI-2020), bamlanivimab (LY-CoV555), mavrilimab, leronlimab (PRO140), AZD7442, lenzilumab, infliximab, adalimumab, JS 016, STI-1499 (COVIGUARD), lanadelumab (Takhzyro), canakinumab (Ilaris), gimsilumab, otilimab, casirivimab/imdevimab (REGN-Cov2), MK-7110 (CD24Fc/SACCOVID), heparin, apixaban, tocilizumab (Actemra), sarilumab (Kevzara), apilimod dimesylate, DNL758, PB1046, dapaglifozin, abivertinib, ATR-002, bemcentinib, acalabrutinib, baricitinib, tofacitinib, losmapimod, famotidine, niclosamide and diminazene.

E49 is the method of E48 wherein the one or more additional agent is selected from the group consisting of remdesivir, dexamethasone, malnupiravir, bamlanivimab, tofacitinib and baricitinib.

It is to be understood that the method of treatment claims can also be construed as appropriate use type claims.

The present invention also provides a method of treating a condition that is mediated by SARS-CoV-2 coronavirus 3C-like protease activity in a patient by administering to said patient a pharmaceutically effective amount of a SARS-CoV-2 protease inhibitor as described herein.

The present invention also provides a method of targeting SARS-CoV-2 inhibition as a means of treating indications caused by SARS-CoV-2-related viral infections.

The present invention also provides a method of identifying cellular or viral pathways interfering with the functioning of the members of which could be used for treating indications caused by SARS-CoV-2 infections by administering a SARS-CoV-2 protease inhibitor as described herein.

The present invention also provides a method of using SARS-CoV-2 protease inhibitors as described herein as tools for understanding mechanism of action of other SARS-CoV-2 inhibitors.

The present invention also provides a method of using SARS-CoV-2 3C-like protease inhibitors for carrying out gene profiling experiments for monitoring the up or down regulation of genes for the purposed of identifying inhibitors for treating indications caused by SARS-CoV-2 infections such as COVID-19.

The present invention further provides a pharmaceutical composition for the treatment of COVID-19 in a mammal containing an amount of a SARS-CoV-2 3C-like protease inhibitor that is effective in treating COVID-19 and a pharmaceutically acceptable carrier.

Another embodiment of the invention is a method of treating COVID-19 in a patient wherein approximately 500 mg/day of (3S)-3-({N-[(4-methoxy-1H-indol-2-yl)carbonyl]-L-leucyl}amino)-2-oxo-4-[(3S)-2-oxopyrrolidin-3-yl] butyl dihydrogen phosphate is administered to the patient. The administration can be intravenous for example by continuous intravenous infusion. The administration can be in a solution volume of 250 mL or less per day.

Another embodiment of the invention is a method of treating COVID-19 in a patient by administration of 0.25 g to 5 g of (3S)-3-({N-[(4-methoxy-1H-indol-2-yl)carbonyl]-L-leucyl}amino)-2-oxo-4-[(3S)-2-oxopyrrolidin-3-yl]butyl dihydrogen phosphate to the patient by continuous intravenous infusion. The administration can be in a intravenous solution volume of 250 mL or less per day. The method can include co-administration of one or more additional therapeutic agents to the patient. The method can include co-administration of one or more additional therapeutic agents selected from the group consisting of remdesivir, (2R,3R,4S,5R)-2-(4-aminopyrrolo[2,1-f][1,2,4]triazin-7-yl)-3,4-dihydroxy-5-(hydroxymethyl) oxolane-2-carbonitrile (GS-441524), Sodium (2S)-2-((S)-2-(((benzyloxy) carbonyl) amino)-4-methylpentanamido)-1-hydroxy-3-(2-oxopyrrolidin-3-yl)propane-1-sulfonate (GC376), dexamethasone, azithromycin, umifenovir and favipiravir.

Another embodiment, F1, of the invention is a pharmaceutical composition comprising (3S)-3-({N-[(4-methoxy-1H-indol-2-yl)carbonyl]-L-leucyl}amino)-2-oxo-4-[(3S)-2-oxopyrrolidin-3-yl]butyl dihydrogen phosphate or a pharmaceutically acceptable salt thereof together with a pharmaceutically acceptable carrier.

Another embodiment, F2, of the invention is the pharmaceutical composition of the immediately preceding embodiment F1 wherein the pharmaceutical composition further comprises a buffering agent.

Another embodiment of the invention, F3, is the pharmaceutical composition of claim the immediately preceding embodiment wherein the buffering agent is selected from the group consisting of phosphoric acid, citric acid, maleic acid, tartaric acid, lactic acid and acetic acid.

Another embodiment of the invention, F4, is the pharmaceutical composition of the immediately preceding embodiment, F3, wherein the buffering agent is citric acid.

Another embodiment of the invention, F5, is the pharmaceutical composition of any one of the three immediately preceding embodiments, F2-F4, wherein the composition is in the form of an aqueous solution and the solution pH of the formulation is in the range of 2 to 6.

Another embodiment of the invention, F6, is the pharmaceutical composition of the immediately preceding embodiment F5 wherein the solution pH of the formulation is in the range of 3 to 5.

Another embodiment of the invention, F7, is the pharmaceutical composition of the immediately preceding embodiment F6 wherein the solution pH of the formulation is in the range of 3.5 to 4.5.

Another embodiment of the invention, F8, is the pharmaceutical composition of F1-F4 wherein the pharmaceutical composition further comprises a bulking agent.

Another embodiment of the invention, F9, is the pharmaceutical composition of F8 wherein the bulking agent is selected from the group consisting of sucrose, lactose, trehalose, mannitol, sorbitol, glucose, raffinose, glycine, histidine, polyvinyl pyrrolidone.

Another embodiment of the invention, F10, is the pharmaceutical composition of F9 wherein the bulking agent is selected from the group consisting of trehalose, sucrose, lactose, mannitol and polyethylene glycol 400.

Another embodiment of the invention is the pharmaceutical composition of any one of F1 through F10 which is in the form of a lyophile or a powder.

Another embodiment of the invention is the pharmaceutical composition of any one of F1 through F10 which is in the form of an aqueous solution.

Another embodiment of the invention is the pharmaceutical composition of any one of F1 through F10 wherein the pharmaceutical composition further comprises a solubilizing agent.

Another embodiment of the invention is the pharmaceutical composition of the immediately preceding embodiment wherein the solubilizing agent is selected from the group consisting of polysorbate 20, Cremophor EL, Kolliphor HS-15, hydroxypropyl-beta-cyclodextrin, sulfobutylether-beta cyclodextrin, gamma cyclodextrin and polysorbate 80.

Another embodiment of the invention is the pharmaceutical composition of the immediately preceding embodiment wherein the solubilizing agent is polysorbate 80 and the buffering agent is citrate.

Another embodiment of the invention is the pharmaceutical composition of the immediately preceding embodiment wherein the composition is an aqueous solution.

Another embodiment of the invention is the pharmaceutical composition of the immediately preceding embodiment wherein the solution pH of the formulation is in the range of about 3.5 to about 4.5.

Another embodiment of the invention is the pharmaceutical composition of the immediately preceding embodiment wherein the polysorbate 80 concentration is about 5 mg/mL and the citrate buffer concentration is about 40 mM.

Another embodiment of the invention is the pharmaceutical composition which comprises the solubilizing agent polysorbate 80 and the buffering agent citrate and wherein the pharmaceutical composition is a powder or a lyophile.

Another embodiment of the invention, M1, is a method of treating a coronavirus infection in a patient comprising administering a therapeutically effective amount of (3S)-3-({N-[(4-methoxy-1H-indol-2-yl)carbonyl]-L-leucyl}amino)-2-oxo-4-[(3S)-2-oxopyrrolidin-3-yl]butyl dihydrogen phosphate or a pharmaceutically acceptable salt thereof to a patient in need thereof.

Another embodiment of the invention, M2, is the method of M1 wherein the coronavirus infection is a SARS-CoV-2, MERS-CoV, 229E-CoV-2, NL63-CoV, OC43-CoV or HKU1-CoV infection.

Another embodiment of the invention, M3, is the method of M2 is a SARS-CoV-2 infection.

Another method of the invention, M4, is the method of claim M1 wherein the (3S)-3-({N-[(4-methoxy-1H-indol-2-yl)carbonyl]-L-leucyl}amino)-2-oxo-4-[(3S)-2-oxopyrrolidin-3-yl]butyl dihydrogen phosphate or a pharmaceutically acceptable salt thereof is administered as a pharmaceutical composition which comprises the (3S)-3-dihydrogen phosphate or a pharmaceutically acceptable salt thereof together with a pharmaceutically acceptable carrier.

Another method of the invention, M5, is a method of treating a coronavirus infection in a patient comprising administering a pharmaceutical composition according to any one of claims F1 to F10.

Another method of the invention, M6, is the method of claim M5 wherein the pharmaceutical composition is a parenteral solution which is administered to the patient intravenously.

DETAILED DESCRIPTION OF THE INVENTION

Figure 1:
FIG. 1: Residue differences between SARS-CoV and SARS-CoV-2, with an inhibitor compound shown at the active site.

For the purposes of the present invention, as described and claimed herein, the following terms are defined as follows:

As used herein, the terms "comprising" and "including" are used in their open, non-limiting sense. The term "treating", as used herein, unless otherwise indicated, means reversing, alleviating, inhibiting the progress of, or preventing the disorder of condition to which such term applies, or one or more symptoms of such disorder or condition. The term "treatment", as used herein, unless otherwise indicated, refers to the act of treating as "treating" is defined immediately above.

The term "alkyl" as used herein refers to a linear or branched-chain saturated hydrocarbyl substituent (i.e., a substituent obtained from a hydrocarbon by removal of a hydrogen); in one embodiment containing from one to six carbon atoms. Non-limiting examples of such substituents include methyl, ethyl, propyl (including n-propyl and isopropyl), butyl (including n-butyl, isobutyl, sec-butyl and tert-butyl), pentyl, isoamyl, hexyl and the like.

The term "alkoxy" refers to a linear or branched-chain saturated hydrocarbyl substituent attached to an oxygen radical (i.e., a substituent obtained from a hydrocarbon alcohol by removal of the hydrogen from the OH); in one embodiment containing from one to six carbon atoms. Non-limiting examples of such substituents include methoxy, ethoxy, propoxy (including n-propoxy and isopropoxy), butoxy (including n-butoxy, isobutoxy, sec-butoxy and tert-butoxy), pentoxy, hexoxy and the like. An alkoxy group which is attached to an alkyl group is referred to as an so alkoxyalkyl. An example of an alkoxyalkyl group is methoxymethyl.

The term "alkylene" refers to an alkanediyl group (i.e. a substituent obtained from a hydrocarbon by removal of two hydrogens); in one embodiment containing from three to five carbons. Non-limiting examples of such groups include propylene, butylene and pentylene.

In some instances, the number of carbon atoms in a hydrocarbyl substituent (i.e., alkyl, cycloalkyl, etc.) is indicated by the prefix "$C_x$-$C_y$-" or "$C_{x-y}$", wherein x is the minimum and y is the maximum number of carbon atoms in the substituent. Thus, for example, "$C_1$-$C_6$-alkyl" or "$C_{1-6}$ alkyl" refers to an alkyl substituent containing from 1 to 6 carbon atoms. Illustrating further, $C_3$-$C_6$cycloalkyl or $C_{3-6}$-cycloalkyl refers to saturated cycloalkyl group containing from 3 to 6 carbon ring atoms.

The term "cycloalkyl" refers to a carbocyclic substituent obtained by removing a hydrogen from a saturated carbocyclic molecule, for example one having three to seven carbon atoms. The term "cycloalkyl" includes monocyclic saturated carbocycles. The term "$C_3$-$C_7$cycloalkyl" means a radical of a three to seven membered ring system which includes the groups cyclopropyl, cyclobutyl, cyclopentyl, cyclohexyl, and cycloheptyl. The term "$C_{3-6}$cycloalkyl" means a radical of a three to six membered ring system which includes the groups cyclopropyl, cyclobutyl, cyclopentyl and cyclohexyl. The term "$C_{3-6}$cycloalkoxy" refers to a three to six membered cycloalkyl group attached to an oxygen radical. Examples include cyclopropoxy, cyclobutoxy, cyclopentoxy and cyclohexoxy. The term "$C_5$-$C_{12}$bicycloalkyl" means bicyclic cycloalkyl moieties such as bicyclopentyl, bicyclohexyl, bicycloheptyl, bicyclooctyl, bicyclononyl, spiropentyl, spirohexyl, spiroheptyl, spirooctyl and spirononyl.

In some instances, the number of atoms in a cyclic substituent containing one or more heteroatoms (i.e., heteroaryl or heterocycloalkyl) is indicated by the prefix "x- to y-membered", wherein x is the minimum and y is the maximum number of atoms forming the cyclic moiety of the substituent. Thus, for example, "4- to 6-membered heterocycloalkyl" refers to a heterocycloalkyl containing from 4 to 6 atoms, including one to three heteroatoms, in the cyclic moiety of the heterocycloalkyl. Likewise the phrase "5- to 6-membered heteroaryl" refers to a heteroaryl containing from 5 to 6 atoms, and "5- to 10-membered heteroaryl" refers to a heteroaryl containing from 5 to 10 atoms, each including one or more heteroatoms, in the cyclic moiety of the heteroaryl. Furthermore the phases "5-membered heteroaryl" and "6-membered heteroaryl" refer to a five membered heteroaromatic ring system and a six membered heteroaromatic ring system, respectively. The heteroatoms present in these ring systems are selected from N, O and S.

The term "hydroxy" or "hydroxyl" refers to —OH. When used in combination with another term(s), the prefix "hydroxy" indicates that the substituent to which the prefix is attached is substituted with one or more hydroxy substituents. Compounds bearing a carbon to which one or more hydroxy substituents include, for example, alcohols, enols and phenol. The term cyano refers to a —CN group. The term "oxo" means an oxygen which is attached to a carbon by a double bond (i.e. when $R^3$ is oxo then $R^3$ together with the carbon to which it is attached are a C=O moiety).

The term "halo" or "halogen" refers to fluorine (which may be depicted as —F), chlorine (which may be depicted as —Cl), bromine (which may be depicted as —Br), or iodine (which may be depicted as —I).

The term "heterocycloalkyl" refers to a substituent obtained by removing a hydrogen from a saturated or partially saturated ring structure containing a total of the specified number of atoms, such as 4 to 6 ring atoms, wherein at least one of the ring atoms is a heteroatom (i.e., oxygen, nitrogen, or sulfur), with the remaining ring atoms being independently selected from the group consisting of carbon, oxygen, nitrogen, and sulfur. In a group that has a heterocycloalkyl substituent, the ring atom of the heterocycloalkyl substituent that is bound to the group may be a nitrogen heteroatom, or it may be a ring carbon atom. Similarly, if the heterocycloalkyl substituent is in turn substituted with a group or substituent, the group or substituent may be bound to a nitrogen heteroatom, or it may be bound to a ring carbon atom.

The term "heteroaryl" refers to an aromatic ring structure containing the specified number of ring atoms in which at least one of the ring atoms is a heteroatom (i.e., oxygen, nitrogen, or sulfur), with the remaining ring atoms being independently selected from the group consisting of carbon, oxygen, nitrogen, and sulfur. Examples of heteroaryl substituents include 6-membered heteroaryl substituents such as pyridyl, pyrazyl, pyrimidinyl, and pyridazinyl; and 5-membered heteroaryl substituents such as triazolyl, imidazolyl, furanyl, thiophenyl, pyrazolyl, pyrrolyl, oxazolyl, isoxazolyl, thiazolyl, 1,2,3-, 1,2,4-, 1,2,5-, or 1,3,4-oxadiazolyl and isothiazolyl. The heteroaryl group can also be a bicyclic heteroaromatic group such as indolyl, benzofuranyl, benzothienyl, benzimidazolyl, benzothiazolyl, benzoxazolyl, benzoisoxazolyl, oxazolopyridinyl, imidazopyridinyl, imidazopyrimidinyl and the like. In a group that has a heteroaryl substituent, the ring atom of the heteroaryl substituent that is bound to the group may be one of the heteroatoms, or it may be a ring carbon atom. Similarly, if the heteroaryl substituent is in turn substituted with a group or substituent, the group or substituent may be bound to one of the heteroatoms, or it may be bound to a ring carbon atom. The term "heteroaryl" also includes pyridyl N-oxides and groups containing a pyridine N-oxide ring. In addition, the heteroaryl group may contain an oxo group such as the one present in a pyridone group. Further examples include furyl, thienyl, oxazolyl, thiazolyl, imidazolyl, pyrazolyl, triazolyl, tetrazolyl, isoxazolyl, isothiazolyl, oxadiazolyl, thiadiazolyl, pyridinyl, pyridazinyl, pyrimidinyl, pyrazinyl, pyridin-2

(1H)-onyl, pyridazin-2(1H)-onyl, pyrimidin-2(1H)-onyl, pyrazin-2(1H)-onyl, imidazo[1,2-a]pyridinyl, and pyrazolo [1,5-a]pyridinyl. The heteroaryl can be further substituted as defined herein.

Examples of single-ring heteroaryls and heterocycloalkyls include furanyl, dihydrofuranyl, tetrahydrofuranyl, thiophenyl, dihydrothiophenyl, tetrahydrothiophenyl, pyrrolyl, isopyrrolyl, pyrrolinyl, pyrrolidinyl, imidazolyl, isoimidazolyl, imidazolinyl, imidazolidinyl, pyrazolyl, pyrazolinyl, pyrazolidinyl, triazolyl, tetrazolyl, dithiolyl, oxathiolyl, oxazolyl, isoxazolyl, thiazolyl, isothiazolyl, thiazolinyl, isothiazolinyl, thiazolidinyl, isothiazolidinyl, thiaoxadiazolyl, oxathiazolyl, oxadiazolyl (including oxadiazolyl, 1,2,4-oxadiazolyl, 1,2,5-oxadiazolyl, or 1,3,4-oxadiazolyl), pyranyl (including 1,2-pyranyl or 1,4-pyranyl), dihydropyranyl, pyridinyl, piperidinyl, diazinyl (including pyridazinyl, pyrimidinyl, piperazinyl, triazinyl (including s-triazinyl, as-triazinyl and v-triazinyl), oxazinyl (including 2H-1,2-oxazinyl, 6H-1,3-oxazinyl, or 2H-1,4-oxazinyl), isoxazinyl (including o-isoxazinyl or p-isoxazinyl), oxazolidinyl, isoxazolidinyl, oxathiazinyl (including 1,2,5-oxathiazinyl or 1,2,6-oxathiazinyl), oxadiazinyl (including 2H-1,2,4-oxadiazinyl or 2H-1,2,5-oxadiazinyl), morpholinyl.

The term "heteroaryl" can also include, when specified as such, ring systems having two rings wherein such rings may be fused and wherein one ring is aromatic and the other ring is not fully part of the conjugated aromatic system (i.e., the heteroaromatic ring can be fused to a cycloalkyl or heterocycloalkyl ring). Non-limiting examples of such ring systems include 5,6,7,8-tetrahydroisoquinolinyl, 5,6,7,8-tetrahydro-quinolinyl, 6,7-dihydro-5H-cyclopenta[b]pyridinyl, 6,7-dihydro-5H-cyclopenta[c]pyridinyl, 1,4,5,6-tetrahydrocyclopenta[c]pyrazolyl, 2,4,5,6-tetrahydrocyclopenta[c]pyrazolyl, 5,6-dihydro-4H-pyrrolo[1,2-b]pyrazolyl, 6,7-dihydro-5H-pyrrolo[1,2-b][1,2,4]triazolyl, 5,6,7,8-tetrahydro-[1,2,4]triazolo[1,5-a]pyridinyl, 4,5,6,7-tetrahydropyrazolo[1,5-a]pyridinyl, 4,5,6,7-tetrahydro-1H-indazolyl and 4,5,6,7-tetrahydro-2H-indazolyl. It is to be understood that if a carbocyclic or heterocyclic moiety may be bonded or otherwise attached to a designated substrate through differing ring atoms without denoting a specific point of attachment, then all possible points are intended, whether through a carbon atom or, for example, a trivalent nitrogen atom. For example, the term "pyridyl" means 2-, 3- or 4-pyridyl, the term "thienyl" means 2- or 3-thienyl, and so forth.

If substituents are described as "independently" having more than one variable, each instance of a substituent is selected independent of the other(s) from the list of variables available. Each substituent therefore may be identical to or different from the other substituent(s).

If substituents are described as being "independently selected" from a group, each instance of a substituent is selected independent of the other(s). Each substituent therefore may be identical to or different from the other substituent(s).

As used herein, the term "Formula I" may be hereinafter referred to as a "compound(s) of the invention," "the present invention," and "compound of Formula I." Such terms are also defined to include all forms of the compound of Formula I, including hydrates, solvates, isomers, crystalline and non-crystalline forms, isomorphs, polymorphs, and metabolites thereof. For example, the compounds of the invention, or pharmaceutically acceptable salts thereof, may exist in unsolvated and solvated forms. When the solvent or water is tightly bound, the complex will have a well-defined stoichiometry independent of humidity. When, however, the solvent or water is weakly bound, as in channel solvates and hygroscopic compounds, the water/solvent content will be dependent on humidity and drying conditions. In such cases, non-stoichiometry will be the norm.

The compounds of the invention may exist as clathrates or other complexes. Included within the scope of the invention are complexes such as clathrates, drug-host inclusion complexes wherein the drug and host are present in stoichiometric or non-stoichiometric amounts. Also included are complexes of the compounds of the invention containing two or more organic and/or inorganic components, which may be in stoichiometric or non-stoichiometric amounts. The resulting complexes may be ionized, partially ionized, or non-ionized. For a review of such complexes, see J. Pharm. Sci., 64 (8), 1269-1288 by Haleblian (August 1975). The compounds of the invention have asymmetric carbon atoms. The carbon-carbon bonds of the compounds of the invention may be depicted herein using a solid line ( ——— ), a solid wedge ( ◥◣ ), or a dotted wedge ( ·····||||| ). The use of a solid line to depict bonds to asymmetric carbon atoms is meant to indicate that all possible stereoisomers (e.g., specific enantiomers, racemic mixtures, etc.) at that carbon atom are included. The use of either a solid or dotted wedge to depict bonds to asymmetric carbon atoms is meant to indicate that only the stereoisomer shown is meant to be included. It is possible that compounds of Formula I may contain more than one asymmetric carbon atom. In those compounds, the use of a solid line to depict bonds to asymmetric carbon atoms is meant to indicate that all possible stereoisomers are meant to be included. For example, unless stated otherwise, it is intended that the compounds of Formula I can exist as enantiomers and diastereomers or as racemates and mixtures thereof. The use of a solid line to depict bonds to one or more asymmetric carbon atoms in a compound of Formula I and the use of a solid or dotted wedge to depict bonds to other asymmetric carbon atoms in the same compound is meant to indicate that a mixture of diastereomers is present.

Stereoisomers of Formula I include cis and trans isomers, optical isomers such as R and S enantiomers, diastereomers, geometric isomers, rotational isomers, conformational isomers, and tautomers of the compounds of the invention, including compounds exhibiting more than one type of isomerism; and mixtures thereof (such as racemates and diastereomeric pairs). Also included are acid addition or base addition salts wherein the counterion is optically active, for example, D-lactate or L-lysine, or racemic, for example, DL-tartrate or DL-arginine.

When any racemate crystallizes, crystals of two different types are possible. The first type is the racemic compound (true racemate) referred to above wherein one homogeneous form of crystal is produced containing both enantiomers in equimolar amounts. The second type is the racemic mixture or conglomerate wherein two forms of crystal are produced in equimolar amounts each comprising a single enantiomer. The compounds of Formula I may exhibit the phenomenon of tautomerism; such tautomers are also regarded as compounds of the invention. All such tautomeric forms, and mixtures thereof, are included within the scope of compounds of Formula I. Tautomers exist as mixtures of a tautomeric set in solution. In solid form, usually one tautomer predominates. Even though one tautomer may be described, the present invention includes all tautomers of the compounds of Formula I and salts thereof.

The phrase "pharmaceutically acceptable salts(s)", as used herein, unless otherwise indicated, includes salts of acidic or basic groups which may be present in the compounds described herein. The compounds used in the methods of the invention that are basic in nature are capable of forming a wide variety of salts with various inorganic and organic acids. The acids that may be used to prepare pharmaceutically acceptable acid addition salts of such basic compounds are those that form non-toxic acid addition salts, i.e., salts containing pharmacologically acceptable anions, such as the acetate, benzenesulfonate, benzoate, bicarbonate, bisulfate, bitartrate, borate, bromide, calcium edetate, camsylate, carbonate, chloride, clavulanate, citrate, dihydrochloride, edetate, edislyate, estolate, esylate, ethylsuccinate, fumarate, gluceptate, gluconate, glutamate, glycollylarsanilate, hexylresorcinate, hydrabamine, hydrobromide, hydrochloride, iodide, isethionate, lactate, lactobionate, laurate, malate, maleate, mandelate, mesylate, methylsulfate, mucate, napsylate, nitrate, oleate, oxalate, pamoate (embonate), palmitate, pantothenate, phosphate/diphosphate, polygalacturonate, salicylate, stearate, subacetate, succinate, tannate, tartrate, teoclate, tosylate, triethiodode, and valerate salts.

With respect to the compounds of the invention used in the methods of the invention, if the compounds also exist as tautomeric forms then this invention relates to those tautomers and the use of all such tautomers and mixtures thereof.

The subject invention also includes compounds and methods of treatment of COVID-19 and methods of inhibiting SARS-CoV-2 with isotopically-labelled compounds, which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine and chlorine, such as $^{2}H$, $^{3}H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. Compounds of the present invention, prodrugs thereof, and pharmaceutically acceptable salts of said compounds or of said prodrugs which contain the aforementioned isotopes and/or isotopes of other atoms are with the scope of this invention. Certain isotopically-labelled compounds of the present invention, for example those into which radioactive isotopes such as $^{3}H$ and $^{14}C$ are incorporated, are useful in drug and/or substrate tissue distribution assays. Tritiated, i.e., $^{3}H$, and carbon-14, i.e., $^{14}C$, isotopes are particularly preferred for their ease of preparation and detectability. Further, substitution with heavier isotopes such as deuterium, i.e., $^{2}H$, can afford certain therapeutic advantages resulting from greater metabolic stability, for example increased in vivo half-life or reduced dosage requirements and, hence, may be preferred in some circumstances. Isotopically labelled compounds used in the methods of this invention and prodrugs thereof can generally be prepared by carrying out the procedures for preparing the compounds disclosed in the art by substituting a readily available isotopically labelled reagent for a non-isotopically labelled reagent.

This invention also encompasses methods using pharmaceutical compositions and methods of treating COVID-19 infections through administering prodrug compounds of the invention. Compounds having free amido or hydroxy groups can be converted into prodrugs. Prodrugs include compounds wherein an amino acid residue, or a polypeptide chain of two or more (e.g., two, three or four) amino acid residues is covalently joined through an ester bond to a hydroxy of compounds used in the methods of this invention. The amino acid residues include but are not limited to the 20 naturally occurring amino acids commonly designated by three letter symbols and also includes 4-hydroxyproline, hydroxylysine, demosine, isodemosine, 3-methylhistidine, norvalin, beta-alanine, gamma-aminobutyric acid, citrulline homocysteine, homoserine, ornithine and methionine sulfone. Additional types of prodrugs are also encompassed. For instance, free hydroxy groups may be derivatized using groups including but not limited to hemisuccinates, phosphate esters, dimethylaminoacetates, and phosphoryloxymethyloxycarbonyls, as outlined in Advanced Drug Delivery Reviews, 1996, 19, 115. Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy)ethyl ethers wherein the acyl group may be an alkyl ester, optionally substituted with groups including but not limited to ether, amine and carboxylic acid functionalities, or where the acyl group is an amino acid ester as described above, are also encompassed. Prodrugs of this type are described in *J. Med. Chem.*, 1996, 29, 10. Free amines can also be derivatized as amides, sulfonamides or phosphonamides. All of these prodrug moieties may incorporate groups including but not limited to ether, amine and carboxylic acid functionalities.

The compounds of the present invention can be used in the methods of the invention in combination with other drugs. For example, dosing a SARS-CoV-2 coronavirus infected patient (i.e. a patient with COVID-19) with the SARS-CoV-2 coronavirus 3CL protease inhibitor of the invention and an interferon, such as interferon alpha, or a pegylated interferon, such as PEG-Intron or Pegasus, may provide a greater clinical benefit than dosing either the interferon, pegylated interferon or the SARS-CoV-2 coronavirus inhibitor alone. Other additional agents that can be used in the methods of the present invention include chloroquine, hydroxychloroquine, azithromycin and remdesivir. Examples of greater clinical benefits could include a larger reduction in COVID-19 symptoms, a faster time to alleviation of symptoms, reduced lung pathology, a larger reduction in the amount of SARS-Cov-2 coronavirus in the patient (viral load), and decreased mortality.

The SARS-Cov-2 coronavirus infects cells which express p-glycoprotein. Some of the SARS-Cov-2 coronavirus 3CL protease inhibitors of the invention are p-glycoprotein substrates. Compounds which inhibit the SARS-Cov-2 coronavirus which are also p-glycoprotein substrates may be dosed with p-glycoprotein inhibitor. Examples of p-glycoprotein inhibitors are verapamil, vinblastine, ketoconazole, nelfinavir, ritonavir or cyclosporine. The p-glycoprotein inhibitors act by inhibiting the efflux of the SARS-Cov-2 coronavirus inhibitors of the invention out of the cell. The inhibition of the p-glycoprotein based efflux will prevent reduction of intracellular concentrations of the SARS-Cov-2 coronavirus inhibitor due to p-glycoprotein efflux. Inhibition of the p-glycoprotein efflux will result in larger intracellular concentrations of the SARS-CoV-2 coronavirus inhibitors. Dosing a SARS-CoV-2 coronavirus infected patient with the SARS-CoV-2 coronavirus 3CL protease inhibitors of the invention and a p-glycoprotein inhibitor may lower the amount of SARS-Cov-2 coronavirus 3CL protease inhibitor required to achieve an efficacious dose by increasing the intracellular concentration of the SARS-CoV-2 coronavirus 3CL protease inhibitor.

Among the agents that may be used to increase the exposure of a mammal to a compound of the present invention are those that can as inhibitors of at least one isoform of the cytochrome P450 (CYP450) enzymes. The isoforms of CYP450 that may be beneficially inhibited included, but are not limited to CYP1A2, CYP2D6, CYP2C9, CYP2C19 and CYP3A4. The compounds used in the methods of the invention include compounds that may be CYP34 substrates and are metabolized by CYP3A4. Dosing a SARS-CoV-2 coronavirus infected patient with a SARS-CoV-2 coronavirus inhibitor which is a CYP3A4 substrate, such as SARS-CoV-2 coronavirus 3CL protease inhibitor, and a CYP3A4 inhibitor, such as ritonavir, nelfinavir or delavirdine, will reduce the metabolism of the SARS-Cov-2 coronavirus inhibitor by CYP3A4. This will result in reduced clearance of the SARS-CoV-2 coronavirus inhibitor and increased SARS-Cov-2 coronavirus inhibitor plasma concentrations. The reduced clearance and higher plasma concentrations may result in a lower efficacious dose of the SARS-CoV-2 coronavirus inhibitor.

Additional therapeutic agents that can be used in combination with the SARS-CoV-2 inhibitors in the methods of the present invention include the following:

PLpro inhibitors: Ribavirin, Valganciclovir, β-Thymidine, Aspartame, Oxprenolol, Doxycycline, Acetophenazine, Iopromide, Riboflavin, Reproterol, 2,2'-Cyclocytidine, Chloramphenicol, Chlorphenesin carbamate, Levodropizine, Cefamandole, Floxuridine, Tigecycline, Pemetrexed, L(+)-Ascorbic acid, Glutathione, Hesperetin, Ademetionine, Masoprocol, Isotretinoin, Dantrolene, Sulfasalazine Anti-bacterial, Silybin, Nicardipine, Sildenafil, Platycodin, Chrysin, Neohesperidin, Baicalin, Sugetriol-3,9-diacetate, (−)-Epigallocatechin gallate, Phaitanthrin D, 2-(3,4-Dihydroxyphenyl)-2-[[2-(3,4-dihydroxyphenyl)-3,4-dihydro-5,7-dihydroxy-2H-1-benzopyran-3-yl]oxy]-3,4-dihydro-2H-1-benzopyran-3,4,5,7-tetrol, 2,2-Di(3-indolyl)-3-indolone, (S)-(1S,2R,4aS,5R,8aS)-1-Formamido-1,4a-dimethyl-6-methylene-5-((E)-2-(2-oxo-2,5-dihydrofuran-3-yl)ethenyl)decahydronaphthalen-2-yl-2-amino-3-phenylpropanoate, Piceatannol, Rosmarinic acid, and Magnolol.

3CLpro inhibitors: Lymecycline, Chlorhexidine, Alfuzosin, Cilastatin, Famotidine, Almitrine, Progabide, Nepafenac, Carvedilol, Amprenavir, Tigecycline, Montelukast, Carminic acid, Mimosine, Flavin, Lutein, Cefpiramide, Phenethicillin, Candoxatril, Nicardipine, Estradiol valerate, Pioglitazone, Conivaptan, Telmisartan, Doxycycline, Oxytetracycline, (1S,2R,4aS,5R,8aS)-1-Formamido-1,4a-dimethyl-6-methylene-5-((E)-2-(2-oxo-2,5-dihydrofuran-3-yl)ethenyl)decahydronaphthalen-2-yl5-((R)-1,2-dithiolan-3-yl) pentanoate, Betulonal, Chrysin-7-O-β-glucuronide, Andrographiside, (1S,2R,4aS,5R,8aS)-1-Formamido-1,4a-dimethyl-6-methylene-5-((E)-2-(2-oxo-2,5-dihydrofuran-3-yl)ethenyl)decahydronaphthalen-2-yl 2-nitrobenzoate, 2β-Hydroxy-3,4-seco-friedelolactone-27-oic acid (S)-(1S,2R,4aS,5R,8aS)-1-Formamido-1,4a-dimethyl-6-methylene-5-((E)-2-(2-oxo-2,5-dihydrofuran-3-yl)ethenyl) decahydronaphthalen-2-yl-2-amino-3-phenylpropanoate, Isodecortinol, Cerevisterol, Hesperidin, Neohesperidin, Andrograpanin, 2-((1R,5R,6R,8aS)-6-Hydroxy-5-(hydroxymethyl)-5,8a-dimethyl-2-methylenedecahydronaphthalen-1-yl)ethyl benzoate, Cosmosiin, Cleistocaltone A, 2,2-Di(3-indolyl)-3-indolone, Biorobin, Gnidicin, Phyllaemblinol, Theaflavin 3,3'-di-O-gallate, Rosmarinic acid, Kouitchenside 1, Oleanolic acid, Stigmast-5-en-3-ol, Deacetylcentapicrin, and Berchemol.

RdRp inhibitors: Valganciclovir, Chlorhexidine, Ceftibuten, Fenoterol, Fludarabine, Itraconazole, Cefuroxime, Atovaquone, Chenodeoxycholic acid, Cromolyn, Pancuronium bromide, Cortisone, Tibolone, Novobiocin, Silybin, Idarubicin Bromocriptine, Diphenoxylate, Benzylpenicilloyl G, Dabigatran etexilate, Betulonal, Gnidicin, 2β,30β-Dihydroxy-3,4-seco-friedelolactone-27-lactone, 14-Deoxy-11,12-didehydroandrographolide, Gniditrin, Theaflavin 3,3'-di-O-gallate, (R)-((1R,5aS,6R,9aS)-1,5a-Dimethyl-7-methylene-3-oxo-6-((E)-2-(2-oxo-2,5-dihydrofuran-3-yl)ethenyl)decahydro-1H-benzo[c]azepin-1-yl)methyl2-amino-3-phenylpropanoate, 2β-Hydroxy-3,4-seco-friedelolactone-27-oic acid, 2-(3,4-Dihydroxyphenyl)-2-[[2-(3,4-dihydroxyphenyl)-3,4-dihydro-5,7-dihydroxy-2H-1-benzopyran-3-yl]oxy]-3,4-dihydro-2H-1-benzopyran-3,4,5,7-tetrol, Phyllaemblicin B, 14-hydroxycyperotundone, Andrographiside, 2-((1R,5R,6R,8aS)-6-Hydroxy-5-(hydroxymethyl)-5,8a-dimethyl-2-methylenedecahydro naphthalen-1-yl)ethyl benzoate, Andrographolide, Sugetriol-3,9-diacetate, Baicalin,(1S,2R,4aS,5R,8aS)-1-Formamido-1,4a-dimethyl-6-methylene-5-((E)-2-(2-oxo-2,5-dihydrofuran-3-yl)ethenyl) decahydronaphthalen-2-yl 5-((R)-1,2-dithiolan-3-yl)pentanoate, 1,7-Dihydroxy-3-methoxyxanthone, 1,2,6-Trimethoxy-8-[(6-O-β-D-xylopyranosyl-β-glucopyranosyl)oxy]-9H-xanthen-9-one, and 1,8-Dihydroxy-6-methoxy-2-[(6-O-β-D-xylopyranosyl-β-D-glucopyranosyl)oxy]-9H-xanthen-9-one, 8-(β-D-Glucopyranosyloxy)-1,3,5-trihydroxy-9H-xanthen-9-one, Additional therapeutic agents that can be used in the methods of the invention include Diosmin, Hesperidin, MK-3207, Venetoclax, Dihydroergocristine, Bolazine, R428, Ditercalinium, Etoposide, Teniposide, UK-432097, Irinotecan, Lumacaftor, Velpatasvir, Eluxadoline, Ledipasvir, Lopinavir/Ritonavir+Ribavirin, Alferon, and prednisone. Other additional agents useful in the methods of the present invention include chloroquine, hydroxychloroquine, azithromycin and remdesivir.

Other additional agents that can be used in the methods of the present invention include α-ketoamides compounds designated as 11r, 13a and 13b, shown below, as described in Zhang, L.; Lin, D.; Sun, X.; Rox, K.; Hilgenfeld, R.; X-ray Structure of Main Protease of the Novel Coronavirus SARS-CoV-2 Enables Design of α-Ketoamide Inhibitors; bioRxiv preprint doi: https://doi.org/10.1101/2020.02.17.952879

13b

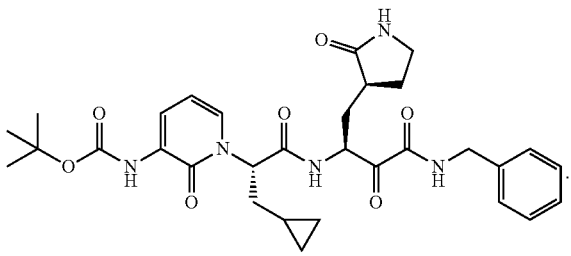

Additional agents that can be used in the methods of the present invention include RIG 1 pathway activators such as those described in U.S. Pat. No. 9,884,876.

Additional therapeutic agents that can be used in the methods and compositions of the invention include one or more agents selected from the group consisting of remdesivir, galidesivir, favilavir/avifavir, mulnupiravir (MK-4482/EIDD 2801), AT-527, AT-301, BLD-2660, favipiravir, camostat, SLV213 emtricatbine/tenofivir, clevudine, dalcetrapib, boceprevir, ABX464, dexamethasone, hydrocortisone, convalescent plasma, gelsolin (Rhu-p65N), monoclonal antibodies, regdanvimab (Regkirova), ravulizumab (Ultomiris), VIR-7831/VIR-7832, BRII-196/BRII-198, COVI-AMG/COVI DROPS (STI-2020), bamlanivimab (LY-CoV555), mavrilimab, leronlimab (PRO140), AZD7442, lenzilumab, infliximab, adalimumab, JS 016, STI-1499 (COVIGUARD), lanadelumab (Takhzyro), canakinumab (Ilaris), gimsilumab, otilimab, casirivimab/imdevimab (REGN-Cov2), MK-7110 (CD24Fc/SACCOVID), heparin, apixaban, tocilizumab (Actemra), sarilumab (Kevzara), apilimod dimesylate, DNL758, PB1046, dapaglifozin, abivertinib, ATR-002, bemcentinib, acalabrutinib, baricitinib, tofacitinib, losmapimod, famotidine, niclosamide and diminazene.

The term "SARS-Cov-2 inhibiting agent" means any SARS-CoV-2 related coronavirus 3C like protease inhibitor compound described herein or a pharmaceutically acceptable salt, hydrate, prodrug, active metabolite or solvate thereof or a compound which inhibits replication of SARS-CoV-2 in any manner.

The term "interfering with or preventing" SARS-CoV-2-related coronavirus ("SARS-CoV-2") viral replication in a cell means to reduce SARS-CoV-2 replication or production of SARS-CoV-2 components necessary for progeny virus in a cell as compared to a cell not being transiently or stably transduced with the ribozyme or a vector encoding the ribozyme. Simple and convenient assays to determine if SARS-CoV-2 viral replication has been reduced include an ELISA assay for the presence, absence, or reduced presence of anti-SARS-CoV-2 antibodies in the blood of the subject (Nasoff, et al., PNAS 88:5462-5466, 1991), RT-PCR (Yu, et al., in Viral Hepatitis and Liver Disease 574-577, Nishioka, Suzuki and Mishiro (Eds.); Springer-Verlag, Tokyo, 1994). Such methods are well known to those of ordinary skill in the art. Alternatively, total RNA from transduced and infected "control" cells can be isolated and subjected to analysis by dot blot or northern blot and probed with SARS-CoV-2 specific DNA to determine if SARS-CoV-2 replication is reduced. Alternatively, reduction of SARS-CoV-2 protein expression can also be used as an indicator of inhibition of SARS-CoV-2 replication. A greater than fifty percent reduction in SARS-CoV-2 replication as compared to control cells typically quantitates a prevention of SARS-CoV-2 replication.

If a SARS-CoV-2 inhibitor compound used in the method of the invention is a base, a desired salt may be prepared by any suitable method known to the art, including treatment of the free base with an inorganic acid (such as hydrochloric acid, hydrobromic acid, sulfuric acid, nitric acid, phosphoric acid, and the like), or with an organic acid (such as acetic acid, maleic acid, succinic acid, mandelic acid, fumaric acid, malonic acid, pyruvic acid, oxalic acid, glycolic acid, salicylic acid, pyranosidyl acid (such as glucuronic acid or galacturonic acid), alpha-hydroxy acid (such as citric acid or tartaric acid), amino acid (such as aspartic acid or glutamic acid), aromatic acid (such as benzoic acid or cinnamic acid), sulfonic acid (such as p-toluenesulfonic acid or ethanesulfonic acid), and the like.

If a SARS-CoV-2 inhibitor compound used in the method of the invention is an acid, a desired salt may be prepared by any suitable method known to the art, including treatment of the free acid with an inorganic or organic base (such as an amine (primary, secondary, or tertiary)), an alkali metal hydroxide, or alkaline earth metal hydroxide. Illustrative examples of suitable salts include organic salts derived from amino acids (such as glycine and arginine), ammonia, primary amines, secondary amines, tertiary amines, and cyclic amines (such as piperidine, morpholine, and piperazine), as well as inorganic salts derived from sodium, calcium, potassium, magnesium, manganese, iron, copper, zinc, aluminum and lithium.

In the case of SARS-CoV-2 inhibitor compounds, prodrugs, salts, or solvates that are solids, it is understood by those skilled in the art that the compounds, prodrugs, salts, and solvates used in the method of the invention, may exist in different polymorph or crystal forms, all of which are intended to be within the scope of the present invention and specified formulas. In addition, the compounds, salts, prodrugs and solvates used in the method of the invention may exist as tautomers, all of which are intended to be within the broad scope of the present invention.

Solubilizing agents may also be used with the compounds of the invention to increase the compounds solubility in water of physiologically acceptable solutions. These solubilizing agents include cyclodextrans, propylene glycol, diethylacetamide, polyethylene glycol, Tween, ethanol and micelle forming agents. Offered solubilizing agents are cyclodextrans, particularly beta cyclodextrans and in particular hydroxypropyl betacyclodextran and sulfobutylether betacyclodextran.

Formulations of (3S)-3-({N-[(4-methoxy-1H-indol-2-yl)carbonyl]-L-leucyl}amino)-2-oxo-4-[(3S)-2-oxopyrrolidin-3-yl]butyl dihydrogen phosphate A particularly preferred compound of the invention, (3S)-3-({N-[(4-methoxy-1H-indol-2-yl)carbonyl]-L-leucyl}amino)-2-oxo-4-[(3S)-2-oxopyrrolidin-3-yl]butyl dihydrogen phosphate (referred to as PF-07304814 in certain instances), can be supplied as a solution or powder-based formulation with or without excipients to produce pharmaceutical compositions suitable for parenteral administration. The concentration of PF-07304814 solution formulations, or the concentration of a lyophilized or powder fill formulation after reconstitution is preferred to be in the range 25-200 mg/mL. The formulation can be reconstituted or diluted for IV administration in sterile water for injection, 0.9% w/v sodium chloride, or 5% w/v dextrose solution. For example, for purposes of IV administration, a daily dose of approximately 3 g of PF-0730814 in an infusion volume of approximately 250 mL or approximately 500 mL will result in an infusion concentration of 12 mg/mL or 6 mg/mL, respectively. As a further example, for purposes of IV administration, a daily dose of approximately 1 g of PF-0730814 in an infusion volume of approximately 250 mL or approximately 500 mL will result in an infusion concentration of 4 mg/mL or 2 mg/mL, respectively. As a further example, for purposes of IV administration, a daily dose of approximately 500 mg of PF-0730814 in an infusion volume of approximately 250 mL or approximately 500 mL will result in an infusion concentration of 2 mg/mL or 1 mg/mL, respectively.

For PF-07304814, there are multiple degradants with pH-dependent mechanisms, and the pH that results in minimum degradation is different for each degradant. Preferable pH values for PF-07304814 formulations (including any solution formulations, solutions prior to lyophilization, reconstituted solutions after lyophilization, and diluted solutions for IV administration) are in the range of approximately pH 2.0 to approximately pH 6.0, and the most preferable pH range is from approximately pH 3.0 to approximately pH 5.0. In order to maintain the required pH, a buffer is optionally added, with preferred buffers being lactic acid, phosphoric acid, acetic acid, and tartaric acid, with the most preferred buffer being citric acid. The preferred molar ratio of PF-07304814 to citrate buffer is approximately 1:1 to approximately 20:1, the more preferred molar ratio is approximately 2:1 to approximately 10:1, and most preferable molar ratio is approximately 4.5:1. The pH of the formulation may be adjusted and controlled by addition of a suitable basic excipient, preferred bases include benzathine, calcium hydroxide, choline, diethylamine, diolamine, magnesium hydroxide, and meglumine; more preferred bases are lysine, piperazine, potassium hydroxide, and tris(hydroxymethyl)aminomethane; and the most preferred base is sodium hydroxide (NaOH).

The PF-07304814 form used in formulations can be the free acid or a suitable salt. In solution, the phosphate group of PF-07304814 is expected to be ionized and negatively charged in the target pH range, and thus cationic species in solution are expected to act as counterions interacting with the phosphate group. Surprisingly, we find that the counterion does not significantly impact the solid state structure of the lyophilized powder, as measured by powder X-ray diffraction (PXRD) or modulated differential scanning calorimetry (mDSC) but can significantly influence the rate of degradation for the primary degradant. Preferred counter-ions to form a salt of PF-07304814 include benzathine, calcium, choline, diethylamine, diolamine, magnesium, meglumine, more preferred counter-ions include lysine, piperazine, potassium, and tris(hydroxymethyl)aminomethane, and the most preferred counter-ion is sodium. A preferable molar ratio of the counterion to PF-07304814 in the pharmaceutical composition formulations (including any solution formulations, solutions prior to lyophilization, reconstituted solutions after lyophilization, and diluted solutions for IV administration) is approximately 0.5:1 to approximately 3:1, and the most preferred molar ratio is approximately 0.5:1 to approximately 2:1.

Unexpectedly, we find that the addition of one or more stabilizing excipients can produce lyophilized formulations with comparable moisture content, crystallinity, and appearance, but can significantly reduce the rate of formation of Degradant 1 (the phosphate cleaved compound). Preferred stabilizing excipients include sugars, polyalcohols, polymers, and amino acids; more preferred excipients include dextran, glycine, lactose, mannitol, polyvinylpyrrolidone, sucrose, and trehalose; and most preferred excipients include polyethylene glycols (PEGs; e.g. PEG300, PEG400, PEG3350). The preferred amount of stabilizing excipient in the lyophilized powder is up to approximately 30% w/w, and the most preferred amount is up to approximately 15% w/w. The preferred amount of total stabilizing excipient in the reconstituted solution after lyophilization is up to approximately 50 mg/mL, and the most preferred amount is up to approximately 20 mg/mL. The preferred amount of total stabilizing excipient in the diluted solution for IV administration is up to 10 mg/mL, and the most preferred amount is up to 4 mg/mL.

For PF-07304814, we find that the addition of a small amount of solubilizing excipient can prevent the precipitation of poorly soluble impurities. Preferred solubilizing excipients include surfactants and complexing excipients (e.g. cyclodextrins); more preferred solubilizing excipients include polyethoxylated castor oil, polyethylene glycol (15)-hydroxystearate, hydroxypropyl-β-cyclodextrin (HP-β-CD), sulfobutylether-β-cyclodextrin (SBE-β-CD), γ-cyclodextrin; and most preferred solubilizing excipients include polysorbate 20 (PS20) or polysorbate 80 (PS80). The preferred amount of solubilizing excipients in the lyophilized powder is up to approximately 15% w/w, and the most preferred amount is up to approximately 5% w/w. The preferred amount of total solubilizing excipient in the reconstituted solution after lyophilization is up to approximately 20 mg/mL, and the most preferred amount is up to approximately 5 mg/mL. The preferred amount of solubilizing excipient in the diluted solution for IV administration is up to 4 mg/mL, and the most preferred amount is up to 1 mg/mL.

For PF-07304814, a lyophilized product is prepared to reduce the water content in the drug product. We find that optimization of the lyophilization cycle can result in low water content that significantly improves the chemical stability. A preferred water content is less than 2% w/w, more preferably less than 1% w/w, and most preferably less than 0.5% w/w. PF-07304814 can be prepared as a solution formulation that can be filled into an appropriate container closure system. A solution formulation can be stored and supplied as a solution, or subsequently freeze-dried to prepare a lyophilized formulation. Alternatively, PF-07304814 can be prepared as a powder in an appropriate container closure system, with a standard or specialty diluent to prepare a solution.

In some cases, the SARS-CoV-2 inhibitor compounds, salts, prodrugs and solvates used in the method of the invention may have chiral centers. When chiral centers are present, the hydroxamate compound, salts, prodrugs and solvates may exist as single stereoisomers, racemates, and/or mixtures of enantiomers and/or disastereomers. All such single stereoisomers, racemates, and mixtures thereof are intended to be within the broad scope of the present invention.

As generally understood by those skilled in the art, an optically pure compound is one that is enantiomerically pure. As used herein, the term "optically pure" is intended to mean a compound comprising at least a sufficient activity. Preferably, an optically pure amount of a single enantiomer to yield a compound having the desired pharmacological pure compound of the invention comprised at least 90% of a single isomer (80% enantiomeric excess), more preferably at least 95% (90% e.e.), even more preferably at least 97.5% (95%) e.e.), and most preferably at least 99% (98% e.e.).

The term "treating", as used herein, unless otherwise indicated, means reversing, alleviating, inhibiting the progress of, or preventing the disorder or condition to which such term applies, or one or more symptoms of such disorder or condition. The term "treatment", as used herein, unless otherwise indicated, refers to the act of treating as "treating" is defined immediately above. In a preferred embodiment of the present invention, "treating" or "treatment" means at least the mitigation of a disease condition in a human, that is alleviated by the inhibition of the activity of the SARS-CoV-2 3C-like protease which is the main protease of SARS-CoV-2, the causative agent for COVID-19. The SARS-CoV-2 virus is to be understood to encompass the initially discovered strain of the virus as well as mutant strains which emerge, such as but not limited to, strains such as B.1.1.7 (UK variant), B.1.351 (South African variant) and P.1 (Brazilian variant). For patients suffering from COVID-19 fever, fatigue, and dry cough are the main manifestations of the disease, while nasal congestion, runny nose, and other symptoms of the upper respiratory tract are rare. Beijing Centers for Diseases Control and Prevention indicated that the typical case of COVID-19 has a progressive aggravation process. COVID-19 can be classified into light, normal, severe, and critical types based on the severity of the disease National Health Commission of the People's Republic of China. Diagnosis and Treatment of Pneumonia Caused by 2019-nCoV (Trial Version 4). Available online: http://www.nhc.gov.cn/jkj/s3577/202002/573340613ab243b3-a7f61df260551dd4/files/c791e5a7ea5149f680fdcb34d-ac0f54e.pdf (accessed on 6 Feb. 2020).: (1) Mild cases—the clinical symptoms were mild, and no pneumonia was found on the chest computed tomography (CT); (2) normal cases—fever, respiratory symptoms, and patients found to have imaging manifestations of pneumonia; (3) severe cases—one of the following three conditions: Respiratory distress, respiratory rate≥30 times/min (in resting state, refers to oxygen saturation 93%), partial arterial oxygen pressure (PaO2)/oxygen absorption concentration (FiO2)≤300 mmHg (1 mmHg=0.133 kPa); (4) critical cases—one of the following three conditions: Respiratory failure and the need for mechanical ventilation, shock, or the associated failure of other organs requiring the intensive care unit. The current clinical data shows that the majority of the deaths occurred in the older patients. However, severe cases have been documented in young adults who have unique factors, particularly those with chronic diseases, such as diabetes or hepatitis B. Those with a long-term use of hormones or immunosuppressants, and decreased immune function, are likely to get severely infected.

Methods of treatment for mitigation of a disease condition such as COVID-19 include the use of one or more of the compounds in the invention in any conventionally acceptable manner. According to certain preferred embodiments of the invention, the compound or compounds used in the methods of the present invention are administered to a mammal, such as a human, in need thereof. Preferably, the mammal in need thereof is infected with a coronavirus such as the causative agent of COVID-19, namely SARS-CoV-2.

The present invention also includes prophylactic methods, comprising administering an effective amount of a SARS-CoV-2 inhibitor of the invention, or a pharmaceutically acceptable salt, prodrug, pharmaceutically active metabolite, or solvate thereof to a mammal, such as a human at risk for infection by SARS-CoV-2. According to certain preferred embodiments, an effective amount of one or more compounds of the invention, or a pharmaceutically acceptable salt, prodrug, pharmaceutically active metabolite, or solvate thereof is administered to a human at risk for infection by SARS-CoV-2, the causative agent for COVID-19. The prophylactic methods of the invention include the use of one or more of the compounds in the invention in any conventionally acceptable manner.

The following are examples of specific embodiments of the invention:

Certain of the compounds used in the methods of the invention are known and can be made by methods known in the art.

Recent evidence indicates that a new coronavirus SARS-Cov-2 is the causative agent of COVID-19. The nucleotide sequence of the SARS-CoV-2 coronavirus as well as the recently determined L- and S-subtypes have recently been determined and made publicly available.

The activity of the inhibitor compounds as inhibitors of SARS-CoV-2 viral activity may be measured by any of the suitable methods available in the art, including in vivo and in vitro assays. The activity of the compounds of the present invention as inhibitors of coronavirus 3C-like protease activity (such as the 3C-like protease of the SARS-CoV-2 coronavirus) may be measured by any of the suitable methods known to those skilled in the art, including in vivo and in vitro assays. Examples of suitable assays for activity measurements include the antiviral cell culture assays described herein as well as the antiprotease assays described herein, such as the assays described in the Example section.

Administration of the SARS-CoV-2 inhibitor compounds and their pharmaceutically acceptable prodrugs, salts, active metabolites, and solvates may be performed according to any of the accepted modes of administration available to those skilled in the art. Illustrative examples of suitable modes of administration include oral, nasal, pulmonary, parenteral, topical, intravenous, injected, transdermal, and rectal. Oral, intravenous, and nasal deliveries are preferred.

A SARS-CoV-2-inhibiting agent may be administered as a pharmaceutical composition in any suitable pharmaceutical form. Suitable pharmaceutical forms include solid, semi-solid, liquid, or lyophilized formulations, such as tablets, powders, capsules, suppositories, suspensions, liposomes, and aerosols. The SARS-CoV-2-inhibiting agent may be prepared as a solution using any of a variety of methodologies. For example, SARS-CoV-2-inhibiting agent can be dissolved with acid (e.g., 1 M HCl) and diluted with a sufficient volume of a solution of 5% dextrose in water (D5W) to yield the desired final concentration of SARS-Cov-2-inhibiting agent (e.g., about 15 mM). Alternatively, a solution of D5W containing about 15 mM HCl can be used to provide a solution of the SARS-CoV-2-inhibiting agent at the appropriate concentration. Further, the SARS-Cov-2-inhibiting agent can be prepared as a suspension using, for example, a 1% solution of carboxymethylcellulose (CMC).

Acceptable methods of preparing suitable pharmaceutical forms of the pharmaceutical compositions are known or may be routinely determined by those skilled in the art. For example, pharmaceutical preparations may be prepared following conventional techniques of the pharmaceutical chemist involving steps such as mixing, granulating, and compressing when necessary for tablet forms, or mixing, filling and dissolving the ingredients as appropriate, to give the desired products for intravenous, oral, parenteral, topical, intravaginal, intranasal, intrabronchial, intraocular, intraaural, and/or rectal administration.

Pharmaceutical compositions of the invention may also include suitable excipients, diluents, vehicles, and carriers, as well as other pharmaceutically active agents, depending upon the intended use. Solid or liquid pharmaceutically acceptable carriers, diluents, vehicles, or excipients may be employed in the pharmaceutical compositions. Illustrative solid carriers include starch, lactose, calcium sulfate dihydrate, terra alba, sucrose, talc, gelatin, pectin, acacia, magnesium stearate, and stearic acid. Illustrative liquid carriers include syrup, peanut oil, olive oil, saline solution, and water. The carrier or diluent may include a suitable prolonged-release material, such as glyceryl monostearate or glyceryl distearate, alone or with a wax. When a liquid carrier is used, the preparation may be in the form of a syrup, elixir, emulsion, soft gelatin capsule, sterile injectable liquid (e.g., solution), or a nonaqueous or aqueous liquid suspension.

Chemical and physical stability influence the choice of storage conditions and shelf life of a pharmaceutical composition and determine the viability of a pharmaceutical product. Chemical stability generally relates to a change in the chemical nature of the constituents within a pharmaceutical composition, which could include the degradation of the active pharmaceutical ingredient (API), the degradation of excipients, the reaction of the API (or its related degradants) with excipients (or their related degradants), or the reaction of constituents within the pharmaceutical composition with the container closure system. The acceptability of degradants in pharmaceutical compositions requires research, which may include identification of the degradant structure, evaluation of the degradant solubility for parenteral products, and assessment of degradant safety (in silico, in vitro, and in vivo). The chemical stability of pro-drug moieties, in particular, is dependent on the identity, position, and local environment of the pro-drug moiety on the active metabolite, as well as the formulation and storage conditions of the drug product. In particular, the hydrolysis of phosphate ester pro-drugs is sensitive to the steric and electronic environment around the pro-drug moiety, the pH of the formulation, and the amount of water in the formulation. Physical stability generally relates to a change in phase of the pharmaceutical composition, which could include a change in the solid state structure of a powder, the precipitation of poorly soluble species from a solution, or the change in structure of a dispersed system. To control the chemical and physical stability of the pharmaceutical compositions, researchers can investigate the method of preparation of the API, the formulation design of the pharmaceutical composition, or the method of preparation of the pharmaceutical composition.

In formulation design, one possible approach to control stability-related challenges is the addition of a pH adjuster or buffering agents to modify and maintain the pH. pH adjustment may modify the solubility of species in solution (e.g. the API, excipients, or degradants), or may modify the rate of formation of specific degradants. However, parenteral pharmaceutical compositions with pH values that deviate from neutral may cause local irritation at the injection site. Furthermore, pH optimization may be non-trivial due to the presence of multiple pH-dependent degradation mechanisms. Consequently, pH selection for a pharmaceutical composition requires careful study and consideration.

Another formulation design approach to control the stability of ionizable APIs is the use of counterions. Counterions can electrostatically interact with ionizable groups of opposite charge and may be able to electronically or sterically stabilize bonds to degradation. Counterions may also modify the ability of APIs to form crystalline structures in a lyophilized or powder formulation, which may impact chemical and physical stability. However, the impact of counterions is difficult to predict and requires experimental investigation of chemical and physical stability, chemical compatibility, and assessment of safety.

Another formulation design approach to control stability is the addition of a stabilizing excipients in a lyophilized formulation. Stabilizing excipients can improve the chemical and physical stability of formulations throughout the freezing and drying steps of a lyophilization process, or on storage of the drug product through its shelf life.

Stabilizing excipients may modify the crystallinity and/or glass transition temperature ($T_g$) of a lyophilized formulation, which may impact the orientation and mobility of species in the solid state, and thus impact the kinetics and thermodynamics of degradation. For water-sensitive degradation mechanisms (e.g. hydrolysis), stabilizing excipients may also displace water from interacting with an API and thus shield the API from degradation, or alternatively may effectively sequester water and thus prevent it from reaction with the API. Stabilizing excipient selection and optimization requires careful consideration of multiple factors to produce a formulation with improved chemical stability, including assessment of the crystallinity and physical stability of the solid state structure, the water sorption-desorption properties of the lyophile, the compatibility of the API and the stabilizing excipients, and the safety of the excipients.

If chemical and physical stability cannot be improved, then an alternative formulation-driven approach is the addition of solubilizing excipients that prevent the precipitation of poorly soluble degradants in parenteral compositions. Solubilizing excipients may also be helpful to prevent the precipitation of poorly soluble API-related impurities, which are challenging to remove via API isolation and purification approaches. Solubilizing excipients may include solvents, complexing excipients, surfactants, or other excipients. However, parenteral administration of many solubilizing excipients can cause adverse safety effects that limit the amount of an excipient that can be used in a specific patient population. For example, in the "Information for the package leaflet regarding polysorbates used as excipients in medicinal products for human use" from the European Medicines Agency as of 19 Nov. 2018, intravenous polysorbate dose levels above 10 mg/kg per dose may have adverse cardiovascular effects and dose levels above 35 mg/kg/day may have adverse hepatotoxic effects. High levels of surfactants can also negatively impact the manufacture or performance of a drug product, which may include foaming during drug product manufacture or during preparation of drug products for parenteral administration, or modification of the solid state structures formed during lyophilization. Consequently, the amount of solubilizing excipient must be studied and optimized to prevent the precipitation of poorly soluble species without introducing additional risks into the drug product.

In the preparation of a pharmaceutical composition, the manufacturing unit operations (e.g. compounding, lyophilization) can expose the formulation to stressors that result in degradation. Furthermore, the preparation can create a pharmaceutical product with different compositions or structures that impact stability. For APIs sensitive to hydrolytic degradation, such as phosphate ester pro-drugs, the amount of residual water content in a powder can significantly impact the chemical stability of the formulation.

A dose of the pharmaceutical composition may contain at least a therapeutically effective amount of a SARS-CoV-2-inhibiting agent and preferably is made up of one or more pharmaceutical dosage units. The selected dose may be administered to a mammal, for example, a human patient, in need of treatment mediated by inhibition of SARS-Cov-2 related coronavirus activity, by any known or suitable method of administering the dose, including topically, for example, as an ointment or cream; orally; rectally, for example, as a suppository; parenterally by injection; intravenously; or continuously by intravaginal, intranasal, intrabronchial, intraaural, or intraocular infusion.

The phrases "therapeutically effective amount" and "effective amount" are intended to mean the amount of an inventive agent that, when administered to a mammal in need of treatment, is sufficient to effect treatment for injury or disease conditions alleviated by the inhibition of SARS-CoV-2 viral replication. The amount of a given SARS-CoV-2-inhibiting agent used in the method of the invention that will be therapeutically effective will vary depending upon factors such as the particular SARS-CoV-2-inhibiting agent, the disease condition and the severity thereof, the identity and characteristics of the mammal in need thereof, which amount may be routinely determined by those skilled in the art.

It will be appreciated that the actual dosages of the SARS-CoV-2-inhibiting agents used in the pharmaceutical compositions of this invention will be selected according to the properties of the particular agent being used, the particular composition formulated, the mode of administration and the particular site, and the host and condition being treated. Optimal dosages for a given set of conditions can be ascertained by those skilled in the art using conventional dosage-determination tests. For oral administration, e.g., a dose that may be employed is from about 0.01 to about 1000 mg/kg body weight, preferably from about 0.1 to about 500 mg/kg body weight, and even more preferably from about 1 to about 500 mg/kg body weight, with courses of treatment repeated at appropriate intervals. For intravenous dosing a dose of up to 5 grams per day may be employed. Intravenous administration can occur for intermittent periods during a day or continuously over a 24-hour period.

The terms "cytochrome P450-inhibiting amount" and "cytochrome P450 enzyme activity-inhibiting amount", as used herein, refer to an amount of a compound required to decrease the activity of cytochrome P450 enzymes or a particular cytochrome P450 enzyme isoform in the presence of such compound. Whether a particular compound of decreases cytochrome P450 enzyme activity, and the amount of such a compound required to do so, can be determined by methods know to those of ordinary skill in the art and the methods described herein.

Protein functions required for coronavirus replication and transcription are encoded by the so-called "replicase" gene. Two overlapping polyproteins are translated from this gene and extensively processed by viral proteases. The C-proximal region is processed at eleven conserved interdomain junctions by the coronavirus main or "3C-like protease. The name "3C-like" protease derives from certain similarities between the coronavirus enzyme and the well-known picornavirus 3C proteases. These include substrate preferences, use of cysteine as an active site nucleophile in catalysis, and similarities in their putative overall polypeptide folds. A comparison of the amino acid sequence of the SARS-Cov-2-associated coronavirus 3C-like protease to that of other known coronaviruses such as SARS-CoV shows the amino acid sequences have approximately 96% shared homology.

Amino acids of the substrate in the protease cleavage site are numbered from the N to the C terminus as follows: -P3-P2-P1-P1'-P2'-P3', with cleavage occurring between the P1 and P1' residues (Schechter & Berger, 1967). Substrate specificity is largely determined by the P2, P1 and P1' positions. Coronavirus main protease cleavage site specificities are highly conserved with a requirement for gluta- mine at P1 and a small amino acid at P1' (*Journal of General Virology*, 83, pp. 595-599 (2002)).

The compounds used in the methods of the present invention can be prepared according to the methods set forth in Reaction Schemes 1 to 17 below.

Scheme 1

Scheme 1 illustrates a synthetic sequence for the preparation of compounds of Formula Ia as shown, wherein a compound of Formula A is treated with a compound of Formula B, wherein X is a halogen atom, most frequently chlorine (see PCT International Application Publication WO 2005/113580). In this case the compound of Formula B is known as a chloroformate, and such methods are well known to those skilled in the art. The reaction is conducted in the presence of a suitable base to consume the hydrogen halide HX produced as a by-product of the reaction. Examples of suitable bases include, but are not limited to, tertiary amines such as N-methyl morpholine (NMM), 2,6-dimethylpyridine, or diisopropylethylamine (DIEA), or inorganic bases such as magnesium oxide (MgO), sodium carbonate ($Na_2CO_3$) or potassium bicarbonate ($KHCO_3$). Suitable solvents include, but are not limited to, aprotic solvents such as dichloromethane ($CH_2Cl_2$), tetrahydrofuran (THF), or acetonitrile ($CH_3CN$). One skilled in the art will appreciate that in the event that the compound of Formula A has $R^2$ being H, the above transformations may afford a product compound of Formula Ia in which $R^2$ may be H or may be ROC(O), depending upon the selection of reaction parameters such as time, temperature, solvent, and equivalents of the compound of Formula E employed.

Scheme 2

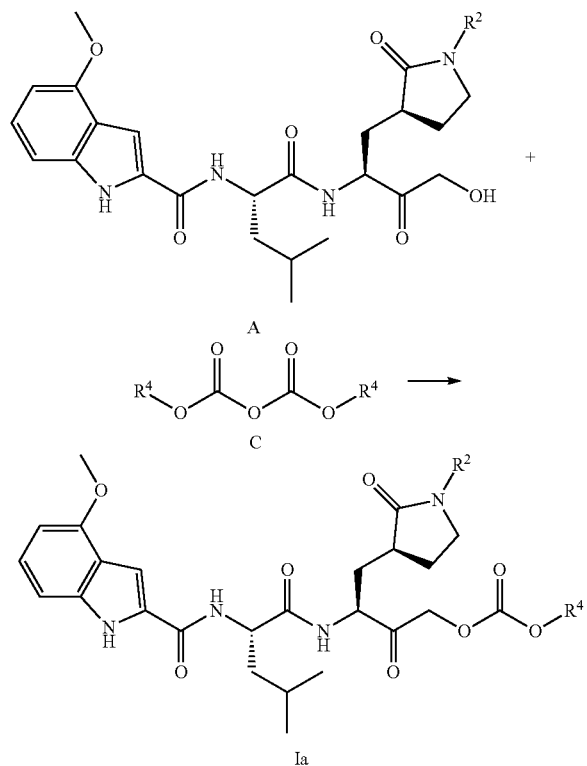

Scheme 2 illustrates a synthetic sequence for the preparation of compounds of Formula 1a as shown, wherein a compound of Formula A is treated with a compound of Formula C, frequently known as a pyrocarbonate by those skilled in the art. The reaction is frequently conducted in the presence of a nucleophilic catalyst to accelerate the reaction. Examples of such nucleophilic catalysts include, but are not limited to, 4-(dimethylamino)pyridine, imidazole or 1,8-diazabicyclo[5.4.0] undec-7-ene (DBU). Suitable solvents include, but are not limited to, $CH_2Cl_2$, THF, pyridine or $CH_3CN$. One skilled in the art will appreciate that in the event that the compound of Formula A has $R^2$ being H, the above transformations may afford a product compound of Formula Ia in which $R^2$ may be or may be $R^4OC(O)$, depending upon the selection of reaction parameters such as time, temperature, solvent, and equivalents of the compound of Formula C employed.

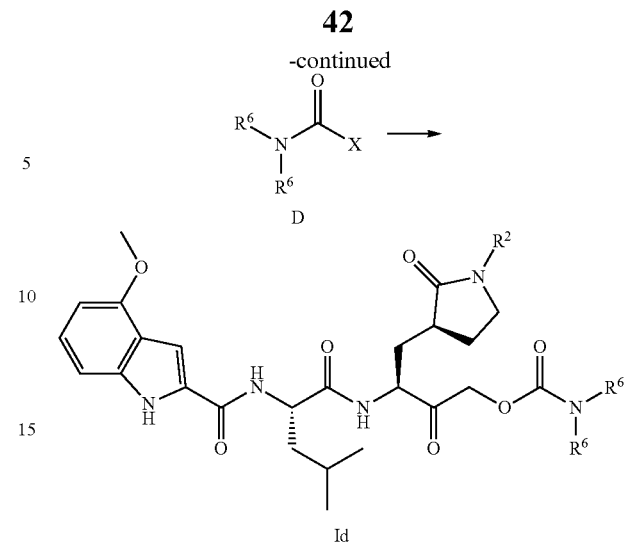

Scheme 3 illustrates a synthetic sequence for the preparation of compounds of Formula Id as shown, wherein a compound of Formula A is treated with a compound of Formula D, wherein X is a halogen atom, most frequently chlorine. In this case the compound of Formula D is known as a carbamoyl chloride, and such methods are well known to those skilled in the art. The reaction is conducted in the presence of a base to consume the hydrogen halide HX produced as a by-product of the reaction. Examples of suitable bases include, but are not limited to, tertiary amines such as N-methyl morpholine, 2,6-dimethylpyridine or diisopropylethylamine, or inorganic bases such as MgO, $Na_2CO_3$ or $KHCO_3$. Suitable solvents include, but are not limited to, $CH_2Cl_2$, THF, or $CH_3CN$. In another embodiment, X may be an imidazole, pyrazole, or triazole ring, linked through one of the heterocyclic N atoms. Such reagents are known to those skilled in the art and are typically prepared from the corresponding amine $(R^6)_2NH$ and 1,1'-carbonyldiimidazole, 1,1'-carbonylbis-1H-pyrazole, or 1,1'-carbonylbis-1H-1,2,3-triazole, most frequently as a preliminary step in the synthetic sequence. One skilled in the art will appreciate that in the event that the compound of Formula A contains $R^2$=H, the above transformations may afford a product compound of Formula 1d in which $R^2$ may be H or may be $(R^6)_2NC(O)$, depending upon the selection of reaction parameters such as time, temperature, solvent, and equivalents of the compound of Formula D employed.

Scheme 3

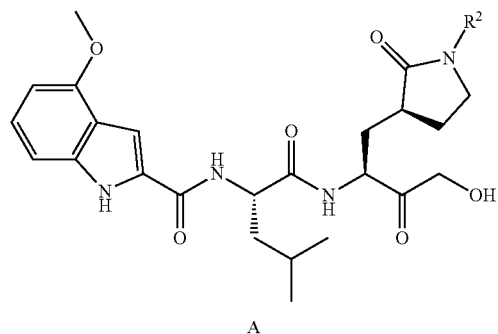

Scheme 4

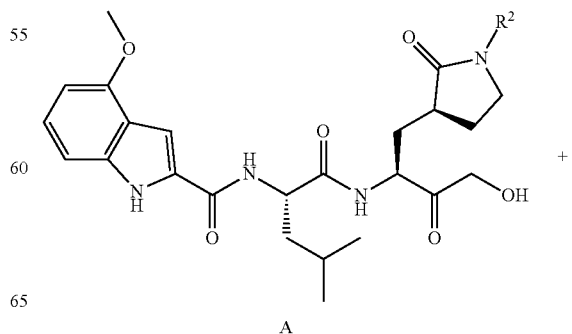

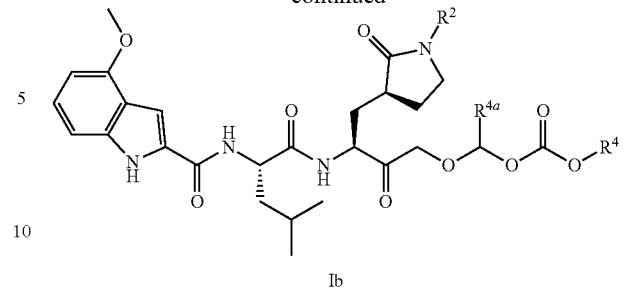

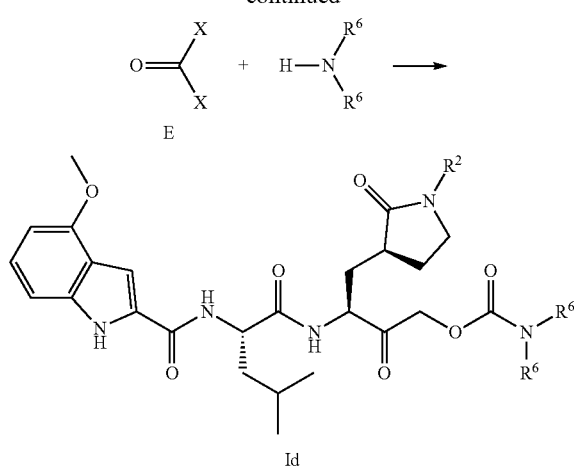

Id

Scheme 4 illustrates a synthetic sequence for the preparation of compounds of Formula 1d as shown, wherein a compound of Formula A is treated with a compound of Formula E, followed after a period of time by treatment with $(R^6)_2$NH. In this embodiment, X may be an imidazole, pyrazole or triazole ring, linked through one of the heterocyclic N atoms, or X may be an N-oxy-imide, linked through the O—N oxygen atom. Examples of such reagents that are commonly used by those skilled in the art include 1,1'-carbonyldiimidazole, 1,1'-carbonylbis-1H-pyrazole, 1,1'-carbonylbis-1H-1,2,3-triazole and 1,1'-[carbonylbis(oxy)]bis-2,5-pyrrolidinedione. The reaction may be conducted in the presence of a nucleophilic catalyst to accelerate the reaction. Examples of such nucleophilic catalysts include, but are not limited to, 4-(dimethylamino)pyridine, imidazole, or DBU. Suitable solvents include, but are not limited to, $CH_2Cl_2$, THF, DMF, DMSO or $CH_3CN$. One skilled in the art will appreciate that in the event that the compound of Formula A contains $R^2$=H, the above transformations may afford a product compound of Formula 1d in which $R^2$ may be H or may be $(R^6)_2NC(O)$, depending upon the selection of reaction parameters such as time, temperature, solvent, and equivalents of of the compound of formula E employed.

Scheme 5

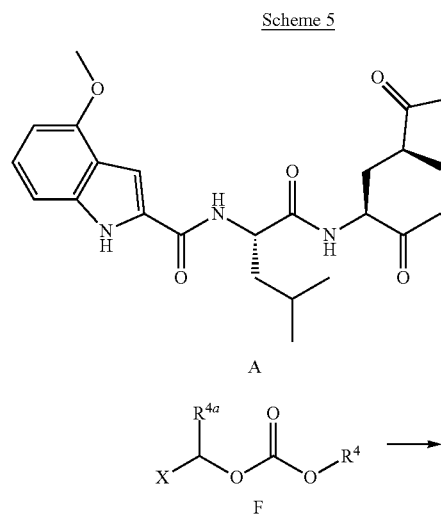

Ib

Scheme 5 illustrates a synthetic sequence for the preparation of compounds of Formula Ib as shown in which $R^4$ is H, methyl or ethyl, wherein a compound of Formula A is treated with a compound of Formula F in which $R^{4a}$ is H, methyl or ethyl and X is a halogen atom, frequently chlorine. Such compounds F are described in the chemical literature and may be commercially available. The reaction is effected by treatment with a base, for example cesium carbonate ($Cs_2CO_3$), in a suitable solvent which may include, but is not limited to, THF, DMF, DMSO or $CH_3CN$. One skilled in the art will appreciate that in the event that the compound of Formula A contains $R^2$=H, the above transformations may afford a product compound of Formula 1 b in which $R^2$ may be H and/or may be $CH(R^{4a})OC(O)OR^4$, depending upon the selection of reaction parameters such as time, temperature, solvent, and equivalents of the compound of Formula F employed.

Scheme 6

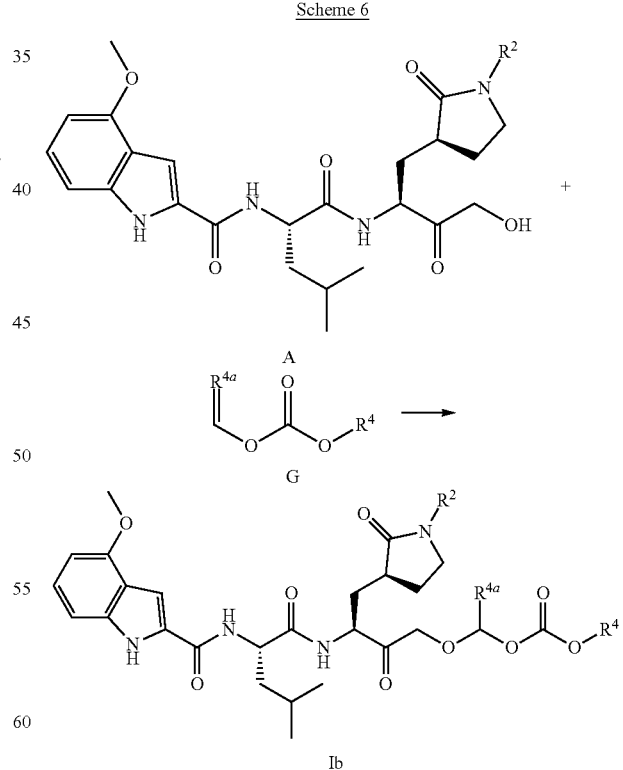

Ib

Scheme 6 illustrates a synthetic sequence for the preparation of compounds of Formula 1 b as shown in which $R^{4a}$ is not equal to H, wherein a compound of Formula A is treated with an olefinic compound of Formula G. Such compounds G are described in the chemical literature and may be commercially available. The reaction is effected by treatment with a catalyst as known to those skilled in the art, which may include but is not limited to an acid, a compound of palladium, or a compound of mercury. Suitable solvents may include, but are not limited to, acetic acid, THF or $CH_3CN$. One skilled in the art will appreciate that in the event that the compound of Formula A contains $R^2$=H, the above transformations may afford a product compound of Formula 1b in which $R^2$ may be H or may be $CH(R^{4a})OC(O)OR^4$, depending upon the selection of reaction parameters such as time, temperature, solvent, and equivalents of the compound of Formula G employed.

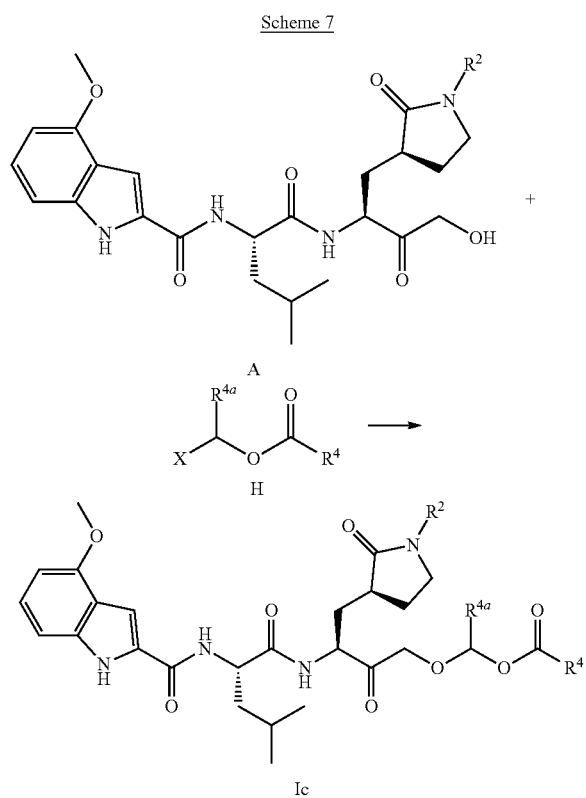

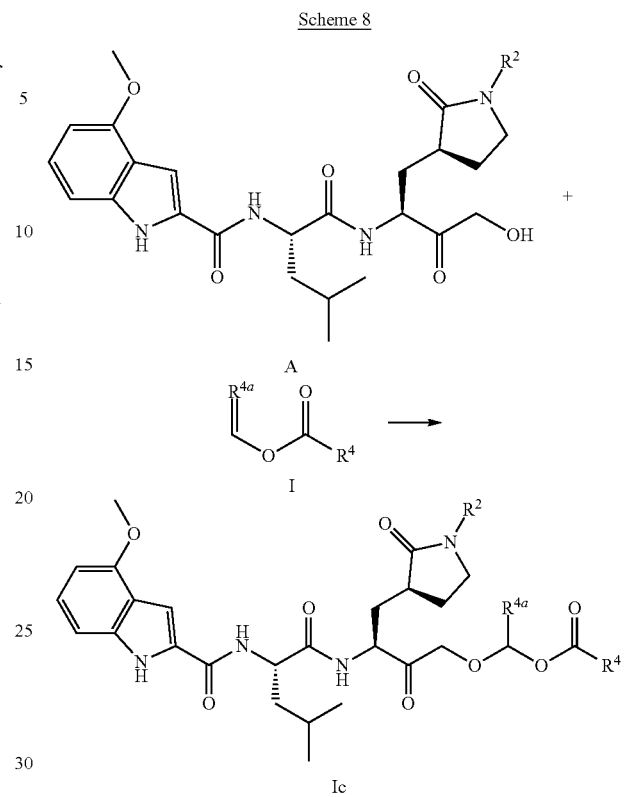

Scheme 8 illustrates a synthetic sequence for the preparation of compounds of Formula Ic as shown in which $R^{4a}$ is not equal to H, wherein a compound of Formula A is treated with an olefinic compound of Formula I. Such compounds I are described in the chemical literature and may be commercially available. The reaction is effected by treatment with a catalyst as known to those skilled in the art, which may include but is not limited to an acid, a compound of palladium, or a compound of mercury. Suitable solvents may include, but are not limited to, acetic acid, THF or $CH_3CN$. One skilled in the art will appreciate that in the event that the compound of Formula A contains $R^2$=H, the above transformations may afford a product compound of Formula 1c in which $R^2$ may be H or may be $CH(R^{4a})OC(O)R^4$, depending upon the selection of reaction parameters such as time, temperature, solvent, and equivalents of the compound of Formula I employed.

Scheme 7 illustrates a synthetic sequence for the preparation of compounds of Formula 1c as shown in which $R^{4a}$ is H, methyl or ethyl, wherein a compound of Formula A is treated with a compound of Formula H in which $R^{4a}$ is H, methyl or ethyl and X is a halogen atom. The reaction is conducted in the presence of a base to consume the hydrogen halide HX produced as a by-product of the reaction. Examples of suitable bases include, but are not limited to, tertiary amines such as N-methyl morpholine, 2,6-dimethylpyridine or diisopropylethylamine, or inorganic bases such as MgO, $Cs_2CO_3$ or $KHCO_3$. Suitable solvents may include, but are not limited to, THF, DMF, DMSO or $CH_3CN$. One skilled in the art will appreciate that in the event that the compound of Formula A contains $R^2$=H, the above transformations may afford a product compound of Formula 1 in which $R^2$ may be H or may be $CH(R^{4a})OC(O)R^4$, depending upon the selection of reaction parameters such as time, temperature, solvent, and equivalents of the compound of Formula H employed.

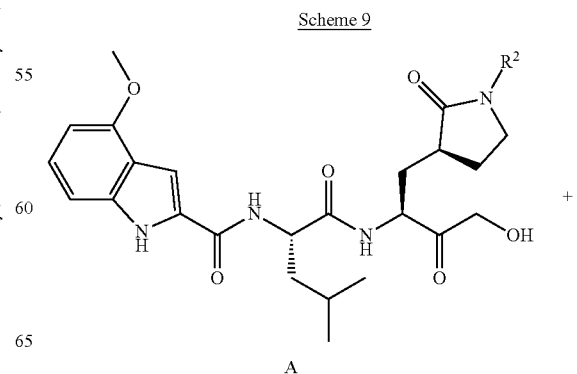

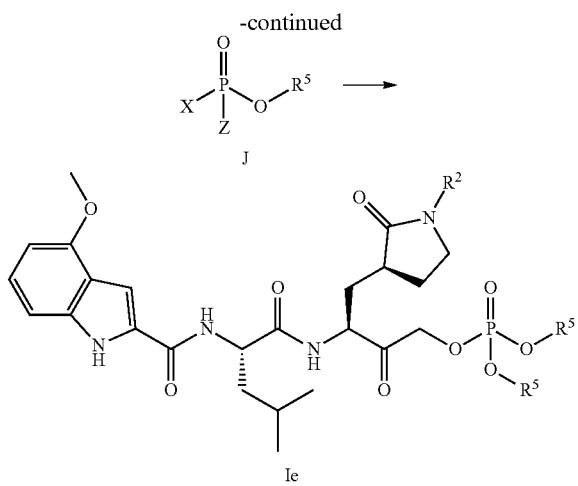

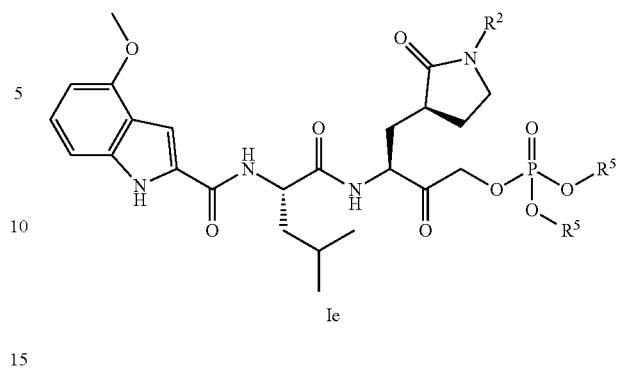

Scheme 9 illustrates a synthetic sequence for the preparation of compounds of Formula Ie as shown, wherein a compound of Formula A is treated with a compound of Formula J, wherein X is typically a halogen atom and Z may be either an $C_1$-$C_6$alkyl group directly linked to phosphorus or a $R^5O$ group linked to phosphorus through the O atom. The product Ie depicted above is where Z is $R^5O$— but it is to be understood that when Z is instead an alkyl group then one of the —$OR^5$ groups shown would instead be that alkyl group. Such methods are well known to those skilled in the art. Compounds J are described in the chemical literature and may be commercially available. The reaction is conducted in the presence of a base to consume the hydrogen halide HX produced as a by-product of the reaction. Examples of suitable bases include, but are not limited to, tertiary amines such as N-methyl morpholine, pyridine, triethylamine or diisopropylethylamine. Suitable solvents include, but are not limited to, $CH_2Cl_2$, DMF, THF or $CH_3CN$. One skilled in the art will appreciate that in the event that the compound of Formula A contains $R^2$=H, the above transformations may afford a product compound of Formula Ie in which $R^2$ may be H or may be $P(O)Z(OR^5)$, depending upon the selection of reaction parameters such as time, temperature, solvent, and equivalents of the compound of Formula J employed.

Scheme 10 illustrates a synthetic sequence for the preparation of compounds of Formula 1e as shown, wherein a compound of Formula A is treated with a compound of Formula K, wherein Alk is typically an alkyl group, such as methyl, ethyl, isopropyl, t-butyl or benzyl. Compounds K are known by those skilled in the art as phosphoramidites and may be commercially available. The reaction is typically conducted in the presence of a nucleophilic catalyst, with 1H-tetrazole being particularly common. During the course of the reaction, an oxidant is generally added prior to the isolation of the compound of Formula 1. Typical oxidants include, but are not limited to, meta-chloroperoxybenzoic acid (mCPBA), hydrogen peroxide ($H_2O_2$) and t-butyl hydroperoxide. Suitable solvents include, but are not limited to, $CH_2Cl_2$, THF or $CH_3CN$. One skilled in the art will appreciate that in the event that the compound of Formula A contains $R^2$=H, the above transformations may afford a product compound of Formula 1 in which $R^2$ may be H or may be $P(O)(OR^5)_2$, depending upon the selection of reaction parameters such as time, temperature, solvent, and equivalents of the compound of Formula K employed.

Scheme 10

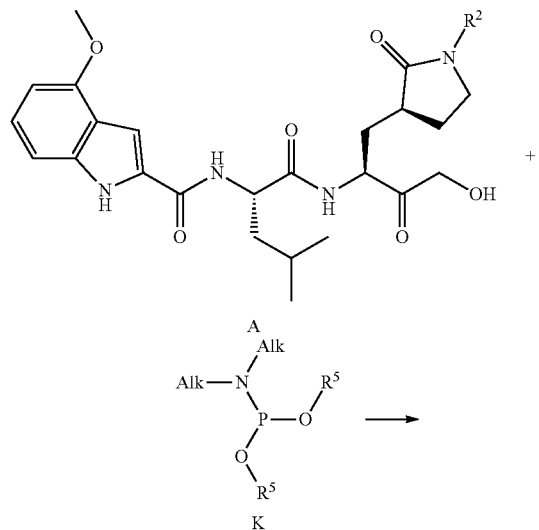

Scheme 11

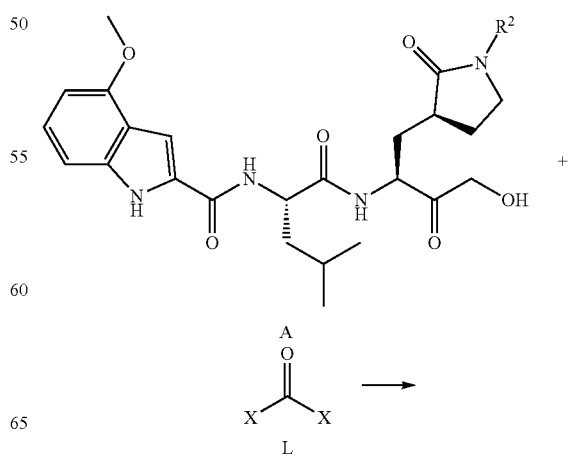

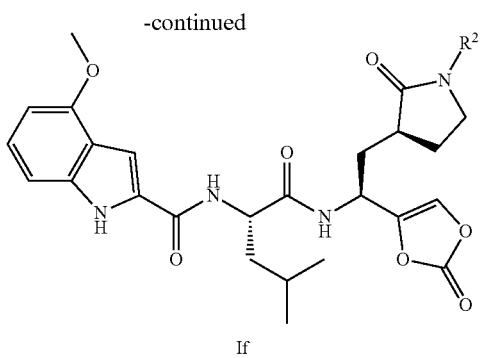

If

Scheme 11 illustrates a synthetic sequence for the preparation of compounds of Formula 1f as shown, wherein a compound of Formula A is treated with a compound of Formula L, wherein either X is a halogen atom, typically chlorine, or an $OCCl_3$ group. Compounds O are known in the chemical literature as phosgene derivatives and are commercially available. The reaction is conducted in the presence of a base to consume the hydrogen halide HX produced as a by-product of the reaction. Examples of suitable bases include, but are not limited to, tertiary amines such as N,N-dimethylaniline, pyridine or N-methylmorpholine. Suitable solvents include, but are not limited to, $CH_2Cl_2$, THF or $CH_3CN$.

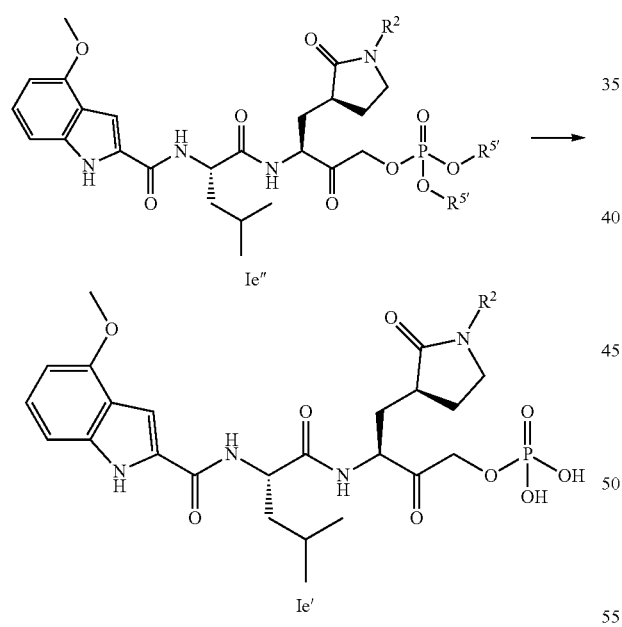

Scheme 12 illustrates a synthetic sequence for the preparation of compounds of Formula Ie' as shown, wherein a compound of Formula 1e'', prepared for example as shown in Scheme 10, is treated with a reagent or reagents that cause cleavage of the $R^{5'}O$ group on phosphorus to liberate an OH group as shown. Such methods are well known to those skilled in the art, and the selection of conditions depends upon the nature of the $R^6O$ group attached to phosphorus. For example, when the $R^{5'}O$ group is $PhCH_2O$, the reaction may be affected by hydrogenation over a palladium catalyst. Alternatively, when the $R^{5'}O$ group is $PhCH_2O$, t-butyl or $CH_2CH_2CN$, the reaction may be affected by exposure of the compound of Formula Ie to acid, with trifluoroacetic acid being especially commonly used. Suitable solvents include, but are not limited to, $CH_2Cl_2$, DMF, THF, or $CH_3CN$.

One skilled in the art will appreciate that it is possible to prepare compounds of the present invention in which $R^2$ may be some other group than H. The following schemes illustrate, in a non-limiting manner, how such other $R^2$ groups may be introduced to provide compounds of Formula A, and to provide ultimately compounds of the present invention, in which $R^2$ is not equal to H.

Scheme 13

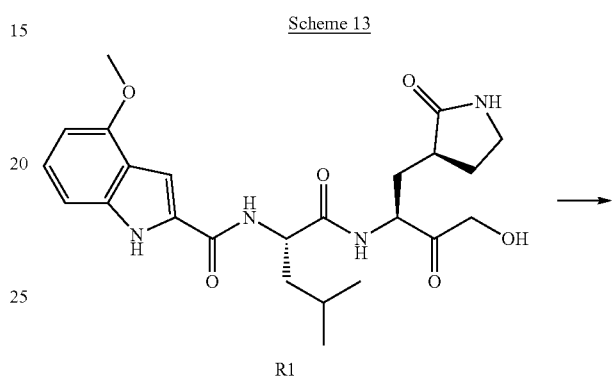

Scheme 13 illustrates a synthetic sequence for the preparation of compounds of Formula R as shown, wherein the compound of Formula R1 (PCT Int. Appl. Pub. WO 2005/113580) is treated with a reagent that silylates the OH group as shown. Such methods are well known to those skilled in the art, and the reaction illustrated may be accomplished by exposure of the compound of Formula R1 to tert-butyldimethylchlorosilane, for example, typically in the presence of imidazole. Suitable solvents include, but are not limited to, $CH_2Cl_2$, DMF, THF, or $CH_3CN$. One skilled in the art will appreciate that other reagents may be used to introduce the tert-butyldimethylsilyl group, and that other silyl ethers closely similar to compounds of Formula R may be prepared by the selection of other appropriate silylating agents, for example triisopropylsilyl or tert-butyldiphenylsilyl ethers.

Scheme 14

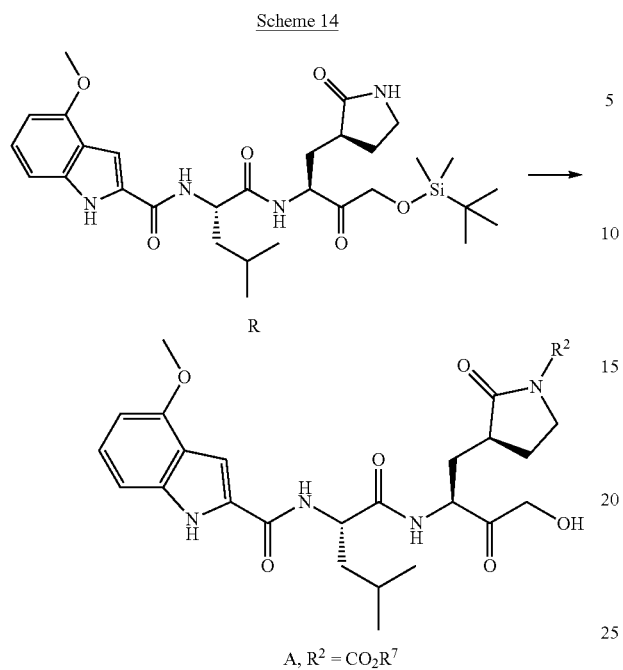

A, R² = CO₂R⁷

Scheme 14 illustrates a synthetic sequence for the preparation of compounds of Formula A as shown, wherein the compound of Formula R is transformed, typically in two synthetic manipulations, into the compound of Formula A in which R² is equal to C(O)OR⁷ as illustrated. In the first manipulation, the compound of Formula R may be treated with a compound of Formula B (R⁷OC(O)X, Scheme 1), wherein X is a halogen atom, most frequently chlorine. In this case the compound of Formula B is known as a chloroformate, and such methods are well known to those skilled in the art. The reaction is conducted in the presence of a base to consume the hydrogen halide HX produced as a by-product of the reaction. Examples of suitable bases include, but are not limited to, tertiary amines such as N-methyl morpholine, 2,6-dimethylpyridine, or diisopropylethylamine, or inorganic bases such as MgO, Na₂CO₃, or KHCO₃. Suitable solvents include, but are not limited to, CH₂Cl₂, THF, or CH₃CN. Alternatively, in the first manipulation, the compound of Formula R may be treated with a compound of Formula C(R⁷OC(O)OC(O)OR⁷, Scheme 2), frequently known as a pyrocarbonate by those skilled in the art. The reaction is frequently conducted in the presence of a nucleophilic catalyst to accelerate the reaction. Examples of such nucleophilic catalysts include, but are not limited to, 4-(dimethylamino)pyridine, imidazole or DBU. Suitable solvents include, but are not limited to, CH₂Cl₂, THF, pyridine or CH₃CN.

In the second manipulation, the silyl ether may be removed to afford the compounds of Formula A as shown. One skilled in the art will understand that the selection of reagents and conditions to effect this transformation will depend upon the nature of the particular C(O)OR⁷ group introduced at the first manipulation, such that the conditions for the second manipulation are not incompatible with the integrity of the C(O)OR⁷ group introduced at the first manipulation. Commonly employed conditions for removal of the silyl ether include exposure to acids, such as trifluoroacetic acid, acetic acid, hydrofluoric, or hydrochloric acid, for example, or alternately exposure to a source of fluoride ion, with tetrabutylammonium fluoride being especially commonly used. One skilled in the art will appreciate that the selection of suitable solvents for the second manipulation will depend upon the reagents selected to effect that transformation and may include, but are not limited to, CH₂Cl₂, THF or CH₃CN.

Scheme 15

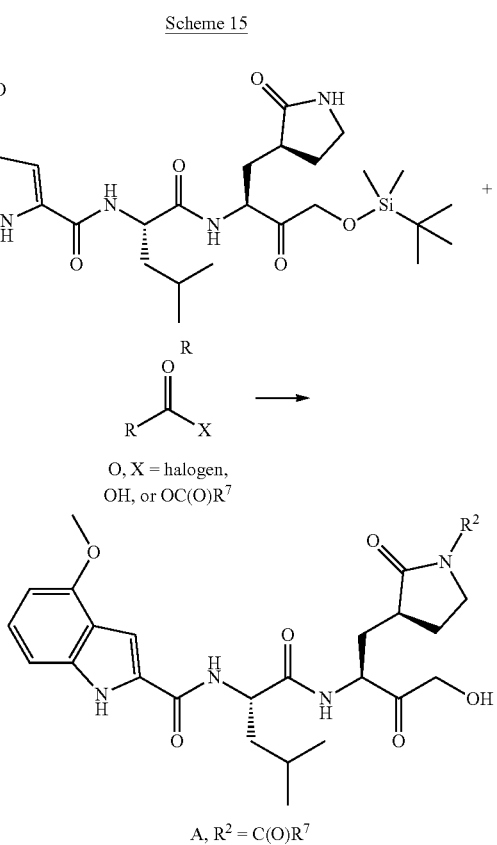

O, X = halogen, OH, or OC(O)R⁷

A, R² = C(O)R⁷

Scheme 15 illustrates a synthetic sequence for the preparation of compounds of Formula A as shown, wherein the compound of Formula R is transformed, typically in two synthetic manipulations, into the compound of Formula A in which R² is equal to C(O)R as illustrated. In the first manipulation, the compound of Formula R is treated with a compound of Formula O, wherein X is typically a halogen atom, OH, or OC(O)R⁷. Such methods are well known to those skilled in the art. For example, when X=a halogen atom, the reaction is conducted in the presence of a base to consume the hydrogen halide HX produced as a by-product of the reaction. Examples of suitable bases include, but are not limited to, tertiary amines such as N-methyl morpholine, 2,6-dimethylpyridine or diisopropylethylamine, or inorganic bases such as MgO, Na₂CO₃ or KHCO₃. Suitable solvents include, but are not limited to, CH₂Cl₂, DMF, THF, or CH₃CN. When X=OH, the compound of Formula O is a carboxylic acid and it is customary to use a reagent or combination of reagents to accelerate the reaction of the carboxylic acid O. One skilled in the art may choose to use, for example, a carbodiimide reagent such as EDC or DCC, optionally in the presence of an auxiliary nucleophile such as HOBt or HOPO. Further, when X=OH, one skilled in the art may choose to use reagents that are suitable for the formation of mixed carboxyl/carbonic anhydrides, such as CDI, isobutyl or ethyl chloroformate, frequently in the presence of a base such as described above. Suitable solvents include, but are not limited to, CH$_2$Cl$_2$, THF, or CH$_3$CN. Another approach commonly used by those skilled in the art when X=OH is to treat the compound of Formula O with a carboxylic acid chloride, for example such as Me$_3$CCOCl, in the presence of a base such as described above to generate a mixed carboxylic anhydride of the Formula R$^7$C(O)O(O)CCMe$_3$. Suitable solvents include, but are not limited to, CH$_2$Cl$_2$, THF, or CH$_3$CN. In many cases it is possible to use a symmetric anhydride of the desired carboxylic acid of Formula O to effect the reaction of Scheme 15, optionally in the presence of a base such as described above, in which case X=O(O)CR and the compound of Formula O is therefore R$^7$C(O)O(O)R$^7$. Suitable solvents include, but are not limited to, CH$_2$Cl$_2$, THF or CH$_3$CN.

In the second manipulation, the silyl ether may be removed to afford the compounds of Formula A as shown. One skilled in the art will understand that the selection of reagents and conditions to effect this transformation will depend upon the nature of the particular C(O)R group introduced at the first manipulation, such that the conditions for the second manipulation are not incompatible with the integrity of the C(O)R group introduced at the first manipulation. Commonly employed conditions for removal of the silyl ether include exposure to acids, such as trifluoroacetic acid, acetic acid, hydrofluoric, or hydrochloric acid, for example, or alternately exposure to a source of fluoride ion, with tetrabutylammonium fluoride being especially commonly used. One skilled in the art will appreciate that the selection of suitable solvents for the second manipulation will depend upon the reagents selected to effect that transformation and may include, but are not limited to, CH$_2$Cl$_2$, THF or CH$_3$CN.

synthetic manipulations, into the compound of Formula A in which R$^2$ is equal to CH$_2$OC(O)OR or CHMeOC(O)OR$^7$ as illustrated. In the first manipulation, the compound of Formula R may be treated with a compound of Formula F (XCH$_2$OC(O)OR$^7$ or XCHMeOC(O)OR$^7$, Scheme 5) in which X is a halogen atom. Such compounds of Formula F are described in the chemical literature and may be commercially available. The reaction is affected by treatment with a base, for example KOtBu or Cs$_2$CO$_3$, in a suitable solvent which may include, but is not limited to, THF, DMF, DMSO, or CH$_3$CN.

In the second manipulation, the silyl ether may be removed to afford the compounds of Formula A as shown. One skilled in the art will understand that the selection of reagents and conditions to effect this transformation may depend upon the nature of the particular CH$_2$OC(O)OR$^7$ or CHMeOC(O)OR$^7$ group introduced at the first manipulation, such that the conditions for the second manipulation are not incompatible with the integrity of the CH$_2$OC(O)OR$^7$ or CHMeOC(O)OR$^7$ group introduced at the first manipulation. The silyl ether may be removed by exposure to a source of fluoride ion, with tetrabutylammonium fluoride being especially suitable. Suitable solvents for the second manipulation may include, but are not limited to, DMF, CH$_2$Cl$_2$, THF or CH$_3$CN.

Scheme 17

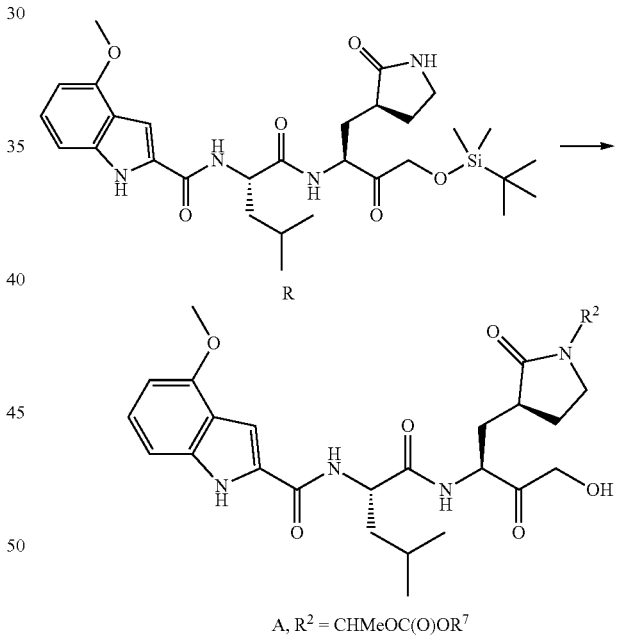

A, R$^2$ = CHMeOC(O)OR$^7$

Scheme 16

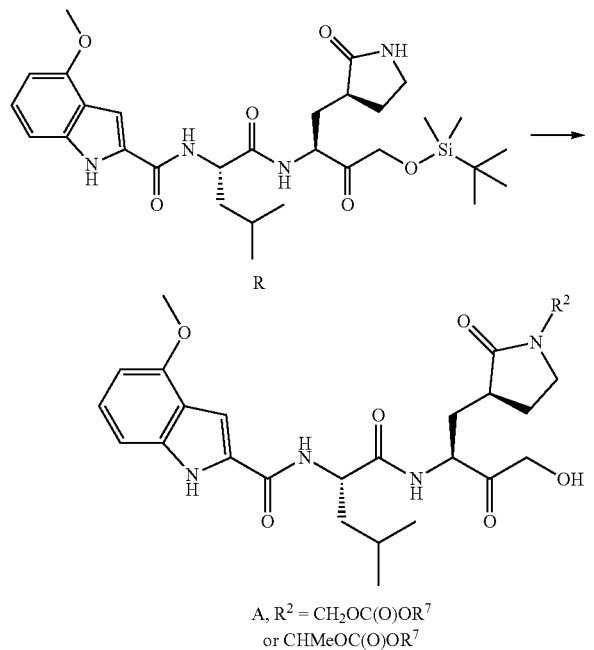

A, R$^2$ = CH$_2$OC(O)OR$^7$
or CHMeOC(O)OR$^7$

Scheme 16 illustrates a synthetic sequence for the preparation of compounds of Formula A as shown, wherein the compound of Formula R is transformed, typically in two Scheme 17 illustrates a synthetic sequence for the preparation of compounds of Formula A as shown, wherein the compound of Formula R is transformed, typically in two synthetic manipulations, into the compound of Formula A in which R$^2$ is equal to CHMeOC(O)OR$^7$ as illustrated. In the first manipulation, the compound of Formula R may be treated with an olefinic compound of Formula G (CH$_2$=CHOC(O)OR$^7$, Scheme 6). Such compounds of Formula G are described in the chemical literature and may be commercially available. The reaction is affected by treatment with a catalyst as known to those skilled in the art, which may include but is not limited to an acid, a compound of palladium, or a compound of mercury. Suitable solvents may include, but are not limited to, $CH_2Cl_2$, THF, or $CH_3CN$.

In the second manipulation, the silyl ether may be removed to afford the compounds of Formula A as shown. One skilled in the art will understand that the selection of reagents and conditions to effect this transformation may depend upon the nature of the particular $CHMeOC(O)OR^7$ group introduced at the first manipulation, such that the conditions for the second manipulation are not incompatible with the integrity of the $CHMeOC(O)OR^7$ group introduced at the first manipulation. The silyl ether may be removed by exposure to a source of fluoride ion, with tetrabutylammonium fluoride being especially suitable. Suitable solvents for the second manipulation may include, but are not limited to, DMF, $CH_2Cl_2$, THF, or $CH_3CN$.

EXAMPLES

The following Examples can be prepared according to the methods described in Schemes 1-17 hereinabove and for Examples 1, 2, 5, 7, 8, 43, 44, 49, 57, 64 and 65 can be prepared as specifically set forth hereinbelow.

Experimental Procedures

The following illustrate the synthesis of various compounds of the present invention. Additional compounds within the scope of this invention may be prepared using the methods illustrated in these Examples, either alone or in combination with techniques generally known in the art. All starting materials in these Preparations and Examples are either commercially available or can be prepared by methods known in the art or as described herein.

All reactions were carried out using continuous stirring under an atmosphere of nitrogen or argon gas unless otherwise noted. When appropriate, reaction apparatuses were dried under dynamic vacuum using a heat gun, and anhydrous solvents (Sure-Seal™ products from Aldrich Chemical Company, Milwaukee, Wisconsin or DriSolv™ products from EMD Chemicals, Gibbstown, NJ) were employed. In some cases, commercial solvents were passed through columns packed with 4 Å molecular sieves, until the following QC standards for water were attained: a) <100 ppm for dichloromethane, toluene, N,N-dimethylformamide, and tetrahydrofuran; b) <180 ppm for methanol, ethanol, 1,4-dioxane, and diisopropylamine. For very sensitive reactions, solvents were further treated with metallic sodium, calcium hydride, or molecular sieves, and distilled just prior to use. Other commercial solvents and reagents were used without further purification. For syntheses referencing procedures in other Examples or Methods, reaction conditions (reaction time and temperature) may vary. Products were generally dried under vacuum before being carried on to further reactions or submitted for biological testing.

When indicated, reactions were heated by microwave irradiation using Biotage Initiator or Personal Chemistry Emrys Optimizer microwaves. Reaction progress was monitored using thin-layer chromatography (TLC), liquid chromatography-mass spectrometry (LCMS), high-performance liquid chromatography (HPLC), and/or gas chromatography-mass spectrometry (GCMS) analyses. TLC was performed on pre-coated silica gel plates with a fluorescence indicator (254 nm excitation wavelength) and visualized under UV light and/or with $I_2$, $KMnO_4$, $CoCl_2$, phosphomolybdic acid, and/or ceric ammonium molybdate stains. LCMS data were acquired on an Agilent 1100 Series instrument with a Leap Technologies autosampler, Gemini C18 columns, acetonitrile/water gradients, and either trifluoroacetic acid, formic acid, or ammonium hydroxide modifiers. The column eluate was analyzed using a Waters ZQ mass spectrometer scanning in both positive and negative ion modes from 100 to 1200 Da. Other similar instruments were also used. HPLC data were generally acquired on an Agilent 1100 Series instrument, using the columns indicated, acetonitrile/water gradients, and either trifluoroacetic acid or ammonium hydroxide modifiers. GCMS data were acquired using a Hewlett Packard 6890 oven with an HP 6890 injector, HP-1 column (12 m×0.2 mm×0.33 μm), and helium carrier gas. The sample was analyzed on an HP 5973 mass selective detector scanning from 50 to 550 Da using electron ionization. Purifications were performed by medium performance liquid chromatography (MPLC) using Isco CombiFlash Companion, AnaLogix IntelliFlash 280, Biotage SP1, or Biotage Isolera One instruments and pre-packed Isco RediSep or Biotage Snap silica cartridges. Chiral purifications were performed by chiral supercritical fluid chromatography (SFC), generally using Berger or Thar instruments; columns such as ChiralPAK-AD, -AS, -IC, Chiralcel-OD, or -OJ columns; and $CO_2$ mixtures with methanol, ethanol, 2-propanol, or acetonitrile, alone or modified using trifluoroacetic acid or propan-2-amine. UV detection was used to trigger fraction collection. For syntheses referencing procedures in other Examples or Methods, purifications may vary: in general, solvents and the solvent ratios used for eluents/gradients were chosen to provide appropriate $R_f$s or retention times.

Mass spectrometry data are reported from LCMS analyses. Mass spectrometry (MS) was performed via atmospheric pressure chemical ionization (AFCI), electrospray ionization (ESI), electron impact ionization (E1) or electron scatter ionization (ES) sources. Proton nuclear magnetic spectroscopy ($^1H$ NMR) chemical shifts are given in parts per million downfield from tetramethylsilane and were recorded on 300, 400, 500, or 600 MHz Varian, Bruker, or Jeol spectrometers. Chemical shifts are expressed in parts per million (ppm, δ) referenced to the deuterated solvent residual peaks (chloroform, 7.26 ppm; $CD_2HOD$, 3.31 ppm; acetonitrile-$d_2$, 1.94 ppm; dimethyl sulfoxide-$d_5$, 2.50 ppm; DHO, 4.79 ppm). The peak shapes are described as follows: s, singlet; d, doublet; t, triplet; q, quartet; quin, quintet; m, multiplet; br s, broad singlet; app, apparent. Analytical SFC data were generally acquired on a Berger analytical instrument as described above. Optical rotation data were acquired on a PerkinElmer model 343 polarimeter using a 1 dm cell. Microanalyses were performed by Quantitative Technologies Inc. and were within 0.4% of the calculated values.

Unless otherwise noted, chemical reactions were performed at room temperature (about 23 degrees Celsius).

Unless noted otherwise, all reactants were obtained commercially and used without further purification, or were prepared using methods known in the literature.

The terms "concentrated", "evaporated", and "concentrated in vacuo" refer to the removal of solvent at reduced pressure on a rotary evaporator with a bath temperature less than 60° C. The abbreviations "min" and "h" stand for "minutes" and "hours," respectively. The term "TLC" refers to thin-layer chromatography, "room temperature or ambient temperature" means a temperature between 18 to 25° C., "GCMS" refers to gas chromatography-mass spectrometry, "LCMS" refers to liquid chromatography-mass spectrometry, "UPLC" refers to ultra-performance liquid chromatography, "HPLC" refers to high-performance liquid chromatography, and "SFC" refers to supercritical fluid chromatography.

Hydrogenation may be performed in a Parr shaker under pressurized hydrogen gas, or in a Thales-nano H-Cube flow hydrogenation apparatus at full hydrogen and a flow rate between 1-2 mL/min at specified temperature.

HPLC, UPLC, LCMS, GCMS, and SFC retention times were measured using the methods noted in the procedures.

In some examples, chiral separations were carried out to separate enantiomers or diastereomers of certain compounds of the invention (in some examples, the separated enantiomers are designated as ENT-1 and ENT-2, according to their order of elution; similarly, separated diastereomers are designated as DIAST-1 and DIAST-2, according to their order of elution). In some examples, the optical rotation of an enantiomer was measured using a polarimeter. According to its observed rotation data (or its specific rotation data), an enantiomer with a clockwise rotation was designated as the (+)-enantiomer and an enantiomer with a counter-clockwise rotation was designated as the (−)-enantiomer. Racemic compounds are indicated either by the absence of drawn or described stereochemistry, or by the presence of (+/−) adjacent to the structure; in this latter case, the indicated stereochemistry represents just one of the two enantiomers that make up the racemic mixture.

The compounds and intermediates described below were named using the naming convention provided with ACD/ChemSketch 2019.1.1, File Version C05H41, Build 110712 (Advanced Chemistry Development, Inc., Toronto, Ontario, Canada). The naming convention provided with ACD/ChemSketch 2019.1.1 is well known by those skilled in the art and it is believed that the naming convention provided with ACD/ChemSketch 2019.1.1 generally comports with the IUPAC (International Union for Pure and Applied Chemistry) recommendations on Nomenclature of Organic Chemistry and the CAS Index rules.

Example 1: (3S)-3-({N-[(4-Methoxy-1H-indol-2-yl)carbonyl]-L-leucyl}amino)-2-oxo-4-[(3S)-2-oxopyrrolidin-3-yl]butyl methyl carbonate (1)

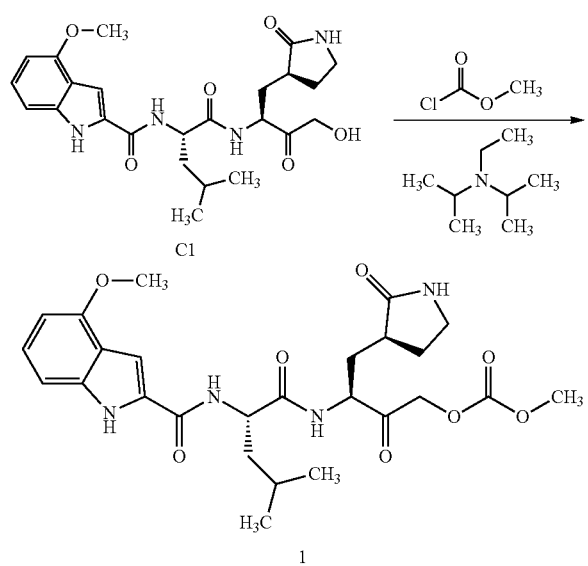

A 0° C. solution of N-[(2S)-1-({(2S)-4-hydroxy-3-oxo-1-[(3S)-2-oxopyrrolidin-3-yl]butan-2-yl}amino)-4-methyl-1-oxopentan-2-yl]-4-methoxy-1H-indole-2-carboxamide (C1) (see Hoffman, R. L. et al., PCT Int. Appl. 2005113580, Dec. 1, 2005; 30 mg, 63 µmol) in tetrahydrofuran (0.64 mL) was treated with N,N-diisopropylethylamine (11 µL, 63 µmol), followed by methyl chloroformate (4.91 µL, 63.5 µmol). The reaction mixture was allowed to warm to room temperature overnight, whereupon an additional equivalent of methyl chloroformate was added. After three days, because the reaction was still incomplete, N,N-dimethylformamide (0.2 mL) was added; 4 hours later, the reaction mixture was diluted with dichloromethane and washed with 1 M hydrochloric acid. The organic layer was dried over sodium sulfate, filtered, and concentrated in vacuo. Purification via silica gel chromatography (Gradient: 0% to 10% methanol in dichloromethane) afforded (3S)-3-({N-[(4-methoxy-1H-indol-2-yl)carbonyl]-L-leucyl}amino)-2-oxo-4-[(3S)-2-oxopyrrolidin-3-yl]butyl methyl carbonate (1) as a solid. Yield: 24 mg, 45 µmol, 71%. LCMS m/z 531.4 [M+H]$^+$. $^1$H NMR (400 MHz, methanol-d$_4$) δ 7.28 (br s, 1H), 7.14 (dd, component of ABX system, J=8, 8 Hz, 1H), 7.02 (d, half of AB quartet, J=8.3 Hz, 1H), 6.50 (d, J=7.7 Hz, 1H), 4.91 (AB quartet, J$_{AB}$=17.4 Hz, Δv$_{AB}$=10.1 Hz, 2H), 4.66-4.57 (m, 2H), 3.92 (s, 3H), 3.76 (s, 3H), 3.29-3.20 (m, 2H), 2.61-2.50 (m, 1H), 2.33-2.22 (m, 1H), 2.09 (ddd, J=14.2, 11.2, 4.7 Hz, 1H), 1.88-1.66 (m, 5H), 1.03 (d, J=6.1 Hz, 3H), 0.99 (d, J=6.2 Hz, 3H).

Example 2: (3S)-3-({N-[(4-Methoxy-1H-indol-2-yl)carbonyl]-L-leucyl}amino)-2-oxo-4-[(3S)-2-oxopyrrolidin-3-yl]butyl propan-2-yl carbonate (2)

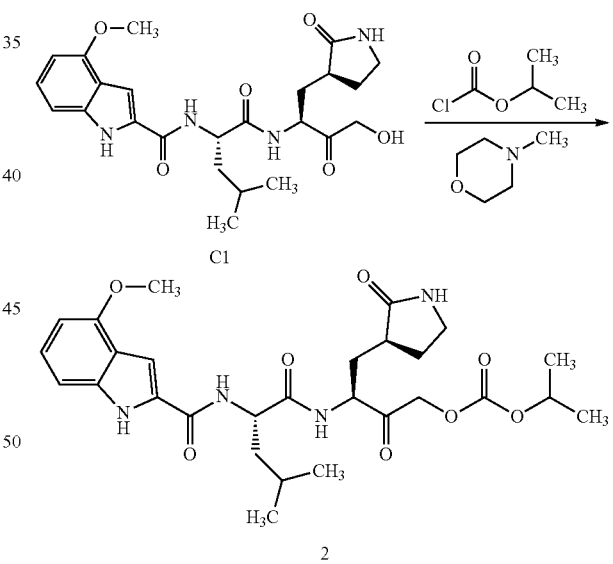

A 0° C. solution of C1 (15 mg, 32 µmol) in tetrahydrofuran (0.32 mL) was treated with 4-methylmorpholine (4.2 µL, 38 µmol), followed by a solution of 2-propyl chloroformate in toluene (1.0 M; 34.8 µL, 34.8 µmol). The reaction mixture was warmed to room temperature; after 5 hours, heat was applied, and stirring was continued at 40° C. overnight, whereupon the reaction mixture was diluted with dichloromethane and treated with 10% aqueous potassium hydrogen sulfate solution. After the organic layer had been dried over sodium sulfate, it was filtered, and the filtrate was concentrated in vacuo. Purification via reversed-phase HPLC (Column: Waters Sunfire C18, 19×100 mm, 5 µm; Mobile phase A: water containing 0.05% trifluoroacetic acid; Mobile phase B: acetonitrile containing 0.05% trifluoroacetic acid; Gradient: 5% to 95% B over 8.54 minutes, then 95% B for 1.46 minutes; Flow rate: 25 mL/minute) provided (3S)-3-({N-[(4-methoxy-1H-indol-2-yl)carbonyl]-L-leucyl}amino)-2-oxo-4-[(3S)-2-oxopyrrolidin-3-yl]butyl propan-2-yl carbonate (2). Yield: 14.5 mg, 26.0 μmol, 81%. LCMS m/z 559.5 [M+H]$^+$. Retention time: 2.73 minutes (Analytical conditions. Column: Waters Atlantis dC18, 4.6× 50 mm, 5 μm; Mobile phase A: water containing 0.05% trifluoroacetic acid (v/v); Mobile phase B: acetonitrile containing 0.05% trifluoroacetic acid (v/v); Gradient: 5.0% to 95% B, linear over 4.0 minutes, then 95% B for 1.0 minute; Flow rate: 2 mL/minute).

Example 3: (3S)-4-[(3S)-1-acetyl-2-oxopyrrolidin-3-yl]-3-({N-[(4-methoxy-1H-indol-2-yl)carbonyl]-L-leucyl}amino)-2-oxobutyl methyl carbonate Example 4: (3S)-4-[(3S)-1-{(1S)-1-[(methoxycarbonyl)oxy]ethyl}-2-oxopyrrolidin-3-yl]-3-({N-[(4-methoxy-1H-indol-2-yl)carbonyl]-L-leucyl}amino)-2-oxobutyl methyl carbonate Example 5: Ethyl (3S)-3-({N-[(4-methoxy-1H-indol-2-yl)carbonyl]-L-leucyl}amino)-2-oxo-4-[(3S)-2-oxopyrrolidin-3-yl]butyl carbonate (5)

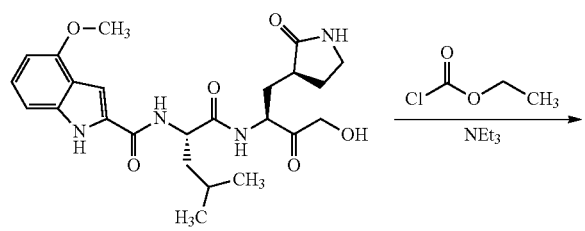

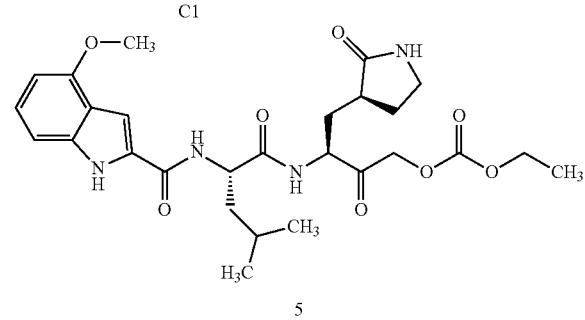

Ethyl chloroformate (29.9 mg, 0.276 mmol) and triethylamine (42.8 mg, 0.423 mmol) were added to a 0° C. solution of C1 (100 mg, 0.212 mmol) in dichloromethane (4.0 mL). The reaction mixture was stirred at 20° C. for 2 hours, whereupon it was diluted with water (3 mL) and extracted with dichloromethane (3×3 mL). The combined organic layers were washed with saturated aqueous sodium chloride solution, dried over sodium sulfate, concentrated in vacuo, and combined with the product of a similar reaction carried out using C1 (50.0 mg, 0.106 mmol). Purification using reversed-phase HPLC (Column: Agela Durashell C18, 40×150 mm, 5 μm; Mobile phase A: 0.225% formic acid in water; Mobile phase B: acetonitrile; Gradient: 26% to 66% B; Flow rate: 50 mL/minute) provided ethyl (3S)-3-({N-[(4-methoxy-1H-indol-2-yl)carbonyl]-L-leucyl}amino)-2-oxo-4-[(3S)-2-oxopyrrolidin-3-yl]butyl carbonate (5) as a white solid. Combined yield: 48.0 mg, 88.1 μmol, 28%. LCMS m/z 545.3 [M+H]$^+$. $^1$H NMR (400 MHz, DMSO-$d_6$) δ11.59 (d, J=2.4 Hz, 1H), 8.59 (d, J=7.9 Hz, 1H), 8.46 (d, J=7.7 Hz, 1H), 7.66 (s, 1H), 7.37 (d, J=2.4 Hz, 1H), 7.09 (dd, component of ABX system, J=8, 8 Hz, 1H), 7.00 (d, half of AB quartet, J=8.2 Hz, 1H), 6.50 (d, J=7.6 Hz, 1H), 4.89 (AB quartet, $J_{AB}$=17.3 Hz, $\Delta v_{AB}$=21.6 Hz, 2H), 4.52-4.37 (m, 2H), 4.13 (q, J=7.1 Hz, 2H), 3.88 (s, 3H), 3.19-3.03 (m, 2H), 2.37-2.25 (m, 1H), 2.13-2.03 (m, 1H), 1.98 (ddd, J=14, 11, 4 Hz, 1H), 1.79-1.50 (m, 5H), 1.21 (t, J=7.1 Hz, 3H), 0.94 (d, J=6.2 Hz, 3H), 0.89 (d, J=6.2 Hz, 3H).

Example 6: methyl (3S)-3-[(2S)-4-[(methoxycarbonyl)oxy]-2-({N-[(4-methoxy-1H-indol-2-yl)carbonyl]-L-leucyl}amino)-3-oxobutyl]-2-oxopyrrolidine-1-carboxylate LCMS m/z 589.5 [M+H]$^+$. Retention time: 2.77 minutes (Analytical conditions. Column: Waters Atlantis dC18, 4.6× 50 mm, 5 μm; Mobile phase A: water containing 0.05% trifluoroacetic acid (v/v); Mobile phase B: acetonitrile containing 0.05% trifluoroacetic acid (v/v); Gradient: 5.0% to 95% B, linear over 4.0 minutes, then 95% B for 1.0 minute; Flow rate: 2 mL/minute).

Examples 7 and 8: tert-Butyl (3S)-3-({N-[(4-methoxy-1H-indol-2-yl)carbonyl]-L-leucyl}amino)-2-oxo-4-[(3S)-2-oxopyrrolidin-3-yl]butyl carbonate (7) and tert-Butyl (3S)-3-[(2S)-4-[(tert-butoxycarbonyl)oxy]-2-({N-[(4-methoxy-1H-indol-2-yl)carbonyl]-L-leucyl}amino)-3-oxobutyl]-2-oxopyrrolidine-1-carboxylate (8)

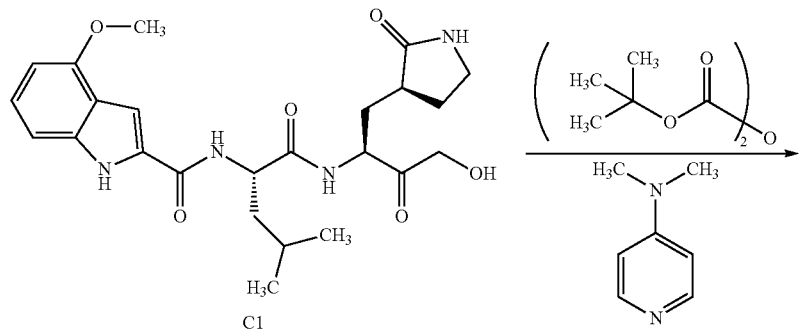

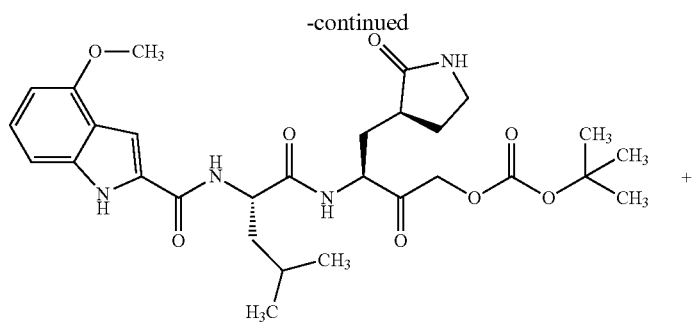

7

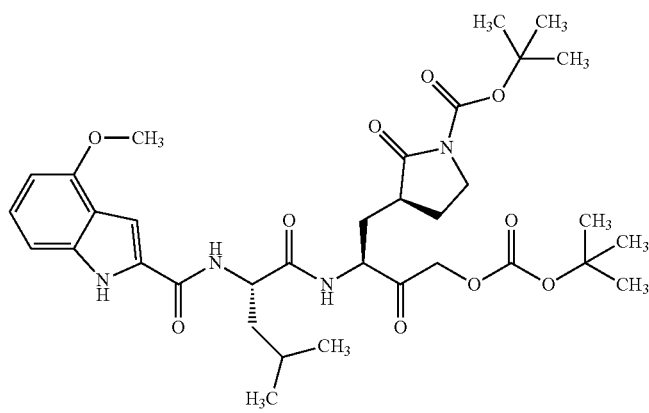

8

4-(Dimethylamino)pyridine (0.13 mg, 1.10 µmol) was added to a solution of C1 (26.8 mg, 56.7 µmol) and di-tert-butyl dicarbonate (12 mg, 55 µmol) in tetrahydrofuran (0.55 mL). After the reaction mixture had been stirred for 1 hour and 40 minutes, it was concentrated in vacuo and purified via silica gel chromatography (Gradient: 0% to 100% ethyl acetate in heptane) to afford tert-butyl (3S)-3-({N-[(4-methoxy-1H-indol-2-yl)carbonyl]-L-leucyl}amino)-2-oxo-4-[(3S)-2-oxopyrrolidin-3-yl]butyl carbonate (7) as a solid. Yield: 7.4 mg, 13 µmol, 24%. LCMS m/z 573.4 [M+H]$^+$. $^1$H NMR (400 MHz, chloroform-d), characteristic peaks: δ 9.53 (br s, 1H), 8.64 (d, J=5.9 Hz, 1H), 7.17 (dd, component of ABX system, J=8, 8 Hz, 1H), 7.10 (br d, J=2 Hz, 1H), 6.99 (d, half of AB quartet, J=8.3 Hz, 1H), 6.83 (br d, J=8.2 Hz, 1H), 6.48 (d, J=7.8 Hz, 1H), 6.10 (br s, 1H), 4.84 (AB quartet, $J_{AB}$=17.2 Hz, $\Delta v_{AB}$=41.0 Hz, 2H), 4.83-4.74 (m, 1H), 4.55-4.46 (m, 1H), 3.93 (s, 3H), 3.34-3.16 (m, 2H), 2.47-2.25 (m, 2H), 1.48 (s, 9H), 1.01-0.94 (m, 6H).

Also isolated was 8, as a solid. $^1$H NMR (400 MHz, chloroform-d), characteristic peaks: δ 8.04 (br s, 1H), 7.76 (br d, J=6.5 Hz, 1H), 7.09 (d, half of AB quartet, J=8.3 Hz, 1H), 6.70 (br s, 1H), 6.49 (d, J=7.8 Hz, 1H), 4.78 (AB quartet, $J_{AB}$=17.8 Hz, $\Delta v_{AB}$=33.3 Hz, 2H), 4.38-4.28 (m, 1H), 3.94 (s, 3H), 3.82-3.69 (m, 1H), 3.38-3.28 (m, 1H), 3.27-3.15 (m, 1H), 2.30-2.17 (m, 1H), 2.04-1.88 (m, 2H), 1.63 (s, 9H), 1.61 (s, 9H), 1.03 (d, J=6.6 Hz, 3H), 0.96 (d, J=6.5 Hz, 3H).

This batch of 8 was further purified via reversed-phase HPLC (Column: Waters Sunfire C18, 19×100 mm, 5 µm; Mobile phase A: water containing 0.05% trifluoroacetic acid; Mobile phase B: acetonitrile containing 0.05% trifluoroacetic acid; Gradient: 45% to 85% B over 8.5 minutes, then 85% to 95% B over 0.5 minutes, then 95% B for 1.0 minute; Flow rate: 25 mL/minute) to provide tert-butyl (3S)-3-[(2S)-4-[(tert-butoxycarbonyl)oxy]-2-({N-[(4-methoxy-1H-indol-2-yl)carbonyl]-L-leucyl}amino)-3-oxobutyl]-2-oxopyrrolidine-1-carboxylate (8). Yield: 13.5 mg, 20.1 µmol, 36%. LCMS m/z 673.7 [M+H]$^+$. Retention time: 3.43 minutes (Analytical conditions. Column: Waters Atlantis dC18, 4.6×50 mm, 5 µm; Mobile phase A: water containing 0.05% trifluoroacetic acid (v/v); Mobile phase B: acetonitrile containing 0.05% trifluoroacetic acid (v/v); Gradient: 5.0% to 95% B, linear over 4.0 minutes, then 95% B for 1.0 minute; Flow rate: 2 mL/minute).

This reversed-phase HPLC purification also provided the tris-tert-butyloxycarbonyl derivative tert-butyl 2-{[(2S)-1-({(2S)-1-[(3S)-1-(tert-butoxycarbonyl)-2-oxopyrrolidin-3-yl]-4-[(tert-butoxycarbonyl)oxy]-3-oxobutan-2-yl}amino)-4-methyl-1-oxopentan-2-yl]carbamoyl}-4-methoxy-1H-indole-1-carboxylate. Yield: 6.2 mg, 8.0 µmol, 14%. $^1$H NMR (400 MHz, chloroform-d) δ 7.70 (br d, J=8.4 Hz, 1H), 7.55 (d, J=8.5 Hz, 1H), 7.33-7.25 (m, 1H, assumed; partially obscured by solvent peak), 6.95 (s, 1H), 6.77-6.66 (m, 1H), 6.67 (d, J=8.0 Hz, 1H), 4.90 (AB quartet, $J_{AB}$=17.5 Hz, $\Delta v_{AB}$=41.3 Hz, 2H), 4.72-4.62 (m, 2H), 3.93 (s, 3H), 3.71-3.61 (m, 1H), 3.54-3.43 (m, 1H), 2.54-2.42 (m, 1H), 1.63 (s, 9H), 1.48 (s, 9H), 1.48 (s, 9H), 1.00 (d, J=6.4 Hz, 6H). LCMS of second (non-8) peak in the pre-purified sample: m/z 773.8 [M+H]$^+$.

Example 9: (1R)-1-({(3S)-3-({N-[(4-methoxy-1H-indol-2-yl)carbonyl]-L-leucyl}amino)-2-oxo-4-[(3S)-2-oxopyrrolidin-3-yl]butyl}oxy)ethyl methyl carbonate Example 10: (1R)-1-({(3S)-3-({N-[(4-methoxy-1H-indol-2-yl)carbonyl]-L-leucyl}amino)-2-oxo-4-[(3S)-2-oxopyrrolidin-3-yl]butyl}oxy)ethyl propan-2-yl carbonate Example 11: (1R)-1-({(3S)-3-({N-[(4-methoxy-1H-indol-2-yl)carbonyl]-L-leucyl}amino)-2-oxo-4-[(3S)-2-oxopyrrolidin-3-yl]butyl}oxy)propyl methyl carbonate Example 12: (1R)-1-({(3S)-3-({N-[(4-methoxy-1H-indol-2-yl)carbonyl]-L-leucyl}amino)-2-oxo-4-[(3S)-2-oxopyrrolidin-3-yl]butyl}oxy)propyl propan-2-yl carbonate Example 13: ({(3S)-3-({N-[(4-methoxy-1H-indol-2-yl)carbonyl]-L-leucyl}amino)-2-oxo-4-[(3S)-2-oxopyrrolidin-3-yl]butyl}oxy)methyl methyl carbonate Example 14: ({(3S)-3-({N-[(4-methoxy-1H-indol-2-yl)carbonyl]-L-leucyl}amino)-2-oxo-4-[(3S)-2-oxopyrrolidin-3-yl]butyl}oxy)methyl propan-2-yl carbonate Example 15: ethyl (1R)-1-({(3S)-3-({N-[(4-methoxy-1H-indol-2-yl)carbonyl]-L-leucyl}amino)-2-oxo-4-[(3S)-2-oxopyrrolidin-3-yl]butyl}oxy)ethyl carbonate Example 16: ethyl (1R)-1-({(3S)-3-({N-[(4-methoxy-1H-indol-2-yl)carbonyl]-L-leucyl}amino)-2-oxo-4-[(3S)-2-oxopyrrolidin-3-yl]butyl}oxy)propyl carbonate Example 17: ethyl ({(3S)-3-({N-[(4-methoxy-1H-indol-2-yl)carbonyl]-L-leucyl}amino)-2-oxo-4-[(3S)-2-oxopyrrolidin-3-yl]butyl}oxy)methyl carbonate Example 18: methyl (3S)-3-[(2S)-4-{[(methoxycarbonyl)oxy]methoxy}-2-({N-[(4-methoxy-1H-indol-2-yl)carbonyl]-L-leucyl}amino)-3-oxobutyl]-2-oxopyrrolidine-1-carboxylate Example 19: tert-butyl (1R)-1-({(3S)-3-({N-[(4-methoxy-1H-indol-2-yl)carbonyl]-L-leucyl}amino)-2-oxo-4-[(3S)-2-oxopyrrolidin-3-yl]butyl}oxy)ethyl carbonate Example 20: tert-butyl (1R)-1-({(3S)-3-({N-[(4-methoxy-1H-indol-2-yl)carbonyl]-L-leucyl}amino)-2-oxo-4-[(3S)-2-oxopyrrolidin-3-yl]butyl}oxy)propyl carbonate Example 21: tert-butyl ({(3S)-3-({N-[(4-methoxy-1H-indol-2-yl)carbonyl]-L-leucyl}amino)-2-oxo-4-[(3S)-2-oxopyrrolidin-3-yl]butyl}oxy)methyl carbonate Example 22: {(3S)-3-[(2S)-4-{[(methoxycarbonyl)oxy]methoxy}-2-({N-[(4-methoxy-1H-indol-2-yl)carbonyl]-L-leucyl}amino)-3-oxobutyl]-2-oxopyrrolidin-1-yl}methyl methyl carbonate Example 23: {[(3S)-4-[(3S)-1-acetyl-2-oxopyrrolidin-3-yl]-3-({N-[(4-methoxy-1H-indol-2-yl)carbonyl]-L-leucyl}amino)-2-oxobutyl]oxy}methyl methyl carbonate Example 24: {[(3S)-4-[(3S)-1-{(1R)-1-[(methoxycarbonyl)oxy]ethyl}-2-oxopyrrolidin-3-yl]-3-({N-[(4-methoxy-1H-indol-2-yl)carbonyl]-L-leucyl}amino)-2-oxobutyl]oxy}methyl methyl carbonate Example 25: (1R)-1-({(3S)-3-({N-[(4-methoxy-1H-indol-2-yl)carbonyl]-L-leucyl}amino)-2-oxo-4-[(3S)-2-oxopyrrolidin-3-yl]butyl}oxy)ethyl 2,2-dimethylpropanoate Example 26: (1S)-1-({(3S)-3-({N-[(4-methoxy-1H-indol-2-yl)carbonyl]-L-leucyl}amino)-2-oxo-4-[(3S)-2-oxopyrrolidin-3-yl]butyl}oxy)ethyl 2-methylpropanoate Example 27: (1S)-1-({(3S)-3-({N-[(4-methoxy-1H-indol-2-yl)carbonyl]-L-leucyl}amino)-2-oxo-4-[(3S)-2-oxopyrrolidin-3-yl]butyl}oxy)ethyl propanoate Example 28: (1S)-1-({(3S)-3-({N-[(4-methoxy-1H-indol-2-yl)carbonyl]-L-leucyl}amino)-2-oxo-4-[(3S)-2-oxopyrrolidin-3-yl]butyl}oxy)propyl 2,2-dimethylpropanoate Example 29: (1S)-1-({(3S)-3-({N-[(4-methoxy-1H-indol-2-yl)carbonyl]-L-leucyl}amino)-2-oxo-4-[(3S)-2-oxopyrrolidin-3-yl]butyl}oxy)propyl 2,2-dimethylpropanoate Example 30: (1S)-1-({(3S)-3-({N-[(4-methoxy-1H-indol-2-yl)carbonyl]-L-leucyl}amino)-2-oxo-4-[(3S)-2-oxopyrrolidin-3-yl]butyl}oxy)propyl 2-methylpropanoate Example 31: (1S)-1-({(3S)-3-({N-[(4-methoxy-1H-indol-2-yl)carbonyl]-L-leucyl}amino)-2-oxo-4-[(3S)-2-oxopyrrolidin-3-yl]butyl}oxy)propyl propanoate Example 32: ({(3S)-3-({N-[(4-methoxy-1H-indol-2-yl)carbonyl]-L-leucyl}amino)-2-oxo-4-[(3S)-2-oxopyrrolidin-3-yl]butyl}oxy)methyl 2,2-dimethylpropanoate Example 33: ({(3S)-3-({N-[(4-methoxy-1H-indol-2-yl)carbonyl]-L-leucyl}amino)-2-oxo-4-[(3S)-2-oxopyrrolidin-3-yl]butyl}oxy)methyl 2,6-dimethylbenzoate Example 34: ({(3S)-3-({N-[(4-methoxy-1H-indol-2-yl)carbonyl]-L-leucyl}amino)-2-oxo-4-[(3S)-2-oxopyrrolidin-3-yl]butyl}oxy)methyl 2-methylpropanoate Example 35: ({(3S)-3-({N-[(4-methoxy-1H-indol-2-yl)carbonyl]-L-leucyl}amino)-2-oxo-4-[(3S)-2-oxopyrrolidin-3-yl]butyl}oxy)methyl D-valinate Example 36: ({(3S)-3-({N-[(4-methoxy-1H-indol-2-yl)carbonyl]-L-leucyl}amino)-2-oxo-4-[(3S)-2-oxopyrrolidin-3-yl]butyl}oxy)methyl N,N-dimethylglycinate Example 37: ({(3S)-3-({N-[(4-methoxy-1H-indol-2-yl)carbonyl]-L-leucyl}amino)-2-oxo-4-[(3S)-2-oxopyrrolidin-3-yl]butyl}oxy)methyl propanoate Example 38: methyl (3S)-3-{(2S)-2-({N-[(4-methoxy-1H-indol-2-yl)carbonyl]-L-leucyl}amino)-3-oxo-4-[(propanoyloxy)methoxy]butyl}-2-oxopyrrolidine-1-carboxylate Example 39: {[(3S)-4-[(3S)-1-acetyl-2-oxopyrrolidin-3-yl]-3-({N-[(4-methoxy-1H-indol-2-yl)carbonyl]-L-leucyl}amino)-2-oxobutyl]oxy}methyl propanoate Example 40: {[(3S)-4-[(3S)-1-{(1S)-1-[(methoxycarbonyl)oxy]ethyl}-2-oxopyrrolidin-3-yl]-3-({N-[(4-methoxy-1H-indol-2-yl)carbonyl]-L-leucyl}amino)-2-oxobutyl]oxy} methyl propanoate Example 41: (3S)-3-({N-[(4-methoxy-1H-indol-2-yl)carbonyl]-L-leucyl}amino)-2-oxo-4-[(3S)-2-oxopyrrolidin-3-yl]butyl 1,4'-bipiperidine-1'-carboxylate LCMS m/z 667.6 [M+H]$^+$. Retention time: 2.16 minutes (Analytical conditions. Column: Waters Atlantis dC18, 4.6× 50 mm, 5 μm; Mobile phase A: water containing 0.05% trifluoroacetic acid (v/v); Mobile phase B: acetonitrile containing 0.05% trifluoroacetic acid (v/v); Gradient: 5.0% to 95% B, linear over 4.0 minutes, then 95% B for 1.0 minute; Flow rate: 2 mL/minute).

Example 42: (3S)-3-({N-[(4-methoxy-1H-indol-2-yl)carbonyl]-L-leucyl}amino)-2-oxo-4-[(3S)-2-oxopyrrolidin-3-yl]butyl [2-(dimethylamino)ethyl] carbamate LCMS m/z 587.6 [M+H]$^+$. Retention time: 1.96 minutes (Analytical conditions. Column: Waters Atlantis dC18, 4.6× 50 mm, 5 μm; Mobile phase A: water containing 0.05% trifluoroacetic acid (v/v); Mobile phase B: acetonitrile containing 0.05% trifluoroacetic acid (v/v); Gradient: 5.0% to 95% B, linear over 4.0 minutes, then 95% B for 1.0 minute; Flow rate: 2 mL/minute).

Example 43: (3S)-3-({N-[(4-Methoxy-1H-indol-2-yl)carbonyl]-L-leucyl}amino)-2-oxo-4-[(3S)-2-oxopyrrolidin-3-yl]butyl [2-(dimethylamino)ethyl] methylcarbamate, trifluoroacetate Salt (43)

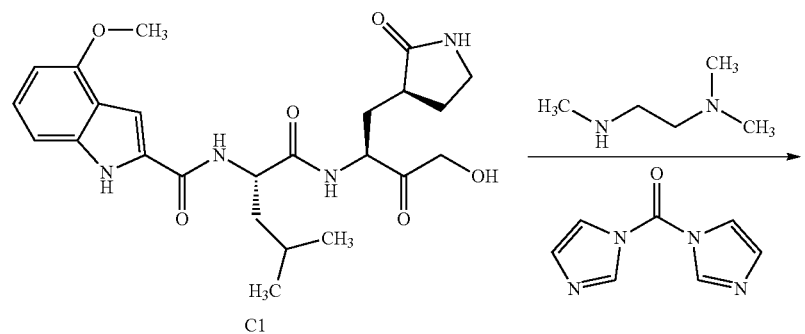

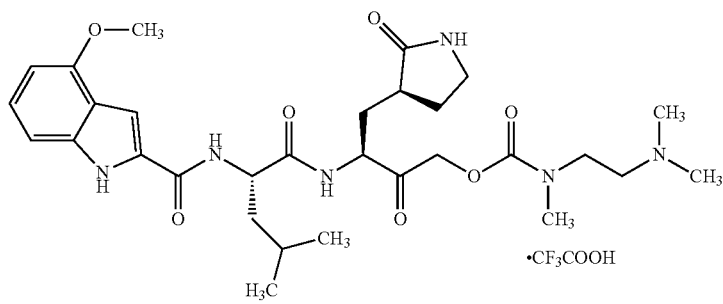

1,1'-Carbonyldiimidazole (6.86 mg, 42.3 µmol) was added to a solution of C1 (20 mg, 42 µmol) in dichloromethane (0.42 mL). The reaction mixture was stirred at room temperature for 1 hour, whereupon N,N,N'-trimethylethane-1,2-diamine (5.50 µL, 42.3 µmol) was added, and stirring was continued overnight. After the reaction mixture had been concentrated in vacuo, the residue was purified via reversed-phase chromatography (Column: Waters Sunfire C18, 19×100 mm, 5 µm; Mobile phase A: water containing 0.05% trifluoroacetic acid; Mobile phase B: acetonitrile containing 0.05% trifluoroacetic acid; Gradient: 5% to 95% B over 8.54 minutes, then 95% B for 1.46 minutes; Flow rate: 25 mL/minute) to afford (3S)-3-({N-[(4-methoxy-1H-indol-2-yl)carbonyl]-L-leucyl}amino)-2-oxo-4-[(3S)-2-oxopyrrolidin-3-yl]butyl [2-(dimethylamino)ethyl]methylcarbamate, trifluoroacetate salt (43). Yield: 16.5 mg, 23.1 µmol, 55%. LCMS m/z 601.6 [M+H]⁺. Retention time: 2.05 minutes (Analytical conditions. Column: Waters Atlantis dC18, 4.6×50 mm, 5 µm; Mobile phase A: water containing 0.05% trifluoroacetic acid (v/v); Mobile phase B: acetonitrile containing 0.05% trifluoroacetic acid (v/v); Gradient: 5.0% to 95% B, linear over 4.0 minutes, then 95% B for 1.0 minute; Flow rate: 2 mL/minute).

Example 44: (3S)-3-({N-[(4-Methoxy-1H-indol-2-yl)carbonyl]-L-leucyl}amino)-2-oxo-4-[(3S)-2-oxopyrrolidin-3-yl]butyl piperidine-1-carboxylate (44)

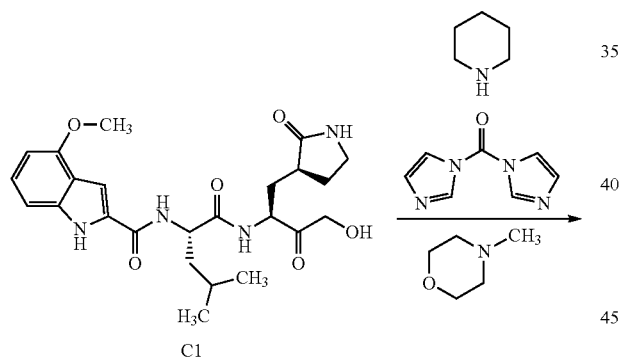

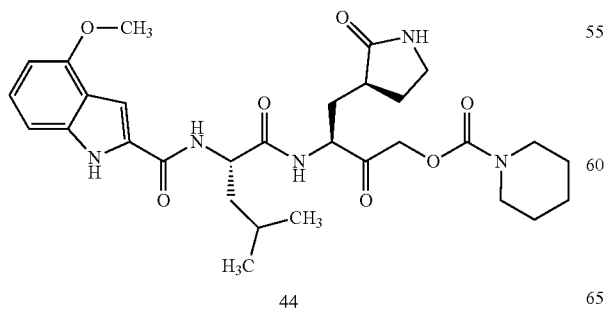

To a solution of C1 (20 mg, 42 µmol) in dichloromethane (0.42 mL) was added 1,1'-carbonyldiimidazole (6.86 mg, 42.3 µmol), followed by 4-methylmorpholine (4.65 µL, 42.3 µmol). After the reaction mixture had been stirred for 1 hour, it was treated with piperidine (4.60 µL, 46.5 µmol) and allowed to stir overnight, whereupon it was partitioned between ethyl acetate and 10% aqueous potassium hydrogen sulfate solution. The organic layer was dried over sodium sulfate, filtered, concentrated in vacuo, and subjected to reversed-phase HPLC (Column: Waters Sunfire C18, 19×100 mm, 5 µm; Mobile phase A: water containing 0.05% trifluoroacetic acid; Mobile phase B: acetonitrile containing 0.05% trifluoroacetic acid; Gradient: 5% to 95% B over 8.54 minutes, then 95% B for 1.46 minutes; Flow rate: 25 mL/minute), providing (3S)-3-({N-[(4-methoxy-1H-indol-2-yl)carbonyl]-L-leucyl}amino)-2-oxo-4-[(3S)-2-oxopyrrolidin-3-yl]butyl piperidine-1-carboxylate (44). Yield: 18.7 mg, 32.0 µmol, 76%. LCMS m/z 584.5 [M+H]⁺. Retention time: 2.75 minutes (Analytical conditions. Column: Waters Atlantis dC18, 4.6×50 mm, 5 µm; Mobile phase A: water containing 0.05% trifluoroacetic acid (v/v); Mobile phase B: acetonitrile containing 0.05% trifluoroacetic acid (v/v); Gradient: 5.0% to 95% B, linear over 4.0 minutes, then 95% B for 1.0 minute; Flow rate: 2 mL/minute).

Example 45: (3S)-4-[(3S)-1-(methoxycarbonyl)-2-oxopyrrolidin-3-yl]-3-({N-[(4-methoxy-1H-indol-2-yl)carbonyl]-L-leucyl}amino)-2-oxobutyl piperidine-1-carboxylate Example 46: (3S)-4-[(3S)-1-acetyl-2-oxopyrrolidin-3-yl]-3-({N-[(4-methoxy-1H-indol-2-yl)carbonyl]-L-leucyl}amino)-2-oxobutyl piperidine-1-carboxylate Example 47: (3S)-4-[(3S)-1-{(1S)-1-[(methoxycarbonyl)oxy]ethyl}-2-oxopyrrolidin-3-yl]-3-({N-[(4-methoxy-1H-indol-2-yl)carbonyl]-L-leucyl}amino)-2-oxobutyl piperidine-1-carboxylate Example 48: (1S)-1-{(3S)-3-[(2S)-4-[(dimethoxyphosphoryl)oxy]-2-({N-[(4-methoxy-1H-indol-2-yl)carbonyl]-L-leucyl}amino)-3-oxobutyl]-2-oxopyrrolidin-1-yl}ethyl methyl carbonate Example 49: (3S)-3-({N-[(4-methoxy-1H-indol-2-yl)carbonyl]-L-leucyl}amino)-2-oxo-4-[(3S)-2-oxopyrrolidin-3-yl]butyl dihydrogen phosphate (49)

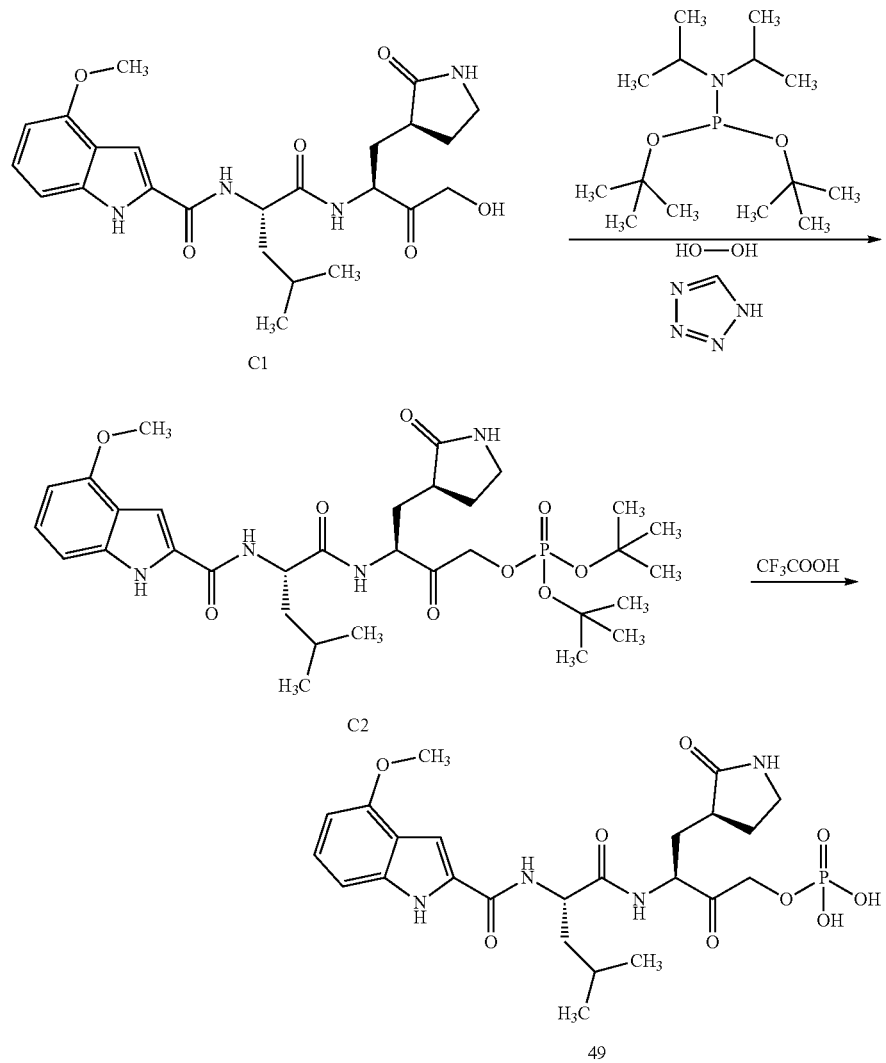

Step 1. Synthesis of di-tert-butyl (3S)-3-({N-[(4-methoxy-1H-indol-2-yl)carbonyl]-L-leucyl}amino)-2-oxo-4-[(3S)-2-oxopyrrolidin-3-yl]butyl phosphate (C2)

To a 0° C. solution of N-[(2S)-1-({(2S)-4-hydroxy-3-oxo-1-[(3S)-2-oxopyrrolidin-3-yl]butan-2-yl}amino)-4-methyl-1-oxopentan-2-yl]-4-methoxy-1H-indole-2-carboxamide (C1) (see Hoffman, R. L. et al., PCT Int. Appl. 2005113580, Dec. 1, 2005; 2.82 g, 5.97 mmol) and 1H-tetrazole (1.25 g, 17.9 mmol) in tetrahydrofuran (60 mL) was added a solution of di-tert-butyl N,N-dipropan-2-ylphosphoramidoite (7.53 mL, 6.62 g, 23.9 mmol) in tetrahydrofuran (0.5 mL). The reaction mixture was warmed to room temperature over 30 minutes and then re-cooled to 0° C. Aqueous hydrogen peroxide solution (50% w/w, 0.80 mL, 11.9 mmol) was added and stirring was continued for 1 hour. The reaction mixture was diluted with water (30 mL) and extracted into dichloromethane (3×20 mL). The combined organic layers were washed with aqueous sodium thiosulfate solution (1 M, 20 mL) and water (20 mL), then dried over magnesium sulfate, filtered, and concentrated in vacuo. Silica gel chromatography (Gradient: 0% to 15% methanol in dichloromethane) afforded C2 as a solid. Yield: 3.60 g, 5.42 mmol, 91%. LCMS m/z 663.5 [M−H]⁻. The $^1$H NMR data for this compound was obtained using a batch from a smaller-scale pilot reaction run under the same conditions.

$^1$H NMR (400 MHz, methanol-$d_4$, $^{31}$P-decoupled) δ 7.27 (s, 1H), 7.15 (t, J=8.1 Hz, 1H), 7.02 (d, J=8.3 Hz, 1H), 6.51 (d, J=7.6 Hz, 1H), 4.75 (AB quartet, $J_{AB}$=17.3 Hz, $\Delta v_{AB}$=26.3 Hz, 2H), 4.70 (dd, J=10.3 Hz, 3.7 Hz, partially overlaps the AB quartet at 4.75 ppm, 1H), 4.64 (dd, J=9.3 Hz, 5.1 Hz, 1H), 3.93 (s, 3H), 3.33-3.20 (m, 2H, assumed; partially obscured by methanol peak), 2.62-2.53 (m, 1H), 2.34-2.25 (m, 1H), 2.11-2.01 (m, 1H), 1.90-1.65 (m, 5H), 1.51-1.43 [multiplet (1H) overlapping two broadened singlets at 1.49 (18H), 19H total], 1.03 (d, J=6.1 Hz, 3H), 1.00 (d, J=6.1 Hz, 3H).

Step 2. Synthesis of (3S)-3-({N-[(4-methoxy-1H-indol-2-yl)carbonyl]-L-leucyl}amino)-2-oxo-4-[(3S)-2-oxopyrrolidin-3-yl]butyl dihydrogen phosphate (1)

Trifluoroacetic acid (2.07 mL, 27.1 mmol) was added to a 0° C. solution of C2 (3.60 g, 5.42 mmol) in dichloromethane (54 mL). After stirring for 1 hour, the reaction mixture was concentrated in vacuo. LCMS analysis at this point indicated conversion to 49: LCMS m/z 553.3 [M+H]$^+$. The residue was slurried in ethanol (15 mL) at 75° C. for 30 minutes and then at room temperature for 2 hours. The solid was collected by filtration to give (3S)-3-({N-[(4-methoxy-1H-indol-2-yl)carbonyl]-L-leucyl}amino)-2-oxo-4-[(3S)-2-oxopyrrolidin-3-yl]butyl dihydrogen phosphate (49) as a solid. Yield: 1.60 g, 2.90 mmol, 54%. $^1$H NMR (400 MHz, methanol-d$_4$, $^{31}$P-decoupled) δ 7.27 (s, 1H), 7.15 (t, J=8.0 Hz, 1H), 7.03 (d, J=8.3 Hz, 1H), 6.51 (d, J=7.7 Hz, 1H), 4.80-4.56 (m, 3H), {4.25-4.19 (m) and 4.02-3.81 [multiplet overlapping singlet at 3.93 (3H)], 4H total}, 3.31-3.18 (m, 2H, assumed; partially obscured by methanol peak), [2.63-2.52 (m) and 2.51-2.38 (m), 1H total], 2.36-2.24 (m, 1H), 2.10-1.98 (m, 1H), 1.94-1.65 (m, 5H), 1.04 (d, J=5.6 Hz, 3H), 1.00 (d, J=5.9 Hz, 3H). Retention time: 6.48 minutes (Analytical conditions. Column: Waters XBridge C18, 4.6× 150 mm, 5 μm; Mobile phase A: water containing 0.1% trifluoroacetic acid; Mobile phase B: acetonitrile containing 0.1% trifluoroacetic acid; Gradient: 5% B for 1.5 minutes, then 5% to 100% B over 8.5 minutes; Flow rate: 1.5 mL/minute).

The compound of Example 49 can also be prepared as a hydrate (designated Form 1) as described below.

Synthesis of (3S)-3-({N-[(4-methoxy-1H-indol-2-yl)carbonyl]-L-leucyl}amino)-2-oxo-4-[(3S)-2-oxopyrrolidin-3-yl]butyl dihydrogen phosphate monohydrate Step 1: Synthesis of methyl (4-methoxy-1H-indole-2-carbonyl)-L-leucinate, (49-B)

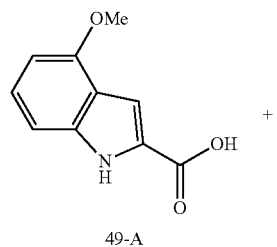

49-A

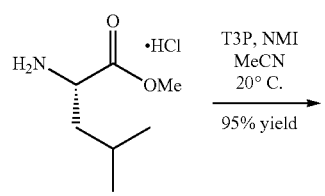

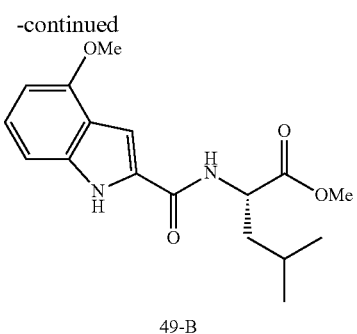

49-B

To a jacket reactor at 20° C. was charged 4-methoxy-1H-indole-2-carboxylic acid (49-A) (1.0 eq, 100 g), acetonitrile (7 mL/g, 700 mL), N-methylimidazole (3.5 eq, 145.8 mL) and L-Leucine methyl ester hydrochloride (1.15 eq, 109 g). 1-Propanephosphonic acid cyclic anhydride (T3P) in acetonitrile (50 mass %, 1.25 eq, 457 mL) was charged dropwise, maintaining temperature below 30° C. The resulting mixture was stirred for 2 h or until <1% 4-methoxy-1H-indole-2-carboxylic acid remained by UPLC analysis. The reaction mixture was filtered through a pad of celite, rinsing with acetonitrile (2 mL/g, 200 mL) and the resulting filtrate was concentrated to ~10 mL/g under reduced pressure, maintaining temperature less than 50° C. Water (1.5 mL/g, 150 mL) was charged and the mixture stirred until solids began to precipitate. Additional water (8 mL/g, 800 mL) was charged dropwise and the resulting slurry granulated for 4 h before filtration. The solids were rinsed with water (5 mL/g, 500 mL) and dried at 50° C. to provide methyl (4-methoxy-1H-indole-2-carbonyl)-L-leucinate (49-B) (158 g) in 95% yield as a white solid.

$^1$H NMR (400 MHz, DMSO-d$_6$) δ 11.57 (s, 1H), 8.62 (d, J=7.8 Hz, 1H), 7.35 (d, J=1.7 Hz, 1H), 7.10 (t, J=7.9 Hz, 1H), 7.01 (d, J=8.2 Hz, 1H), 6.51 (d, J=7.6 Hz, 1H), 4.58-4.44 (m, 1H), 3.89 (s, 3H), 3.65 (s, 3H), 1.85-1.62 (m, 2H), 1.64-1.53 (m, 1H), 0.93 (d, J=6.4 Hz, 3H), 0.89 (d, J=6.4 Hz, 3H).

$^{13}$C NMR (101 MHz, DMSO-d6) δ 173.14, 161.20, 153.65, 137.88, 129.54, 124.57, 118.05, 105.41, 101.16, 99.26, 55.09, 51.91, 50.51, 39.38, 24.44, 22.85, 21.16.

Step 2: Synthesis of (4-methoxy-1H-indole-2-carbonyl)-L-leucine, (49-C)

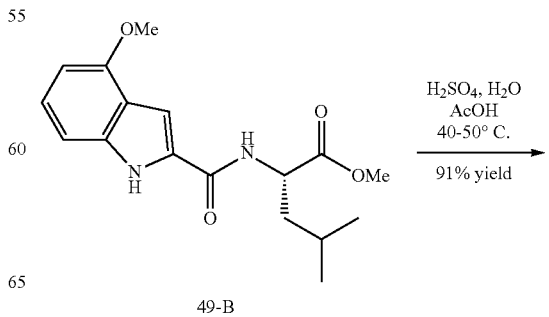

49-B

-continued

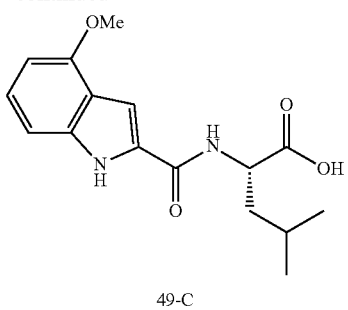

49-C

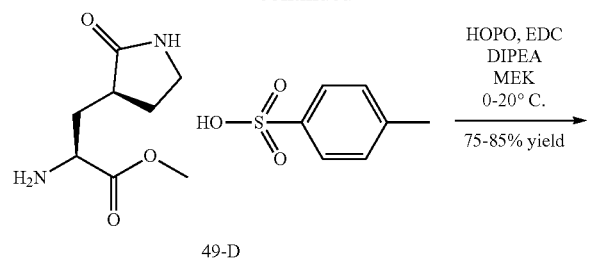

49-D

To a jacketed reactor was charged methyl (4-methoxy-1H-indole-2-carbonyl)-L-leucinate (49-B) (1.0 eq, 158 g), acetic acid (5 mL/g, 790 mL) and water (1 mL/g, 158 mL). Sulfuric acid (1.5 eq, 39.7 mL) was charged over 30 minutes. The mixture was warmed to 50° C. and held for 18-24 h or until the reaction contained approximately 5% remaining methyl (4-methoxy-1H-indole-2-carbonyl)-L-leucinate. The reaction was distilled under reduced pressure to remove byproducts methanol or methyl acetate. When the reaction reached completion (less 1% remaining methyl (4-methoxy-1H-indole-2-carbonyl)-L-leucinate), water (7 mL/g, 1106 mL) was charged over 2 h. After stirring for 1 h, the mixture was cooled to 20° C. over 30 minutes, then held at 20° C. for 3 h. The solids were isolated by filtration, rinsing with water (2×2 mL/g, 316 mL). The solids were dried on the filter, then in a vacuum oven at 50° C. to produce (4-methoxy-1H-indole-2-carbonyl)-L-leucine, (49-C) (137 g) as a white solid in 91% yield.

¹H NMR (400 MHz, DMSO-d6) δ 11.55 (s, 1H), 8.50 (d, J=8.0 Hz, 1H), 7.34 (d, J=1.6 Hz, 1H), 7.10 (t, J=7.9 Hz, 1H), 7.01 (d, J=8.2 Hz, 1H), 6.51 (d, J=7.6 Hz, 1H), 4.54-4.36 (m, 1H), 3.89 (s, 3H), 1.81-1.66 (m, 2H), 1.63-1.53 (m, 1H), 0.93 (d, J=6.3 Hz, 3H), 0.89 (d, J=6.3 Hz, 3H).

¹³C NMR (101 MHz, DMSO-d6) δ 174.22, 161.11, 153.63, 137.82, 129.80, 124.43, 118.06, 105.40, 100.96, 99.22, 55.07, 50.41, 24.51, 22.96, 21.13. (peak around 39.5 under DMSO peak).

Step 3: Synthesis of methyl (S)-2-((S)-2-(4-methoxy-1H-indole-2-carboxamido)-4-methylpentanamido)-3-((S)-2-oxopyrrolidin-3-yl)propanoate, (49-E)

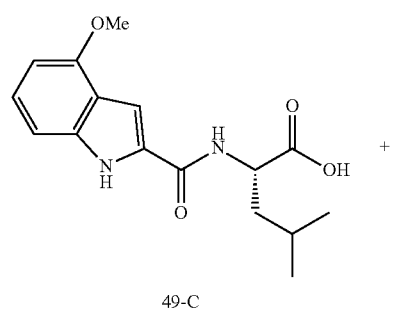

49-C

+

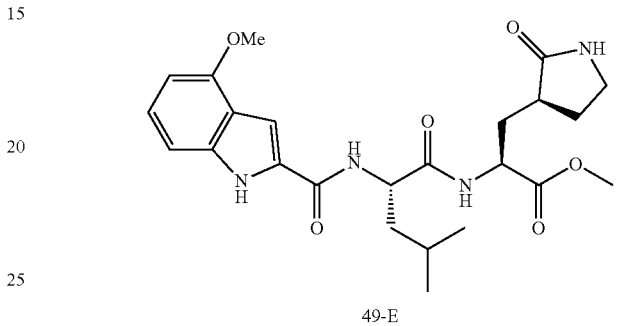

49-E

To a jacketed reactor was charged (4-methoxy-1H-indole-2-carbonyl)-L-leucine (49-C) (1.0 eq, 10.0 g), methyl (S)-2-amino-3-((S)-2-oxopyrrolidin-3-yl)propanoate 4-methylbenzenesulfonate (49-D) (1.05 eq, 12.4 g), 2-hydroxypyridine N-oxide (0.025 eq, 0.91 g) and methyl ethyl ketone (5 mL/g, 50 mL). The resulting slurry was cooled to 0° C. and N,N-diisopropylethylamine (2.25 eq, 12.9) was charged. 1-(3-Dimethylaminopropyl)-3-ethyl-carbodiimide hydrochloride (1.2 eq, 7.86 g) was charged in a single portion and the mixture stirred for 20 min, then warmed to 20° C. and stirred for at least 8 h, or until less than 1% (4-methoxy-1H-indole-2-carbonyl)-L-leucine (49-C) remained by UPLC. An aqueous solution of saturated brine (23.5 mass %, 3.5 mL/g, 35 mL) was added to the reaction, followed by a solution of phosphoric acid (1.5 eq, 5.68 g) in water (3 mL/g, 30 mL). The resulting biphasic mixture was stirred for 15 minutes, then the layers were separated. The organic layer was washed aqueous saturated brine (23.5 mass %, 3.5 mL/g, 35 mL). The organic layer was concentrated under reduced pressure (250 mbar, 50° C.) to 5 mL/g, then methyl tert-butyl ether (5 mL/g, 50 mL) was charged and the distillation repeated. Additional methyl tert-butyl ether (5 mL/g, 50 mL) was charged and the mixture cooled to 35° C. over 15 minutes. Then, another portion of methyl tert-butyl ether (2.5 mL/g, 25 mL) was charged slowly, resulting in precipitation. The slurry was granulated for 30 minutes before a final portion of methyl tert-butyl ether (2.5 mL/g, 25 mL) was charged to achieve a final solvent ratio of approximately 4:1 methyl tert-butyl ether:methyl ethyl ketone. The final slurry was granulated for 30 minutes, then cooled to 10° C. at 0.25° C./min and held for 4 h. The final slurry was filtered, rinsing with methyl tert-butyl ether (2.5 mL/g, 25 mL) and dried on the filter, then in a vacuum oven at 25° C. The product methyl (S)-2-((S)-2-(4-methoxy-1H-indole-2-carboxamido)-4-methylpentanamido)-3-((S)-2-oxopyrrolidin-3-yl)propanoate, (49-E) was isolated as a methyl tert-butyl ether solvate in 75-85% yield.

Step 4: Synthesis of N—((S)-1-(((S)-4-chloro-3-oxo-1-((S)-2-oxopyrrolidin-3-yl)butan-2-yl)amino)-4-methyl-1-oxopentan-2-yl)-4-methoxy-1H-indole-2-carboxamide, (49-F)

Step 5: Synthesis of di-tert-butyl ((S)-3-((S)-2-(4-methoxy-1H-indole-2-carboxamido)-4-methylpentanamido)-2-oxo-4-((S)-2-oxopyrrolidin-3-yl)butyl) phosphate, (49-G)

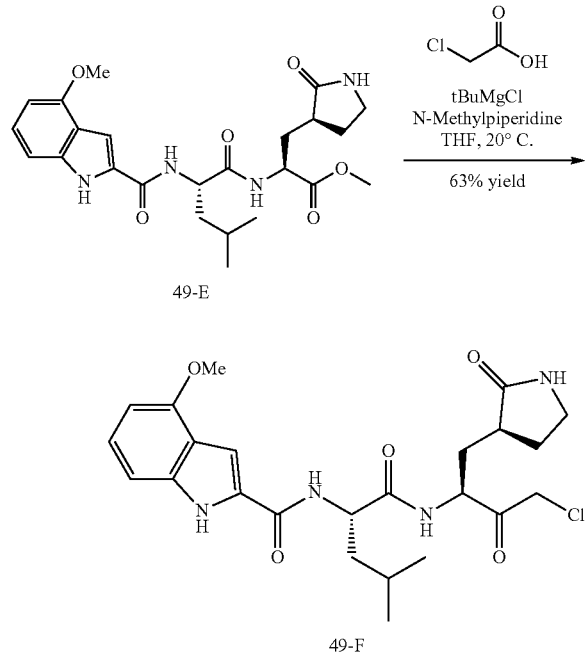

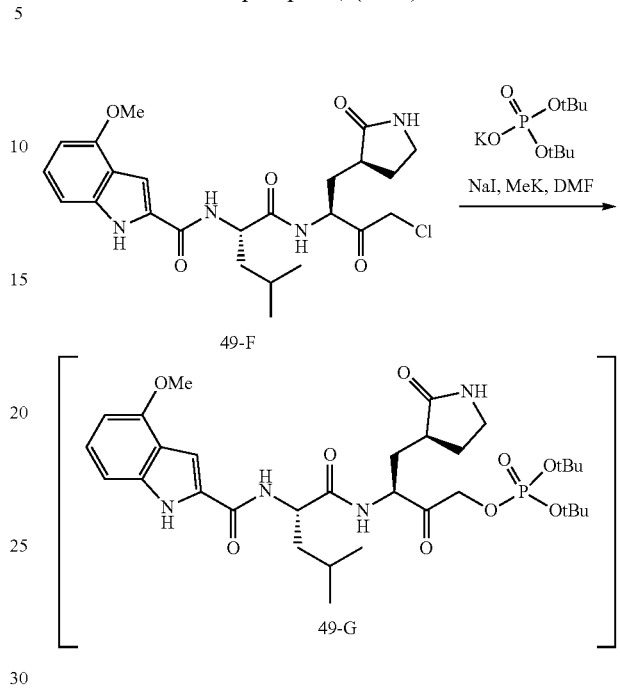

A jacketed reactor at 20° C. is charged with tert-butyl magnesium chloride in tetrahydrofuran (1M, 21 eq, 32 g) and N-methylpiperidine (10.5 eq, 1.71 g). A mixture of methyl (S)-2-((S)-2-(4-methoxy-1H-indole-2-carboxamido)-4-methylpentanamido)-3-((S)-2-oxopyrrolidin-3-yl)propanoate, (49-E) (1.0 eq, 1.0 g), chloroacetic acid (2.5 eq, 0.40 g) and THF (10 mL/g, 10 mL) were added via addition funnel to the reactor, maintaining the temperature below 25° C. After addition was complete, the mixture was held until the reaction was complete (98% consumption of (49-E)). The reaction was then concentrated under reduced pressure (150 mbar, temperature maintained below 30° C.) to ~20 mL/g, then cooled to 20° C. A second reactor was charged with aqueous citric acid (25 wt %, 20 mL/g, 20 mL) and 2-methyltetrahydrofuran (10 mL/g, 10 mL) and cooled to 10° C. The reaction mixture was slowly added to the citric acid and 2-methyltetrahydrofuran, maintaining reaction temperature under 15° C. Upon completion, the mixture was warmed to 20° C. and the layers separated. The organic layer was washed with aqueous sodium bicarbonate solution (1.14 M, 10 mL/g, 10 mL), then a more dilute aqueous sodium bicarbonate solution (0.6 M, 10 mL/g, 10 mL), then brine (12 mass %, 10 mL/g, 10 mL). The organic solution was concentrated at atmospheric pressure 10 mL/g and displaced with 2-methyltetrahydrofuran. The mixture was cooled to 20° C. over 4 h and granulated at 20° C. before filtering and washing with 2-methyltetrahydrofuran (3 mL/g, 3 mL). The solids were dried at 50° C. in a vacuum oven to provide N—((S)-1-(((S)-4-chloro-3-oxo-1-((S)-2-oxopyrrolidin-3-yl)butan-2-yl)amino)-4-methyl-1-oxopentan-2-yl)-4-methoxy-1H-indole-2-carboxamide, (49-F) as a 2-methyltetrahydrofuran solvate (~10 wt %) in 63% yield.

To a jacketed reactor at 25° C. was charged N—((S)-1-(((S)-4-chloro-3-oxo-1-((S)-2-oxopyrrolidin-3-yl)butan-2-yl)amino)-4-methyl-1-oxopentan-2-yl)-4-methoxy-1H-indole-2-carboxamide, (49-F) (1.0 eq, 7.30 g) methyl ethyl ketone (12.5 mL/g, 91 mL) and N,N-dimethylformamide (2.5 mL/g, 18 mL). Then, potassium di-tert-butyl phosphate (2.0 eq, 7.5 g) and sodium iodide (0.20 eq, 0.45 g) were charged. The mixture was stirred for 48-72 h until both N—((S)-1-(((S)-4-chloro-3-oxo-1-((S)-2-oxopyrrolidin-3-yl)butan-2-yl)amino)-4-methyl-1-oxopentan-2-yl)-4-methoxy-1H-indole-2-carboxamide, (49-F) and the corresponding iodide compound were present less than 2% by UPLC. Water (10 mL/g, 73 mL) was charged followed by methyl tert-butyl ether (5 mL/g, 37 mL). The biphasic mixture was stirred for 5 minutes, then the aqueous layer discarded. The organic layer was washed with twice with water (2×10 mL/g, 73 mL), then concentrated under reduced pressure to 5 mL/g, maintaining temperature below 35° C. Methyl ethyl ketone (15 mL/g, 110 mL) was charged to the reactor and the mixture was concentrated again under reduced pressure to 5 mL/g, maintaining temperature below 35° C. This was repeated a third time, or until water content was >0.5%. The mixture was diluted with methyl ethyl ketone (5 mL/g, 36 mL) and carried forward to the next step.

$^{1}$HNMR (400 MHz, DMSO-d6): δ 11.55 (d, J=1.8 Hz, 1H), 8.59 (d, J=8.0 Hz, 1H), 8.43 (d, J=8.0 Hz, 1H), 7.63 (s, 1H), 7.36 (d, J=1.6 Hz, 1H), 7.09 (t, J=7.9 Hz, 1H), 7.00 (d, J=8.2 Hz, 1H), 6.50 (d, J=7.6 Hz, 1H), 4.74 (dd, J=17.5, 7.9 Hz, 1H), 4.61 (dd, J=17.5, 7.2 Hz, 1H), 4.53-4.43 (m, 2H), 3.88 (s, 3H), 3.15-3.03 (m, 2H), 2.32 (m, 1H), 2.06 (m, 1H), 1.97 (m, 1H), 1.72 (m, 2H), 1.62 (m, 2H), 1.52 (m, 1H), 1.40 (s, 9H), 1.39 (s, 9H), 0.94 (d, J=6.2 Hz, 3H), 0.90 (d, J=6.2 Hz, 3H).

$^{13}$CNMR (101 MHz, DMSO-d6): δ 203.1 (d, J=7.4 Hz), 178.8, 173.4, 161.6, 154.1, 138.3, 130.3, 124.9, 118.5, 105.9, 101.7, 99.7, 82.6 (dd, J=7.2, 4.4 Hz), 68.7 (d, J=5.8 Hz), 55.5, 54.0, 51.9, 49.1, 37.7, 31.8, 29.9, 29.8, 27.6, 27.3, 24.9, 23.5, 21.9.

Step 6: Synthesis of (3S)-3-({N-[(4-methoxy-1H-indol-2-yl)carbonyl]-L-leucyl}amino)-2-oxo-4-[(3S)-2-oxopyrrolidin-3-yl]butyl dihydrogen phosphate, methyl ethyl ketone solvate

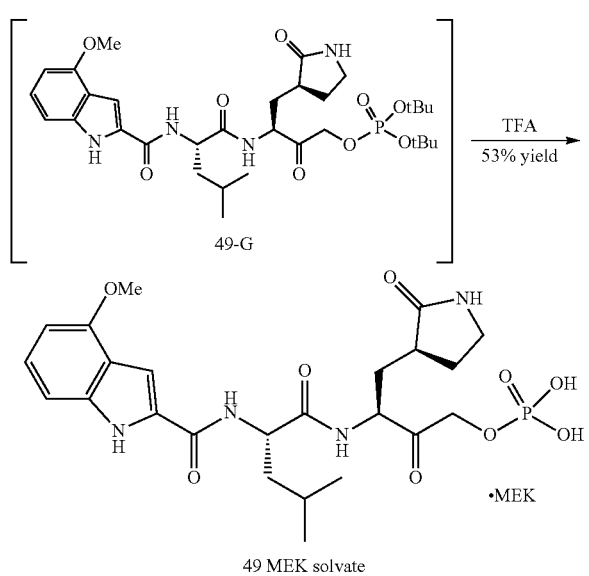

49-G

49 MEK solvate

To the solution of di-tert-butyl ((S)-3-((S)-2-(4-methoxy-1H-indole-2-carboxamido)-4-methylpentanamido)-2-oxo-4-((S)-2-oxopyrrolidin-3-yl)butyl) phosphate, (49-G) in methyl ethyl ketone from the previous step, trifluoroacetic acid (20 eq, 23 mL) was charged. The mixture was warmed to 30° C., or until >98% consumption of di-tert-butyl ((S)-3-((S)-2-(4-methoxy-1H-indole-2-carboxamido)-4-methylpentanamido)-2-oxo-4-((S)-2-oxopyrrolidin-3-yl) butyl) phosphate, (49-G) (or the corresponding mono-tert-butyl phosphonate ester) has occurred. The mixture was cooled to 20° C. and granulated for 1 h, then filtered and washed with methyl ethyl ketone (3 mL/g, 22 mL). The product was dried at 40° C. for 5 h to provide (3S)-3-({N-[(4-methoxy-1H-indol-2-yl)carbonyl]-L-leucyl}amino)-2-oxo-4-[(3S)-2-oxopyrrolidin-3-yl]butyl dihydrogen phosphate, methyl ethyl ketone solvate as a white solid (4.9 g) in 53% yield.

$^1$HNMR (400 MHz, DMSO-d6): δ 11.57 (d, J=1.8 Hz, 1H), 8.52 (d, J=8.0 Hz, 1H), 8.42 (d, J=8.0 Hz, 1H), 7.63 (s, 1H), 7.36 (d, J=1.6 Hz, 1H), 7.09 (t, J=7.8 Hz, 1H), 7.00 (d, J=8.2 Hz, 1H), 6.50 (d, J=7.6 Hz, 1H), 4.68 (dd, J=17.6, 8.1 Hz, 1H), 4.57 (dd, J=17.6, 7.2 Hz, 1H), 4.53-4.43 (m, 2H), 3.88 (s, 3H), 3.15-3.03 (m, 2H), 2.42 (q, J=7.3 Hz, 2H), 2.32 (m, 1H), 2.06 (s and m, 4H), 1.95 (m, 1H), 1.77-1.51 (m, 5H), 0.94 (d, J=6.2 Hz, 3H), 0.90 (t, J=7.1 Hz, 3H), 0.89 (d, J=6.2 Hz, 3H).

$^{13}$CNMR (101 MHz, DMSO-d6): δ 209.3, 203.9 (d, J=7.4 Hz), 178.8, 173.3, 161.6, 154.1, 138.3, 130.4, 124.9, 118.5, 105.9, 101.6, 99.7, 68.2 (d, J=4.8 Hz), 55.5, 54.0, 51.9, 37.8, 36.3, 31.2, 29.8, 27.6, 24.9, 23.5, 21.9, 8.1.

Figure 9:
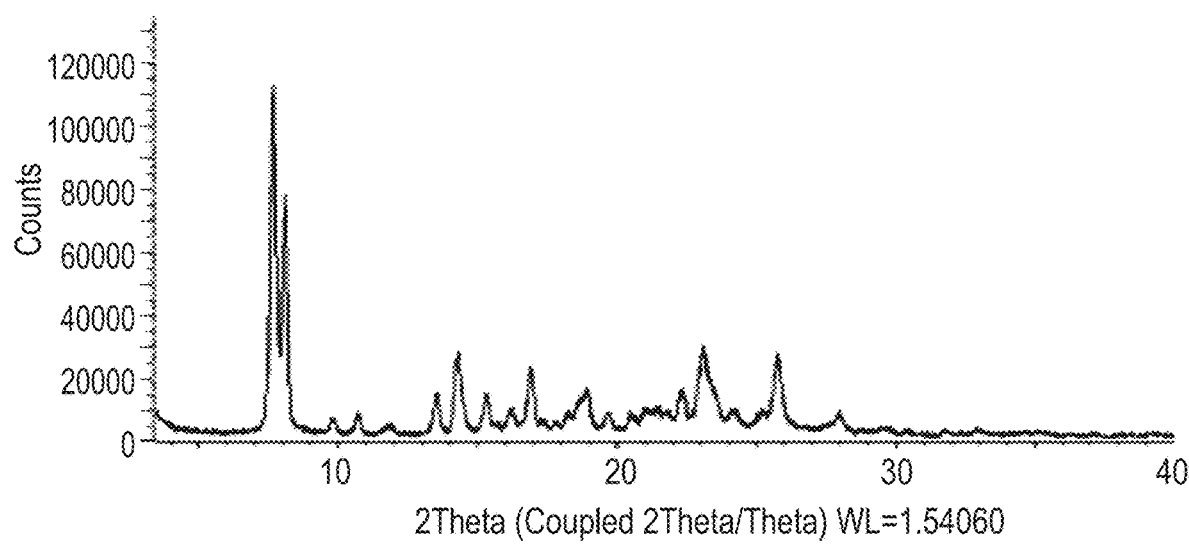
FIG. 9: PXRD of (3S)-3-({N-[(4-methoxy-1H-indol-2-yl)carbonyl]-L-leucyl}amino)-2-oxo-4-[(3S)-2-oxopyrrolidin-3-yl]butyl dihydrogen phosphate, methyl ethyl ketone solvate.

A Powder X-ray diffraction pattern of (3S)-3-({N-[(4-methoxy-1H-indol-2-yl)carbonyl]-L-leucyl}amino)-2-oxo-4-[(3S)-2-oxopyrrolidin-3-yl]butyl dihydrogen phosphate, methyl ethyl ketone solvate is provided in FIG. 9.

Step 7: Synthesis of (3S)-3-({N-[(4-methoxy-1H-indol-2-yl)carbonyl]-L-leucyl}amino)-2-oxo-4-[(3S)-2-oxopyrrolidin-3-yl]butyl dihydrogen phosphate hydrate

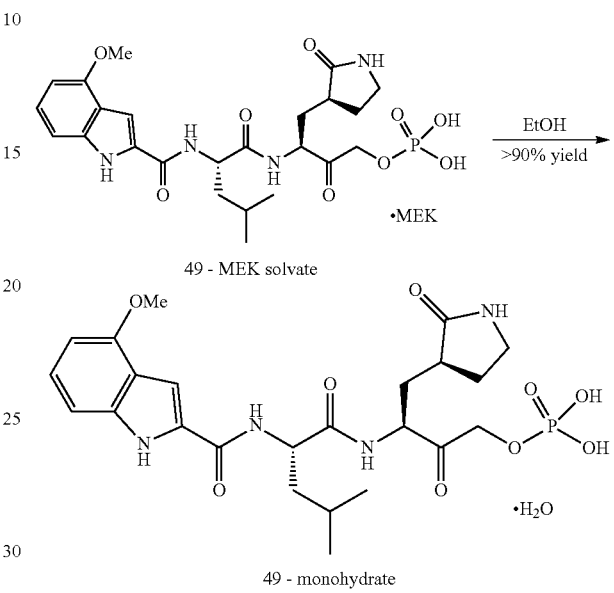

49 - MEK solvate

49 - monohydrate

To a jacketed reactor was added (3S)-3-({N-[(4-methoxy-1H-indol-2-yl)carbonyl]-L-leucyl}amino)-2-oxo-4-[(3S)-2-oxopyrrolidin-3-yl]butyl dihydrogen phosphate, methyl ethyl ketone solvate (1.0 eq, 35.7 g) and anhydrous ethanol (15 mL/g, 536 mL). The slurry was warmed to 40° C. over 30 minutes and held for at least 1 h. A sample of the slurry was taken to confirm the desired polymorph was present. If conversion was incomplete, the slurry was held for additional time. The slurry was cooled to 10° C. over 2 h and granulated for 2 h, and then filtered, washing with ethanol (4 mL/g, 140 mL). The solids were dried at 50° C. overnight to provide (3S)-3-({N-[(4-methoxy-1H-indol-2-yl)carbonyl]-L-leucyl}amino)-2-oxo-4-[(3S)-2-oxopyrrolidin-3-yl]butyl dihydrogen phosphate monohydrate in 98% yield.

The (3S)-3-({N-[(4-methoxy-1H-indol-2-yl)carbonyl]-L-leucyl}amino)-2-oxo-4-[(3S)-2-oxopyrrolidin-3-yl]butyl dihydrogen phosphate hydrate prepared above, designated Form 1, was characterized using powder X-ray diffraction, solid state NMR and Raman spectroscopy as described below.

Powder X-Ray Diffraction

The powder X-ray diffraction pattern was generated using a Bruker AXS D8 Endeavor diffractometer equipped with a Cu radiation source. The tube voltage and amperage were set to 40 kV and 40 mA, respectively. The motorized divergence slits were set at constant illumination of 11 mm. Diffracted radiation was detected using a LYNXEYE XE-T energy dispersive X-ray detector, with the position sensitive detector (PSD) opening set at 4.00°. Data was collected on the theta-theta goniometer at the Cu wavelength from 2.0 to 55.0 degrees 2-theta (° 2θ) using a step size of 0.019° 2θ and a time per step of 0.2 seconds. Samples were prepared for analysis by placing them in a silicon low background small divot holder and rotated at 15 rpm during data collection.

Data were analyzed in DIFFRAC.EVA V5.0 software. Peak lists were prepared using reflections with a relative intensity ≥5% of the most intense band in each respective diffraction pattern. A typical error of ±0.2° 2θ in peak positions (USP-941) applies to this data. The minor error associated with this measurement can occur because of a variety of factors including: (a) sample preparation (e.g. sample height), (b) instrument characteristics, (c) instrument calibration, (d) operator input (e.g. in determining the peak locations), and (e) the nature of the material (e.g. preferred orientation and transparency effects).

To obtain the absolute peak positions, the powder pattern should be aligned against a reference. This could either be the simulated powder pattern from the crystal structure of the same form solved at room temperature, or an internal standard e.g. silica or corundum. The collected powder pattern of Form 1 (3S)-3-({N-[(4-methoxy-1H-indol-2-yl)carbonyl]-L-leucyl}amino)-2-oxo-4-[(3S)-2-oxopyrrolidin-3-yl]butyldihydrogen phosphate hydrate was aligned to the powder pattern of the same material containing internal standard, Si (SRM 640e).

Figure 3:
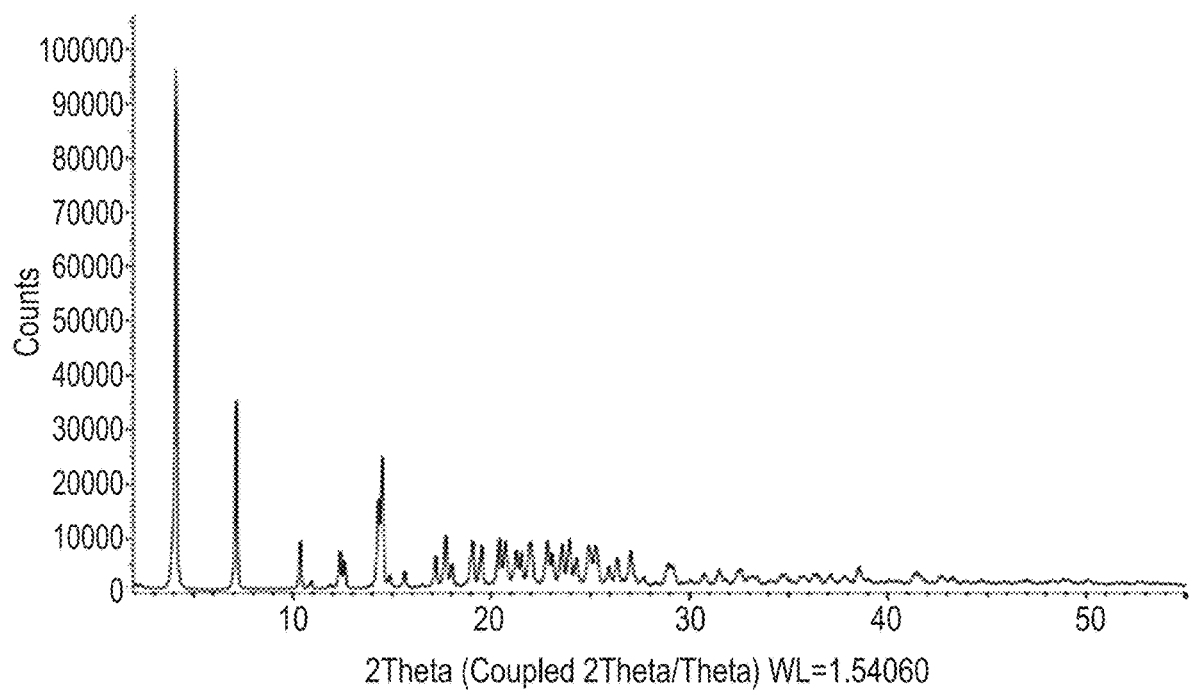
FIG. 3: PXRD pattern of Form 1 of (3S)-3-({N-[(4-methoxy-1H-indol-2-yl)carbonyl]-L-leucyl}amino)-2-oxo-4-[(3S)-2-oxopyrrolidin-3-yl]butyl dihydrogen phosphate hydrate.

The PXRD profile for the Form 1 (3S)-3-({N-[(4-methoxy-1H-indol-2-yl)carbonyl]-L-leucyl}amino)-2-oxo-4-[(3S)-2-oxopyrrolidin-3-yl]butyl dihydrogen phosphate hydrate is provided in FIG. 3 and the corresponding 2-theta peak list and relative intensity is provided in Table PXRD-1 below (the values are ±0.2 2-Theta).

Table PXRD-1: PXRD Peak List for Form 1.

| Angle, Degrees 2-Theta (°2θ) ± 0.2 °2θ | Relative Intensity, % |
|---|---|
| 4.1 | 100.0 |
| 7.2 | 39.4 |
| 10.4 | 10.2 |
| 12.4 | 8.0 |
| 12.6 | 5.9 |
| 14.3 | 19.0 |
| 14.5 | 27.9 |
| 17.2 | 6.5 |
| 17.7 | 11.1 |
| 19.1 | 10.0 |
| 19.6 | 8.8 |
| 20.4 | 10.1 |
| 20.7 | 9.6 |
| 21.3 | 7.4 |
| 21.5 | 6.9 |
| 22.0 | 8.7 |
| 22.8 | 9.3 |
| 23.1 | 6.6 |
| 23.6 | 8.5 |
| 24.0 | 9.6 |
| 24.3 | 5.3 |
| 24.9 | 8.1 |
| 25.3 | 8.2 |
| 26.4 | 5.6 |
| 27.0 | 7.0 |

Characteristic PXRD peaks for Form 1 are peaks at 4.1 and 7.2; at 4.1, 7.2 and 10.4; and at 4.1, 7.2, 10.4 and 14.5 2-theta positions (each being ±0.2 2-Theta), respectively.

Solid State NMR

Figure 4:
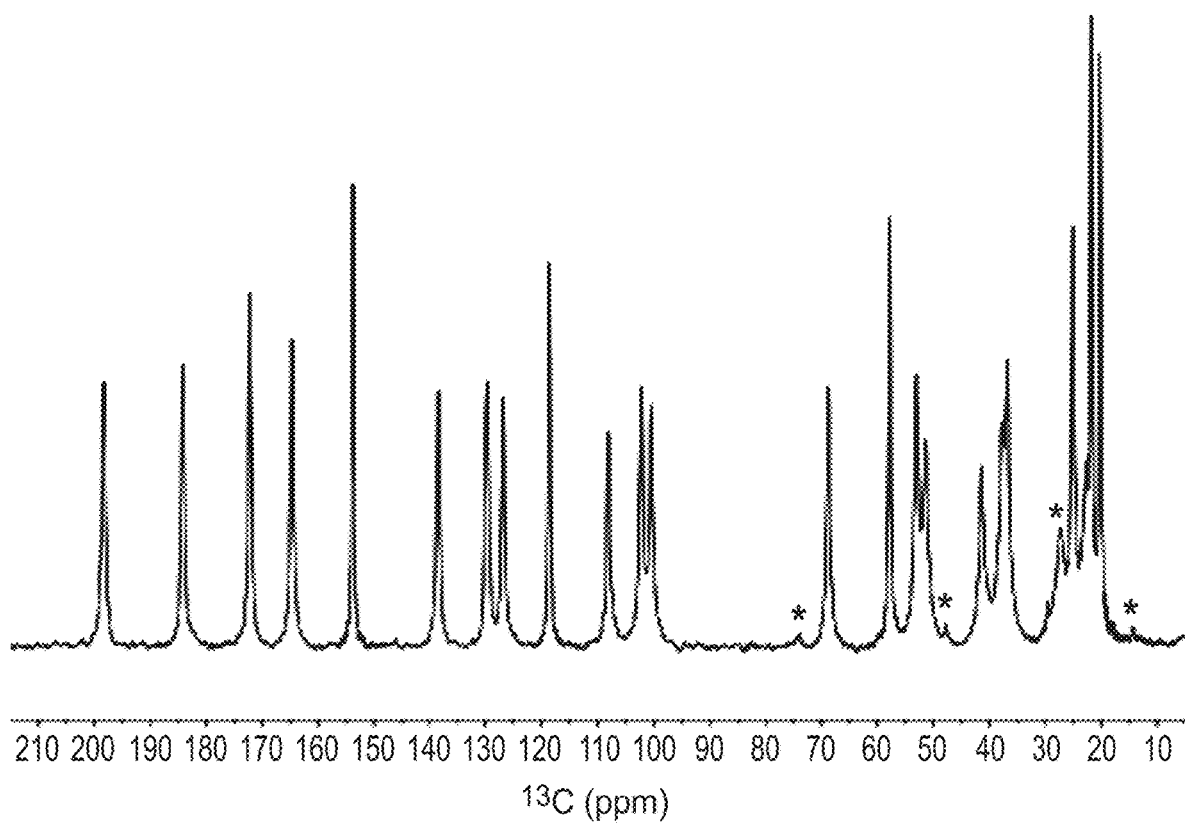
FIG. 4: $^{13}$C solid state NMR spectrum of Form 1 of (3S)-3-({N-[(4-methoxy-1H-indol-2-yl)carbonyl]-L-leucyl}amino)-2-oxo-4-[(3S)-2-oxopyrrolidin-3-yl]butyl dihydrogen phosphate hydrate.

Solid state NMR (ssNMR) analysis was conducted on a Bruker-BioSpin Avance Neo 400 MHz ($^1$H frequency) NMR spectrometer. $^{13}$C ssNMR spectra were collected on a 4 mm MAS probe at a magic angle spinning rate of 12.5 kHz. The temperature was regulated to 20° C. Cross-polarization (CP) spectra were recorded with a 3 ms CP contact time and recycle delay of 3.5 seconds. A phase modulated proton decoupling field of ~100 kHz was applied during spectral acquisition. Carbon spectral referencing is relative to neat tetramethylsilane, carried out by setting the high-frequency signal from an external sample of α-glycine to 176.5 ppm. $^{15}$N ssNMR spectra were collected using the same instrument and probe as the $^{13}$C spectra, at a spinning rate of 12.5 kHz with the temperature regulated to 20° C. Cross-polarisation (CP) spectra were recorded with a 10 ms CP contact time and a recycle delay of 3.5 seconds. Nitrogen spectral referencing is relative to neat nitromethane, carried out by setting the signal from an external sample of glycine to −346.8 ppm. The $^{13}$C and $^{15}$N solid state NMR spectra are provided in FIGS. 4 and 5, respectively.

Automatic peak picking was performed using ACD Labs 2017 Spectrus Processor software with a threshold value of 3% relative intensity used for preliminary peak selection. The output of the automated peak picking was visually checked to ensure validity and adjustments were manually made if necessary. Although specific $^{13}$C and $^{15}$N ssNMR peak values are reported herein there does exist a range for these peak values due to differences in instruments, samples, and sample preparation. A typical variability for $^{13}$C and $^{15}$N chemical shift x-axis values is on the order of plus or minus 0.2 ppm for a crystalline solid. The ssNMR peak heights reported herein are relative intensities. The ssNMR intensities can vary depending on the actual setup of the experimental parameters and the thermal history of the sample.

Table NMR-1: $^{13}$C ssNMR Peak List for Form 1.

| $^{13}$C δ (ppm) ± 0.2 ppm | Relative Intensity, % |
|---|---|
| 20.1 | 94.0 |
| 21.7 | 100.0 |
| 25.0 | 66.2 |
| 27.2 | 17.6 |
| 36.8 | 44.7 |
| 37.7 | 34.7 |
| 41.4 | 27.7 |
| 51.4 | 31.8 |
| 53.0 | 42.4 |
| 57.8 | 67.8 |
| 68.8 | 40.4 |
| 100.5 | 37.6 |
| 102.2 | 40.4 |
| 108.1 | 33.0 |
| 118.6 | 60.2 |
| 126.9 | 38.7 |
| 129.8 | 41.2 |
| 138.6 | 39.7 |
| 153.8 | 73.0 |
| 164.7 | 48.0 |
| 172.2 | 55.4 |
| 184.2 | 43.9 |
| 198.4 | 41.1 |

Characteristic $^{13}$C peaks for Form 1 are at 21.7, 153.8 and 172.2 ppm; at 21.7, 153.8, 172.2 and 118.6 ppm; and at 21.7, 153.8, 172.2, 118.6 and 57.8 ppm (each ±0.2 ppm).

Table NMR-2: $^{15}$N ssNMR Peak List for Form 1.

| $^{15}$N δ, (ppm) ± 0.2 ppm | Rel. Intensity, % |
|---|---|
| −260.8 | 100.0 |
| −256.9 | 100.0 |
| −252.1 | 51.0 |
| −248.0 | 61.3 |

Characteristic $^{15}$N peaks for Form 1 are at −260.8 and −256.9 ppm; at −260.8, −256.9 and −248.0 ppm; and at −260.8, −256.9, −248.0 and −252.1 ppm (each ±0.2 ppm).

Raman Spectroscopy

Raman spectra were collected using a RAM II FT-Raman module attached to a Vertex 70 spectrometer (Bruker Optik GmbH). The instrument is equipped with a 1064 nm solid-state (Nd:YAG) laser and a liquid nitrogen cooled germanium detector. Prior to data acquisition, instrument performance and calibration verifications were conducted using a white light source, and polystyrene and naphthalene references.

Samples were prepared and analysed in truncated NMR tubes. A sample rotator (Ventacon, UK) was used during measurement to maximise the volume of material exposed to the laser during data collection. The backscattered Raman signal from the sample was optimized and data were collected at a spectral resolution of 2 cm$^{-1}$ using a laser power of 500 mW. A Blackmann-Harris 4-term apodization function was applied to minimise spectral aberrations. Spectra were generated between 3500 and 50 cm$^{-1}$ with the number of scans adjusted accordingly to ensure adequate signal to noise.

Spectra were normalised by setting the intensity of the most intense peak to 2.00. Peaks were then identified using the automatic peak picking function in the OPUS v8.2 software (Bruker Optik GmbH) with the sensitivity set to 2%. Peak positions and relative peak intensities were extracted and tabulated. The variability in the peak positions with this experimental configuration is within ±2 cm$^{-1}$.

It is expected that, since FT-Raman and dispersive Raman are similar techniques, peak positions reported in this document for FT-Raman spectra would be consistent with those which would be observed using a dispersive Raman measurement, assuming appropriate instrument calibration.

Table Raman-1: Peak List Extracted from the FT Raman Spectrum Collected from Form 1.

| Wavenumber (cm$^{-1}$) ± 2 cm$^{-1}$ | Relative Intensity (%) |
| --- | --- |
| 409 | 8.1 |
| 465 | 9.8 |
| 545 | 10.0 |
| 631 | 10.5 |
| 704 | 12.9 |
| 818 | 9.3 |
| 859 | 8.4 |
| 905 | 9.0 |
| 989 | 35.0 |
| 1056 | 20.5 |
| 1100 | 10.8 |
| 1132 | 11.3 |
| 1168 | 12.4 |
| 1217 | 42.9 |
| 1244 | 20.3 |
| 1271 | 29.6 |
| 1299 | 18.1 |
| 1320 | 11.4 |
| 1360 | 19.9 |
| 1381 | 40.5 |
| 1421 | 31.4 |
| 1431 | 35.4 |
| 1452 | 22.3 |
| 1517 | 62.9 |
| 1552 | 52.7 |
| 1584 | 14.8 |
| 1620 | 31.4 |
| 1640 | 100.0 |
| 1749 | 6.0 |
| 2726 | 5.3 |
| 2843 | 9.5 |
| 2872 | 14.2 |
| 2968 | 25.9 |
| 3074 | 9.7 |

Characteristic Raman peaks for Form 1 are at 1271, 1421 and 1217 cm$^{-1}$; at 1271, 1421, 1217 and 1640 cm$^{-1}$; at 1271, 1421, 1217, 1640 and 3074 cm$^{-1}$ (each ±2 cm$^{-1}$).

Powder X-Ray diffraction, solid state NMR and Raman spectroscopy techniques as described above were also used to characterize (3S)-3-({N-[(4-methoxy-1H-indol-2-yl)carbonyl]-L-leucyl}amino)-2-oxo-4-[(3S)-2-oxopyrrolidin-3-yl]butyl dihydrogen phosphate, methyl ethyl ketone solvate which was re-worked to improve its crystallinity. A re-work of the (3S)-3-({N-[(4-methoxy-1H-indol-2-yl)carbonyl]-L-leucyl}amino)-2-oxo-4-[(3S)-2-oxopyrrolidin-3-yl]butyl dihydrogen phosphate, methyl ethyl ketone solvate was performed to improve crystallinity of the sample before the solid-state characterization. This was executed via a 40° C. to 10° C. heat-cool re-slurry cycles of (3S)-3-({N-[(4-methoxy-1H-indol-2-yl)carbonyl]-L-leucyl}amino)-2-oxo-4-[(3S)-2-oxopyrrolidin-3-yl]butyl dihydrogen phosphate, methyl ethyl ketone solvate in methyl ethyl ketone using 0.5° C./min heating and cooling rates with a 10 minutes hold period at each temperature over 24 hours. The resulting crystalline (3S)-3-({N-[(4-methoxy-1H-indol-2-yl)carbonyl]-L-leucyl}amino)-2-oxo-4-[(3S)-2-oxopyrrolidin-3-yl]butyl dihydrogen phosphate, methyl ethyl ketone solvate was then characterized.

Figure 10:
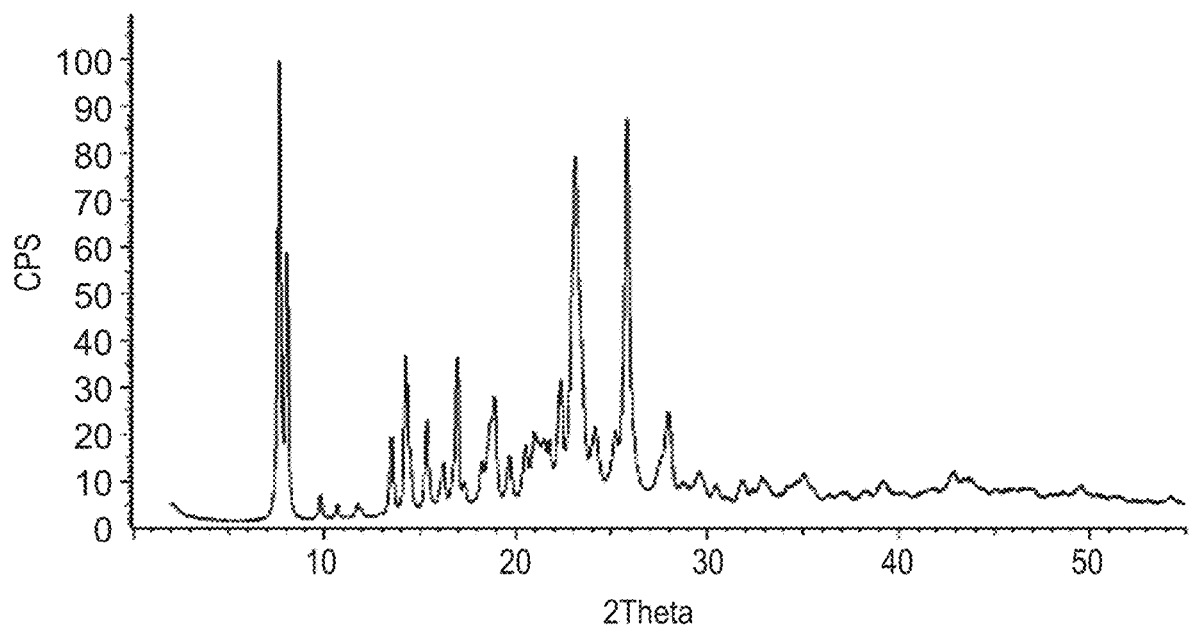
FIG. 10: PXRD of (3S)-3-({N-[(4-methoxy-1H-indol-2-yl)carbonyl]-L-leucyl}amino)-2-oxo-4-[(3S)-2-oxopyrrolidin-3-yl]butyl dihydrogen phosphate, methyl ethyl ketone solvate after re-work.
Figure 11:
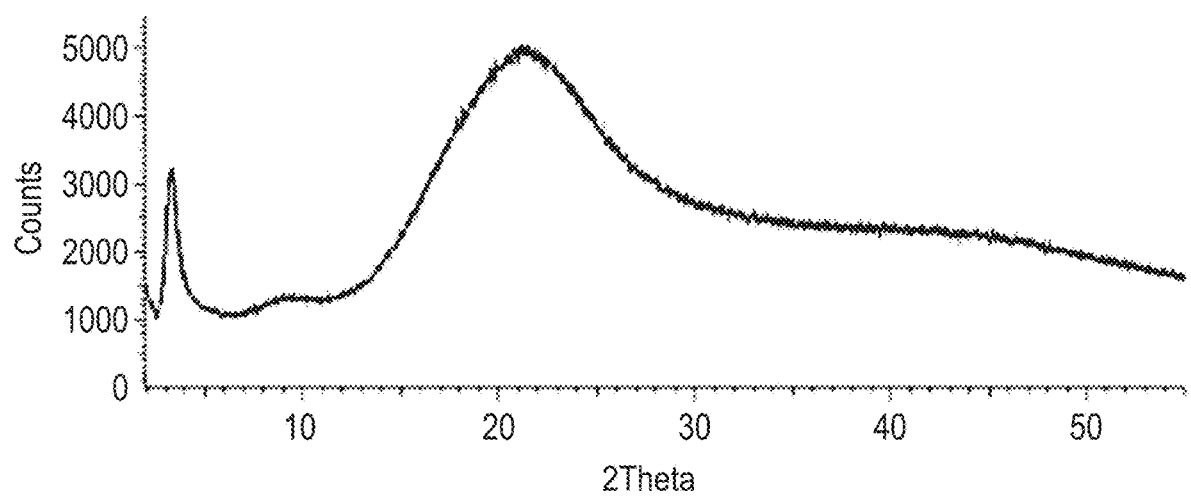
FIG. 11: PXRD pattern of (3S)-3-({N-[(4-methoxy-1H-indol-2-yl)carbonyl]-L-leucyl}amino)-2-oxo-4-[(3S)-2-oxopyrrolidin-3-yl]butyl dihydrogen phosphate amorphous sodium salt.
Figure 12:
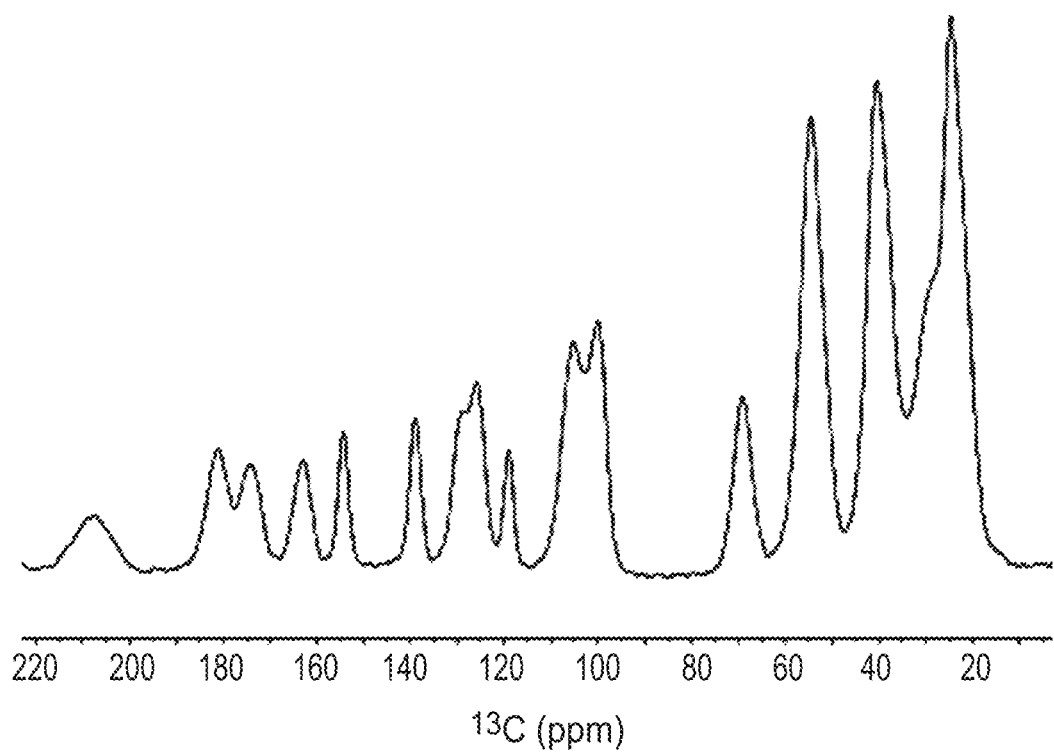
FIG. 12: $^{13}$C solid state NMR spectrum of (3S)-3-({N-[(4-methoxy-1H-indol-2-yl)carbonyl]-L-leucyl}amino)-2-oxo-4-[(3S)-2-oxopyrrolidin-3-yl]butyl dihydrogen phosphate amorphous sodium salt.
Figure 13:
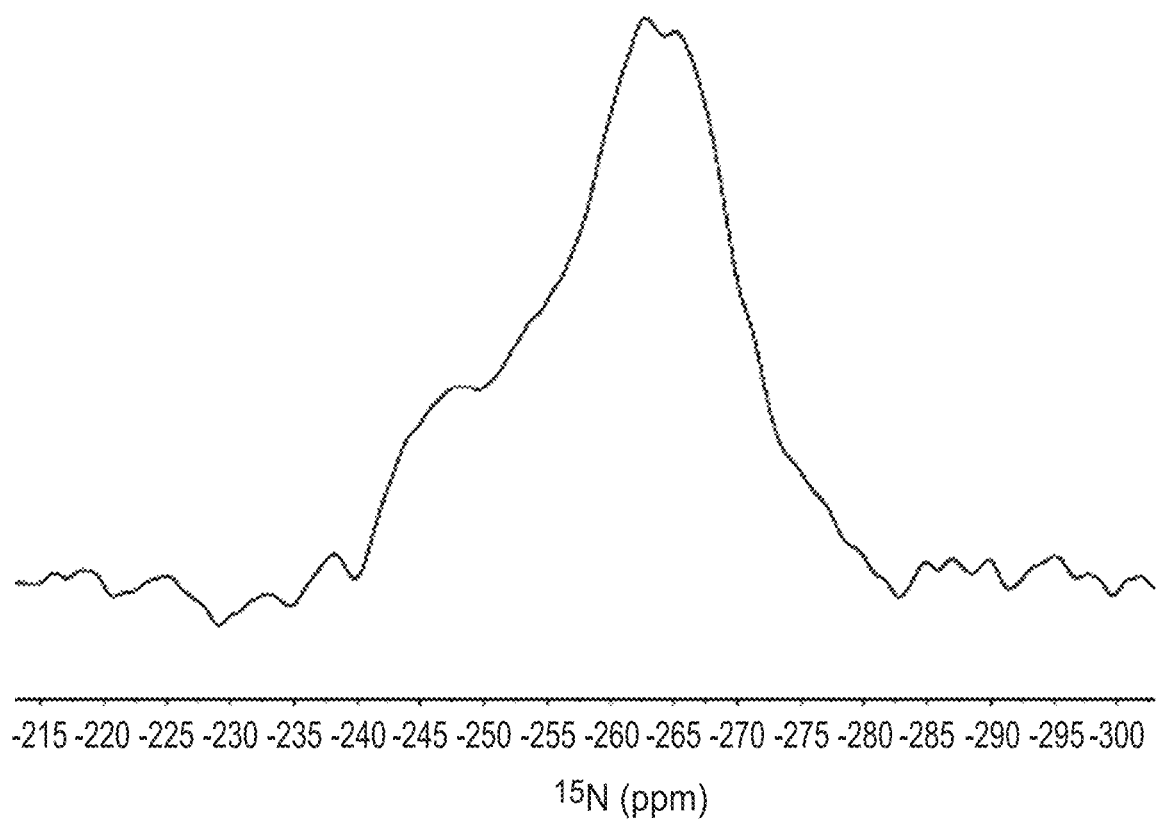
FIG. 13: $^{15}$N solid state NMR spectrum of (3S)-3-({N-[(4-methoxy-1H-indol-2-yl)carbonyl]-L-leucyl}amino)-2-oxo-4-[(3S)-2-oxopyrrolidin-3-yl]butyl dihydrogen phosphate amorphous sodium salt.
Figure 14:
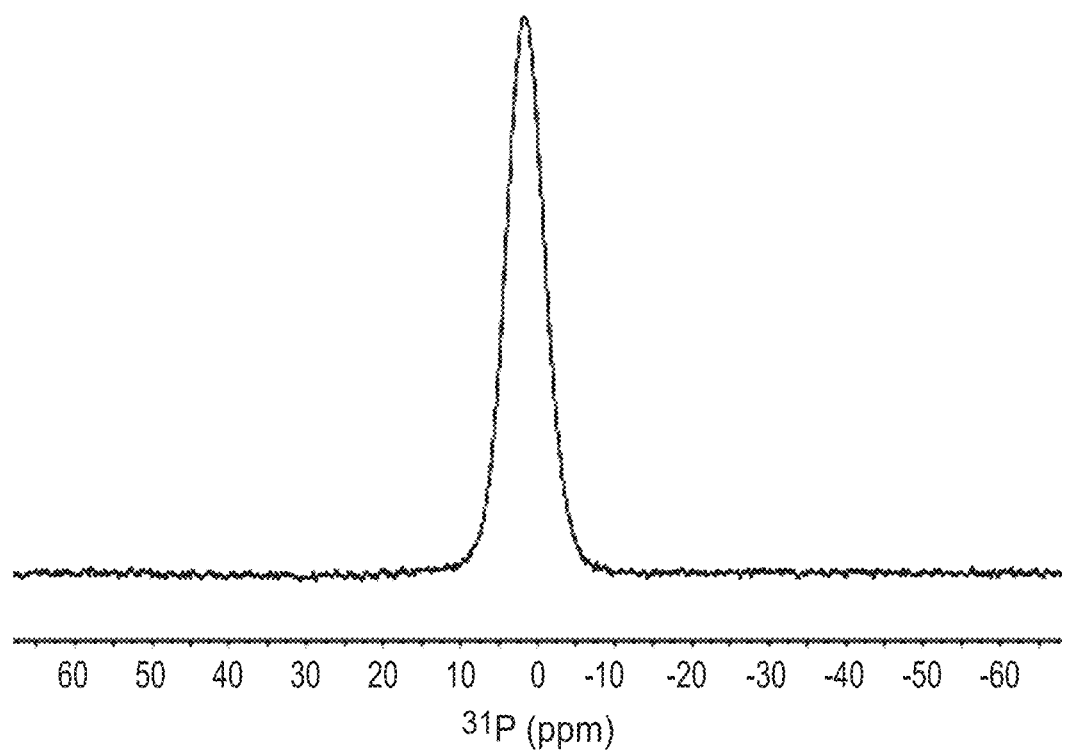
FIG. 14: $^{31}$P solid state NMR spectrum of (3S)-3-({N-[(4-methoxy-1H-indol-2-yl)carbonyl]-L-leucyl}amino)-2-oxo-4-[(3S)-2-oxopyrrolidin-3-yl]butyl dihydrogen phosphate amorphous sodium salt.
Figure 15:
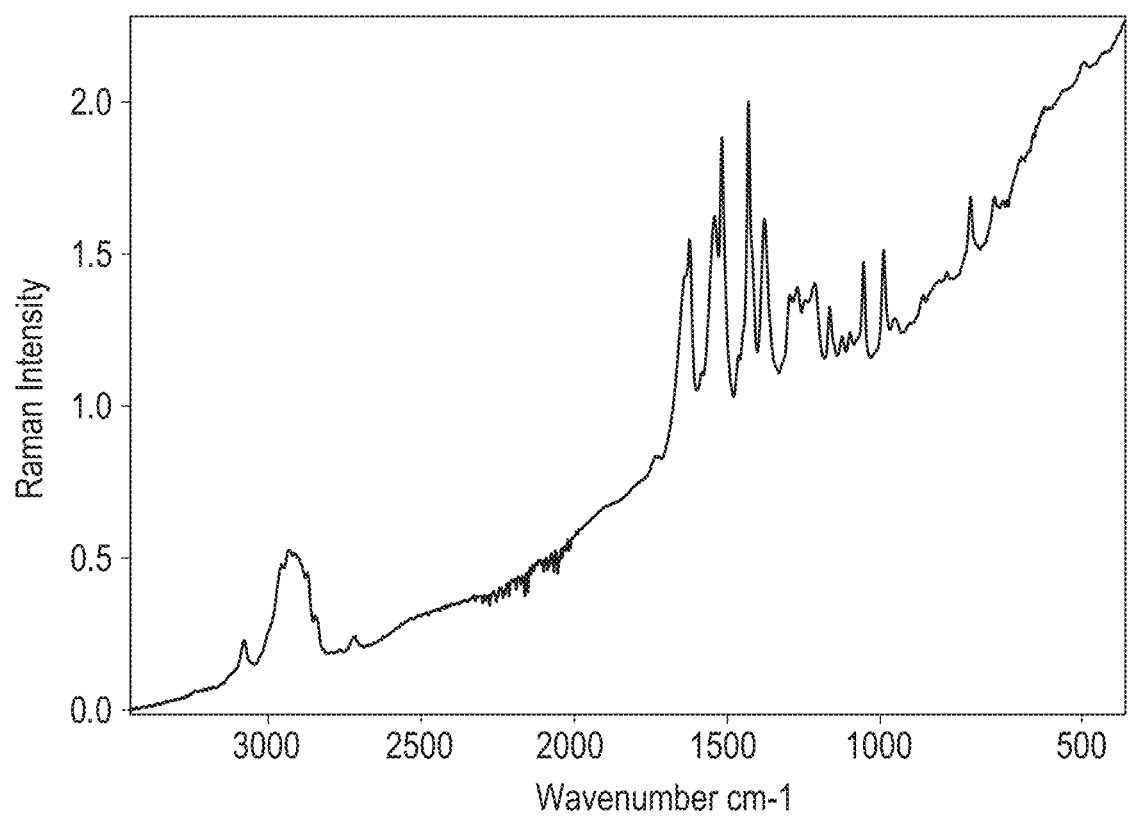
FIG. 15: Raman spectrum of (3S)-3-({N-[(4-methoxy-1H-indol-2-yl)carbonyl]-L-leucyl}amino)-2-oxo-4-[(3S)-2-oxopyrrolidin-3-yl]butyl dihydrogen phosphate amorphous sodium salt.
Figure 16:
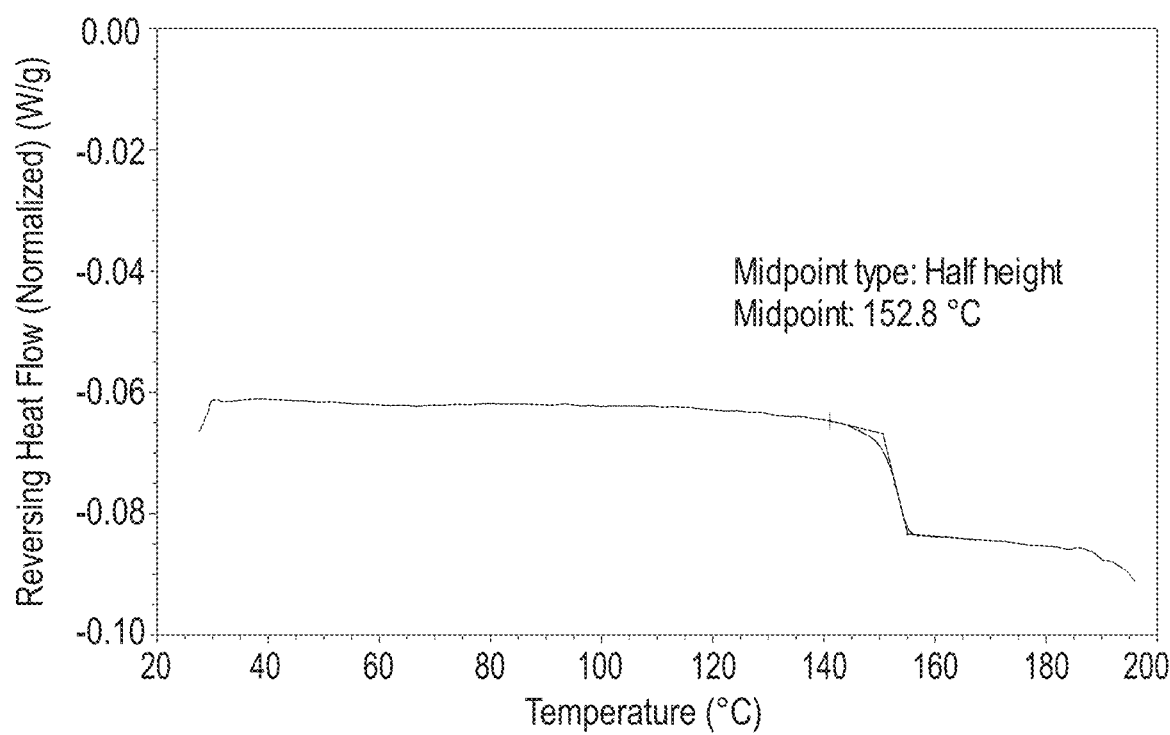
FIG. 16: Modulated DSC for glass transition determination of (3S)-3-({N-[(4-methoxy-1H-indol-2-yl)carbonyl]-L-leucyl}amino)-2-oxo-4-[(3S)-2-oxopyrrolidin-3-yl]butyl dihydrogen phosphate amorphous sodium salt.

Powder X-Ray Diffraction of (3S)-3-({N-[(4-methoxy-1H-indol-2-yl)carbonyl]-L-leucyl}amino)-2-oxo-4-[(3S)-2-oxopyrrolidin-3-yl]butyl dihydrogen phosphate, methyl ethyl ketone solvate The collected powder X-ray diffraction pattern of (3S)-3-({N-[(4-methoxy-1H-indol-2-yl)carbonyl]-L-leucyl}amino)-2-oxo-4-[(3S)-2-oxopyrrolidin-3-yl]butyl dihydrogen phosphate, methyl ethyl ketone solvate was aligned to the powder pattern of the same material containing internal standard, Si (SRM 640e). The PXRD profile for this material is provided in FIG. 10 and the corresponding peak list is provided in Table PXRD-2.

Characteristic peaks for the MEK solvate are peaks at 7.7, 8.1, 17.0, 23.1 and 25.8 2-theta positions.

Table PXRD-2: PXRD Peak List for MEK Solvate.

| Angle, Degrees 2-Theta (°2θ) ± 0.2° 2θ | Relative Intensity, % |
| --- | --- |
| 7.7 | 100.0 |
| 8.1 | 58.0 |
| 9.8 | 5.1 |
| 13.5 | 16.6 |
| 14.3 | 33.9 |
| 15.4 | 18.9 |
| 16.2 | 9.7 |
| 17.0 | 31.6 |
| 18.3 | 8.9 |
| 18.9 | 22.8 |
| 19.7 | 8.8 |
| 20.5 | 11.3 |
| 21.0 | 12.2 |
| 21.5 | 11.6 |
| 21.8 | 11.5 |
| 22.4 | 24.5 |
| 23.1 | 73.8 |
| 24.2 | 14.1 |
| 25.2 | 13.0 |
| 25.8 | 83.2 |
| 28.0 | 18.1 |
| 29.6 | 5.2 |

Characteristic PXRD peaks for the MEK solvate include but are not limited to 7.7, 8.1 and 23.1; 7.7, 8.1, 17.0 and 23.1; and 7.7, 8.1, 17.0, 23.1 and 25.8 (each degrees 2-theta±0.2 degrees 2-theta).

Table NMR-3: $^{13}$C ssNMR Peak List for MEK Solvate.

| $^{13}$C δ (ppm) ± 0.2 ppm | Relative Intensity % |
|---|---|
| 7.2 | 77.9 |
| 21.1 | 79.3 |
| 23.0 | 87.4 |
| 25.1 | 75.6 |
| 27.0 | 62.6 |
| 27.7 | 82.9 |
| 34.0 | 47.9 |
| 36.3 | 65.8 |
| 38.8 | 75.8 |
| 42.2 | 100.0 |
| 52.3 | 78.4 |
| 57.0 | 74.5 |
| 69.3 | 64.2 |
| 98.9 | 64.7 |
| 101.2 | 54.5 |
| 106.0 | 55.2 |
| 118.4 | 36.1 |
| 128.3 | 54.1 |
| 129.6 | 40.9 |
| 139.0 | 38.0 |
| 153.7 | 44.8 |
| 161.9 | 39.7 |
| 172.9 | 53.4 |
| 183.2 | 48.3 |
| 206.4 | 57.1 |
| 215.8 | 38.5 |

Characteristic $^{13}$C ssNMR peaks for the MEK solvate include 7.2, 206.4 and 215.8; 7.2, 206.4, 215.8 and 42.2; and 7.2, 206.4, 215.8, 42.2 and 101.2 (each ppm±0.2 ppm).

Table NMR-4: $^{15}$N ssNMR Peak List for MEK Solvate.

| $^{15}$N δ (ppm) | Relative Intensity, % |
|---|---|
| −272.9 | 96.5 |
| −266.4 | 100.0 |
| −251.8 | 93.7 |
| −244.6 | 93.1 |

Table Raman-2: Peak List Extracted from the FT Raman Spectrum Collected from MEK Solvate

| Wavenumber (cm$^{-1}$) ± 2 cm$^{-1}$ | Relative Intensity (%) |
|---|---|
| 446 | 23.9 |
| 511 | 20.8 |
| 568 | 19.2 |
| 596 | 19.6 |
| 628 | 22.0 |
| 705 | 29.8 |
| 780 | 18.4 |
| 802 | 20.2 |
| 819 | 20.2 |
| 861 | 17.5 |
| 909 | 17.0 |
| 956 | 18.4 |
| 988 | 40.3 |
| 1058 | 32.9 |
| 1077 | 16.5 |
| 1099 | 25.3 |
| 1125 | 18.1 |
| 1170 | 25.7 |
| 1216 | 37.5 |
| 1230 | 31.8 |
| 1253 | 45.1 |
| 1265 | 59.0 |
| 1298 | 27.7 |
| 1322 | 21.8 |
| 1359 | 29.7 |
| 1379 | 64.8 |
| 1433 | 61.9 |
| 1467 | 26.6 |
| 1511 | 100.0 |
| 1558 | 36.9 |
| 1585 | 26.9 |
| 1620 | 47.7 |
| 1644 | 90.6 |
| 1679 | 17.2 |
| 1699 | 16.9 |
| 1736 | 16.6 |
| 2721 | 6.1 |
| 2894 | 26.4 |
| 2939 | 26.6 |
| 2958 | 18.9 |
| 3081 | 13.3 |

Characteristic Raman peaks for the MEK solvate include but are not limited to those at 1511, 1644 and 3081 cm$^{-1}$, 1511, 1644, 3081 and 1265 cm$^{-1}$, and 1511, 1644, 3081 and 1265 and 446 cm$^{-1}$, each ±2 cm$^{-1}$.

Preparation of Amorphous Free Acid Form of (3S)-3-({N-[(4-methoxy-1H-indol-2-yl)carbonyl]-L-leucyl}amino)-2-oxo-4-[(3S)-2-oxopyrrolidin-3-yl] butyl di hydrogen phosphate; (amorphous free acid form of PF-07304814)

The amorphous free acid PF-07304814-00 is manufactured by adding 220 mL water to 1 g of (3S)-3-({N-[(4-methoxy-1H-indol-2-yl)carbonyl]-L-leucyl}amino)-2-oxo-4-[(3S)-2-oxopyrrolidin-3-yl]butyl dihydrogen phosphate (PF-07304814) in a Duran flask with a stirrer bar. The sample was stirred at 500 rpm at ambient conditions for 1 hour, then the solution filtered using a syringe filter. The water from the filtered solution was subsequently removed over 18 hours via centrifuge evaporation under vacuum using a Genevac EZ-2 Elite evaporator. Approximately 0.9 g solid material was recovered.

Powder X-Ray Diffraction

The powder X-ray diffraction pattern was generated using a Bruker AXS D8 Endeavor diffractometer equipped with a Cu radiation source. The tube voltage and amperage were set to 40 kV and 40 mA, respectively. The motorized divergence slits were set at constant illumination of 11 mm. Diffracted radiation was detected using a LYNXEYE XE-T energy dispersive X-ray detector, with the position sensitive detector (PSD) opening set at 4.00°. Data was collected on the theta-theta goniometer at the Cu wavelength from 2.0 to 55.0 degrees 2-theta (° 2θ) using a step size of 0.019° 2θ and a time per step of 0.2 seconds. Samples were prepared for analysis by placing them in a silicon low background small divot holder and rotated at 15 rpm during data collection. Data were analyzed in DIFFRAC.EVA V5.0 software. The PXRD profile collected for the API is provided in FIG. 1 is typical for amorphous material Solid State NMR Solid state NMR (ssNMR) analysis was conducted on a Bruker Avance III HD 400 MHz ($^1$H frequency) NMR spectrometer using a 4 mm MAS probe at a magic angle spinning rate of 8 kHz with the temperature was regulated to 20° C. $^{13}$C cross-polarization (CP) spectra with TOSS spinning sideband suppression were recorded with a 1 ms CP contact time and recycle delay of 2 seconds. A phase modulated proton decoupling field of ~100 kHz was applied during spectral acquisition. Carbon spectral referencing is relative to neat tetramethylsilane, carried out by setting the high-frequency signal from an external sample of adamantane to 38.5 ppm. $^{15}$N CP spectra were recorded with a 1 ms CP contact time and a recycle delay of 2 seconds. Nitrogen spectral referencing is relative to neat nitromethane, carried out by setting the signal from an external sample of glycine to −346.8 ppm. $^{31}$P spectra were collected using the same MAS probe as the $^{13}$C and $^{15}$N spectra, at a spinning rate of 10 kHz. $^{31}$P CP spectra were recorded with a 4 ms CP contact time and a recycle delay of 2 seconds. Phosphorous spectral referencing is relative to an external sample of 85% H$_3$PO$_4$.

Peak picking was performed using ACD Labs 2019 Spectrus Processor software. The ssNMR peak heights reported herein are relative intensities. The ssNMR intensities can vary depending on the actual setup of the experimental parameters and the thermal history of the sample. Due to the relatively high line width and noise for a number of $^{13}$C peaks there is an estimated ±0.4-0.5 ppm range for the quoted peak positions for some of the lines. The resonance at 204 ppm is particularly broad and the quoted peak position is likely to be ±1.5 ppm. The error is estimated to be ±0.2 ppm for the remaining peaks. The error is estimated to be ±0.2 ppm for the $^{31}$P peak. The $^{15}$N chemical shift information is derived from a deconvolution of the observed spectrum and the quoted intensity information should be used as a guide only. The estimated $^{15}$N error is ±1.5 ppm.

$^{13}$C ssNMR peak list for PF-07304814 amorphous free acid. Estimated error is ±0.2 ppm unless stated otherwise.

| $^{13}$C δ (ppm) | Relative Intensity, % |
| --- | --- |
| 24.6 | 100.0 |
| 40.2 ± 0.5 | 59.4 |
| 54.8 | 79.5 |
| 69.5 | 22.2 |
| 100.4 ± 0.5 | 34.2 |
| 105.3 ± 0.5 | 33.9 |
| 118.9 | 61.0 |
| 128.8 | 56.2 |
| 138.9 | 62.6 |
| 154.3 | 55.1 |
| 162.9 | 39.9 |
| 175.0 ± 0.4 | 29.8 |
| 181.8 ± 0.4 | 33.1 |
| 204 ± 1.5 | 12.5 |

Characteristic $^{13}$C ssNMR peaks for amorphous free acid form of (3S)-3-({N-[(4-methoxy-1H-indol-2-yl)carbonyl]-L-leucyl}amino)-2-oxo-4-[(3S)-2-oxopyrrolidin-3-yl]butyl dihydrogen phosphate are $^{13}$C ssNMR peaks at 175.0±0.4, 204±1.5 and 181.8±0.4 ppm; peaks at 175.0±0.4, 204±1.5, 181.8±0.4 and 54.8±0.2 ppm; and peaks at 175.0±0.4, 204±1.5, 181.8±0.4, 54.8±0.2 and 162.9±0.2 ppm; and a combination of $^{13}$C ssNMR peaks at 175.0±0.4 and 204±1.5 and a $^{31}$P peak at −0.8±0.2 ppm.

$^{15}$N ssNMR of the amorphous free acid found peaks at −264±1.5 ppm with relative intensity of 100% and −249±1.5 ppm.

$^{31}$P ssNMR of the amorphous free acid found a peak at −0.8±0.2 ppm.

Raman Spectroscopy

Raman spectra were collected using a RAM II FT-Raman module attached to a Vertex 70 spectrometer (Bruker Optik GmbH). The instrument is equipped with a 1064 nm solid-state (Nd:YAG) laser and a liquid nitrogen cooled germanium detector. Prior to data acquisition, instrument performance and calibration verifications were conducted using a white light source, and polystyrene and naphthalene references.

Samples were prepared and analysed in truncated NMR tubes. A sample rotator (Ventacon, UK) was used during measurement to maximise the volume of material exposed to the laser during data collection. The backscattered Raman signal from the sample was optimized and data were collected at a spectral resolution of 2 cm$^{-1}$ using a laser power of 500 mW. A Blackmann-Harris 4-term apodization function was applied to minimise spectral aberrations. Spectra were generated between 3500 and 50 cm$^{-1}$ with the number of scans adjusted accordingly to ensure adequate signal to noise.

Spectra were normalised by to the intensity of the most intense peak to 2.00. Peaks were then identified using the automatic peak picking function in the OPUS v8.2 software (Bruker Optik GmbH) with the sensitivity set to 3%. Peak positions and relative peak intensities were extracted and tabulated. The variability in the peak positions with this experimental configuration is within ±2 cm$^{-1}$.

It is expected that, since FT-Raman and dispersive Raman are similar techniques, peak positions reported in this document for FT-Raman spectra would be consistent with those which would be observed using a dispersive Raman measurement, assuming appropriate instrument calibration.

| Wavenumber (cm$^{-1}$) ± 2 cm$^{-1}$ | Relative Intensity (%) |
| --- | --- |
| 336 | 30.6 |
| 630 | 24.3 |
| 706 | 31.2 |
| 861 | 22.1 |
| 907 | 17.5 |
| 956 | 22.9 |
| 990 | 46.8 |
| 1055 | 43.8 |
| 1101 | 25.5 |
| 1125 | 25.6 |
| 1166 | 35.2 |
| 1216 | 45.0 |
| 1247 | 42.7 |
| 1272 | 47.7 |
| 1380 | 65.5 |
| 1431 | 100.0 |
| 1518 | 99.8 |
| 1549 | 62.8 |
| 1623 | 79.5 |
| 1742 | 12.9 |
| 2718 | 17.0 |
| 2847 | 27.7 |
| 2933 | 44.4 |
| 3078 | 17.2 |

Modulated DSC

The glass transition temperature of the amorphous free acid was measured by modulated differential scanning calorimetry (MDSC). A sample weighing 1.6 mg was placed into a TA Instruments T Zero Aluminium Pan, it was gently pressed down to improve contact with the base of the pan and to allow a better flow of heat through the sample. The pan was enclosed using a T Zero Aluminium Lid. Analysis was performed using a TA Instruments Discovery DSC utilising the following procedure. In order to remove any residual water from the sample the temperature was equilibrated at 25° C. and then increased linearly at 10° C./min to 115° C. and then decreased at 10° C./min to 25° C. The temperature was held isothermally at 25° C. for 10 minutes and then increased at 2° C./min whilst applying a temperature modulation of 0.636° C. over a period of 60 s. Analysis was performed using Trios (version 4.5.0.42498). A glass transition with midpoint (half height) was observed at 132.2° C. in the reversing heat flow.

Preparation of amorphous sodium salt of (3S)-3-({N-[(4-methoxy-1H-indol-2-yl)carbonyl]-L-leucyl}amino)-2-oxo-4-[(3S)-2-oxopyrrolidin-3-yl] butyl dihydrogen phosphate The amorphous sodium salt of (3S)-3-({N-[(4-methoxy-1H-indol-2-yl)carbonyl]-L-leucyl}amino)-2-oxo-4-[(3S)-2-oxopyrrolidin-3-yl]butyl dihydrogen phosphate is manufacturing via lyophilization using the following procedure. 2.577 g of (3S)-3-({N-[(4-methoxy-1H-indol-2-yl)carbonyl]-L-leucyl}amino)-2-oxo-4-[(3S)-2-oxopyrrolidin-3-yl] butyl dihydrogen phosphate (equivalent to 2.5 g corrected for potency (Potency=0.97, 2.5/0.97=2.577 g)) was weighed using an analytical/micro balance and added to an appropriately sized vessel. Approximately 12 mL of Water for Injection (WFI) was added and mixed. 4.575 mL of 1M NaOH was added and mixed until fully dissolved. The solution was made up to 25 mL volume with WFI and mixed. The solution was filtered using a 0.2 µm sterilizing grade filter and filled into glass vials (target volume of 10.9 mL). The vials were placed on a tray and the tray was loaded into the lyophilizer (LyoStar).

The lyophilizer was sealed and the shelf temperature was cooled to −45° C. at a rate of 0.5° C. per minute and held for 1 hour. A vacuum pressure was set to 150 mTorr and the lyophilizer was held for 1 hour. The shelf temperature was then heated to 25° C. at a rate of 0.5° C. per minute and held for 20 hours. After primary drying completion, the shelf temperature was heated to 40° C. at a rate of 0.5° C. per minute and held for 10 hours. At the conclusion of secondary drying, the chamber was backfilled with nitrogen and the shelf temperature was chilled to 5° C. Samples were stoppered within the lyophilier, the vacuum was released, and the samples were removed, capped and labelled.

After lyophilization the sample appeared as a cake to powder with a white to off-white/yellow/brown color. The lyophilized samples show minimal evidence of meltback, collapse, and shrinkage.

Powder X-Ray Diffraction

The powder X-ray diffraction pattern was generated using a Bruker AXS D8 Endeavor diffractometer equipped with a copper (Cu) radiation source. The tube voltage and amperage were set to 40 kV and 40 mA, respectively. The motorized divergence slits were set at constant illumination of 11 mm. Diffracted radiation was detected using a LYNX-EYE XE-T energy dispersive X-ray detector, with the position sensitive detector (PSD) opening set at 4.00°. Data was collected on the theta-theta goniometer at the Cu wavelength from 2.0 to 55.0 degrees 2-theta (° 2θ) using a step size of 0.019° 2θ and a time per step of 0.2 seconds. Samples were prepared for analysis by placing them in a silicon low background small divot holder and rotated at 15 rpm during data collection. Data were analyzed in DIFFRAC.EVA V5.0 software. The PXRD profile collected for the API is provided in FIG. 1 and consists of amorphous halo with a single broad peak observed at low angle at 3.3° θ.

Solid State NMR

Solid state NMR (ssNMR) analysis was conducted on a Bruker AVANCE NEO 400 MHz ($^1$H frequency) NMR spectrometer using a 4 mm MAS probe at a magic angle spinning rate of 12.5 kHz with the temperature was regulated to 25° C. $^{13}$C cross-polarization (CP) spectra were recorded with a 3 ms CP contact time and recycle delay of 3 seconds. A phase modulated proton decoupling field of ~100 kHz was applied during spectral acquisition. Carbon spectral referencing is relative to neat tetramethylsilane, carried out by setting the high-frequency signal from an external sample of L-alanine to 177.8 ppm. $^{15}$N CP spectra were recorded with a 10 ms CP contact time and a recycle delay of 3 seconds. Nitrogen spectral referencing is relative to neat nitromethane, carried out by setting the signal from an external sample of glycine to −346.8 ppm. $^{31}$P CP spectra were recorded with a 4 ms CP contact time and a recycle delay of 3 seconds. Phosphorous spectral referencing is relative to an external sample of ammonium dihydrogen phosphate, by setting the signal to 0.8 ppm.

Peak picking was performed using ACD Labs 2019 Spectrus Processor software. The ssNMR peak heights reported herein are relative intensities. The ssNMR intensities can vary depending on the actual setup of the experimental parameters and the thermal history of the sample. Due to the relatively high line width for a number of $^{13}$C peaks, combined with resonance overlaps and noise levels there is an estimated ±0.4-0.5 ppm range for the quoted peak positions for some of the peaks. The resonance at ~208 ppm is particularly broad and noisy, so the quoted peak position is likely to be ±1.5 ppm. The error is estimated to be ±0.2 ppm for the remaining $^{13}$C peaks. The error is estimated to be ±0.2 ppm for the $^{31}$P peak. The $^{15}$N chemical shift information is derived from a deconvolution of the observed spectrum and the quoted intensity information should be used as a guide only. The estimated $^{15}$N error is ±1.5 ppm. The characteristic peaks for the amorphous sodium salt of (3S)-3-({N-[(4-methoxy-1H-indol-2-yl)carbonyl]-L-leucyl} amino)-2-oxo-4-[(3S)-2-oxopyrrolidin-3-yl]butyl dihydrogen phosphate are 126.0±0.4 ppm, 181.0±0.4 ppm, 208.0±1.5 ppm, 174.1±0.4 ppm and 163.1±0.2 ppm for $^{13}$C and 1.9±0.2 ppm for $^{31}$P.

Raman Spectroscopy

Raman spectra were collected using a RAM II FT-Raman module attached to a Vertex 70 spectrometer (Bruker Optik, GmbH). The instrument is equipped with a 1064 nm solid-state (Nd:YAG) laser and a liquid nitrogen cooled germanium detector. Prior to data acquisition, instrument performance and calibration verifications were conducted using a white light source, and polystyrene and naphthalene references.

The sample was analysed directly from the glass vial it was supplied in. The backscattered Raman signal from the sample was optimised and data were collected at a spectral resolution of 2 cm$^{-1}$ using a laser power of 750 mW. A Blackmann-Harris 4-term apodization function was applied to minimise spectral aberrations. Spectra were generated between 3500 and 50 cm$^{-1}$ with the number of scans adjusted accordingly to ensure adequate signal to noise. Three separate measurements were taken to ensure the measurement was representative of the bulk material.

The three measurements were averaged using the averaging function in OPUS v8.2 software and this spectrum was normalised by setting the intensity of the most intense peak to 2.00. Peaks were then identified using the automatic peak picking function in the OPUS v8.2 software (Bruker Optik GmbH) with the sensitivity set to 2%. Peak positions and relative peak intensities were extracted and tabulated. The variability in the peak positions with this experimental configuration is within ±2 cm$^{-1}$.

It is expected that, since FT-Raman and dispersive Raman are similar techniques, peak positions reported in this document for FT-Raman spectra would be consistent with those which would be observed using a dispersive Raman measurement, assuming appropriate instrument calibration.

Modulated DSC

The glass transition temperature of the amorphous sodium salt of (3S)-3-({N-[(4-methoxy-1H-indol-2-yl)carbonyl]-L-leucyl}amino)-2-oxo-4-[(3S)-2-oxopyrrolidin-3-yl]butyl dihydrogen phosphate was measured by modulated differential scanning calorimetry (MDSC). A sample weighing 1.8 mg was placed into a TA Instruments T Zero Aluminium Pan, it was gently pressed down to improve contact with the base of the pan and to allow a better flow of heat through the sample. The pan was enclosed using a T Zero Aluminium Lid. Analysis was performed using a TA Instruments Discovery DSC utilising the following procedure. The temperature was held isothermally at 25° C. for 5 minutes and then increased at 2° C./min to 200° C. whilst applying a temperature modulation of 0.636° C. over a period of 60 seconds.

Analysis was performed using Trios (version 4.5.0.42498). A glass transition with midpoint (half height) was observed at 152.8° C. in the reversing heat flow.

Table NMR-5: $^{13}$C ssNMR peak list for (3S)-3-({N-[(4-methoxy-1H-indol-2-yl)carbonyl]-L-leucyl}amino)-2-oxo-4-[(3S)-2-oxopyrrolidin-3-yl]butyl dihydrogen phosphate amorphous sodium salt.

| $^{13}$C δ (ppm) | Relative Intensity, % |
|---|---|
| 24.8 ± 0.2 | 100.0 |
| 40.6 ± 0.4 | 90.0 |
| 54.6 ± 0.2 | 83.5 |
| 69.2 ± 0.2 | 31.0 |
| 100.0 ± 0.4 | 43.2 |
| 105.3 ± 0.4 | 41.0 |
| 119.1 ± 0.2 | 19.8 |
| 126.0 ± 0.4 | 32.4 |
| 129.1 ± 0.5 | 27.9 |
| 139.0 ± 0.2 | 26.4 |
| 154.3 ± 0.2 | 23.4 |
| 163.1 ± 0.2 | 18.1 |
| 174.1 ± 0.4 | 17.2 |
| 181.0 ± 0.4 | 20.4 |
| 208 ± 1.5 | 7.6 |

Characteristic $^{13}$C ssNMR peaks for the (3S)-3-({N-[(4-methoxy-1H-indol-2-yl)carbonyl]-L-leucyl}amino)-2-oxo-4-[(3S)-2-oxopyrrolidin-3-yl]butyl dihydrogen phosphate amorphous sodium salt include peaks at 126.0±0.4 ppm, 181.0±0.4 ppm and 208.0±1.5 ppm; peaks at 126.0±0.4 ppm, 181.0±0.4 ppm, 208.0±1.5 ppm and 174.1±0.4 ppm; and peaks at 126.0±0.4 ppm, 181.0±0.4 ppm, 208.0±1.5 ppm, 174.1±0.4 ppm and 163.1±0.2 ppm.

$^{15}$N ssNMR of (3S)-3-({N-[(4-methoxy-1H-indol-2-yl)carbonyl]-L-leucyl}amino)-2-oxo-4-[(3S)-2-oxopyrrolidin-3-yl]butyl dihydrogen phosphate amorphous sodium salt resulted in $^{15}$N peaks at δ −263 ppm with relative intensity of 100% and −248 ppm with relative intensity of 37%.

Due to the poor signal to noise ratio (S/N) and broad, overlapping signals, there is insufficient distinction, within the stated error, to select diagnostic $^{15}$N ssNMR peaks for (3S)-3-({N-[(4-methoxy-1H-indol-2-yl)carbonyl]-L-leucyl}amino)-2-oxo-4-[(3S)-2-oxopyrrolidin-3-yl]butyl dihydrogen phosphate amorphous sodium salt compared to other forms of (3S)-3-({N-[(4-methoxy-1H-indol-2-yl)carbonyl]-L-leucyl}amino)-2-oxo-4-[(3S)-2-oxopyrrolidin-3-yl]butyl dihydrogen phosphate.

$^{31}$P ssNMR of (3S)-3-({N-[(4-methoxy-1H-indol-2-yl)carbonyl]-L-leucyl}amino)-2-oxo-4-[(3S)-2-oxopyrrolidin-3-yl]butyl dihydrogen phosphate amorphous sodium salt resulted in a characteristic $^{31}$P peak at δ 1.9 ppm±0.2 ppm with relative intensity of 100%.

Characteristic $^{13}$C ssNMR and $^{31}$P ssNMR peaks for the (3S)-3-({N-[(4-methoxy-1H-indol-2-yl)carbonyl]-L-leucyl}amino)-2-oxo-4-[(3S)-2-oxopyrrolidin-3-yl]butyl dihydrogen phosphate amorphous sodium salt include $^{13}$C peaks at 126.0±0.4 ppm, 181.0±0.4 ppm and a $^{31}$P peak at 1.9 ppm±0.2 ppm.

Table Raman-3: Peak list extracted from the FT Raman spectrum collected from (3S)-3-({N-[(4-methoxy-1H-indol-2-yl)carbonyl]-L-leucyl}amino)-2-oxo-4-[(3S)-2-oxopyrrolidin-3-yl]butyl dihydrogen phosphate amorphous sodium salt

| Wavenumber (cm$^{-1}$) | Relative Intensity (%) |
|---|---|
| 706 | 84.4 |
| 990 | 75.6 |
| 1055 | 73.6 |
| 1125 | 61.4 |
| 1165 | 66.3 |
| 1215 | 70.2 |
| 1271 | 69.6 |
| 1379 | 80.7 |
| 1431 | 100.0 |
| 1518 | 94.2 |
| 1542 | 81.2 |
| 1623 | 77.5 |
| 2934 | 26.2 |
| 3078 | 11.4 |

Preparation of (3S)-3-({N-[(4-methoxy-1H-indol-2-yl)carbonyl]-L-leucyl}amino)-2-oxo-4-[(3S)-2-oxopyrrolidin-3-yl]butyl dihydrogen phosphate dimethylsulfoxide (DMSO) solvate: A jacketed reactor at 20° C. was charged with (3S)-3-({N-[(4-methoxy-1H-indol-2-yl)carbonyl]-L-leucyl}amino)-2-oxo-4-[(3S)-2-oxopyrrolidin-3-yl]butyl dihydrogen phosphate Methyl Ethyl Ketone solvate (1.0 eq, 50 g), Dimethylsulfoxide (100 mL, 2 mL/g) and 2-Propanol (100 mL, 2 mL/g). The mixture was stirred at 20° C. until a clear solution was obtained. The solution was heated to 30° C. and Isopropanol (800 mL, 16 mL/g) is added. The resulting slurry was cooled to 10° C. over 2 h and granulated for a minimum of 1 h before filtering and washing with 2-Propanol (200 mL, 4 mL/g). The solids were dried at 60° C. in a vacuum oven overnight to provide (3S)-3-({N-[(4-methoxy-1H-indol-2-yl)carbonyl]-L-leucyl}amino)-2-oxo-4-[(3S)-2-oxopyrrolidin-3-yl]butyl dihydrogen phosphate as a Dimethylsulfoxide solvate (~12 wt %) in 83% yield. Dimethylsulfoxide solvate is isolated for ambient humidity<30% RH. Higher ambient humidity results in isolation of the dimethylsulfoxide solvate hydrate.

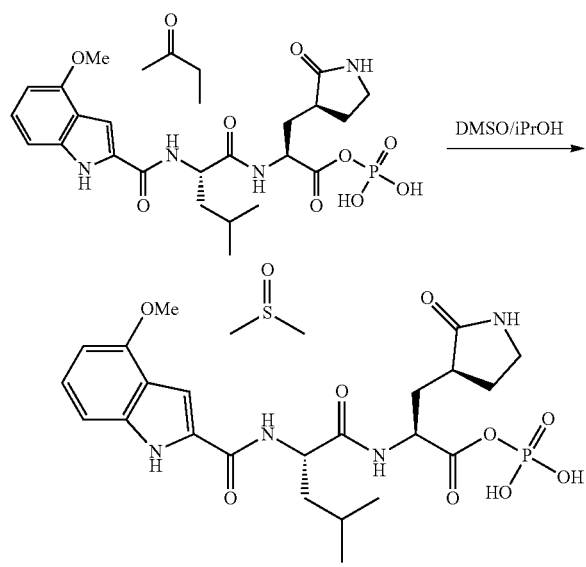

Exposing the dimethylsulfoxide solvate of (3S)-3-({N-[(4-methoxy-1H-indol-2-yl)carbonyl]-L-leucyl}amino)-2-oxo-4-[(3S)-2-oxopyrrolidin-3-yl]butyl dihydrogen phosphate to 50% relative humidity yields a dimethylsulfoxide solvate hydrate.

Powder X-Ray Diffraction

The powder X-ray diffraction pattern for the DMSO solvate of (3S)-3-({N-[(4-methoxy-1H-indol-2-yl)carbonyl]-L-leucyl}amino)-2-oxo-4-[(3S)-2-oxopyrrolidin-3-yl]butyl dihydrogen phosphate was generated using a Bruker AXS D8 Endeavor diffractometer equipped with a copper (Cu) radiation source, wavelength of 1.5406 Å. The tube voltage and amperage were set to 40 kV and 40 mA, respectively. The motorized divergence slits were set at constant illumination of 11 mm. Diffracted radiation was detected using a LYNXEYE XE-T energy dispersive X-ray detector, with the position sensitive detector (PSD) opening set at 4.00°. Data was collected on the theta-theta goniometer at the Cu wavelength from 2.0 to 55.0 degrees 2-theta (° 2θ) using a step size of 0.019° 2θ and a time per step of 0.2 seconds. Samples were prepared for analysis by placing them in a silicon low background small divot holder and rotated at 15 rpm during data collection. The ambient lab relative humidity during this characterization was 13.6%.

The powder X-ray diffraction pattern for the DMSO solvate hydrate was generated using a Bruker AXS D8 Discover diffractometer equipped with an Anton-Paar CHC+ sample chamber and a Cu radiation source wavelength of 1.5406 Å. The tube voltage and amperage were set to 40 kV and 40 mA, respectively. The motorized divergence slits were set at constant illumination of 10 mm. Diffracted radiation was detected using a LYNXEYE XE energy dispersive X-ray detector, with the PSD opening set at 2.95°. Data was collected on the theta-theta goniometer at the Cu wavelength from 5.0 to 40.0 degrees ° 2θ using a step size of 0.01° 2θ and a time per step of 0.2 seconds. Samples were prepared for analysis by placing them in a sample holder with a silicon low background insert and equilibrated for at least 2 hours at 25° C. and 50% relative humidity (RH) prior to data collection.

Data were analyzed in DIFFRAC.EVA V5.0 software. Peak lists were prepared using reflections with a relative intensity ≥5% of the most intense band in each respective diffraction pattern. A typical error of ±0.2° 2θ in peak positions (USP-941) applies to this data. The minor error associated with this measurement can occur because of a variety of factors including: (a) sample preparation (e.g. sample height), (b) instrument characteristics, (c) instrument calibration, (d) operator input (e.g. in determining the peak locations), and (e) the nature of the material (e.g. preferred orientation and transparency effects).

Figure 17:
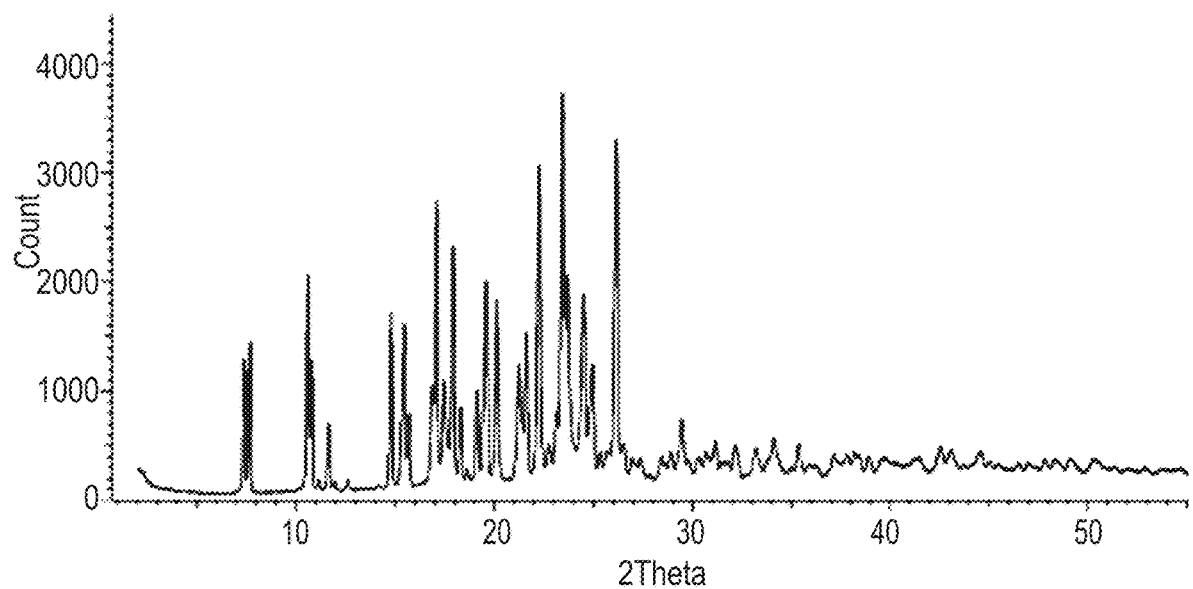
FIG. 17: PXRD pattern of (3S)-3-({N-[(4-methoxy-1H-indol-2-yl)carbonyl]-L-leucyl}amino)-2-oxo-4-[(3S)-2-oxopyrrolidin-3-yl]butyl dihydrogen phosphate, DMSO solvate.
Figure 18:
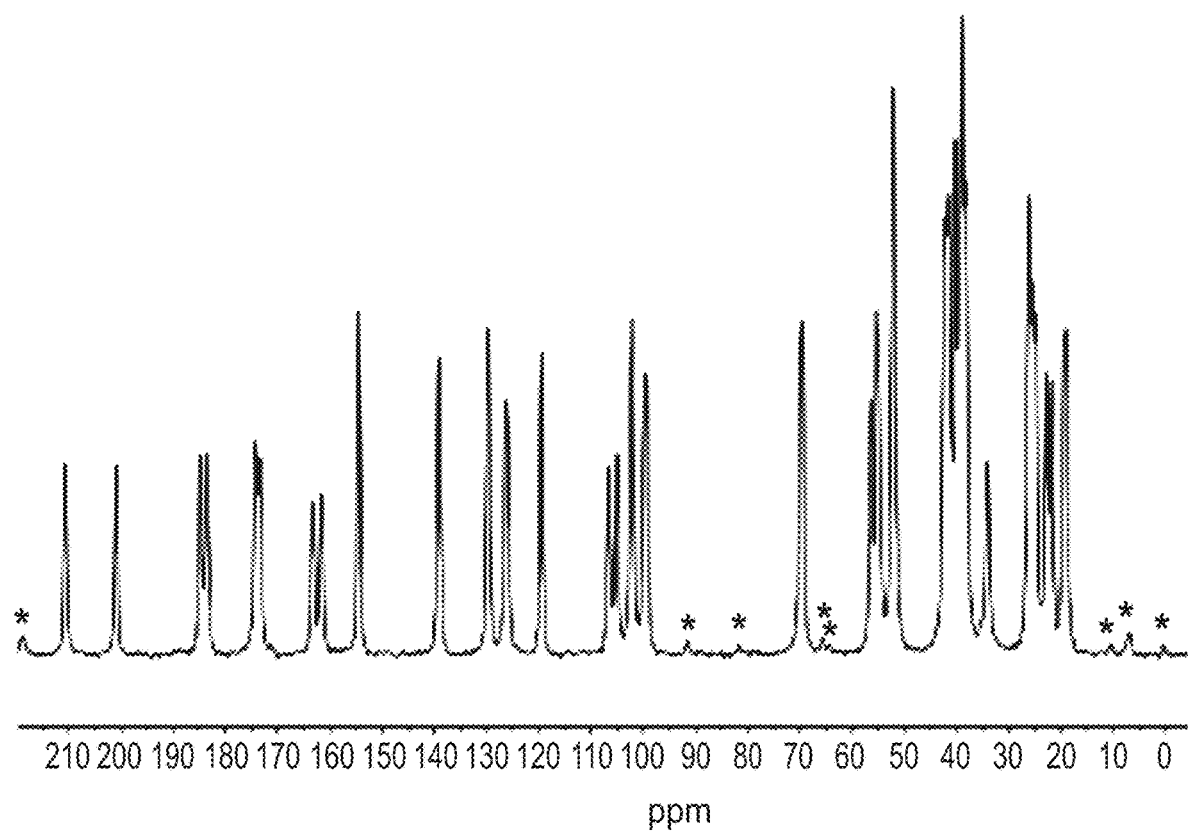
FIG. 18: $^{13}$C ssNMR spectrum of (3S)-3-({N-[(4-methoxy-1H-indol-2-yl)carbonyl]-L-leucyl}amino)-2-oxo-4-[(3S)-2-oxopyrrolidin-3-yl]butyl dihydrogen phosphate, DMSO solvate.
Figure 20:
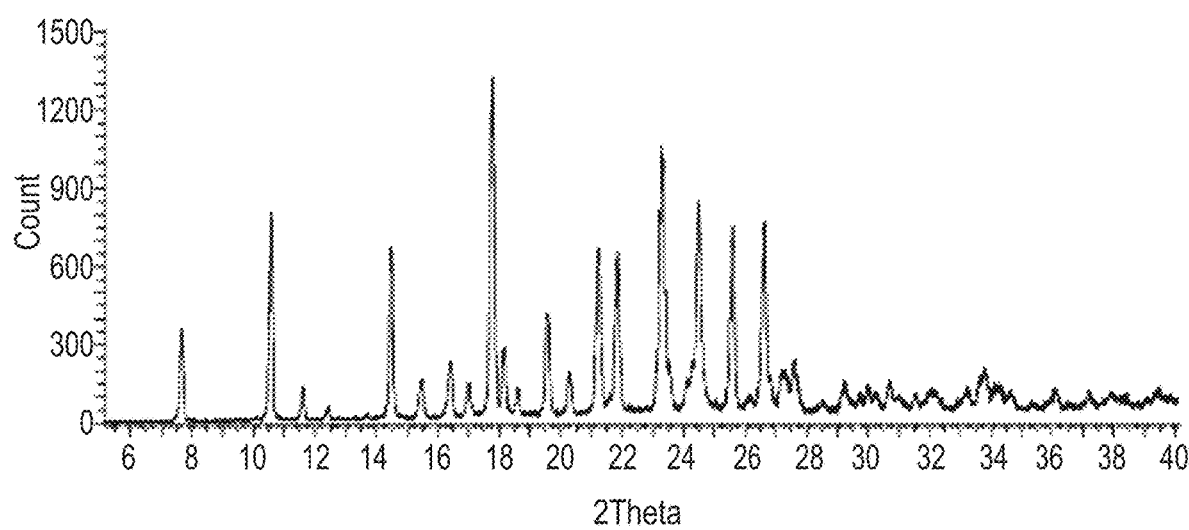
FIG. 20: PXRD pattern of (3S)-3-({N-[(4-methoxy-1H-indol-2-yl)carbonyl]-L-leucyl}amino)-2-oxo-4-[(3S)-2-oxopyrrolidin-3-yl]butyl dihydrogen phosphate, DMSO solvate hydrate.
Figure 21:
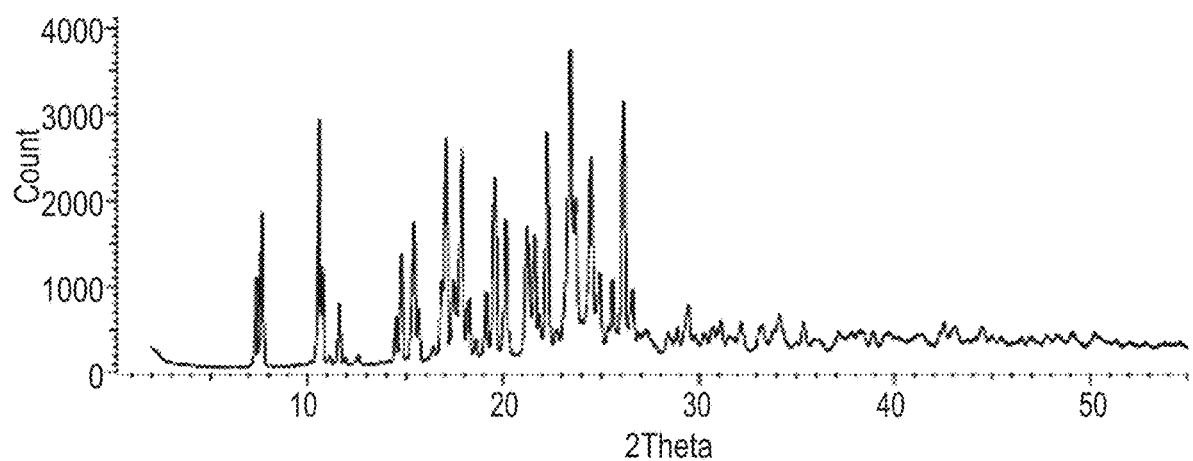
FIG. 21: PXRD pattern of a mixture of (3S)-3-({N-[(4-methoxy-1H-indol-2-yl)carbonyl]-L-leucyl}amino)-2-oxo-4-[(3S)-2-oxopyrrolidin-3-yl]butyl dihydrogen phosphate, DMSO solvate hydrate and (3S)-3-({N-[(4-methoxy-1H-indol-2-yl)carbonyl]-L-leucyl}amino)-2-oxo-4-[(3S)-2-oxopyrrolidin-3-yl]butyl dihydrogen phosphate, DMSO solvate.

To obtain the absolute peak positions, the powder pattern should be aligned against a reference. This could either be the simulated powder pattern from the crystal structure of the same form solved at room temperature, or an internal standard e.g. silica or corundum. The collected powder pattern of the DMSO solvate of (3S)-3-({N-[(4-methoxy-1H-indol-2-yl)carbonyl]-L-leucyl}amino)-2-oxo-4-[(3S)-2-oxopyrrolidin-3-yl]butyl dihydrogen phosphate was aligned to the powder pattern of the same material containing internal standard, Si (SRM 640e). The collected powder pattern of the DMSO solvate hydrate of (3S)-3-({N-[(4-methoxy-1H-indol-2-yl)carbonyl]-L-leucyl}amino)-2-oxo-4-[(3S)-2-oxopyrrolidin-3-yl]butyl dihydrogen phosphate was aligned to the simulated powder pattern from the crystal structure. The PXRD spectrums for the DMSO solvate and DMSO solvate hydrate are provided in FIG. 17 and FIG. 20, respectively, and the corresponding peak lists are provided in Table PXRD-3 and Table PXRD-4, respectively. Characteristic peaks for the DMSO solvate are peaks at 7.4, 10.8, 14.8, 22.3 and 26.2 2-theta positions (degrees 2-theta±0.2 degrees 2-theta). Characteristic peaks for the DMSO solvate hydrate are peaks at 14.5, 17.8, 21.9, 25.6 and 26.6 2-theta positions (degrees 2-theta±0.2 degrees 2-theta). It may be possible the material to be characterised with a combination of the characteristic peaks of the DMSO solvate and DMSO solvate hydrate when a mixture of the two solid forms is present. An example of the PXRD pattern for a mixture of the DMSO solvate and the DMSO solvate hydrate is shown in FIG. 21.

Table PXRD-3: PXRD peak list for (3S)-3-({N-[(4-methoxy-1H-2-yl)carbonyl]-L-leucyl}amino)-2-oxo-4-[(3S)-2-oxopyrrolidin-3-yl]butyl dihydrogen phosphate DMSO solvate.

| Angle, Degrees 2-Theta (°2θ) ± 0.2 °2θ | Relative Intensity (%) |
|---|---|
| 7.4 | 32.9 |
| 7.7 | 37.1 |
| 10.6 | 54.1 |
| 10.8 | 33.0 |
| 11.6 | 17.1 |
| 14.8 | 44.7 |
| 15.4 | 42.3 |
| 15.7 | 18.7 |
| 16.9 | 25.1 |
| 17.1 | 74.0 |
| 17.4 | 37.4 |
| 17.9 | 59.9 |
| 18.3 | 19.3 |
| 19.2 | 23.2 |
| 19.6 | 49.8 |
| 20.2 | 46.2 |
| 21.3 | 41.8 |
| 21.6 | 37.6 |
| 22.3 | 80.0 |
| 22.8 | 8.3 |
| 23.2 | 15.6 |
| 23.5 | 100.0 |
| 23.7 | 51.9 |
| 24.5 | 46.6 |

-continued

| Angle, Degrees 2-Theta (°2θ) ± 0.2 °2θ | Relative Intensity (%) |
|---|---|
| 25.0 | 28.5 |
| 25.4 | 6.2 |
| 25.7 | 5.5 |
| 26.2 | 89.9 |
| 26.5 | 8.3 |
| 27.4 | 5.5 |
| 28.4 | 5.7 |
| 28.9 | 7.0 |
| 29.5 | 15.7 |

Table PXRD-4: PXRD Peak List for (3S)-3-({N-[(4-methoxy-1H-indol-2-yl)carbonyl]-L-leucyl}amino)-2-oxo-4-[(3S)-2-oxopyrrolidin-3-yl]butyl dihydrogen phosphate DMSO solvate hydrate.

| Angle, Degrees 2-Theta (°2θ) ± 0.2° 2θ | Relative Intensity (%) |
|---|---|
| 7.7 | 26.4 |
| 10.6 | 64.2 |
| 11.6 | 9.1 |
| 14.5 | 52.2 |
| 15.5 | 10.7 |
| 16.4 | 15.4 |
| 17.0 | 9.0 |
| 17.8 | 100.0 |
| 18.2 | 20.0 |
| 18.6 | 8.2 |
| 19.6 | 30.7 |
| 20.3 | 13.5 |
| 21.2 | 51.8 |
| 21.9 | 50.1 |
| 23.3 | 83.0 |
| 23.5 | 12.0 |
| 24.1 | 8.1 |
| 24.3 | 15.4 |
| 24.5 | 63.8 |
| 25.6 | 58.2 |
| 26.6 | 57.9 |
| 26.8 | 13.9 |
| 27.2 | 17.0 |
| 27.3 | 10.3 |
| 27.6 | 14.4 |
| 29.2 | 9.6 |
| 30.0 | 5.6 |

Solid State NMR

Solid state NMR (ssNMR) analysis was conducted on a CPMAS probe positioned into a Bruker-BioSpin Avance III 500 MHz ($^1$H frequency) NMR spectrometer. Material was packed into a $ZrO_2$ rotor and capped with an o-ring cap. A magic angle spinning rate of 15.0 kHz was used.

$^{13}$C ssNMR spectra were collected using a proton decoupled cross-polarization magic angle spinning (CPMAS) experiment. A phase modulated proton decoupling field of 80-100 kHz was applied during spectral acquisition. The cross-polarization contact time was set to 2 ms. Spectra were collected with a recycle delay of 3.5 seconds. The number of scans was adjusted to obtain an adequate signal to noise ratio. The $^{13}$C chemical shift scale was referenced using an $^{13}$C CPMAS experiment on an external standard of crystalline adamantane, setting its up-field resonance to 29.5 ppm (as determined from neat TMS).

Automatic peak picking was performed using Bruker-BioSpin TopSpin version 3.6 software. Generally, a threshold value of 5% relative intensity was used for preliminary peak selection. The output of the automated peak picking was visually checked to ensure validity and adjustments were manually made, if necessary. Although specific solid-state NMR peak values are reported herein there does exist a range for these peak values due to differences in instruments, samples, and sample preparation. This is common practice in the art of solid-state NMR because of the variation inherent in peak positions. A typical variability for $^{13}$C chemical shift x-axis value is on the order of ±0.2 ppm for a crystalline solid and ±0.5 ppm for an amorphous solid. The solid-state NMR peak heights reported herein are relative intensities. Solid state NMR intensities can vary depending on the actual setup of the experimental parameters and the thermal history of the sample.

Table NMR-6: $^{13}$C ssNMR Peak List for (3S)-3-({N-[(4-methoxy-1H-indol-2-yl)carbonyl]-L-leucyl}amino)-2-oxo-4-[(3S)-2-oxopyrrolidin-3-yl]butyl dihydrogen phosphate DMSO solvate.

| $^{13}$C δ (ppm) ± 0.2 ppm | Relative Intensity (%) |
|---|---|
| 210.7 | 30 |
| 201.0 | 30 |
| 184.8 | 31 |
| 183.5 | 31 |
| 174.1 | 33 |
| 173.4 | 31 |
| 163.3 | 24 |
| 161.6 | 25 |
| 154.5 | 54 |
| 139.2 | 47 |
| 129.7 | 51 |
| 126.3 | 39 |
| 126.1 | 40 |
| 119.5 | 48 |
| 106.6 | 29 |
| 105.1 | 31 |
| 102.2 | 52 |
| 99.7 | 44 |
| 99.5 | 43 |
| 69.9 | 50 |
| 69.6 | 52 |
| 56.5 | 40 |
| 55.4 | 54 |
| 55.0 | 43 |
| 52.1 | 89 |
| 42.2 | 68 |
| 41.6 | 72 |
| 40.3 | 81 |
| 39.5 | 68 |
| 39.0 | 100 |
| 38.3 | 74 |
| 34.2 | 30 |
| 26.2 | 72 |
| 25.5 | 59 |
| 25.0 | 53 |
| 22.8 | 44 |
| 21.8 | 43 |
| 19.4 | 50 |
| 19.0 | 51 |

Raman Spectroscopy

Raman spectra were collected using a RAM II FT-Raman module attached to a Vertex 70 spectrometer (Bruker Optik GmbH). The instrument is equipped with a 1064 nm solid-state (Nd:YAG) laser and a liquid nitrogen cooled germanium detector. Prior to data acquisition, instrument performance and calibration verifications were conducted using a white light source, and polystyrene and naphthalene references.

Samples were analysed directly from the glass vials they were supplied in; two individual measurements were conducted for each sample at different positions to maximise the volume of material exposed to the laser during data collection. The backscattered Raman signal from the sample was optimized and data were collected at a spectral resolution of 2 cm$^{-1}$ using a laser power of 1000 mW. A Blackmann-Harris 4-term apodization function was applied to minimise spectral aberrations. Spectra were generated between 3500 and 50 cm$^{-1}$ with the number of scans adjusted accordingly to ensure adequate signal to noise.

Spectra were normalised by setting the intensity of the most intense peak to 2.00. Peaks were then identified using the automatic peak picking function in the OPUS v8.2 software (Bruker Optik GmbH) with the sensitivity set to 2%. Peak positions and relative peak intensities were extracted and tabulated. The variability in the peak positions with this experimental configuration is within ±2 cm$^{-1}$.

It is expected that, since FT-Raman and dispersive Raman are similar techniques, peak positions reported in this document for FT-Raman spectra would be consistent with those which would be observed using a dispersive Raman measurement, assuming appropriate instrument calibration.

Figure 19:
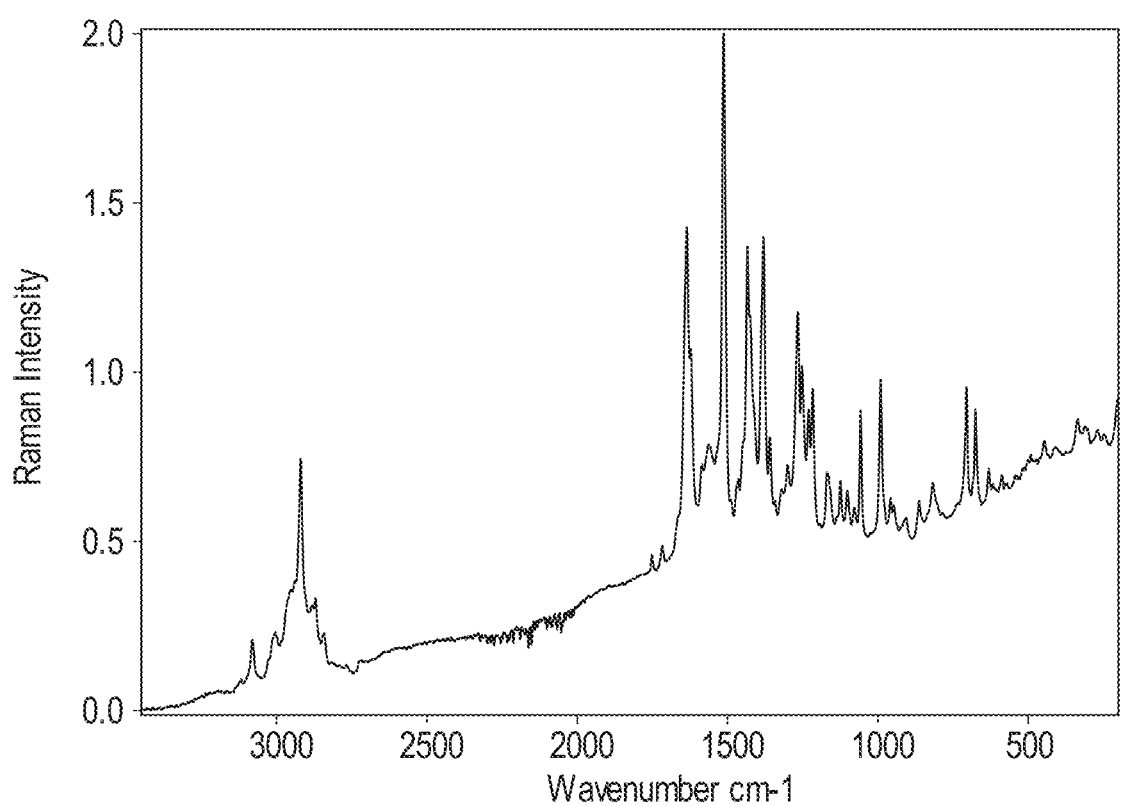
FIG. 19: Raman spectrum of (3S)-3-({N-[(4-methoxy-1H-indol-2-yl)carbonyl]-L-leucyl}amino)-2-oxo-4-[(3S)-2-oxopyrrolidin-3-yl]butyl dihydrogen phosphate, DMSO solvate.

The Raman spectrum collected from the DMSO solvate is presented in FIG. 19. It is noted that the Raman data for the DMSO solvate and DMSO solvate hydrate are equivalent positions within the stated error of ±2 cm$^{-1}$.

Table Raman-4: Peak List Extracted from the FT Raman Spectrum Collected from (3S)-3-({N-[(4-methoxy-1H-indol-2-yl)carbonyl]-L-leucyl}amino)-2-oxo-4-[(3S)-2-oxopyrrolidin-3-yl]butyl dihydrogen phosphate DMSO solvate

| Wavenumber (cm$^{-1}$) ± 2 cm$^{-1}$ | Relative Intensity (%) |
|---|---|
| 334 | 43.0 |
| 446 | 39.8 |
| 588 | 34.7 |
| 631 | 35.7 |
| 675 | 44.6 |
| 705 | 47.9 |
| 817 | 33.6 |
| 863 | 30.9 |
| 958 | 31.4 |
| 991 | 49.1 |
| 1058 | 44.3 |
| 1078 | 30.0 |
| 1101 | 32.4 |
| 1125 | 34.0 |
| 1169 | 35.2 |
| 1217 | 47.5 |
| 1230 | 44.6 |
| 1253 | 51.0 |
| 1266 | 58.9 |
| 1300 | 36.3 |
| 1359 | 40.4 |
| 1380 | 69.9 |
| 1434 | 68.5 |
| 1513 | 100.0 |
| 1563 | 39.3 |
| 1636 | 71.4 |
| 1717 | 24.4 |
| 1751 | 23.1 |
| 2871 | 16.5 |
| 2919 | 37.3 |
| 3004 | 11.6 |
| 3081 | 10.4 |

Characteristic PXRD peaks for (3S)-3-({N-[(4-methoxy-1H-indol-2-yl)carbonyl]-L-leucyl}amino)-2-oxo-4-[(3S)-2-oxopyrrolidin-3-yl]butyl dihydrogen phosphate DMSO solvate include peaks at 7.4±0.2, 14.8±0.2 and 26.2±0.2 degrees 2-theta; peaks at 7.4±0.2, 10.8±0.2, 14.8±0.2 and 26.2±0.2 degrees 2-theta; and peaks at 7.4±0.2, 10.8±0.2, 14.8±0.2, 22.3±0.2 and 26.2±0.2 degrees 2-theta.

Characteristic $^{13}$C ssNMR peaks for (3S)-3-({N-[(4-methoxy-1H-indol-2-yl)carbonyl]-L-leucyl}amino)-2-oxo-4-[(3S)-2-oxopyrrolidin-3-yl]butyl dihydrogen phosphate DMSO solvate include $^{13}$C peaks at 173.4±0.2, 210.7±0.2 and 26.2±0.2 ppm; peaks at 173.4±0.2, 210.7±0.2 and 22.8±0.2 ppm; and peaks at 173.4±0.2, 210.7±0.2, 26.2±0.2, 22.8±0.2 and 25.5±0.2 ppm.

Characteristic Raman peaks for (3S)-3-({N-[(4-methoxy-1H-indol-2-yl)carbonyl]-L-leucyl}amino)-2-oxo-4-[(3S)-2-oxopyrrolidin-3-yl]butyl dihydrogen phosphate DMSO solvate include Raman peaks at 1717±2 and 675±2 cm$^{-1}$.

A characteristic combination of PXRD peaks and $^{13}$C ssNMR peaks for (3S)-3-({N-[(4-methoxy-1H-indol-2-yl)carbonyl]-L-leucyl}amino)-2-oxo-4-[(3S)-2-oxopyrrolidin-3-yl]butyl dihydrogen phosphate DMSO solvate include PXRD peaks at 7.4±0.2, 14.8±0.2 and 26.2±0.2 degrees 2-theta and $^{13}$C ssNMR peaks at 173.4±0.2, 210.7±0.2 and 26.2±0.2 ppm.

A characteristic combination of PXRD peaks and Raman peaks for (3S)-3-({N-[(4-methoxy-1H-indol-2-yl)carbonyl]-L-leucyl}amino)-2-oxo-4-[(3S)-2-oxopyrrolidin-3-yl]butyl dihydrogen phosphate DMSO solvate include PXRD peaks at 7.4±0.2, 14.8±0.2 and 26.2±0.2 degrees 2-theta and Raman peaks at 1717±2 and 675±2 cm$^{-1}$.

A characteristic combination of $^{13}$C ssNMR peaks and Raman peaks for (3S)-3-({N-[(4-methoxy-1H-indol-2-yl)carbonyl]-L-leucyl}amino)-2-oxo-4-[(3S)-2-oxopyrrolidin-3-yl]butyl dihydrogen phosphate DMSO solvate include $^{13}$C ssNMR peaks at 173.4±0.2, 210.7±0.2 and 26.2±0.2 ppm and Raman peaks at 1717±2 and 675±2 cm$^{-1}$.

Characteristic PXRD peaks for (3S)-3-({N-[(4-methoxy-1H-indol-2-yl)carbonyl]-L-leucyl}amino)-2-oxo-4-[(3S)-2-oxopyrrolidin-3-yl]butyl dihydrogen phosphate DMSO solvate hydrate include peaks at 14.5±0.2, 25.6±0.2 and 26.6±0.2 degrees 2-theta; peaks at 14.5±0.2, 21.9±0.2, 25.6±0.2 and 26.6±0.2 degrees 2-theta; and peaks at 14.5±0.2, 17.8±0.2, 21.9±0.2, 25.6±0.2 and 26.6±0.2 degrees 2-theta.

Formulation Examples for (3S)-3-({N-[(4-methoxy-1H-indol-2-yl)carbonyl]-L-leucyl}amino)-2-oxo-4-[(3S)-2-oxopyrrolidin-3-yl]butyl dihydrogen phosphate Lyophile Formulations of (3S)-3-({N-[(4-methoxy-1H-indol-2-yl)carbonyl]-L-leucyl}amino)-2-oxo-4-[(3S)-2-oxopyrrolidin-3-yl]butyl dihydrogen phosphate (3S)-3-({N-[(4-methoxy-1H-indol-2-yl)carbonyl]-L-leucyl}amino)-2-oxo-4-[(3S)-2-oxopyrrolidin-3-yl]butyl dihydrogen phosphate is preferably formulated by forming a solution then performing a freeze-drying process to manufacture a lyophile. The (3S)-3-({N-[(4-methoxy-1H-indol-2-yl)carbonyl]-L-leucyl}amino)-2-oxo-4-[(3S)-2-oxopyrrolidin-3-yl]butyl dihydrogen phosphate form can be as the free acid or as a suitable salt. Preferred counter-ions to form a salt of (3S)-3-({N-[(4-methoxy-1H-indol-2-yl)carbonyl]-L-leucyl}amino)-2-oxo-4-[(3S)-2-oxopyrrolidin-3-yl]butyl dihydrogen phosphate (i.e. the salt of the phosphate moiety) include choline, meglumine, benzathine, diethylamine, tris (hydroxymethyl)aminomethane, diolamine, piperazine, more preferred counter-ions include potassium, magnesium, and calcium, and most preferred counter-ion is sodium. The lyophilized solution is preferably formulated in the range of pH 2 to pH 6, more preferably pH 3 to pH 5 and most preferably in the range pH 3.5 to pH 4.5. In order to maintain the required pH the formulation is buffered, with preferred buffers being lactic acid, phosphoric acid, acetic acid, and tartaric acid, with the most preferred buffer being citric acid. The pH of the formulation may be adjusted and controlled by addition of a suitable basic excipient, preferred bases include choline, meglumine, benzathine, diethylamine, tris(hydroxymethyl)aminomethane, diolamine, piperazine, more preferred bases are potassium hydroxide, magnesium hydroxide, and calcium hydroxide, and the most preferred base is sodium hydroxide.

A bulking agent, tonicity modifier, or water scavenging excipient may also be included, where preferred excipients include sugars, polyalcohols, polymers, and amino acids, more preferred excipients include dextran, polyvinylpyrrolidone, and glycine, and most preferred excipients include trehalose, sucrose, lactose, mannitol, polyethylene glycol 400, and polyethylene glycol 3350. Furthermore, the formulation may include a solubilizing agent, where preferred excipients include surfactants and complexing agents (e.g. cyclodextrins), with more preferred excipients of polysorbate 20, Cremophor EL, Kolliphor HS-15, hydroxypropyl-beta-cyclodextrin, sulfobutylether-beta cyclodextrin, gamma cyclodextrin, and most preferred polysorbate 80.

The water content of the lyophilized formulation following manufacture is preferred to be <2% w/w, more preferably <1% w/w, and most preferably <0.5% w/w. The concentration of (3S)-3-({N-[(4-methoxy-1H-indol-2-yl)carbonyl]-L-leucyl}amino)-2-oxo-4-[(3S)-2-oxopyrrolidin-3-yl]butyl dihydrogen phosphate before lyophilization and after reconstitution is preferred to be in the range 10-300 mg/mL, more preferably 25-150 mg/mL, and most preferably in the range 50-125 mg/mL. The formulation can be reconstituted and diluted in sterile water for injection, 0.9% w/v sodium chloride (Normal Saline), or 5% w/v dextrose solution.

Powder in a Bottle Formulation:

(3S)-3-({N-[(4-methoxy-1H-indol-2-yl)carbonyl]-L-leucyl}amino)-2-oxo-4-[(3S)-2-oxopyrrolidin-3-yl]butyl dihydrogen phosphate can also be formulated as a powder. In this case, (3S)-3-({N-[(4-methoxy-1H-indol-2-yl)carbonyl]-L-leucyl}amino)-2-oxo-4-[(3S)-2-oxopyrrolidin-3-yl]butyl dihydrogen phosphate can be filled into a vial as a powder and reconstituted to a suitable pH. The (3S)-3-({N-[(4-methoxy-1H-indol-2-yl)carbonyl]-L-leucyl}amino)-2-oxo-4-[(3S)-2-oxopyrrolidin-3-yl]butyl dihydrogen phosphate can be added as the free acid or as a suitable salt. Preferred counter-ions to form a salt of (3S)-3-({N-[(4-methoxy-1H-indol-2-yl)carbonyl]-L-leucyl}amino)-2-oxo-4-[(3S)-2-oxopyrrolidin-3-yl]butyl dihydrogen phosphate include choline, meglumine, benzathine, diethylamine, tris(hydroxymethyl)aminomethane, diolamine, piperazine, more preferred counter-ions include potassium, magnesium, and calcium, and the most preferred counter-ion is sodium. Following reconstitution of the solution the preferred range of pH 2 to pH 6, more preferably pH 3 to pH 5 and most preferably in the range pH 3.5 to pH 4.5. In order to maintain the required pH the formulation is buffered with preferred buffers being lactic acid, phosphoric acid, acetic acid, and tartaric acid, with the most preferred buffer being citric acid. The pH of the formulation is adjusted controlled by inclusion of a suitable base, preferred bases include choline, meglumine, benzathine, diethylamine, tris(hydroxymethyl)aminomethane, diolamine, piperazine, more preferred bases are potassium hydroxide, magnesium hydroxide, and calcium hydroxide, and the most preferred base is sodium hydroxide.

A bulking agent, tonicity modifier, or water scavenging excipient may also be included, where preferred excipients include sugars, polyalcohols, polymers, and amino acids, more preferred excipients include dextran, polyvinylpyrrolidone, and glycine, and most excipients include trehalose, sucrose, lactose, mannitol, polyethylene glycol 400, and polyethylene glycol 3350. Furthermore, the formulation may include a solubilizing agent, where preferred excipients include surfactants and complexing agents (e.g. cyclodextrins), with more preferred excipients of polysorbate 20, Cremophor EL, Kolliphor HS-15, hydroxypropyl-beta-cyclodextrin, sulfobutylether-beta cyclodextrin, gamma cyclodextrin, and most preferred polysorbate 80.

The concentration of (3S)-3-({N-[(4-methoxy-1H-indol-2-yl)carbonyl]-L-leucyl}amino)-2-oxo-4-[(3S)-2-oxopyrrolidin-3-yl]butyl dihydrogen phosphate after reconstitution is preferred to be in the range 10-300 mg/mL, more preferably 25-150 mg/mL, and most preferably in the range 50-125 mg/mL. The formulation can be reconstituted and diluted in sterile water for injection, 0.9% w/v sodium chloride (Normal Saline), or 5% w/v dextrose solution.

General Methodologies for PF-07304814 Formulation Examples

Karl Fischer Assessment of Water Content

The moisture content of lyophilized samples was determined by a coulometric method using a Karl Fisher (KF) Titrator (Mettler Toledo C30) equipped with double pin platinum electrode DM143-SC, connected to an Analytical Balance (Mettler Toledo XP56). Hydranal Coulomat AD (Fluke) was used as the KF vessel solution. The instrument was conditioned until the background drift was below 20 mg/min. Samples were analyzed after an initial water check passed for system suitability criteria per guidelines. Briefly, 100 mg of sample was placed in a test tube and placed on an analytical balance. The balance was then tared, and sample quickly transferred to the KF vessel and stoppered. The empty tube was weighed again on the balance to check for residual sample, if any. The sample was automatically titrated and results of the experiment were printed out as sample size and water content. Samples were measured in duplicates and the % moisture content was reported as averaged value.

Ultra-High Performance Liquid Chromatography (UPLC) Assessment of Purity

Determination of assay and purity of PF-07304814 was performed using a gradient UPLC method with UV detection. The column used for analysis has a pentafluorophenyl with TMS end capping stationary phase. The mobile phase was prepared by mixing aqueous ammonium formate and ammonium formate in methanol. Impurities were defined by their relative retention times (RRT) based on the PF-07304814 peak. Assay was quantitated by comparing the corresponding peak area from a sample solution chromatogram to that of the PF-07304814 peak from a Standard solution of a known concentration. Area Percent (%) of each impurity peak was calculated by comparing the impurity peak area to that of Total peak area (Sum of peak area from PF-07304814 and impurities).

Modulated Differential Scanning Calorimetry (mDSC) Characterization

Lyophilized samples were analyzed using a TA Instruments DSC Q1000 instrument. The software for analysis is Universal Analysis 2000 (version 4.5 A, build 4.5.0.5). Briefly, the sample was sealed in an aluminum pan and the temperature was ramped from −20 to 200° C. at a rate of 2° C./min, modulated ±0.53° C. every 100 seconds. The $T_g$ and other thermal events were analyzed.

Powder X-Ray Diffraction (PXRD) Characterization

Lyophilized samples were analyzed via PXRD to assess the structure of the lyophile using a Rigaku Miniflex 600 diffractometer. The diffractometer was used with a 40 kV/15 mA tube power and a scintillation detector. The slit condition used was Varied+Fixed system, with incident beam path settings of 5.0°, 10.0 mm for the IHS, and 1.25° for the DS, and diffracted beam settings of 0.3 mm for the RS. The samples were analyzed in step mode, beginning at a 2θ of 2° and ending at 40°, with a step of 0.02° for a 1 second duration. Raw data was processed using Rigaku PDXL software (version 1.8.0.3).

Formulation Examples for (3S)-3-({N-[(4-methoxy-1H-indol-2-yl)carbonyl]-L-leucyl}amino)-2-oxo-4-[(3S)-2-oxopyrrolidin-3-yl]butyl dihydrogen phosphate (PF-07304814): pH, Buffer, and PF-07304814 Concentration of PF-07304814 Formulations Formulation pH To evaluate possible pH ranges for PF-07304814 formulations, PF-07304814 formulations were prepared at pH 1 to pH 7 and the chemical stability was evaluated by HPLC over time.

Approximately 1.35 mg of PF-07304814 was weighed into 20 mL scintillation vials, with 2 replicates per pH value. To each vial, 7 mL of purified water was added, followed by a predicted amount of 0.01 M, 0.1 M, or 1 M HCl or NaOH. The pH of each formulation was measured, and if off by more than +/−0.2 units, the pH was adjusted using 0.01 M HCl or NaOH until the target pH was achieved. Purified water was then added to a target volume of 10 mL. The vials were then capped, mixed, and placed on stability at room temperature. After 1, 3, and 6 days, 150 μL aliquots of each formulation were removed and transferred to an HPLC vial for analysis of purity.

From the experimental data in the pH Stability Table below, the preferred pH range is approximately pH 2 to approximately pH 6, and the most preferred pH range is approximately pH 3 to approximately pH 5. This preferred pH applies to the solution prior to lyophilization, the reconstituted solution after lyophilization, and the diluted solution for IV administration.

pH Stability Table: The chemical stability of an approximately 0.13 mg/mL PF-07304814 solution was evaluated as a function of pH over 6 days at room temperature to understand the optimal pH range. The total impurities, as determined by UPLC determination of chromatographic purity, is reported.

pH Stability Table

| pH | Total Impurities (%) | | |
|---|---|---|---|
| | 1 day | 3 days | 6 days |
| 1.0 | 12.6 | 25.8 | 44.9 |
| 1.9 | 3.2 | 5.4 | 8.9 |
| 2.9 | 2.0 | 2.5 | 3.0 |
| 4.2 | 3.0 | 3.8 | 6.5 |
| 5.1 | 4.8 | 8.8 | 16.0 |
| 5.9 | 7.9 | 15.3 | 25.0 |
| 6.9 | 13.6 | 24.9 | 32.7 |

Buffer Composition

To evaluate possible buffer compositions for PF-07304814 formulations, PF-07304814 formulations were prepared with no buffer, with citrate buffer, and with lactate buffer. For each of these formulations, the chemical stability and pH were evaluated by HPLC over time.

Concentrated stock solutions were prepared in 250 mL volumetric flasks, such that the final pH would be 3, 4, or 5 after addition of PF-07304814 to a concentration of approximately 25 mg/mL. For stock solutions without buffer, a specified amount of 1 M NaOH was added, and then the flask was filled to volume with purified water. For the citrate buffers, approximately 1471 mg of sodium citrate dihydrate was added to each flask along with a specified amount 1 M NaOH, and then the flask was filled to volume with purified water. For the lactate buffers, approximately 1868 mg of sodium lactate (60% w/w) was added to each flask along with a specified amount 1 M NaOH, and then the flask was filled to volume with purified water.

Approximately 75 mg of PF-07304814 was weighed into 3 mL glass vials. To each vial, 1.2 mL of purified water was added, followed by 1.5 mL of the concentrated stock solution. The pH of each formulation was then measured, and if off by more than +/−0.2 units, the pH was adjusted using 0.1 M HCl or NaOH until the target pH was achieved. Purified water was then added to a target volume of 3 mL. The resultant formulations should have either no buffer, a 10 mM citrate buffer, or a 20 mM lactate buffer with final pH values of 3, 4, and 5 for each formulation. The vials were then stoppered, capped, mixed, and placed on stability at 25° C. After 4 days, the solution pH was measured and 50 μL aliquots of each formulation were transferred to an HPLC vial for analysis of purity.

From the experimental data in the Buffer Composition Table below, no significant differences in total impurities were observed across the different formulations at a specific pH, which suggests that there were no chemical compatibility issues between the buffers tested and PF-07304814. There were no significant trends in the qualitative impurity profile that formed as a function of the buffer used (data not shown). However, the inclusion of citrate buffer at 10 mM does appear to enable greater control of the pH at pH values of approximately 3 and 4, as compared to samples without a buffer. Consequently, in order to keep the drug product within the target pH specification, and in turn, to limit unwanted pH-dependent degradation, a citrate buffer was selected at a molar ratio of 4.5:1 for PF-07304814 to buffer. This preferred buffer composition applies to the solution prior to lyophilization, the lyophilized powder, the reconstituted solution after lyophilization, and the diluted solution for IV administration.

Buffer Composition Table: The chemical stability of 25 mg/mL PF-07304814 formulations at 45 mM were evaluated at 3 different pH levels (3, 4, and 5) without buffer, with 10 mM citrate buffer, and with 20 mM lactate buffer to understand the optimal buffer composition. The increase in total impurities is reported as the difference between the initial total impurities and the measured total impurities after 4 days at 25° C.

Buffer Composition Table

| Target pH | Buffer | Buffer Concentration (mM) | PF-07304814:Buffer Molar Ratio | Increase in Total Impurities (%) - 4 days | pH Change - 4 days |
|---|---|---|---|---|---|
| 3 | None | 0 | — | 0.8 | 0.4 |
|   | Citrate | 10 | 4.5:1 | 1.2 | 0.1 |
|   | Lactate | 20 | 2.3:1 | 1.2 | 0.3 |
| 4 | None | 0 | — | 1.4 | 0.2 |
|   | Citrate | 10 | 4.5:1 | 1.5 | 0.0 |
|   | Lactate | 20 | 2.3:1 | 1.6 | −0.1 |
| 5 | None | 0 | — | 4.3 | 0.1 |
|   | Citrate | 10 | 4.5:1 | 4.1 | −0.2 |
|   | Lactate | 20 | 2.3:1 | 3.6 | −0.1 |

PF-07304814 Concentration

To evaluate possible PF-07304814 concentrations in solution prior to lyophilization and in the reconstituted lyophile solutions, PF-07304814 formulations were prepared at approximately 50, approximately 100, and approximately 200 mg/mL, while keeping a fixed ratio of PF-07304814 to citrate buffer of 4.5:1. For each of these formulations, the chemical stability and pH were evaluated by HPLC over time.

Concentrated buffer solutions were first prepared in 250 mL volumetric flasks, such that the final pH value would be 4 after addition of PF-07304814 to a concentration of approximately 50 mg/mL, approximately 100 mg/mL, or approximately 200 mg/mL. For the 50 mg/mL PF-07304814 formulation, a 40 mM citrate buffer was prepared by adding 2.94 g of sodium citrate dihydrate and 27.4 mL of 1 N NaOH and diluting to volume with purified water. For the 100 mg/mL PF-07304814 formulation, an 80 mM citrate buffer was prepared by adding 5.88 g of sodium citrate dihydrate and 55.5 mL of 1 N NaOH and diluting to volume with purified water. For the 200 mg/mL PF-07304814 formulation, a 160 mM citrate buffer was prepared by adding 11.76 g of sodium citrate dihydrate and 112.5 mL of 1 N NaOH and diluting to volume with purified water.

Approximately 200 mg, approximately 400 mg, or approximately 800 mg of PF-07304814 was weighed into 10 mL glass vials. To each vial, 2 mL of the appropriate concentrated buffer solution was added, followed by 2 mL of purified water. The pH of each formulation was then measured, and if off by more than +/−0.2 units, the pH was adjusted using 0.1 M HCl or NaOH until the target pH was achieved. The resultant formulations should have PF-07304814 concentrations of approximately 50 mg/mL, approximately 100 mg/mL, or approximately 200 mg/mL with 20 mM, 40 mM, or 80 mM citrate buffer, respectively. The vials were then stoppered, capped, mixed, and placed on stability at 25° C. After 3, 6, and 13 days, the solution pH was measured, and aliquots of each formulation were transferred to an HPLC vial for analysis of purity.

From the experimental data in the Formulation Chemical Stability Table below, the chemical stability of PF-07304814 formulations was comparable across PF-07304814 concentrations of 50 mg/mL to 200 mg/mL. The tested concentrations behave comparably. This preferred PF-07304814 concentration range supports possible solutions prior to lyophilization and reconstituted solutions after lyophilization. Formulations with lower PF-07304814 concentrations from approximately 1 mg/mL to approximately 25 mg/mL also have acceptable chemical stability, as demonstrated in the examples in the pH Stability and Buffer Composition Table, above, which may further cover possible diluted solutions for IV administration.

Formulation Chemical Stability Table: The chemical stability of PF-07304814 formulations were evaluated at 3 different PF-07304814 concentrations (50 mg/mL, 100 mg/mL and 200 mg/mL) with a fixed PF-07304814 to citrate buffer molar ratio of 4.5:1. The increase in total impurities is reported as the difference between the initial total impurities and the measured total impurities after 3, 6, or 13 days at 25° C.

Formulation Chemical Stability Table

| pH at Day 0 | PF-07304814 Concentration (mg/mL) | Citrate Buffer Concentration (mM) | PF-07304814:Buffer Molar Ratio | Increase in Total Impurities (%) | | |
|---|---|---|---|---|---|---|
|  |  |  |  | Day 3 | Day 6 | Day 13 |
| 4.0 | 200 | 80 | 4.5:1 | 0.9 | 1.8 | 4.2 |
| 4.0 | 100 | 40 | 4.5:1 | 1.0 | 1.7 | 4.2 |
| 4.0 | 50 | 20 | 4.5:1 | 0.7 | 1.7 | 3.8 |

Formulation Example 1: Preparation of 100 mg/mL (3S)-3-({N-[(4-methoxy-1H-indol-2-yl)carbonyl]-L-leucyl}amino)-2-oxo-4-[(3S)-2-oxopyrrolidin-3-yl] butyl dihydrogen phosphate as a Solution in Citrate Buffer Step 1: Preparation of 250 mL preparation of 80 mM sodium citrate buffer 5.89 g of sodium citrate dihydrate (USP Grade) added to 250 mL volumetric flask. 125 mL of purified water added to volumetric flask, followed by 55.5 mL of 1 N sodium hydroxide solution. Solution diluted to target volume with purified water and inverted to mix until homogeneous. Solution was vacuum filtered through a 0.2 um nylon filter.

Drug Product Formulation Example 1 A 5 mL of 80 mM sodium citrate buffer solution was added to 20 mL beaker with magnetic flea. 1.03 g of (3S)-3-({N-[(4-methoxy-1H-indol-2-yl)carbonyl]-L-leucyl}amino)-2-oxo-4-[(3S)-2-oxopyrrolidin-3-yl]butyl dihydrogen phosphate (as the Form 1 hydrate) was added to the beaker to form a solution and mixed for 25 minutes. 3 mL of purified water added to beaker and mixed for 5 minutes. Solution titrated to target pH of 4 using 1 N sodium hydroxide solution or 1 N hydrochloric acid solution (Fisher Chemical). Solution diluted to target volume in volumetric flask or to target mass based on density with purified water and inverted to mix until homogeneous. The solution was syringe filtered through a 0.2 um PVDF filter. The final composition of the formulation was 10 mL of a pH 4 solution with ~100 mg/mL (3S)-3-({N-[(4-methoxy-1H-indol-2-yl)carbonyl]-L-leucyl}amino)-2-oxo-4-[(3S)-2-oxopyrrolidin-3-yl]butyl dihydrogen phosphate, form 1 hydrate and 40 mM citrate buffer (molar ratio of PF-07304814 to citrate of 4.5:1).

Drug Product Formulation Example 1B 5 mL of refrigerated 80 mM sodium citrate buffer solution was added to 20 mL beaker with magnetic flea. The beaker was placed in a water bath controlled to 2-8° C. 1.03 g of (3S)-3-({N-[(4-methoxy-1H-indol-2-yl)carbonyl]-L-leucyl}amino)-2-oxo-4-[(3S)-2-oxopyrrolidin-3-yl]butyl dihydrogen phosphate (as the Form 1 hydrate) was added to the beaker to form a solution and mixed for 25 minutes. 3 mL of refrigerated purified water added to beaker and mixed for 5 minutes. Solution titrated to target pH of 4 using 1 N sodium hydroxide solution or 1 N hydrochloric acid solution (Fisher Chemical). Solution diluted to target volume in volumetric flask or to target mass based on density with purified water and inverted to mix until homogeneous. The solution was syringe filtered through a 0.2 um PVDF filter. The final composition of the formulation was 10 mL of a pH 4 solution with ~100 mg/mL (3S)-3-({N-[(4-methoxy-1H-indol-2-yl)carbonyl]-L-leucyl}amino)-2-oxo-4-[(3S)-2-oxopyrrolidin-3-yl]butyl dihydrogen phosphate, form 1 hydrate and 40 mM citrate buffer (molar ratio of PF-07304814 to citrate of 4.5:1).

Drug Product Formulation Example 1C 3 mL of refrigerated purified water was added to 20 mL beaker with magnetic flea. The beaker was placed in a water bath controlled to 2-8° C. 1.03 g of (3S)-3-({N-[(4-methoxy-1H-indol-2-yl)carbonyl]-L-leucyl}amino)-2-oxo-4-[(3S)-2-oxopyrrolidin-3-yl]butyl dihydrogen phosphate, form 1 hydrate was added to the beaker to form a suspension and mixed for 5 minutes. 5 mL of refrigerated 80 mM sodium citrate buffer solution was added to the beaker to form a solution and mixed for 25 minutes. Solution titrated to target pH of 4 using 1 N sodium hydroxide solution or 1 N hydrochloric acid solution (Fisher Chemical). Solution diluted to target volume in volumetric flask or to target mass based on density with purified water and inverted to mix until homogeneous. Solution was syringe filtered through a 0.2 um PVDF filter. Final composition of the formulation was ~100 mg/mL (3S)-3-({N-[(4-methoxy-1H-indol-2-yl)carbonyl]-L-leucyl}amino)-2-oxo-4-[(3S)-2-oxopyrrolidin-3-yl]butyl dihydrogen phosphate, form 1 hydrate, 40 mM citrate buffer, and pH 4 (molar ratio of PF-07304814 to citrate of 4.5:1).

Drug Product Formulation Example 1D 5 mL of purified water was added to 20 mL beaker with magnetic flea. 77.1 mg of citric acid anhydrous (USP grade, Fisher Chemical) was added to the beaker, followed by 0.92 mL of 1 N sodium hydroxide solution, and mixed for 5 minutes. 0.517 g of (3S)-3-({N-[(4-methoxy-1H-indol-2-yl)carbonyl]-L-leucyl}amino)-2-oxo-4-[(3S)-2-oxopyrrolidin-3-yl]butyl dihydrogen phosphate, form 1 hydrate was added to the beaker to form a solution and mixed for 5 minutes. 1.12 mL of 1 N sodium hydroxide solution added to beaker and mixed for 5 minutes. 0.556 g of (3S)-3-({N-[(4-methoxy-1H-indol-2-yl)carbonyl]-L-leucyl}amino)-2-oxo-4-[(3S)-2-oxopyrrolidin-3-yl]butyl dihydrogen phosphate, form 1 hydrate was added to the beaker to form a solution and mixed for 5 minutes. Solution titrated to target pH of 4 using 0.29 mL of 1 N sodium hydroxide solution. Solution diluted to target volume in volumetric flask or to target mass based on density with purified water and inverted to mix until homogeneous. The solution was syringe filtered through a 0.2 um PVDF filter. The final composition of the formulation was 10 mL of a pH 4 solution with ~100 mg/mL (3S)-3-({N-[(4-methoxy-1H-indol-2-yl)carbonyl]-L-leucyl}amino)-2-oxo-4-[(3S)-2-oxopyrrolidin-3-yl]butyl dihydrogen phosphate, form 1 hydrate and 40 mM citrate buffer (molar ratio of PF-07304814 to citrate of 4.5:1).

Drug Product Formulation 1E

Preparation of 100 mg/mL (3S)-3-({N-[(4-methoxy-1H-indol-2-yl)carbonyl]-L-leucyl}amino)-4-[(3S)-2-oxypyrrolidin-3-yl)butyl dihydrogen phosphate (PF-07304814) Solution with 5 mg/mL Polysorbate 80

To prevent the precipitation of poorly soluble PF-07304814-related impurities or degradants, we investigated the preparation of formulations with solubilizing excipients, and specifically, with polysorbate 80. The composition of the formulation was consistent with Examples 1A-1D, with 100 mg/mL of PF-07304814, a pH of 4.0, a citrate buffer at 40 mM (molar ratio of PF-07304814 to citrate of approximately 4.5:1), and an approximate ratio of sodium to PF-07304814 of approximately 1.3:1. The solution also included 5 mg/mL Polysorbate 80. To further confirm that such solutions could be lyophilized without significant degradation to produce a lyophile, lyophilization cycle development was pursued. The polysorbate 80 content of the lyophilized powder was approximately 4% w/w.

Preparation of 80 mM Sodium Citrate Buffer 5.89 g of sodium citrate dihydrate (USP Grade) added to 250 mL volumetric flask. 125 mL of purified water added to volumetric flask, followed by 55.5 mL of 1 N sodium hydroxide solution. Solution diluted to target volume with purified water and inverted to mix until homogeneous. Solution was vacuum filtered through a 0.2 μm nylon filter.

Preparation of 250 mg/mL Polysorbate 80 Solution 2.50 g of polysorbate 80 (NF Grade, Spectrum) added to 10 mL volumetric flask. Solution diluted to target volume with purified water and inverted to mix until homogeneous.

Preparation of Drug Product Formulation—100 mg/mL PF-07304814 Solution with 5 mg/mL Polysorbate 80

5.0 mL of refrigerated 80 mM sodium citrate buffer solution was added to 20 mL beaker with magnetic flea. The beaker was placed in a water bath controlled to 2-8° C. Approximately 1.04 g of (3S)-3-({N-[(4-methoxy-1H-indol-2-yl)carbonyl]-L-leucyl}amino)-2-oxo-4-[(3S)-2-oxopyrrolidin-3-yl]butyl dihydrogen phosphate, form 1 hydrate was added to the beaker to form a solution and mixed for approximately 25 minutes. 3.0 mL of refrigerated purified water added to beaker and mixed for 5 minutes. Solution diluted to target mass of 10.35 g with purified water and mixed via stir bar until homogeneous. The solution was syringe filtered through a 0.2 μm PVDF filter. The final composition of the formulation was approximately 10 mL of a pH 4 solution with approximately 100 mg/mL (3S)-3-({N-[(4-methoxy-1H-indol-2-yl)carbonyl]-L-leucyl}amino)-2-oxo-4-[(3S)-2-oxopyrrolidin-3-yl]butyl dihydrogen phosphate, form 1 hydrate, 40 mM citrate buffer, and 5 mg/mL polysorbate 80. (molar ratio of PF-07304814 to citrate of 4.5:1).

Dilution of Drug Product Formulations

To confirm that the presence of a solubilizing excipient can help prevent the precipitation of poorly soluble impurities or degradants, formulations were prepared with and without polysorbate 80, diluted in a manner consistent with how they would be prepared for IV administration, and monitored for the formation of visible and sub-visible particulates. Importantly, a small amount of polysorbate 80 (5 mg/mL) in the pharmaceutical composition (before and after reconstitution) can significantly reduce the formation of particulates in diluted solutions for IV administration.

Formulations with 0 and 5 mg/mL polysorbate 80 were prepared as described above in Drug Product Formulation 1D and 1E, respectively. Formulations were then diluted to 25 mg/mL of (3S)-3-({N-[(4-methoxy-1H-indol-2-yl)carbonyl]-L-leucyl}amino)-2-oxo-4-[(3S)-2-oxopyrrolidin-3-yl]butyl dihydrogen phosphate in either 0.9% w/v Sodium Chloride Injection (USP, B. Braun) or 5% w/v Dextrose Injection (USP, B. Braun). For 25 mg/mL dilutions of (3S)-3-({N-[(4-methoxy-1H-indol-2-yl)carbonyl]-L-leucyl}amino)-2-oxo-4-[(3S)-2-oxopyrrolidin-3-yl]butyl dihydrogen phosphate, 3.0 mL of 0.9% w/v Sodium Chloride Injection or 5% w/v Dextrose Injection was added to a vial, followed by 1.0 mL of formulation. All solutions were stoppered, inverted to mix, and stored at room temperature for two days. The resultant dilutions were then analyzed for visible particulates via USP<790> and sub-visible particulates via dynamic flow imaging after 0, 1, and 2 days.

Visible Particulate Analysis

Visual inspection was performed on diluted formulation samples and diluent placebos to monitor visible particulate formation. When tested in accordance with the USP<790> method, samples with polysorbate 80 were 'essentially free from particulates' for 2 days. Samples without polysorbate 80, had >10 visible particulates immediately after dilution. Particulates are associated with API-related impurities.

Subvisible Particulate Analysis

The 25 mg/mL diluted formulation samples and diluent placebos were analyzed by dynamic flow imaging over two days. Utilizing a FlowCam 8100 with a calibrated 10× objective, 1.00 mL of solution was sampled from each vial and run through a clean liquid flow cell. During the image acquisition process, a 4-100 µm equivalent spherical diameter (ESD) pre-filter was applied to align with the size constraints defined by the flow-cell. The results of the acquisitions were exported from the FlowCam 8100 to the Lumetics Link software for further processing. Using Lumetics Link, the entire particle population of each run was filtered into sub-visible size ranges (4-10 µm, 10-25 µm, 25-50 µm, and 50-100 µm). From this analysis, the majority of particulates were observed between 4-10 µm in size. Greater than 90% of the particulates are below 25 µm in size utilizing ESD. Importantly, the data indicated substantially less particulates in drug product samples containing polysorbate 80 as compared to drug products without polysorbate 80. The reduction in particulates with polysorbate 80 is consistent with the visual inspection results and demonstrate that polysorbate 80 solubilizes API-related impurities that cause the formation of visible and sub-visible particulates. The subvisible particulate counts are comparable to placebo. Results are reported in the Particulate Data Table for Day 0, but consistent trends are observed at Day 1 and Day 2.

Particulate Data Table: Subvisible particulate count per mL of 100 mg/mL formulations of (3S)-3-({N-[(4-methoxy-1H-indol-2-yl)carbonyl]-L-leucyl}amino)-2-oxo-4-[(3S)-2-oxopyrrolidin-3-yl]butyl dihydrogen phosphate with 0 or 5 mg/mL of polysorbate 80 diluted in saline or dextrose to a concentration of 25 mg/mL (3S)-3-({N-[(4-methoxy-1H-indol-2-yl)carbonyl]-L-leucyl}amino)-2-oxo-4-[(3S)-2-oxopyrrolidin-3-yl]butyl di hydrogen phosphate. Analysis was performed via dynamic flow imaging. Data reported is on day 0, within several hours of dilution.

| | Particulate Counts per mL in Saline Dilutions | | |
|---|---|---|---|
| Particulate Size (µm) | Placebo | Without polysorbate 80 | With polysorbate 80 |
| 4-10 | 37 | 378 | 65 |
| 10-25 | 10 | 226 | 13 |
| 25-50 | 3 | 63 | 11 |
| 50-100 | 0 | 10 | 0 |

| | Particulate Counts per mL in Dextrose Dilutions | | |
|---|---|---|---|
| Particulate Size (µm) | Placebo | Without polysorbate 80 | With polysorbate 80 |
| 4-10 | 307 | 629 | 65 |
| 10-25 | 72 | 220 | 10 |
| 25-50 | 10 | 37 | 3 |
| 50-100 | 0 | 7 | 0 |

Formulation Example 2: Lyophilization of 100 mg/mL (3S)-3-({N-[(4-methoxy-1H-indol-2-yl)carbonyl]-L-leucyl}amino)-2-oxo-4-[(3S)-2-oxopyrrolidin-3-yl]butyl dihydrogen phosphate, form 1 hydrate Solution 10 mL of filtered 100 mg/mL solution of (3S)-3-({N-[(4-methoxy-1H-indol-2-yl)carbonyl]-L-leucyl}amino)-2-oxo-4-[(3S)-2-oxopyrrolidin-3-yl]butyl dihydrogen phosphate, form 1 hydrate solution (as prepared in Formulation Example 1D above) was filled into 20 mL vials with a 20 mm neck diameter and partially stoppered. The filled and partially stoppered vials were placed on a tray and the tray was loaded into the lyophilizer (LyoStar). The lyophilizer was sealed and the shelf temperature was cooled to −45° C. at a rate of 0.5° C. per minute and held for 1 hour. A vacuum pressure was set to 150 mTorr and the lyophilizer was held for 1 hour. The shelf temperature was then heated to 25° C. at a rate of 0.5° C. per minute and held for 27 hours. At the conclusion of primary drying, the chamber was backfilled with nitrogen and the shelf temperature was chilled to 5° C. Samples were stoppered within the lyophilizer, the vacuum was released, and the samples were removed to provide the product as a lyophile in a vial.

Characterization of the PF-07304814 Lyophile

Figure 22:
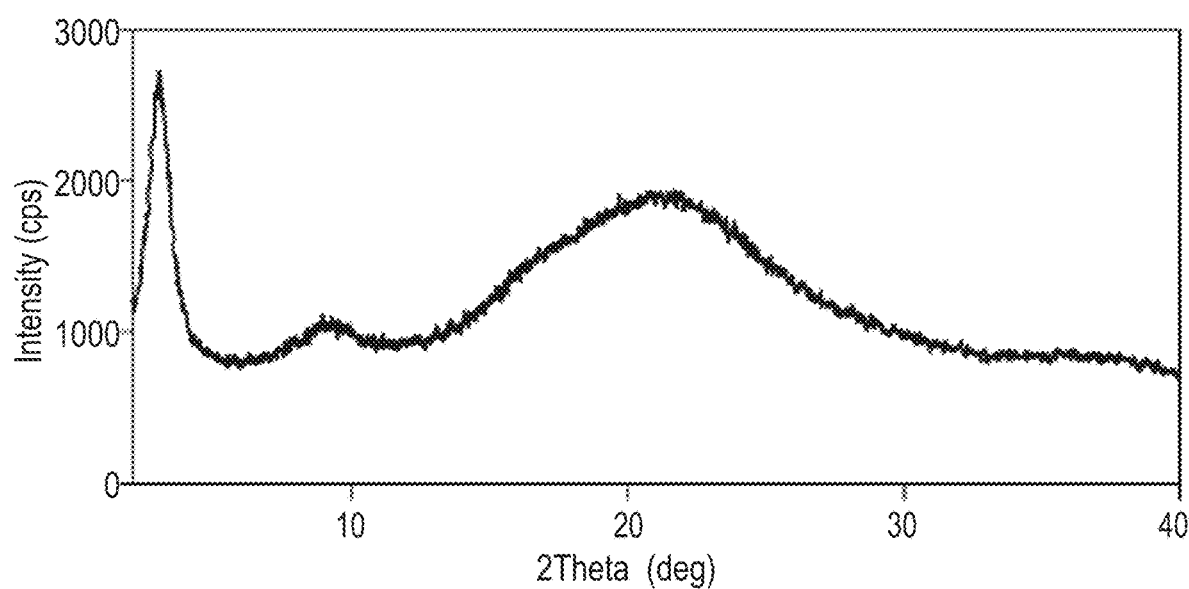
FIG. 22: Representative PXRD diffraction pattern of a lyophilized drug product of PF-07304814.

After lyophilization the sample appeared as a cake to powder with a white to off-white/yellow/brown color. The lyophilized samples show minimal evidence of meltback, collapse, and shrinkage. The water content of the lyophilized powder, as measured by Karl Fischer, was approximately 0.6% w/w. The chromatographic purity of the samples, as measured by UPLC, changed by approximately 0.1% between pre- and post-lyophilization. A single $T_g$ was observed via mDSC with a temperature of 109.4° C. Lyophilized samples appear to be predominantly amorphous in structure as measured by PXRD, with one broad peak observed at 2θ of approximately 3.0° (see FIG. 22).

Formulation Example 2 A: Lyophilization of 100 mg/mL PF-07304814 Solution with 5 mg/mL Polysorbate 80 at 10.9 mL Fill Volume To prevent the precipitation of poorly soluble PF-07304814-related impurities or degradants, we investigated the preparation of formulations with solubilizing excipients, and specifically, with polysorbate 80. The composition of the formulation was consistent with Example 2, with 100 mg/mL of PF-07304814, a pH of 4.0, a citrate buffer at 40 mM (molar ratio of PF-07304814 to citrate of approximately 4.5:1), and an approximate ratio of sodium to PF-07304814 of approximately 1.3:1. The solution also included 5 mg/mL Polysorbate 80. To further confirm that such solutions could be lyophilized without significant degradation to produce a lyophile, lyophilization cycle development was pursued. The polysorbate 80 content of the lyophilized powder was approximately 4% w/w.

Lyophilization of 100 mg/mL PF-07304814 Solution with 5 mg/mL Polysorbate 80 at 10.9 mL Fill Volume 10.9 mL of filtered 100 mg/mL PF-07304814 solution (from Formulation 1E above) was filled into 20 mL vials with a 20 mm neck diameter and partially stoppered. The filled and partially stoppered vials were placed on a tray and the tray was loaded into the lyophilizer. The lyophilizer was sealed and the shelf temperature was cooled to −45° C. at a rate of 0.5° C. per minute and held for 1 hour. A vacuum pressure was set to 150 mTorr and the lyophilizer was held for 1 hour. The shelf temperature was then heated to 25° C. at a rate of 0.5° C. per minute and held for 27 hours. At the conclusion of secondary drying, the chamber was backfilled with nitrogen and the shelf temperature was chilled to 5° C. Samples were stoppered within the lyophilizer, the vacuum was released, and the samples were removed.

Characterization of PF-07304814 Lyophile Prepared with 5 mg/mL Polysorbate 80 at 10.9 mL Fill Volume After lyophilization the sample appeared as a cake to powder with a white to off-white/yellow/brown color. The lyophilized samples show minimal evidence of meltback, collapse, and shrinkage. The water content of the lyophilized powder, as measured by Karl Fischer, was approximately 0.5% w/w. The chromatographic purity of the samples, as measured by UPLC, changed by approximately 0.1% between pre- and post-lyophilization. A single $T_g$ was observed via mDSC with a temperature of 101.2° C.

Figure 23:
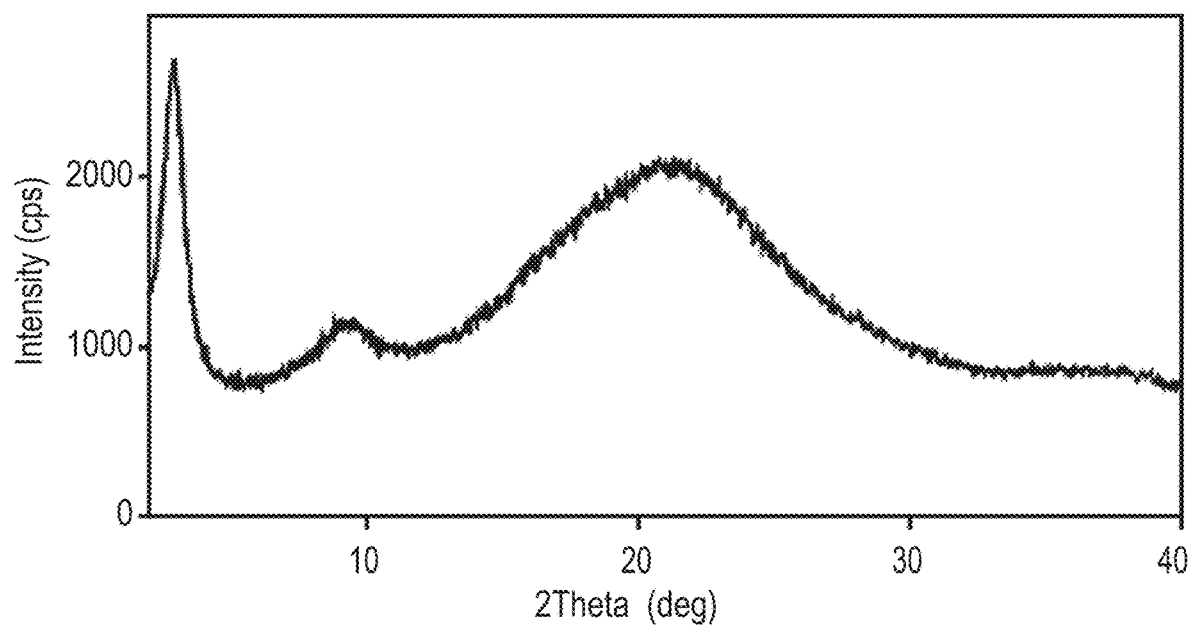
FIG. 23: PXRD characterization of PF-07304814 Lyophile Prepared with 5 mg/mL Polysorbate 80.

Lyophilized samples appear to be predominantly amorphous in structure as measured by PXRD, with one broad peak observed at 2θ of approximately 3.0° (see FIG. 23).

Formulation Example 2B: Lyophilization of 100 mg/mL PF-07304814 Solution with 5 mg/mL Polysorbate 80 at 5.45 mL Fill Volume 5.45 mL of filtered 100 mg/mL PF-07304814 solution was filled into 20 mL vials with a 20 mm neck diameter and partially stoppered. The filled and partially stoppered vials were placed on a tray and the tray was loaded into the lyophilizer. The lyophilizer was sealed and the shelf temperature was cooled to −45° C. at a rate of 0.5° C. per minute and held for 1.5 hours. A vacuum pressure was set to 150 mTorr and the lyophilizer was held for 1 hour. The shelf temperature was then heated to 25° C. at a rate of 0.5° C. per minute and held for 16.7 hours. The shelf temperature was then heated to 40° C. at a rate of 0.2° C. per minute and held for 6.7 hours. At the conclusion of secondary drying, the chamber was backfilled with nitrogen and the shelf temperature was chilled to 5° C. Samples were stoppered within the lyophilizer, the vacuum was released, and the samples were removed.

Formulation Example 3: Reconstitution of (3S)-3-({N-[(4-methoxy-1H-indol-2-yl) carbonyl]-L-leucyl}amino)-2-oxo-4-[(3S)-2-oxopyrrolidin-3-yl] butyl dihydrogen phosphate Lyophile and Dilution of the Resulting Solution 9.2 mL of sterile water for injection was injected through the stopper into the lyophilized vial from Formulation Example 2, above, to reconstitute the drug product to an aqueous solution with a target volume of 10 mL. The vial was then inverted to mix until the lyophile was fully reconstituted, which took less than one minute. The pH of the reconstituted solution was within +/−0.2 units of the pre-lyophilization pH.

After reconstitution, the solution was then withdrawn from the vial and diluted with 0.9% w/v sodium chloride (Normal Saline) or 5% w/v dextrose solution to provide an (3S)-3-({N-[(4-methoxy-1H-indol-2-yl)carbonyl]-L-leucyl}amino)-2-oxo-4-[(3S)-2-oxopyrrolidin-3-yl]butyl dihydrogen phosphate solution of the desired concentration (for example to a concentration of 25 mg/mL). The resulting diluted solution can then be used for parenteral administration, such as intravenous administration and particularly for intravenous infusion.

Formulation Example 3 Å: Reconstitution of PF-07304814 Lyophile Prepared with 5 mg/mL Polysorbate 80 at 10.9 mL Fill Volume 10.0 mL of sterile water for injection was injected through the stopper into the lyophilized vial, from Example 2 Å above, to reconstitute the drug product to a target volume of 10.9 mL. The vial was then inverted to mix until the lyophile was fully reconstituted, which took approximately two to three minutes. The pH of the reconstituted solution was within +/−0.2 units of the pre-lyophilization pH.

Formulation Example 4: Preparation and Lyophilization of 100 mg/mL PF-07304814 Solution with Potassium Counterion To investigate the feasibility of preparing solutions with an alternative counterion, excipients with sodium were removed or replaced from the solution preparation with excipients that did not contain a counterion or contained potassium as a counterion. Specifically, citric acid was substituted for sodium citrate dihydrate, and potassium hydroxide was substituted for NaOH. The resultant composition of the formulation was 100 mg/mL of PF-07304814, a pH of 4.0, a citrate buffer at 40 mM, and an approximate ratio of potassium to PF-07304814 of approximately 1.3:1. To further confirm that such solutions could be lyophilized without significant degradation to produce a lyophile, lyophilization cycle development was pursued. Characterization of the resultant lyophiles demonstrates an acceptable appearance and structure.

Preparation of 80 mM Citric Acid Buffer with Potassium Counterion 1.54 g of citric acid anhydrous added to a 100 mL volumetric flask. Approximately 50 mL of purified water was added to the volumetric flask, followed by 5.17 mL of 50% w/v potassium hydroxide solution. The solution was diluted to target volume with purified water and inverted to mix until homogeneous. The solution was vacuum filtered through a 0.2 μm PVDF filter.

Preparation of 100 mg/mL PF-07304814 Solution with Potassium Counterion 15.0 mL of refrigerated 80 mM citric acid buffer solution was added to a 50 mL beaker with a magnetic flea. The beaker was placed in a water bath controlled to 2-8° C. Approximately 3.12 g of PF-07304814 was added to the beaker to form a solution and mixed for approximately 25 minutes. 9.0 mL of refrigerated purified water was added to the beaker and mixed for 5 minutes. The solution was diluted to target mass of 31.05 g with purified water and mixed via stir bar until homogeneous. The solution was syringe filtered through a 0.2 μm PVDF filter. The final composition of the formulation was approximately 30 mL of a pH 4.0 solution with approximately 100 mg/mL PF-07304814 and 40 mM citrate buffer (molar ratio of PF-07304814 to citrate of 4.5:1). This formulation contained potassium as the counterion due to the potassium hydroxide used to prepare the citrate buffer.

Lyophilization of 100 mg/mL PF-07304814 Solution with Potassium Counterion 5 mL of filtered 100 mg/mL PF-07304814 solution was filled into 6 mL vials with a 20 mm neck diameter and partially stoppered. The filled and partially stoppered vials were placed on a tray and the tray was loaded into the lyophilizer. The lyophilizer was sealed and the shelf temperature was cooled to −45° C. at a rate of 0.5° C. per minute and held for 1 hour. A vacuum pressure was set to 150 mTorr and the lyophilizer was held for 1 hour. The shelf temperature was then heated to 25° C. at a rate of 0.5° C. per minute and held for 20 hours. At the conclusion of secondary drying, the chamber was backfilled with nitrogen and the shelf temperature was chilled to 5° C. Samples were stoppered within the lyophilizer, the vacuum was released, and the samples were removed.

Characterization of PF-07304814 Lyophile Prepared with Potassium Counterion

After lyophilization the sample appeared as a cake to powder with a white to off-white/yellow/brown color. The lyophilized samples show minimal evidence of collapse or shrinkage. The water content of the lyophilized powder, as measured by Karl Fischer, was approximately 0.5% w/w. The chromatographic purity of the samples, as measured by UPLC, changed by approximately 0.1% between pre- and post-lyophilization. A single $T_g$ was observed via mDSC with a temperature of 108.9° C.

Figure 24:
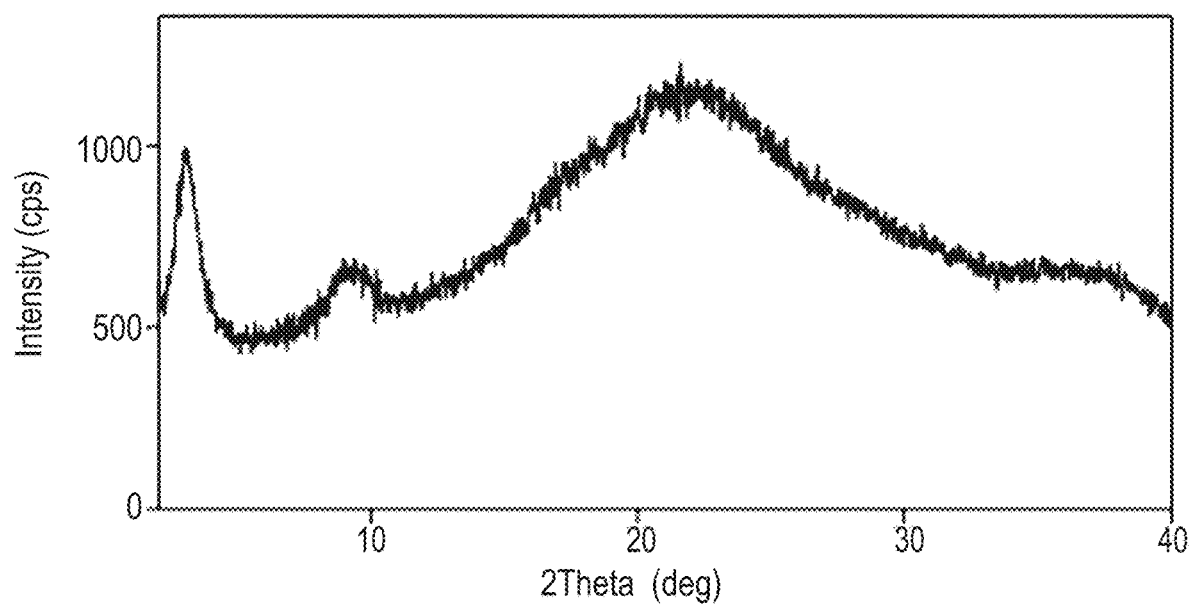
FIG. 24: PXRD diffraction pattern from a lyophilized drug product of PF-07304814, with a potassium counterion.
Figure 25:
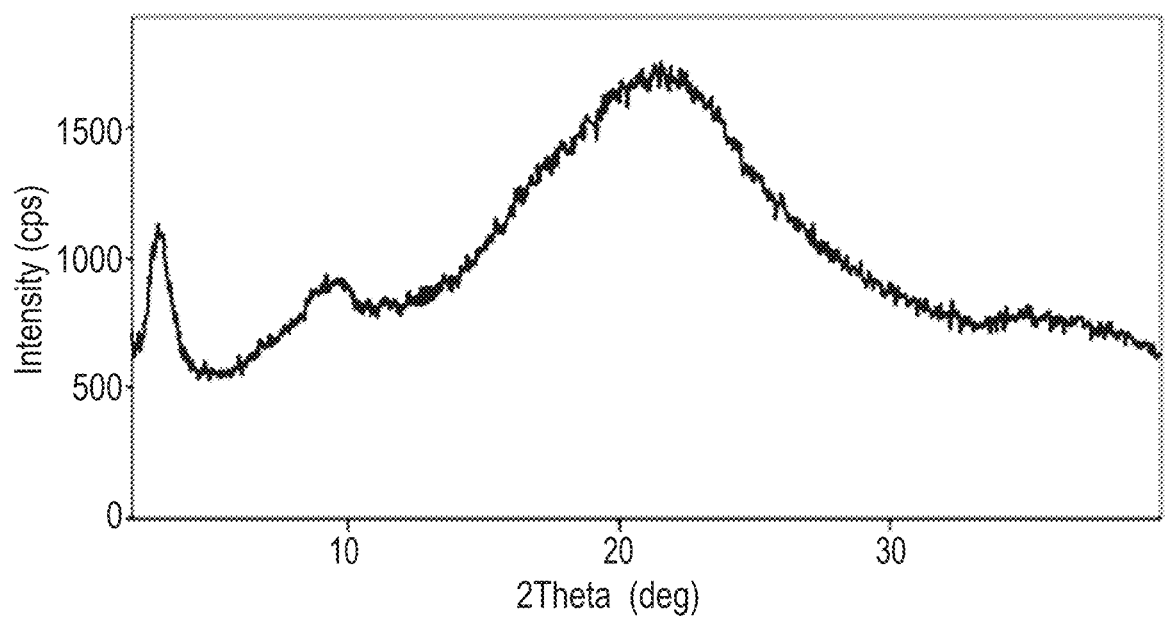
FIG. 25: PXRD diffraction pattern from a lyophilized drug product of PF-07304814, with a piperazine counterion.

Lyophilized samples appear to be predominantly amorphous in structure as measured by PXRD, with one broad peak observed at a 28 of approximately 3.0° (see FIG. 24).

Formulation Example 5: Preparation and Lyophilization of 100 mg/mL PF-07304814 Solution with Piperazine Counterion To investigate the impact of the PF-07304814 counterion on the chemical stability of the formulation, excipients with sodium were removed or replaced with excipients that did not contain a counterion or contained piperazine as a counterion. Specifically, citric acid was substituted for sodium citrate dihydrate, and piperazine was substituted for NaOH. The resultant composition of the formulation was 100 mg/mL of PF-07304814, a pH of 4.0, a citrate buffer at 40 mM (molar ratio of PF-07304814 to citrate of 4.5:1), and an approximate ratio of piperazine to PF-07304814 of approximately 0.6:1. To further confirm that such solutions could be lyophilized without significant degradation to produce a lyophile, lyophilization cycle development was pursued. Lyophilized samples were subsequently placed on accelerated stability, and surprisingly, a significant reduction in degradation to Degradant 1 was observed.

Preparation of 160 mM Citric Acid Buffer 3.07 g of citric acid anhydrous and 4.03 g of piperazine were added to a 100 mL volumetric flask. The solution was diluted to target volume with purified water and inverted to mix until homogeneous. The solution was vacuum filtered through a 0.2 μm PVDF filter.

Preparation of 100 mg/mL PF-07304814 Solution with Piperazine Counterion 25 mL of refrigerated purified water was added to a 100 mL beaker with a magnetic flea and mixed via stir bar. The beaker was placed in a water bath controlled to 2-8° C. Approximately 6.24 g of PF-07304814 was added to the beaker to form a suspension and mixed for approximately 5 minutes. 15 mL of refrigerated 160 mM citric acid buffer solution (containing piperazine) was added to the beaker and mixed via stir bar until homogeneous. The solution was diluted to target volume of 60 mL with purified water and mixed via stir bar until homogeneous. The pH of the solution was checked. The pH was adjusted to target using 1 N HCl. The solution was syringe filtered through a 0.2 μm PVDF filter. The final composition of the formulation was approximately 60 mL of a pH 4.0 solution with approximately 100 mg/mL PF-07304814 and 40 mM citrate buffer (molar ratio of PF-07304814 to citrate of 4.5:1). This solution contained piperazine as the counterion due to the piperazine used to prepare the citrate buffer.

Lyophilization of 100 mg/mL PF-07304814 Solution with Piperazine Counterion 5 mL of filtered 100 mg/mL PF-07304814 solution with a piperazine counterion was filled into 6 mL vials with a 20 mm neck diameter and partially stoppered. The filled and partially stoppered vials were placed on a tray and the tray was loaded into the lyophilizer (LyoStar). The lyophilizer was sealed and the shelf temperature was cooled to −45° C. at a rate of 0.5° C. per minute and held for 1 hour. A vacuum pressure was set to 150 mTorr and the lyophilizer was held for 1 hour. The shelf temperature was then heated to 25° C. at a rate of 0.5° C. per minute and held for 20 hours. The shelf temperature was then heated to 40° C. at a rate of 0.2° C. per minute and held for 10 hours. At the conclusion of secondary drying, the chamber was backfilled with nitrogen and the shelf temperature was chilled to 5° C. Samples were stoppered within the lyophilizer, the vacuum was released, and the samples were removed.

Characterization of PF-07304814 Lyophile Prepared with Piperazine Counterion

After lyophilization the sample appeared as a cake to powder with a white to off-white/yellow/brown color. The lyophilized samples show minimal evidence of collapse or shrinkage. The water content of the lyophilized powder, as measured by Karl Fischer, was approximately 0.3% w/w. The chromatographic purity of the samples, as measured by UPLC, changed by approximately 0.3% between pre- and post-lyophilization. A single $T_g$ was observed via mDSC with a temperature of 102.7° C.

Lyophilized samples appear to be predominantly amorphous in structure as measured by PXRD, with one broad peak observed at 28 of approximately 3.0° (see FIG. 24).

Accelerated Stability of PF-07304814 Lyophile Prepared with Piperazine Counterion Lyophilized formulations prepared with different counterions, as described in Formulation Example 3 (sodium) and Formulation Example 5 (piperazine), were placed on accelerated stability at 40° C./75% relative humidity (RH). Two vials were tested for each formulation after 0 and 4 weeks of storage. A first vial was kept as a solid and a second vial was reconstituted with 4.6 mL of water. Data from this accelerated stability study is shown in Accelerated Stability Table, below. This data shows the use of the piperazine counterion reduces the total degradation and degradation to Degradant 1 (phosphate cleaved compound i.e. the parent compound N-((1S)-1-{[((1S)-3-hydroxy-2-oxo-1-{[(3S)-2-oxopyrrolidin-3-yl]methyl}propyl)amino]carbonyl}-3-methylbutyl)-4-methoxy-1H-indole-2-carboxamide) on accelerated stability (after 4 weeks).

Accelerated Stability Table: Lyophilized formulations of PF-07304814 prepared with a sodium or piperazine counterion were placed on accelerated stability. Results are reported at the start of the accelerated stability study to demonstrate that the lyophilized drug products are comparable in terms of water content and pH post-reconstitution. The change in total impurities and Degradant 1, as measured by HPLC, is reported.

| Counterion | pH - 0 Weeks | Water Content (% w/w) - 0 Weeks | Change in Total Impurities (%) - 4 wks. | Change in Degradant 1 (%) - 4 wks. |
|---|---|---|---|---|
| Sodium | 3.8 | 0.2 | 0.9 | 0.7 |
| Piperazine | 4.0 | 0.3 | 0.5 | 0.2 |

Formulation Example 6: Preparation and Lyophilization of 100 mg/mL PF-07304814 Solution with Polyethylene Glycols (PEGs)

To improve the chemical stability of the lyophilized formulation, we investigated the preparation of formulations with stabilizing excipients, and specifically, with PEG400 and PEG3350. The composition of the formulations were consistent with Formulation Example 1D, with 100 mg/mL of PF-07304814, a pH of 4.0, a citrate buffer at 40 mM (molar ratio of PF-07304814 to citrate of 4.5:1), and an approximate ratio of sodium to PF-07304814 of approximately 1.3:1. To further confirm that such solutions could be lyophilized without significant degradation to produce a lyophile, lyophilization cycle development was pursued. The PEG400 or PEG3350 content of the lyophilized powder was approximately 8% w/w, when included on their own, and the total PEG content of the lyophilized powder when both were included was approximately 15% w/w. Lyophilized samples were subsequently placed on accelerated stability, and surprisingly, a significant reduction in total degradation and degradation to Degradant 1 was observed.

Preparation of 160 mM Citrate Buffer 11.77 g of sodium citrate dihydrate and 111 mL of 1 N NaOH were added to a 250 mL volumetric flask. The solution was diluted to target volume with purified water and inverted to mix until homogeneous. The solution was vacuum filtered through a 0.2 µm PVDF filter.

Preparation of Bulk Formulation 280 mL of refrigerated purified water was added to a 500 mL beaker with magnetic flea. The beaker was placed in a water bath controlled to 2-8° C. Approximately 68.6 g of PF-07304814 was added to the beaker to form a suspension and mixed for approximately 5 minutes. 165 mL of 160 mM citric acid buffer solution was added to the beaker and mixed via stir bar until homogeneous.

Preparation of 100 mg/mL PF-07304814 Solution with 10 mg/mL PEG400

52 mL of the bulk formulation was added to a 100 mL beaker with magnetic flea. Approximately 700 mg of PEG400 was added by mass and mixed until homogeneous. The solution was diluted to a total volume of 70 mL and syringe filtered through a 0.2 µm PVDF filter. The final composition was approximately 70 mL of a pH 4.0 solution with approximately 100 mg/mL PF-07304814, 40 mM citrate buffer (molar ratio of PF-07304814 to citrate of 4.5:1), and 10 mg/mL PEG400.

Preparation of 100 mg/mL PF-07304814 Solution with 10 mg/mL PEG3350

52 mL of the bulk formulation was added to a 100 mL beaker with magnetic flea. Approximately 700 mg of PEG3350 was added by mass and mixed until homogeneous. The solution was diluted to a total volume of 70 mL and syringe filtered through a 0.2 µm PVDF filter. The final composition was approximately 70 mL of a pH 4.0 solution with approximately 100 mg/mL PF-07304814, 40 mM citrate buffer (molar ratio of PF-07304814 to citrate of 4.5:1), and 10 mg/mL PEG3350.

Preparation of 100 mg/mL PF-07304814 Solution with 10 mg/mL PEG400 and 10 mg/mL PEG3350

52 mL of the bulk formulation was added to a 100 mL beaker with magnetic flea. Approximately 700 mg of PEG400 and approximately 700 mg of PEG3350 were added by mass and mixed until homogeneous. The solution was diluted to a total volume of 70 mL and syringe filtered through a 0.2 µm PVDF filter. The final composition was approximately 70 mL of a pH 4.0 solution with approximately 100 mg/mL PF-07304814, 40 mM citrate buffer (molar ratio of PF-07304814 to citrate of 4.5:1), 10 mg/mL PEG400, and 10 mg/mL PEG3350.

Lyophilization of 100 mg/mL PF-07304814 Solutions Prepared with PEGs 5 mL of filtered 100 mg/mL PF-07304814 solutions with PEGs were filled into 6 mL vials with a 20 mm neck diameter and partially stoppered. The filled and partially stoppered vials were placed on a tray and the tray was loaded into the lyophilizer (LyoStar). The lyophilizer was sealed and the shelf temperature was cooled to −45° C. at a rate of 0.5° C. per minute and held for 1 hour. A vacuum pressure was set to 150 mTorr and the lyophilizer was held for 1 hour. The shelf temperature was then heated to 25° C. at a rate of 0.5° C. per minute and held for 20 hours. The shelf temperature was then heated to 40° C. at a rate of 0.2° C. per minute and held for 10 hours. At the conclusion of secondary drying, the chamber was backfilled with nitrogen and the shelf temperature was chilled to 5° C. Samples were stoppered within the lyophilizer, the vacuum was released, and the samples were removed.

Characterization of 100 mg/mL PF-07304814 Lyophiles Prepared with PEGs

Figure 26A:
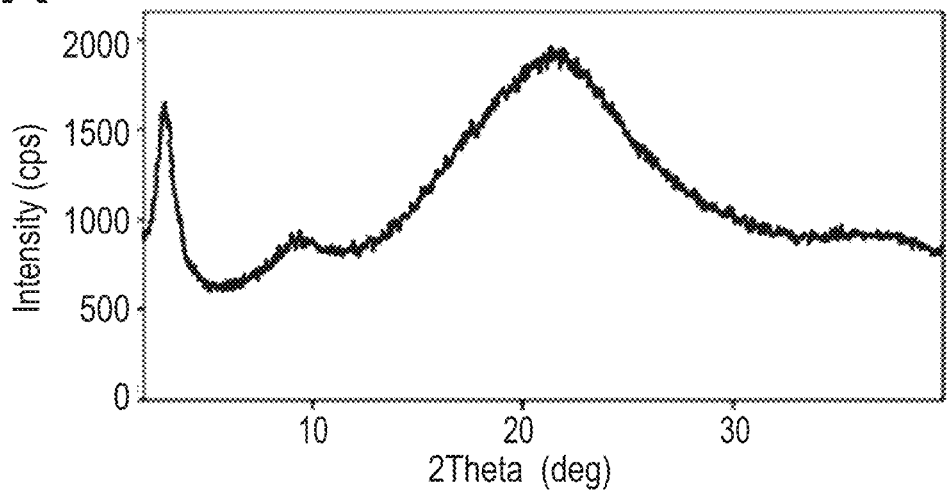
FIG. 26A: PXRD diffraction pattern from a lyophilized drug product of PF-07304814 with 10 mg/mL PEG400.
Figure 26B:
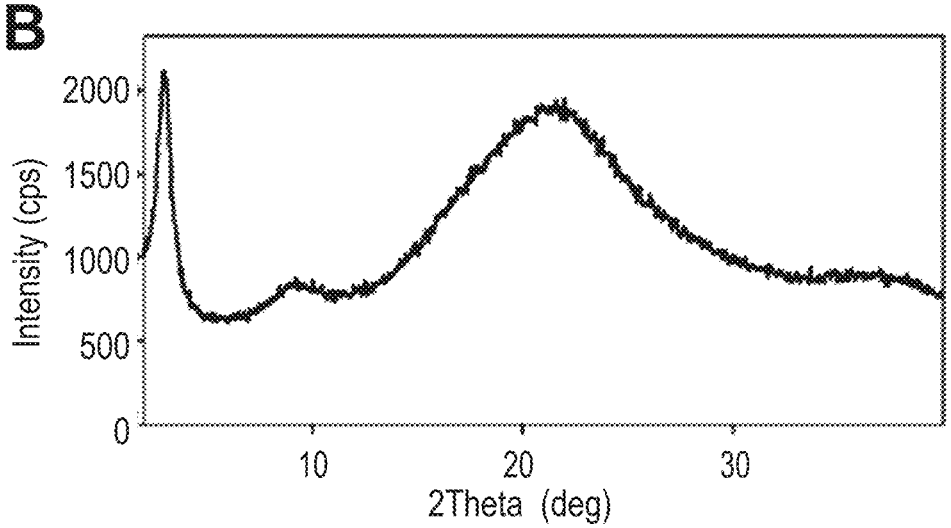
FIG. 26B: PXRD diffraction pattern from a lyophilized drug product of PF-07304814 with 10 mg/mL PEG3350.
Figure 26C:
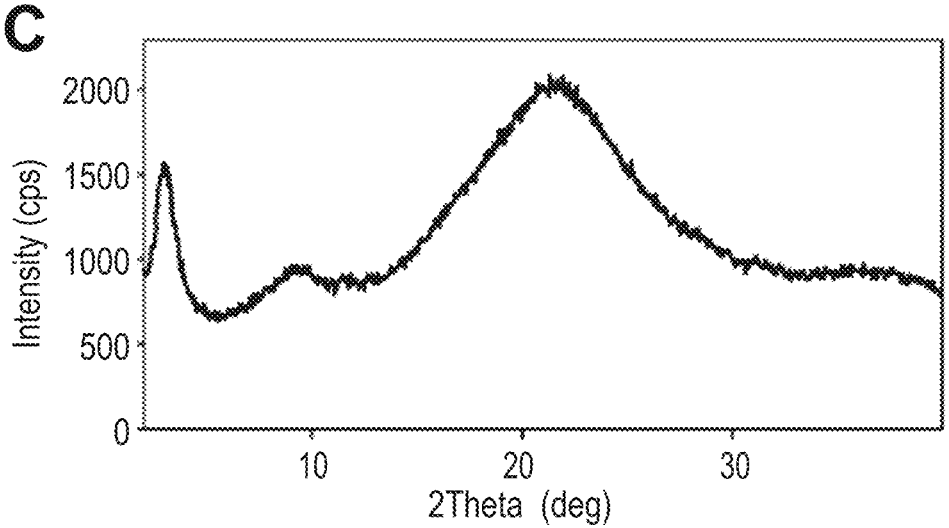
FIG. 26C: PXRD diffraction pattern from a lyophilized drug product of PF-07304814 with 10 mg/mL PEG 400/10 mg/mL PEG3350.

After lyophilization all samples appeared as a cake to powder with a white to off-white/yellow/brown color. The water content of the lyophilized powder, as measured by Karl Fischer, was approximately 0.2% w/w for all three samples. The chromatographic purity of all three samples, as measured by UPLC, changed by approximately 0.1% between pre- and post-lyophilization. A single $T_g$ was observed via mDSC for all three samples at 91.8, 92.4, and 76.3° C. for the samples with 10 mg/mL PEG400, 10 mg/mL PEG3350, and 10 mg/mL PEG400/10 mg/mL PEG3350, respectively. Lyophilized samples appear to be predominantly amorphous in structure as measured by PXRD, with one broad peak observed at 2θ of approximately 3.0° (See FIG. 26).

Accelerated Stability of PF-07304814 Lyophiles Prepared with PEGs

Lyophilized formulations prepared with different combinations of PEG400, PEG3350, and PS80, as described in Example 3 (PS80) and Example 7 (PEGs), were placed on accelerated stability at 40° C./75% relative humidity (RH). Two vials were tested for each formulation after 0 and 4 weeks of storage. A first vial was kept as a solid and a second vial was reconstituted with 4.6 mL of water. Data from this accelerated stability study is shown in PEG Accelerated Stability Table, below. The experimental data shows inclusion of PEGs reduces both the total degradation and the degradation to Degradant 1 on stability (after 4 weeks), with the greatest benefit coming from the inclusion of both PEG400 and PEG3350. Lyophilized formulations of PF-07304814 prepared with PS80, PEG400, or PEG3350 were placed on accelerated stability.

Results are reported at the start of the accelerated stability study to demonstrate that the lyophilized drug products are comparable in terms of pH and water content. The change in total impurities and Degradant 1, as measured by HPLC, is reported as the average of measurements from two vials.

PEG Accelerated Stability Table

| Formulation | pH - 0 Wks. | Water Content (% w/w) - 0 Wks. | Change in Total Impurities (%) - 4 wks. | Change in Degradant 1 (%) - 4 wks. |
|---|---|---|---|---|
| 5 mg/mL PS80 | 3.8 | 0.2 | 0.9 | 0.7 |
| 10 mg/mL PEG400 | 3.9 | 0.2 | 0.7 | 0.5 |
| 10 mg/mL PEG3350 | 3.9 | 0.2 | 0.8 | 0.6 |
| 10 mg/mL PEG400 10 mg/mL PEG3350 | 3.9 | 0.2 | 0.5 | 0.4 |

Formulation Example 7: Preparation and Lyophilization of 100 mg/mL PF-07304814 Solution Using PF-07304814 Purified Via Recrystallization of a Dimethyl Sulfoxide (DMSO) Solvate To investigate the impact of using PF-07304814 derived from an alternative purification scheme as the starting material, drug product formulations shown in Starting API Table, below, were prepared with PF-07304814 hydrate obtained through conversion of a PF-07304814 DMSO solvate (PF-07304814 Lot 1) into a DMSO solvate that is isostructural to the hydrate (PF-07304814 Lot 2) or from unconverted PF-07304814 DMSO solvate (PF-07304814 Lot 3). The composition of the formulations were consistent with Drug Product Formulation 1E, with 100 mg/mL of PF-07304814, a pH of 4.0, a citrate buffer at 40 mM (molar ratio of PF-07304814 to citrate of 4.5:1), an approximate ratio of sodium to PF-07304814 of approximately 1.3:1, and approximately 5 mg/mL of polysorbate 80. To confirm whether the presence of DMSO impacted the ability to produce a lyophilized formulation, lyophilization cycle development was pursued. The polysorbate 80 content of the lyophilized powder was approximately 4% w/w.

Starting API Table: Description of PF-07304814 Lots derived from a DMSO purification method.

| PF-07304814 Lot | PF-07304814 Form by PXRD | Residual DMSO in PF-07304814 (% w/w) |
|---|---|---|
| 1 | PF-07304814 Hydrate | 0.1 |
| 2 | PF-07304814 DMSO solvate isostructural to hydrate | 6.0 |
| 3 | PF-07304814 DMSO Solvate | 12.0 |

Preparation of 160 mM Citrate Buffer

Approximately 47.04 g of sodium citrate dihydrate, 44.4 mL of 10 N NaOH, and 700 mL of purified water were added to a container and mixed until all ingredients were dissolved. The solution was brought to a final volume of 1.0 L with purified water and the solution was vacuum filtered through a 0.2 μm PVDF filter.

Preparation of 100 mg/mL Polysorbate 80 Solution

Approximately 10 g of polysorbate 80 was added to a container and was brought to a final volume of 100.0 mL by weight. The liquid was mixed until a homogenous solution was achieved.

Preparation of 100 mg/mL PF-07304814 Solution using PF-07304814 Purified via Recrystallization of a dimethyl sulfoxide (DMSO) solvate Drug product formulations were prepared in similar fashion to Drug Product Example 1C. Specifically, 8.5 mL of refrigerated purified water was added to a 20 mL beaker with magnetic flea and mixed. The beaker was placed in a water bath controlled to 2-8° C. For each preparation, approximately 2.0 g of PF-07304814 (adjusted for DMSO content) was added to the beaker and mixed until a homogenous wetted suspension was achieved. The wetted PF-07304814 in each suspension was dissolved by adding approximately 5.0 mL of refrigerated 160 mM citrate buffer, followed by approximately 1.0 mL of 100 mg/mL polysorbate 80 solution. The solution was mixed, diluted to a target volume of 20 mL with purified water, mixed, and filtered through a 0.2 μm PVDF syringe filter. The final composition of the formulation was approximately 20 mL of a pH 4.0 solution with approximately 100 mg/mL PF-07304814, 40 mM citrate buffer (molar ratio of PF-07304814 to citrate of 4.5:1), and 5 mg/mL polysorbate 80.

Lyophilization of 100 mg/mL PF-07304814 Solution Using PF-07304814 Purified Via Recrystallization of a DMSO Solvate 5.45 mL of filtered 100 mg/mL PF-07304814 drug product solution, as described above, was filled into 20 mL vials with a 20 mm neck diameter and partially stoppered. The filled and partially stoppered vials were placed on a tray and the tray was loaded into the lyophilizer (LyoStar). The lyophilizer was sealed and the shelf temperature was cooled to −45° C. at a rate of 0.5° C. per minute and held for 90 minutes. A vacuum pressure was set to 150 mTorr and the lyophilizer was held for 1 hour. The shelf temperature was then heated to 25° C. at a rate of 0.5° C. per minute and held for 1000 minutes. The shelf temperature was then heated to 40° C. at a rate of 0.2° C. per minute and held for 400 minutes. At the conclusion of secondary drying, the chamber was backfilled with nitrogen and the shelf temperature was chilled to 5° C. Samples were stoppered within the lyophilizer, the vacuum was released, and the samples were removed.

Characterization of PF-07304814 Lyophiles Prepared Using PF-07304814 Purified Via Recrystallization of a DMSO Solvate After lyophilization the sample appeared as a cake to powder with a white to off-white/yellow/brown color. The lyophilized samples show minimal evidence of collapse or shrinkage. The chromatographic purity of the samples changed by approximately 0.1% between pre- and post-lyophilization analysis. A single $T_g$ was observed in each sample via mDSC as shown in the $T_g$ and DMSO Level Table, below.

$T_g$ and DMSO Level Table: $T_g$ of lyophilized drug products prepared with PF-07304814 derived from a DMSO purification process.

| PF-07304814 Lot Used in Lyophile | DMSO Level in PF-07304814 (% w/w) | Lyophile Tg |
|---|---|---|
| 1 | 0.12% | 103.9° C. |
| 2 | 6% | 74.2° C. |
| 3 | 12% | 68.8° C. |

Figure 27A:
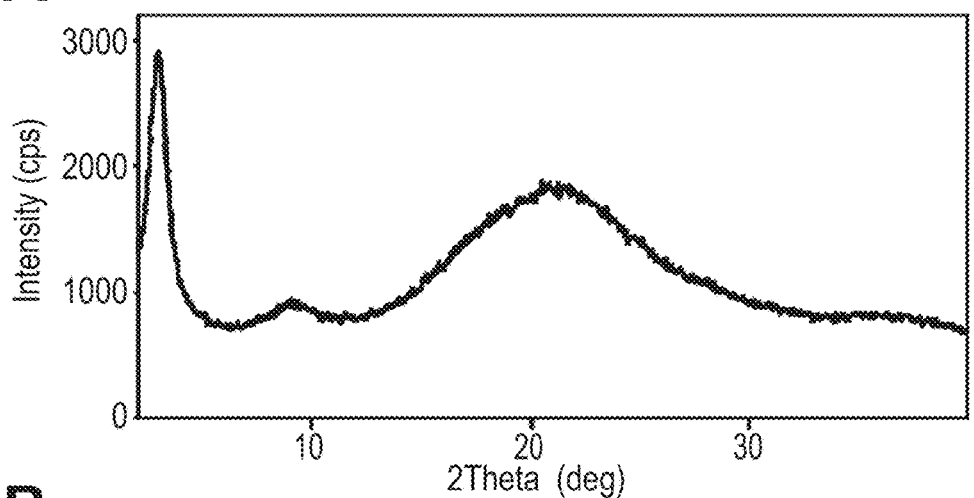
FIG. 27A: PXRD diffraction pattern for a lyophilized drug product prepared from PF-07304814 Lot 1 (0.12% DMSO).
Figure 27B:
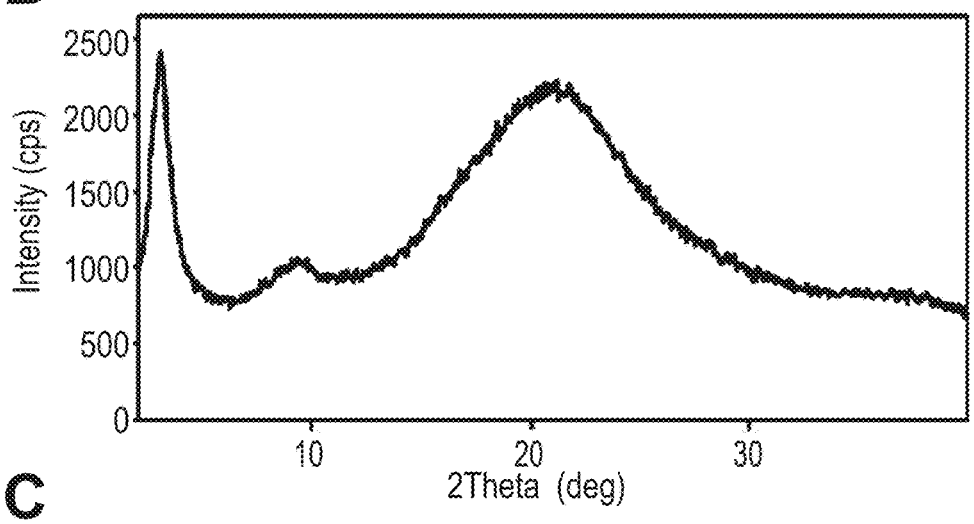
FIG. 27B: PXRD diffraction pattern for a lyophilized drug product prepared from PF-07304814 Lot 2 (6% DMSO).
Figure 27C:
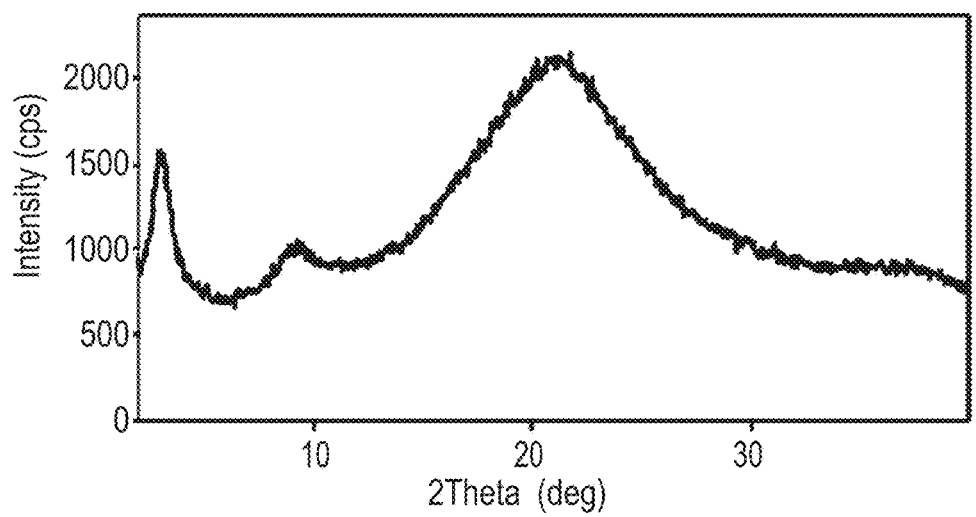
FIG. 27C: PXRD diffraction pattern for a lyophilized drug product prepared from PF-07304814 Lot 3 (12% DMSO).
Figure 28:
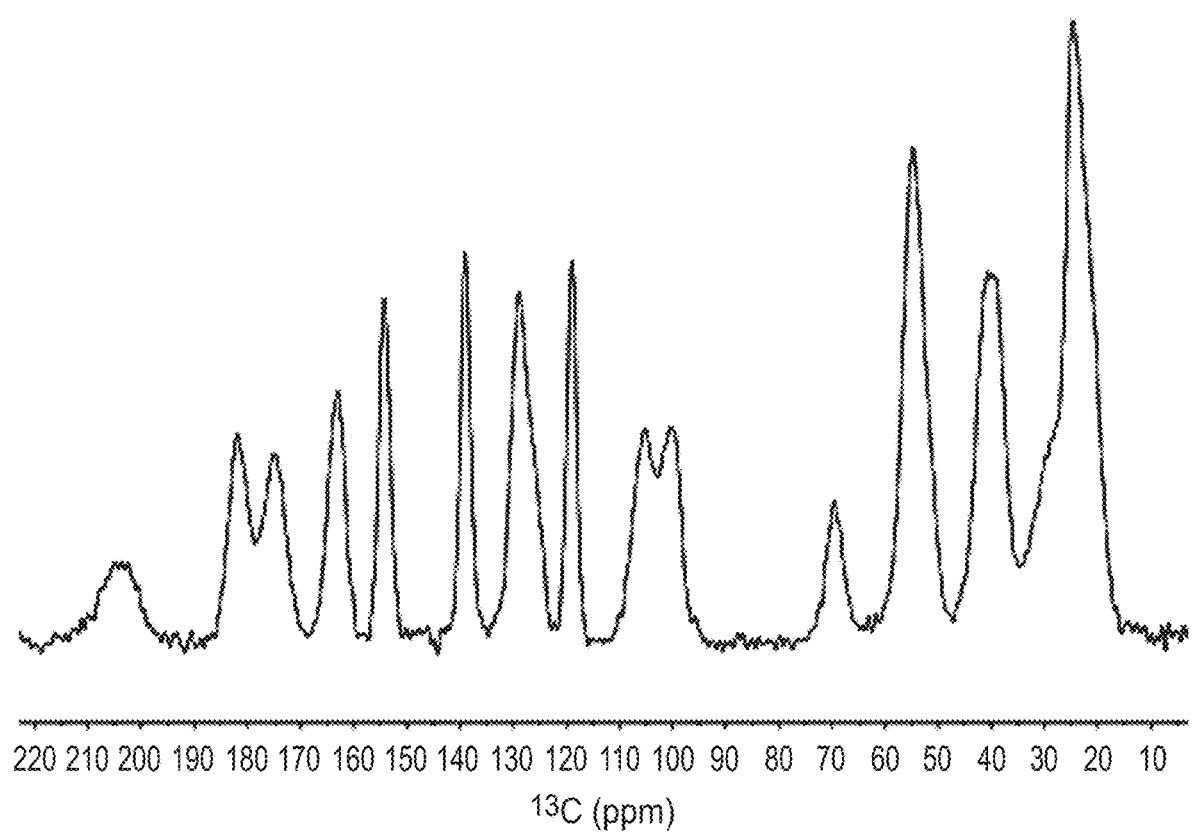
FIG. 28: $^{13}$C solid state NMR spectrum of PF-07304814 amorphous free acid.

Lyophilized samples appear to be predominantly amorphous in structure as measured via PXRD, with one broad peak observed at 2θ of approximately 3.0° (see FIG. 27).

Example 50: (3S)-3-({N-[(4-methoxy-1H-indol-2-yl)carbonyl]-L-leucyl}amino)-2-oxo-4-[(3S)-2-oxopyrrolidin-3-yl]butyl dimethyl phosphate LCMS m/z 581.5 [M+H]$^+$. Retention time: 2.36 minutes (Analytical conditions. Column: Waters Atlantis dC18, 4.6×50 mm, 5 µm; Mobile phase A: water containing 0.05% trifluoroacetic acid (v/v); Mobile phase B: acetonitrile containing 0.05% trifluoroacetic acid (v/v); Gradient: 5.0% to 95% B, linear over 4.0 minutes, then 95% B for 1.0 minute; Flow rate: 2 mL/minute).

Example 51: (3S)-3-({N-[(4-methoxy-1H-indol-2-yl)carbonyl]-L-leucyl}amino)-2-oxo-4-[(3S)-2-oxopyrrolidin-3-yl]butyl dipropan-2-yl phosphate Example 52: (3S)-4-[(3S)-1-acetyl-2-oxopyrrolidin-3-yl]-3-({N-[(4-methoxy-1H-indol-2-yl)carbonyl]-L-leucyl}amino)-2-oxobutyl dimethyl phosphate Example 53: 4-methoxy-N-[(2S)-4-methyl-1-({(2S)-4-[(2-oxido-4-phenyl-1,3,2-dioxa phosphinan-2-yl)oxy]-3-oxo-1-[(3S)-2-oxopyrrolidin-3-yl]butan-2-yl}amino)-1-oxopentan-2-yl]-1H-indole-2-carboxamide Example 54: diethyl (3S)-3-({N-[(4-methoxy-1H-indol-2-yl)carbonyl]-L-leucyl}amino)-2-oxo-4-[(3S)-2-oxopyrrolidin-3-yl]butyl phosphate LCMS m/z 609.5 [M+H]$^+$. Retention time: 2.53 minutes (Analytical conditions. Column: Waters Atlantis dC18, 4.6×50 mm, 5 µm; Mobile phase A: water containing 0.05% trifluoroacetic acid (v/v); Mobile phase B: acetonitrile containing 0.05% trifluoroacetic acid (v/v); Gradient: 5.0% to 95% B, linear over 4.0 minutes, then 95% B for 1.0 minute; Flow rate: 2 mL/minute).

Example 55: methyl (3S)-3-[(2S)-4-[(dimethoxyphosphoryl)oxy]-2-({N-[(4-methoxy-1H-indol-2-yl)carbonyl]-L-leucyl}amino)-3-oxobutyl]-2-oxopyrrolidine-1-carboxylate Example 56: (1S)-1-{(3S)-3-[(2S)-2-({N-[(4-methoxy-1H-indol-2-yl)carbonyl]-L-leucyl}amino)-2-(2-oxo-1,3-dioxol-4-yl)ethyl]-2-oxopyrrolidin-1-yl}ethyl methyl carbonate Example 57: 4-Methoxy-N-[(2S)-4-methyl-1-oxo-1-({(1S)-1-(2-oxo-1,3-dioxol-4-yl)-2-[(3S)-2-oxopyrrolidin-3-yl]ethyl}amino)pentan-2-yl]-1H-indole-2-carboxamide (57)

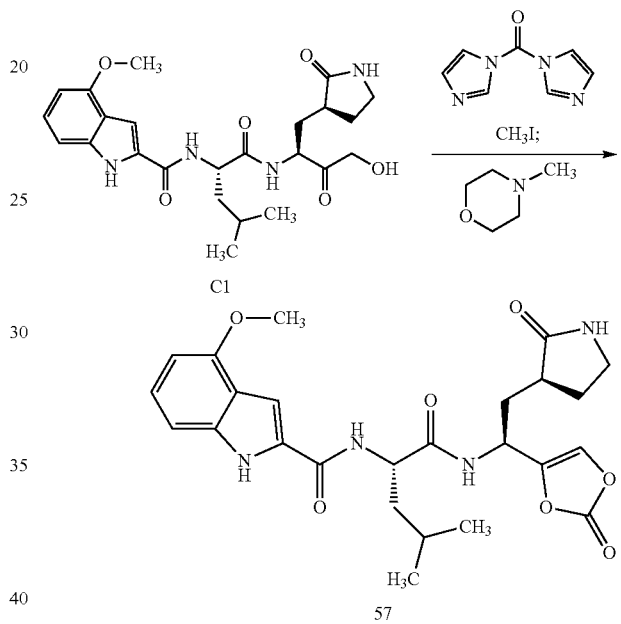

Iodomethane (10.5 µL, 0.169 mmol) was added to a solution of 1,1'-carbonyldiimidazole (13.7 mg, 84.5 µmol) in 1,2-dichloroethane (0.84 mL). The resulting mixture was stirred for 30 minutes, whereupon C1 (40 mg, 85 µmol) was added, followed by 4-methylmorpholine (18.5 µL, 0.168 mmol). The reaction mixture was stirred at room temperature until conversion to the activated ester was complete by LCMS analysis; it was then heated at 80° C. overnight. After being combined with a similar reaction carried out using C1 (20 mg, 42 µmol), the reaction mixture was partitioned between ethyl acetate and 10% aqueous potassium hydrogen sulfate solution. The organic layer was dried over sodium sulfate, filtered, concentrated in vacuo, and purified via reversed-phase HPLC (Column: Waters Sunfire C18, 19×100 mm, 5 µm; Mobile phase A: water containing 0.05% trifluoroacetic acid; Mobile phase B: acetonitrile containing 0.05% trifluoroacetic acid; Gradient: 25% to 45% B over 8.5 minutes, then 45% to 95% B over 0.5 minutes, then 95% B for 1.0 minute; Flow rate: 25 mL/minute) to afford 4-methoxy-N-[(2S)-4-methyl-1-oxo-1-({(1S)-1-(2-oxo-1,3-dioxol-4-yl)-2-[(3S)-2-oxopyrrolidin-3-yl]ethyl}amino)pentan-2-yl]-1H-indole-2-carboxamide (57). Combined yield: 3.5 mg, 7.0 µmol, 6%. LCMS m/z 499.4 [M+H]$^+$. Retention time: 2.47 minutes (Analytical conditions. Column: Waters Atlantis dC18, 4.6×50 mm, 5 µm; Mobile phase A: water containing 0.05% trifluoroacetic acid (v/v); Mobile phase B: acetonitrile containing 0.05% trifluoroacetic acid (v/v); Gradient: 5.0% to 95% B, linear over 4.0 minutes, then 95% B for 1.0 minute; Flow rate: 2 mL/minute).

Example 58: N-[(2S)-1-{[(1S)-2-[(3S)-1-acetyl-2-oxopyrrolidin-3-yl]-1-(2-oxo-1,3-dioxol-4-yl)ethyl]amino}-4-methyl-1-oxopentan-2-yl]-4-methoxy-1H-indole-2-carboxamide Example 59: methyl (3S)-3-[(2S)-2-({N-[(4-methoxy-1H-indol-2-yl)carbonyl]-L-leucyl}amino)-2-(2-oxo-1,3-dioxol-4-yl)ethyl]-2-oxopyrrolidine-1-carboxylate Example 60: (1S)-1-{(3S)-3-[(2S)-4-hydroxy-2-({N-[(4-methoxy-1H-indol-2-yl)carbonyl]-L-leucyl}amino)-3-oxobutyl]-2-oxopyrrolidin-1-yl}ethyl methyl carbonate Example 61: N-[(2S)-1-({(2S)-1-[(3S)-1-acetyl-2-oxopyrrolidin-3-yl]-4-hydroxy-3-oxobutan-2-yl}amino)-4-methyl-1-oxopentan-2-yl]-4-methoxy-1H-indole-2-carboxamide Example 62: methyl (3S)-3-[(2S)-4-hydroxy-2-({N-[(4-methoxy-1H-indol-2-yl)carbonyl]-L-leucyl}amino)-3-oxobutyl]-2-oxopyrrolidine-1-carboxylate Example 63: {(3S)-3-[(2S)-4-hydroxy-2-({N-[(4-methoxy-1H-indol-2-yl)carbonyl]-L-leucyl}amino)-3-oxobutyl]-2-oxopyrrolidin-1-yl}methyl methyl carbonate Example 64: Benzyl (3S)-3-({N-[(4-methoxy-1H-indol-2-yl)carbonyl]-L-leucyl}amino)-2-oxo-4-[(3S)-2-oxopyrrolidin-3-yl]butyl carbonate (64)

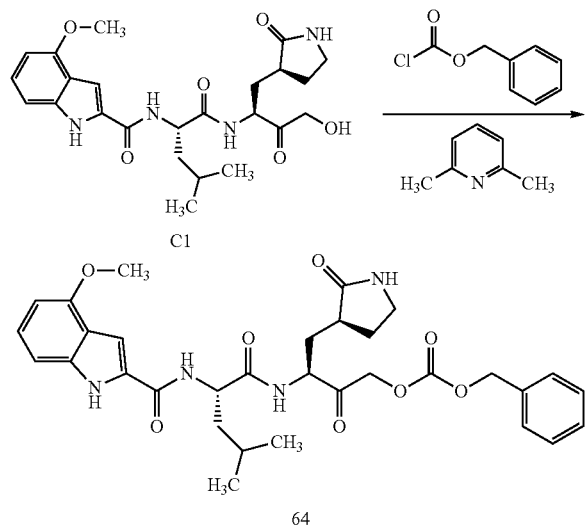

A 0° C. solution of C1 (15 mg, 32 μmol) in tetrahydrofuran (0.32 mL) was treated with 2,6-dimethylpyridine (4.4 μL, 38 μmol), followed by benzyl chloroformate (4.98 μL, 34.9 μmol). The reaction mixture was allowed to warm to room temperature and stirred for 28 hours, whereupon an additional equivalent of benzyl chloroformate was added, and the temperature was increased to 40° C. After the reaction mixture had stirred overnight at 40° C., it was heated to 60° C. for 2 hours, then diluted with dichloromethane and washed with 10% aqueous potassium hydrogen sulfate solution. The organic layer was dried over sodium sulfate, filtered, and concentrated in vacuo; purification of the residue via reversed-phase HPLC (Column: Waters Sunfire C18, 19×100 mm, 5 μm; Mobile phase A: water containing 0.05% trifluoroacetic acid; Mobile phase B: acetonitrile containing 0.05% trifluoroacetic acid; Gradient: 30% to 70% B over 8.5 minutes, then 70% to 95% B over 0.5 minutes, then 95% B for 1.0 minute; Flow rate: 25 mL/minute) afforded benzyl (3S)-3-({N-[(4-methoxy-1H-indol-2-yl)carbonyl]-L-leucyl}amino)-2-oxo-4-[(3S)-2-oxopyrrolidin-3-yl]butyl carbonate (64). Yield: 11.6 mg, 19.1 μmol, 60%. LCMS m/z 607.5 [M+H]$^+$. Retention time: 2.92 minutes (Analytical conditions. Column: Waters Atlantis dC18, 4.6×50 mm, 5 μm; Mobile phase A: water containing 0.05% trifluoroacetic acid (v/v); Mobile phase B: acetonitrile containing 0.05% trifluoroacetic acid (v/v); Gradient: 5.0% to 95% B, linear over 4.0 minutes, then 95% B for 1.0 minute; Flow rate: 2 mL/minute).

Example 65: (3S)-3-({N-[(4-Methoxy-1H-indol-2-yl)carbonyl]-L-leucyl}amino)-2-oxo-4-[(3S)-2-oxopyrrolidin-3-yl]butyl 2-methylpyrrolidine-1-carboxylate (65)

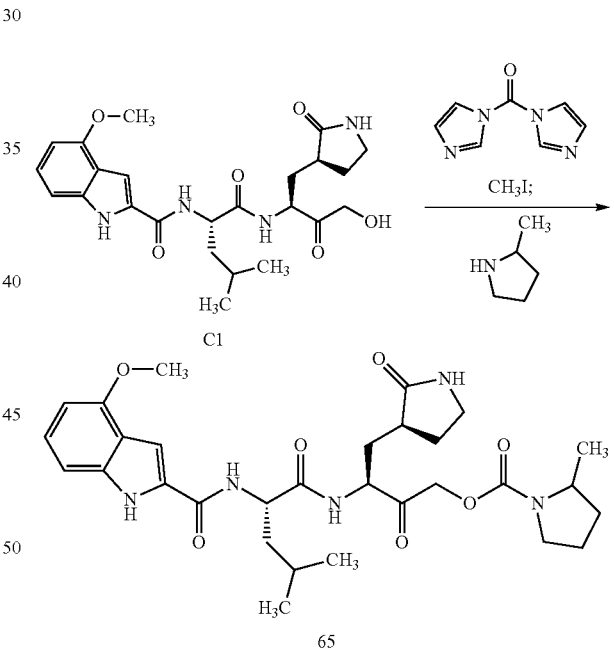

Iodomethane (2.63 μL, 42.2 μmol) was added to a solution of 1,1'-carbonyldiimidazole (3.43 mg, 21.2 μmol) in dichloromethane (0.21 mL). After the resulting mixture had been stirred for 30 minutes, C1 (10 mg, 21 μmol) was added. Following an additional hour of stirring, the reaction mixture was treated with 2-methylpyrrolidine (2.16 μL, 21.2 μmol) and stirred for 2.5 hours, whereupon it was concentrated in vacuo. Purification using reversed-phase HPLC (Column: Waters Sunfire C18, 19×100 mm, 5 μm; Mobile phase A: water containing 0.05% trifluoroacetic acid; Mobile phase B: acetonitrile containing 0.05% trifluoroacetic acid; Gradient: 5% to 95% B over 8.54 minutes, then 95% B for 1.46 minutes; Flow rate: 25 mL/minute) afforded (3S)-3-({N-[(4-methoxy-1H-indol-2-yl)carbonyl]-L-leucyl}amino)-2-oxo-4-[(3S)-2-oxopyrrolidin-3-yl]butyl 2-methylpyrrolidine-1-carboxylate (65). Yield: 7.6 mg, 13 µmol, 61%. LCMS m/z 584.6 [M+H]+. Retention time: 2.70 minutes (Analytical conditions. Column: Waters Atlantis dC18, 4.6×50 mm, 5 µm; Mobile phase A: water containing 0.05% trifluoroacetic acid (v/v); Mobile phase B: acetonitrile containing 0.05% trifluoroacetic acid (v/v); Gradient: 5.0% to 95% B, linear over 4.0 minutes, then 95% B for 1.0 minute; Flow rate: 2 mL/minute).

Docking Experiments

Methods:

Homology Modeling. The sequence of 3C-like proteinase in SARS and COVID-19 can be found in references from the RCSB (e.g., 3IWM)[1] and the NCBI (e.g., Reference Sequence: YP_009725301.1 NCBI)[2].

SARS 3C Protease Sequence (PDB 3IWM):

SGFRKMAFPSGKVEGCMVQVTCGTTTLNGLWLDDTVYCPRHVICTAEDML

NPNYEDLLIRKSNHSFLVQAGNVQLRVI

GHSMQNCLLRLKVDTSNPKTPKYKFVRIQPGQTFSVLACYNGSPSGVYQC

AMRPNHTIKGSFLNGSCGSVGFNIDYDCV

SFCYMHHMELPTGVHAGTDLEGKFYGPFVDRQTAQAAGTDTTITLNVLAW

LYAAVINGDRWFLNRFTTTLNDFNLVA

MKYNYEPLTQDHVDILGPLSAQTGIAVLDMCAALKELLQNGMNGRTILGS

TILEDEFTPFDVVRQCSGVTFQ

The sequence immediately above is also being provided in the required text file format and is designated as SEQ No. 1.

New Wuhan Coronavirus SARS-CoV-2 Sequence (Same Section, 6Y84):

SGFRKMAFPSGKVEGCMVQVTCGTTTLNGLWLDDVVYCPRHVICTSEDML

NPNYEDLLIRKSNHNFLVQAGNVQLRVI

GHSMQNCVLKLKVDTANPKTPKYKFVRIQPGQTFSVLACYNGSPSGVYQC

AMRPNFTIKGSFLNGSCGSVGFNIDYDCV

SFCYMHHMELPTGVHAGTDLEGNFYGPFVDRQTAQAAGTDTTITVNVLAW

LYAAVINGDRWFLNRFTTTLNDFNLVA

MKYNYEPLTQDHVDILGPLSAQTGIAVLDMCASLKELLQNGMNGRTILGS

ALLEDEFTPFDVVRQCSGVTFQ

The sequence immediately above is also being provided in the required text file format and is designated as SEQ No. 2. A homology model was built from a crystal structure of SARS 3C-like protease in Pfizer's database using Schrödinger's PRIMES. Minimization of the homology model in complex with ligands was used to remove clashes with ligands containing benzothiazole ketones or a benzyl side chains after examining the protein conformations of other SARS 3C-like crystal structures with these ligand moieties. Relaxation of residues in the 185-190 loop, His41 and Met49 to led to three differently minimized versions of the homology model. The catalytic Cys was mutated to Gly (C145G) to facilitate AGDOCK core docking and subsequent scoring without a clash with the catalytic Cys.

Docking: Compounds are docked into the homology models using core docking[4] with AGDOCK[5]. The docking is performed without forming the protein-ligand covalent bond. Instead, a common core that included the lactam side chain and reactive ketone was identified in the ligands and held fixed in the crystal structure orientation as a mimic of covalent docking (See FIG. 2). The affinity measure for AGDOCK core docking is HT Score[6].

Method References:
1. http://www.rcsb.org/structure/3IWM
2. https://www.ncbi.nih.gov/proten/YP_009725301.1
3. Schrödinger Release 2019-1: Prime, Schrödinger, LLC, New York, NY; 2019.
4. Daniel K. Gehlhaar, Gennady M. Verkhivker, Paul A. Rejto, Christopher J. Sherman, David R. Fogel, Lawrence J. Fogel, Stephan T. Freer, Molecular recognition of the inhibitor AG-1343 by HIV-1 protease: conformationally flexible docking by evolutionary programming, Chemistry & Biology, Volume 2, Issue 5, 1995, Pages 317-324.
5. Daniel K. Gehlhaar, Djamal Bouzida, and Paul A. Rejto, Reduced Dimensionality in Ligand-Protein Structure Prediction: Covalent Inhibitors of Serine Proteases and Design of Site-Directed Combinatorial Libraries Rational Drug Design. Jul. 7, 1999, 292-311.
6. Tami J. Marrone, Brock A. Luty, Peter W. Röse, Discovering high-affinity ligands from the computationally predicted structures and affinities of small molecules bound to a target: A virtual screening approach. Perspectives in Drug Discovery and Design 20, 209-230 (2000).

Results:

Homology model: The sequence homology between SARS-CoV and SARS-CoV-2 is 96.1%. There are 12 of 306 residues that are different (T35V, A465, S65N, L86V, R88K, S94A, H134F, K180N, L202V, A267S, T285A & I286L highlighted in cyan in Figure A) which translates to 96.1% identity.

The ligand associated with the crystal structure used to build the homology model is Compound B, N-((1S)-1-{[(((1S)-3-hydroxy-2-oxo-1-{[(3S)-2-oxopyrrolidin-3-yl]methyl}propyl)amino]carbonyl}-3-methylbutyl)-4-methoxy-1H-indole-2-carboxamide. The amino acid residue nearest to Compound B, N-((1S)-1-{[(((1S)-3-hydroxy-2-oxo-1-{[(3S)-2-oxopyrrolidin-3-yl]methyl}propyl)amino]carbonyl}-3-methylbutyl)-4-methoxy-1H-indole-2-carboxamide, that differed between SARS 3C-like protease and SARS-CoV-2 3C-like protease model is A46S, and the minimum distance from $C_{alpha}$ to ligand is 8.3 Å. Other residues are between 11 Å and 38 Å from the nearest atom in Compound B.

TABLE 1

Approximate distances from $C_{alpha}$ atoms in SARS-CoV-2 to Compound B, N-((1S)-1-{[(((1S)-3-hydroxy-2-oxo-1-{[(3S)-2-oxopyrrolidin-3-yl]methyl}propyl)amino]carbonyl}-3-methylbutyl)-4-methoxy-1H-indole-2-carboxamide

| SARS-CoV-2 Amino Acid Residues | Distance to Nearest Atom in Compound B (Angstroms) |
|---|---|
| T35V | ~19 |
| A46S | ~8 |
| S65N | ~16 |
| L86V | ~11 |
| R88K | ~15 |
| S94A | ~24 |
| H134F | ~14 |
| K180N | ~13 |
| L202V | ~27 |
| A267S | ~38 |
| T285A | ~34 |
| I286L | ~31 |

FIG. 1 depicts the residue differences between SARS-CoV and SARS-CoV-2. Residue changes are highlighted in cyan in this ribbon depiction of SARS-CoV-2 homology model. The Compound B, N-((1S)-1-{[((1S)-3-hydroxy-2-oxo-1-{[(3S)-2-oxopyrrolidin-3-yl]methyl}propyl)amino]carbonyl}-3-methylbutyl)-4-methoxy-1H-indole-2-carboxamide, location is shown in magenta. The approximate distance between the C-alpha of a SARS-CoV-2 amino acid residue and the closest atom in the Compound B, N-((1S)-1-{[((1S)-3-hydroxy-2-oxo-1-{[(3S)-2-oxopyrrolidin-3-yl]methyl}propyl)amino] carbonyl}-3-methylbutyl)-4-methoxy-1H-indole-2-carboxamide, is shown in Table 1, above.

Docking Results:

The approximately 96% homology of SARS-CoV-2 3CL to SARS-CoV 3CL and the similarity between ligands allows a comparison of the RMSD between the peptide backbone of xtal ligand in SARS-CoV (see FIG. 2) and the docked ligand in the SARS-CoV-2 3CL model. The core-docked ligand RMSD to the peptide backbone did not differ by more than 0.32 Å (average 0.28 Å). See FIG. 2 for an example. In the case of Compound B, N-((1S)-1-{[((1S)-3-hydroxy-2-oxo-1-{[(3S)-2-oxopyrrolidin-3-yl]methyl}propyl)amino]carbonyl}-3-methylbutyl)-4-methoxy-1H-indole-2-carboxamide; the RMSD for the whole molecule was 0.37 Å.

Figure 2:
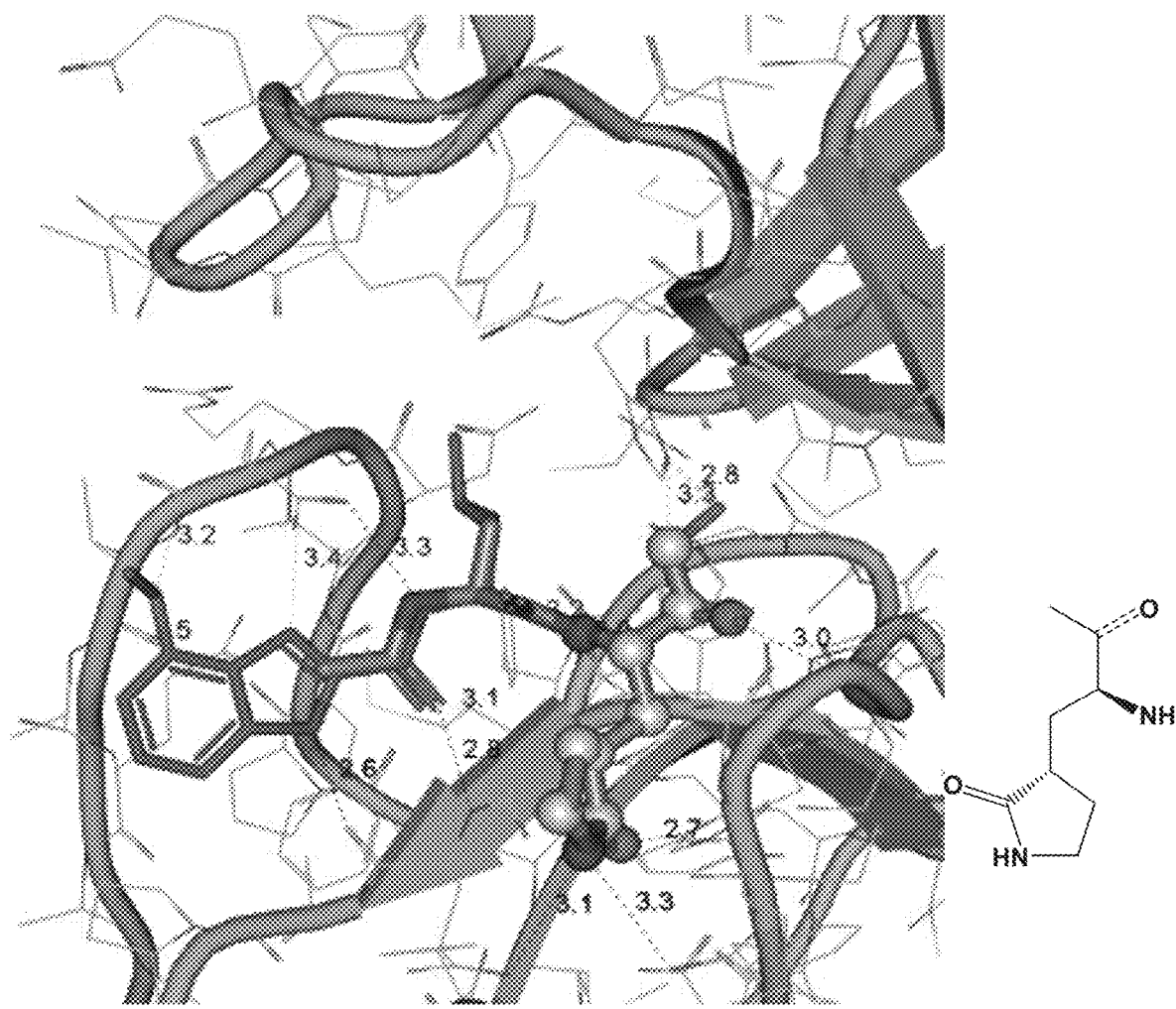
FIG. 2: Binding site of homology model of SARS-CoV-2 3CL with a core-docked ligand (Compound B, N-((1S)-1-{[((1S)-3-hydroxy-2-oxo-1-{[(3S)-2-oxopyrrolidin-3-yl]methyl}propyl)amino]carbonyl}-3-methylbutyl)-4-methoxy-1H-indole-2-carboxamide).

FIG. 2. Binding site of homology model of SARS-CoV-2 3CL with a core-docked ligand (Compound B, N-((1S)-1-{[((1S)-3-hydroxy-2-oxo-1-{[(3S)-2-oxopyrrolidin-3-yl]methyl}propyl)amino]carbonyl}-3-methylbutyl)-4-methoxy-1H-indole-2-carboxamide) present (purple carbons, red oxygen, blue nitrogen). Part of the crystal structure of Compound B, N-((1S)-1-{[((1S)-3-hydroxy-2-oxo-1-{[(3S)-2-oxopyrrolidin-3-yl]methyl} propyl)amino]carbonyl}-3-methylbutyl)-4-methoxy-1H-indole-2-carboxamide, (peptide backbone, lactam side chain and attacked ketone) was used to measure the RMSD of the different ligands to that backbone (grey carbons, thick stick). The core used for core docking is shown as 11 heavy atoms in ball representation (light blue carbons) and in the inset chemical structure. Distances shown in Angstroms.

The docking result(s) in Table 2 below indicate that the compound(s) have predicted affinities ($\Delta G_{bind}$, kcal/mol) that are generally commensurate with target recognition and binding. The effective potency can differ from the AG binding terms depending on several factors such as cell uptake, efflux, cofactor competition or substrate competition.

TABLE 2

| Compound | Predicted $\Delta G_{bind}$ (kcal/mol) | Chemical Name of Docked Compounds |
|---|---|---|
| B | −9.5 | N-((1S)-1-{[((1S)-3-hydroxy-2-oxo-1-{[(3S)-2-oxopyrrolidin-3-yl]methyl}propyl)amino] carbonyl}-3-methylbutyl)-4-methoxy-1H-indole-2-carboxamide |

The compounds described above are analyzed by a FRET biochemical assay and by in vitro virological assays using cell culture techniques.

Protection from SARS Infection: Neutral Red Endpoint

The ability of compounds to protect cells against infection by the SARS coronavirus is measured by a cell viability assay similar to that described in Borenfreund, E., and Puerner, J. 1985. Toxicity determined in vitro by morphological alterations and neutral red absorption Toxicology Letters. 24:119-124, utilizing neutral red staining as an endpoint. Briefly, medium containing appropriate concentrations of compound or medium only is added to Vero cells. Cells are infected with SARS-associated virus or mock-infected with medium only. One to seven days later, the medium is removed and medium containing neutral red is added to the test plates. Following incubation at 37° C. for two hours, cells are washed twice with PBS and a 50% EtOH, 1% acetic acid solution is added. The cells are shaken for 1 to 2 minutes and incubated at 37° C. for 5 to 10 minutes. The amount of neutral red is quantified spectrophotometrically at 540 nm. Data is expressed as the percent of neutral red in wells of compound-treated cells compared to neutral red in wells of uninfected, compound-free cells. The fifty percent effective concentration (EC50) is calculated as the concentration of compound that increases the percent of neutral red production in infected, compound-treated cells to 50% of that produced by uninfected, compound-free cells. The 50% cytotoxicity concentration (CC50) is calculated as the concentration of compound that decreases the percentage of neutral red produced in uninfected, compound-treated cells to 50% of that produced in uninfected, compound-free cells. The therapeutic index is calculated by dividing the cytotoxicity (CC50) by the antiviral activity (EC50).

Protection from SARS-CoV-2 Infection: Glo Endpoint

The ability of compounds to protect cells against infection by the SARS-CoV-2 coronavirus can also be measured by a cell viability assay utilizing luciferase to measure intracellular ATP as an endpoint. Briefly, medium containing appropriate concentrations of compound or medium only is added to Vero cells. Cells are infected with SARS-CoV-2 virus or mock-infected with medium only. One to seven days later, the medium is removed and the amount of intracellular ATP is measured as per Promega Technical Bulletin No. 288: CellTiter-Glo® Luminescent Cell Viability Assay (Promega, Madison, WI). The CellTiter-Glo® reagent is added to the test plates and following incubation at 37° C. for 1.25 hours, the amount of signal is quantified using a luminometer at 490 nm. Data is expressed as the percent of luminescent signal from wells of compound-treated cells compared to the luminescent signal from wells of uninfected, compound-free cells. The fifty percent effective concentration (EC50) is calculated as the concentration of compound that increases the percent of the luminescent signal from infected, compound-treated cells to 50% of the luminescent signal from uninfected, compound-free cells. The 50% cytotoxicity concentration (CC50) is calculated as the concentration of compound that decreases the percentage of the luminescent signal from uninfected, compound-treated cells to 50% of the luminescent signal from uninfected, compound-free cells. The therapeutic index is calculated by dividing the cytotoxicity (CC50) by the antiviral activity (EC50).

Cytotoxicity

The ability of compounds to cause cytotoxicity in cells is measured by a cell viability assay similar to that described in Weislow, O. S., Kiser, R., Fine, D. L., Bader, J., Shoemaker, R. H., and Boyd, M. R. 1989. New Soluble-Formazan Assay for HIV-1 Cytopathic Effects: Application to High-Flux Screening of Synthetic and Natural Products for AIDS-Antiviral Activity. Journal of the National Cancer Institute 81(08): 577-586, utilizing formazan as an endpoint. Briefly, Vero cells are resuspended in medium containing appropriate concentrations of compound or medium only. One to seven days later, XTT and PMS are added to the test plates and following incubation at 37° C. for two hours the amount of formazan produced is quantified spectrophotometrically at 540 nm. Data is expressed as the percent of formazan produced in compound-treated cells compared to formazan produced in wells of compound-free cells. The 50% cytotoxicity concentration (CC50) is calculated as the concentration of compound that decreases the percentage of formazan produced in uninfected, compound-treated cells to 50% of that produced in uninfected, compound-free cells.

Protection from SARS-CoV-2 Coronavirus Infection

The ability of compounds to protect cells against infection by SARS-CoV-2 is measured by a cell viability assay similar to that described in Weislow, O. S., Kiser, R., Fine, D. L., Bader, J., Shoemaker, R. H., and Boyd, M. R. 1989. New Soluble-Formazan Assay for HIV-1 Cytopathic Effects: Application to High-Flux Screening of Synthetic and Natural Products for AIDS-Antiviral Activity. Journal of the National Cancer Institute 81(08): 577-586, utilizing formazan as an endpoint. Briefly, medium containing appropriate concentrations of compound or medium only is added to MRC-5 cells. Cells are infected with human coronavirus SARS-CoV-2 or mock-infected with medium only. One to seven days later, XTI and PMS are added to the test plates and following incubation at 37° C. for two hours the amount of formazan produced is quantified spectrophotometrically at 540 nm. Data is expressed as the percent of formazan in wells of compound-treated cells compared to formazan in wells of uninfected, compound-free cells. The fifty percent effective concentration (EC50) is calculated as the concentration of compound that increases the percent of formazan production in infected, compound-treated cells to 50% of that produced by uninfected, compound-free cells. The 50% cytotoxicity concentration (CC50) is calculated as the concentration of compound that decreases the percentage of formazan produced in uninfected, compound-treated cells to 50% of that produced in uninfected, compound-free cells. The therapeutic index is calculated by dividing the cytotoxicity (CC50) by the antiviral activity (EC50).

SARS-CoV-2 Coronavirus 3C Protease FRET Assay and Analysis

Proteolytic activity of SARS-CoV-2 Coronavirus 3CL protease is measured using a continuous fluorescence resonance energy transfer assay. The SARS-CoV-2 3CL$^{pro}$ FRET assay measures the protease catalyzed cleavage of TAMRA-SIT-SAVLQSGFRKMK-(DABCYL)-OH to TAMRA-SIT-SAVLQ and SGFRKMK(DABCYL)-OH. The fluorescence of the cleaved TAMRA (ex. 558 nm/em. 581 nm) peptide was measured using a TECAN SAFIRE fluorescence plate reader over the course of 10 min. Typical reaction solutions contained 20 mM HEPES (pH 7.0), 1 mM EDTA, 4.0 uM FRET substrate, 4% DMSO and 0.005% Tween-20. Assays were initiated with the addition of 25 nM SARS 3CL$^{pro}$ (nucleotide sequence 9985-10902 of the Urbani strain of SARS coronavirus complete genome sequence (NCBI accession number AY278741)). Percent inhibition was determined in duplicate at 0.001 mM level of inhibitor. Data was analyzed with the non-linear regression analysis program Kalidagraph using the equation:

$$FU = \text{offset} + (\text{limit})(1 - e^{-(k_{obs})t})$$

where offset equals the fluorescence signal of the uncleaved peptide substrate, and limit equals the fluorescence of fully cleaved peptide substrate. The kobs is the first order rate constant for this reaction, and in the absence of any inhibitor represents the utilization of substrate. In an enzyme start reaction which contains an irreversible inhibitors, and where the calculated limit is less than 20% of the theoretical maximum limit, the calculated kobs represents the rate of inactivation of coronavirus 3C protease. The slope (kobs/I) of a plot of kobs vs. [I] is a measure of the avidity of the inhibitor for an enzyme. For very fast irreversible inhibitors, kobs/I is calculated from observations at only one or two [I] rather than as a slope.

Alternatively, the compounds may be assessed using the SARS CoV-2 FRET Assay below.

SARS CoV-2 Protease FRET Assay and Analysis

The proteolytic activity of the main protease, 3CLpro, of SARS-CoV-2 was monitored using a continuous fluorescence resonance energy transfer (FRET) assay. The SARS-CoV-2 3CLpro assay measures the activity of fulllength SARS-CoV-2 3CL protease to cleave a synthetic fluorogenic substrate peptide with the following sequence Dabcyl-KT-SAVLQ-SGFRKME-Edans modelled on a consensus peptide. The fluorescence of the cleaved Edans peptide (excitation 340 nm/emission 490 nm) is measured using a fluorescence intensity protocol on a Flexstation reader (Molecular Devices). The fluorescent signal is reduced in the presence of N-((1S)-1-{[((1S)-3-hydroxy-2-oxo-1-{[(3S)-2-oxopyrrolidin-3-yl]methyl}propyl)amino]carbonyl}-3-methylbutyl)-4-methoxy-1H-indole-2-carboxamide, a potent inhibitor of SARS-CoV-2 3CL pro. The assay reaction buffer contained 20 mM Tris-HCl (pH 7.3), 100 nM NaCl, 1 mM EDTA, 5 mM TCEP and 25 µM peptide substrate. Enzyme reactions were initiated with the addition of 15 nM SARS-CoV-2 3CL protease and allowed to proceed for 60 min at 23° C. Percent inhibition or activity was calculated based on control wells containing no compound (0% inhibition/100% activity) and a control compound (100% inhibition/0% activity). $IC_{50}$ values were generated using a four-parameter fit model using ABASE software (IDBS). $K_i$ values were fit to the Morrison equation with the enzyme concentration parameter fixed to 15 nM, the $K_m$ parameter fixed to 14 µM and the substrate concentration parameter fixed to 25 uM using Activity Base software (IDBS).

The compound of Example 49, (3S)-3-({N-[(4-methoxy-1H-indol-2-yl)carbonyl]-L-leucyl}amino)-2-oxo-4-[(3S)-2-oxopyrrolidin-3-yl]butyl dihydrogen phosphate, when evaluated in the above assay had an $IC_{50}$ of 350 nM (95% confidence interval of 330 nM to 380 nM with n=7) and a Ki of 137 nM (95% confidence interval of 136 nM to 137 nM with n=7).

The parent compound N-((1S)-1-{[((1S)-3-hydroxy-2-oxo-1-{[(3S)-2-oxopyrrolidin-3-yl]methyl}propyl)amino] carbonyl}-3-methylbutyl)-4-methoxy-1H-indole-2-carboxamide which is formed in vivo after administration of (3S)-3-({N-[(4-methoxy-1H-indol-2-yl)carbonyl]-L-leucyl} amino)-2-oxo-4-[(3S)-2-oxopyrrolidin-3-yl]butyl dihydrogen phosphate, has been assessed in various cellular assays and has been found to exhibit antiviral activity against SARS-CoV-2. Cellular assays employing A549-ACE2 (human lung) cells and USA-WA1/2020 SARS-CoV-2 at NYU Langone, Primary Human Airway Epithelial (HAE) (human lung) cells and Washington SARS-CoV-2 at NYU Langone and HeLa-ACE2 (human cervical) and USA-WA1/2020 SARS-CoV-2 at Scripps.

The antiviral activity of N-((1S)-1-{[((1S)-3-hydroxy-2-oxo-1-{[(3S)-2-oxopyrrolidin-3-yl]methyl}propyl)amino] carbonyl}-3-methylbutyl)-4-methoxy-1H-indole-2-carboxamide and remdesivir were evaluated against SARS-CoV-2 in A549-ACE2 cells using a high content imaging assay quantifying virus N protein with a mAb. Cytotoxicity of both compounds was evaluated in uninfected cells by monitoring cell viability based on quantitation of ATP. In A549-ACE2 cells, N-((1S)-{[-((1S)-3-hydroxy-2-oxo-1-{[(3S)-2-oxopyrrolidin-3-yl]methyl}propyl)amino} carbonyl}-3-methylbutyl)-4-methoxy-1H-indole-2-carboxamide inhibited SARS-CoV-2 viral replication with an $EC_{50}/EC_{50}$ value of 0.221/0.734 µM at 24 hours post infection and 0.158/0.439 µM after 48 hours. N-((1S)-1-{[((1S)-3-hydroxy-2-oxo-1-{[(3S)-2-oxopyrrolidin-3-yl]methyl}propyl)amino] carbonyl}-3-methylbutyl)-4-methoxy-1H-indole-2-carboxamide demonstrated $CC_{50}$ values of >10 µM at both time points, resulting in a TI of >46 at 24 hour and >65 after 48 hours post viral infection. As a comparison, remdesivir inhibited SARS-CoV-2 viral replication with an $EC_{50}/EC_{90}$ value of 0.442/1.19 µM at 24 hours post infection and 0.238/0.592 µM after 48 hours.

The antiviral activity of the parent compound N-((1S)-1-{[((1S)-3-hydroxy-2-oxo-1-{[(3S)-2-oxopyrrolidin-3-yl]methyl}propyl)amino] carbonyl}-3-methylbutyl)-4-methoxy-1H-indole-2-carboxamide against SARS-CoV-2 was assessed in polarized HAE cells where the kinetics of virus production in the absence or presence of different concentrations of drugs were assessed by quantifying the infectious virions in culture media collected at 12 hour intervals up to 3 days post infection, using virus plaque assay in Vero cells. Due to the approach taken, $EC_{50}/EC_{90}$ values were not generated however the results have similar trends as to those observed for antiviral efficacy in the A549-ACE2 assay, confirming the potential activity of N-((1S)-1-{[((1S)-3-hydroxy-2-oxo-1-{[(3S)-2-oxopyrrolidin-3-yl]methyl}propyl)amino] carbonyl}-3-methylbutyl)-4-methoxy-1H-indole-2-carboxamide in a physiologically relevant cell type. At all tested concentrations, the parent compound N-((1S)-1-{[((1S)-3-hydroxy-2-oxo-1-{[(3S)-2-oxopyrrolidin-3-yl]methyl}propyl)amino] carbonyl}-3-methylbutyl)-4-methoxy-1H-indole-2-carboxamide potently inhibited SARS-CoV-2 virus production at various time points with the most significant reduction at 48 hours post-infection. At 0.025 µM, 0.5 µM and 10 µM N-((1S)-1-{[((1S)-3-hydroxy-2-oxo-1-{[(3S)-2-oxopyrrolidin-3-yl]methyl}propyl)amino] carbonyl}-3-methylbutyl)-4-methoxy-1H-indole-2-carboxamide resulted in an estimated 22.5, 31.3 and 2590 fold reduction in virion replication whereas remdesivir resulted in 5.09, 93.1 and 2590 fold reduction in virion replication when tested at the same concentrations.

The in vitro potency of the parent compound N-((1S)-1-{[((1S)-3-hydroxy-2-oxo-1-{[(3S)-2-oxopyrrolidin-3-yl]methyl}propyl)amino] carbonyl}-3-methylbutyl)-4-methoxy-1H-indole-2-carboxamide alone and in combination with remdesivir was evaluated against SARS-CoV-2 in a human cervical cancer HeLa-ACE2 cells. HeLa-ACE2 cells were infected with SARS-CoV-2 and incubated with N-((1S)-1-{[((1S)-3-hydroxy-2-oxo-1-{[(3S)-2-oxopyrrolidin-3-yl]methyl}propyl)amino] carbonyl}-3-methylbutyl)-4-methoxy-1H-indole-2-carboxamide-containing media. At 24 hours post infection and drug treatment, cells were fixed and viral proteins were detected using convalescent human polyclonal sera from COVID-19 patients and a secondary mAb, and quantified using high content imaging. Results indicated that N-((1S)-1-{[((1S)-3-hydroxy-2-oxo-1-{[(3S)-2-oxopyrrolidin-3-yl]methyl}propyl)amino] carbonyl}-3-methylbutyl)-4-methoxy-1H-indole-2-carboxamide alone inhibited SARS-CoV-2 replication with an average EC50 of 0.144 µM and EC90 of 0.398 µM, consistent with the same potency as in A549-ACE2 cells. No host cell cytotoxicity was observed.

The parent compound N-((1S)-1-{[((1S)-3-hydroxy-2-oxo-1-{[(3S)-2-oxopyrrolidin-3-yl]methyl}propyl) amino] carbonyl}-3-methylbutyl)-4-methoxy-1H-indole-2-carboxamide was evaluated against 3CLpro from a variety of other coronaviruses representing alpha, beta and gamma groups of coronaviridae, using biochemical Fluorescence Resonance Energy Transfer (FRET) protease activity assays. The assays are analogous to the FRET assay above and can employ the full-length protease sequences from the indicated viruses. The parent compound N-((1S)-1-{[((1S)-3-hydroxy-2-oxo-1-{[(3S)-2-oxopyrrolidin-3-yl]methyl}propyl)amino]carbonyl}-3-methylbutyl)-4-methoxy-1H-indole-2-carboxamide demonstrated potent inhibitory activity against all tested coronavirus 3CLpro including members of alpha-coronaviruses (NL63-CoV, PEDV-CoV-2, FIPV-CoV-2), beta-coronaviruses (HKU4-CoV, HKU5-CoV, HKU9-CoV, MHV-CoV, OC43-CoV, HKU1-CoV), and gamma-coronavirus (IBV-CoV-2), with Ki values and tested enzyme concentrations included in Table 3. This inhibitory activity is restricted to coronavirus 3CL proteases as N-((1S)-1-{[((1S)-3-hydroxy-2-oxo-1-{[(3S)-2-oxopyrrolidin-3-yl]methyl}propyl) amino]carbonyl}-3-methylbutyl)-4-methoxy-1H-indole-2-carboxamide was inactive against a panel of human proteases and HIV protease. N-((1S)-1-{[((1S)-3-hydroxy-2-oxo-1-{[(3S)-2-oxopyrrolidin-3-yl]methyl}propyl) amino]carbonyl}-3-methylbutyl)-4-methoxy-1H-indole-2-carboxamide showed detectable activity against human cathepsin B but with a 1000-fold margin compared to 3CLpro (Table 4). These data collectively support N-((1S)-1-{[((1S)-3-hydroxy-2-oxo-1-{[(3S)-2-oxopyrrolidin-3-yl]methyl} propyl)amino]carbonyl}-3-methylbutyl)-4-methoxy-1H-indole-2-carboxamide as a pan coronavirus 3 CL protease inhibitor.

TABLE 3

Activity of parent compound N-((1S)-1-{[((1S)-3-hydroxy-2-oxo-1-{[(3S)-2-oxopyrrolidin-3-yl]methyl} propyl)amino] carbonyl}-3-methylbutyl)-4-methoxy-1H-indole-2-carboxamide against 3CLpro of coronaviruses

| Virus | $K_i$ (nM) | $[E]_T$ (nM) |
|---|---|---|
| Alpha-CoV | | |
| NL63-CoV | 0.8 ± 0.5 | 170 ± 4 |
| 229E-COV-2 | 1.5 ± 0.8 | 118 ± 3 |
| PEDV-CoV-2 | 0.3 ± 0.1 | 40 ± 1 |
| FIPV-CoV-2 | 0.1 ± 0.1 | 37 ± 1 |
| Beta-CoV | | |
| HKU1-CoV | 0.9 ± 0.2 | 57 ± 1 |
| HKU4-CoV | 0.03 ± 0.08 | 60 ± 1 |
| HKU5-CoV | 0.03 ± 0.1 | 75 ± 1 |
| HKU9-CoV | 0.8 ± 0.6 | 264 ± 5 |
| MHV-CoV | 1.2 ± 0.9 | 75 ± 4 |
| OC43-CoV | 0.5 ± 0.1 | 52 ± 1 |
| Gamma-CoV | | |
| IBV-CoV-2 | 4.0 ± 0.4 | 30 ± 1 |

TABLE 4

Activity of parent compound N-((1S)-1-{[((1S)-3-hydroxy-2-oxo-1-{[(3S)-2-oxopyrrolidin-3-yl]methyl}propyl) amino]carbonyl}-3-methylbutyl)-4-methoxy-1H-indole-2-carboxamide against human proteases and HIV protease

| Protease | $IC_{50}$ µM |
|---|---|
| SAR-Cov2 3CLpro | 0.00692 |
| Human Cathepsin B | 6.12 |
| Human Elastase | >33.3 |
| Human Chymotrypsin | >100 |
| Human Thrombin | >100 |
| Human Caspase 2 | >33.3 |
| Human Cathepsin D | >11.1 |
| HIV-1 protease | >11.1 |

Thermal Shift Binding Data of parent compound N-((1S)-1-{[((1S)-3-hydroxy-2-oxo-1-{[(3S)-2-oxopyrrolidin-3-yl]methyl} propyl)amino]carbonyl}-3-methylbutyl)-4-methoxy-1H-indole-2-carboxamide with SARS-CoV-2 3CLpro indicates tight and specific binding to SARS-CoV-2 3CL in vitro.

Figure 7:
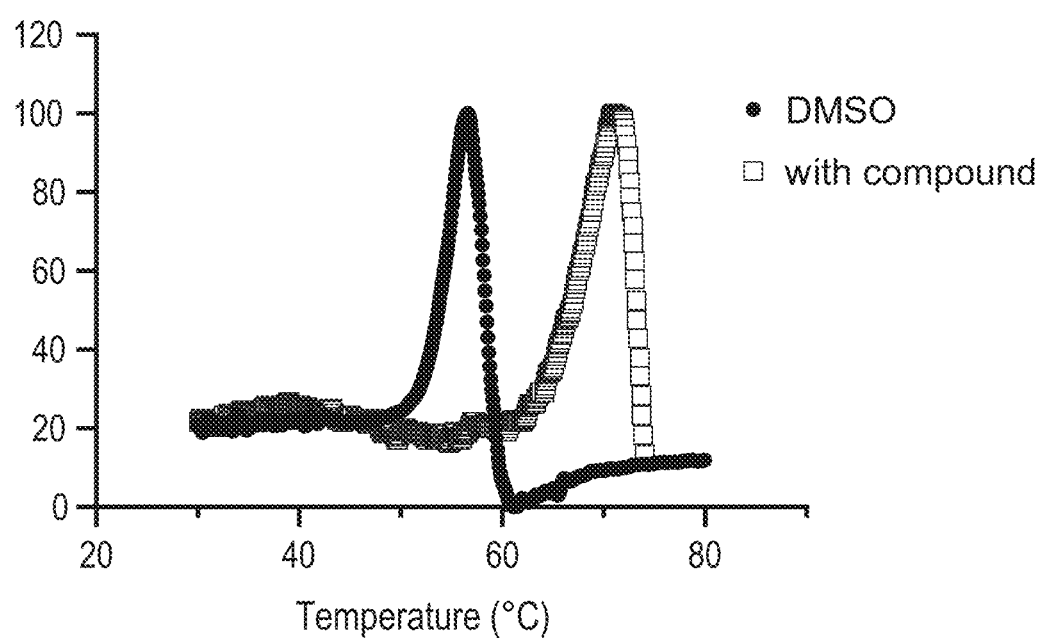
FIG. 7: Representative thermal shift binding data of the parent compound N-((1S)-1-{[((1S)-3-hydroxy-2-oxo-1-{[(3S)-2-oxopyrrolidin-3-yl]methyl}propyl)amino]carbonyl}-3-methyl butyl)-4-methoxy-1H-indole-2-carboxamide with SARS-CoV-2 3CLpro.

In view of the ability of N-((1S)-1-{[((1S)-3-hydroxy-2-oxo-1-{[(3S)-2-oxopyrrolidin-3-yl]methyl} propyl)amino]carbonyl}-3-methylbutyl)-4-methoxy-1H-indole-2-carboxamide to potently inhibit SARS-CoV-2 3CLpro with a Ki value of 0.27 nM further studies were undertaken. Studies of the X-ray co-crystal structure of N-((1S)-1-{[((1S)-3-hydroxy-2-oxo-1-{[(3S)-2-oxopyrrolidin-3-yl]methyl}propyl)amino]carbonyl}-3-methylbutyl)-4-methoxy-1H-indole-2-carboxamide and SARS-CoV-2 3CLpro is consistent with the compound binding to the 3CL enzyme with a covalent and reversible interaction at catalytic cysteine residue of the active site, thus inhibiting the activity of the 3CLpro. A thermal-shift assay was also used to evaluate the direct binding between N-((1S)-1-{[((1S)-3-hydroxy-2-oxo-1-{[(3S)-2-oxopyrrolidin-3-yl] methyl} propyl)amino]carbonyl}-3-methylbutyl)-4-methoxy-1H-indole-2-carboxamide and its target protein, SARS-CoV-2 3CLpro. The melting temperature of SARS-CoV-2 3CLpro was shifted by 14.6° C. upon binding of N-((1S)-1-{[((1S)-3-hydroxy-2-oxo-1-{[(3S)-2-oxopyrrolidin-3-yl]methyl}propyl) amino]carbonyl}-3-methylbutyl)-4-methoxy-1H-indole-2-carboxamide, from 55.9+/−0.11° C. (n=16) to 70.5+/−0.12° C. (n=8). The melting temperature (Tm) was calculated as the mid-log of the transition phase from the native to the denatured protein using a Boltzmann model in Protein Thermal Shift Software v1.3. These data support tight and specific binding of the parent compound N-((1S)-1-{[((1S)-3-hydroxy-2-oxo-1-{[(3S)-2oxopyrrolidin-3yl]-methyl}propyl) amino]carbonyl}-3-methylbutyl)-4-methoxy-1H-indole-2-carboxamide to SARS-CoV-2 3CLpro (see FIG. 7) and, thereby, provide further evidence for the molecular mechanism of this parent compound as an inhibitor of SARS-CoV-2 3CLpro.

SARS-CoV-2 cellular antiviral activity is inhibited by (3S)-3-({N-[(4-methoxy-1H-indol-2-yl)carbonyl]-L-leucyl}amino)-2-oxo-4-[(3S)-2-oxopyrrolidin-3-yl]butyl dihydrogen phosphate and its parent compound N-((1S)-1-{[((1S)-3-hydroxy-2-oxo-1-{[(3S)-2-oxopyrrolidin-3-yl]methyl}propyl) amino]carbonyl}-3-methylbutyl)-4-methoxy-1H-indole-2-carboxamide in vitro.

The antiviral activity of (3S)-3-({N-[(4-methoxy-1H-indol-2-yl)carbonyl]-L-leucyl}amino)-2-oxo-4-[(3S)-2-oxopyrrolidin-3-yl]butyl dihydrogen phosphate and its parent compound N-((1S)-1-{[((1S)-3-hydroxy-2-oxo-1-{[(3S)-2-oxopyrrolidin-3-yl]methyl}propyl)amino]carbonyl}-3-methylbutyl)-4-methoxy-1H-indole-2-carboxamide against SARS-CoV-2 in cell culture were further evaluated with a cytopathic effect (CPE) assay using either VeroE6 cells enriched for ACE2 (VeroE6-enACE2) receptor or VeroE6 cells constitutively expressing EGFP (VeroE6-EGFP). These cell lines were infected with the SARS-CoV-2 Washington strain 1 or the BetaCov GHB-03021/2020 strain, respectively, which have identical 3CLpro amino acid sequences. N-((1S)-1-{[((1S)-3-hydroxy-2-oxo-1-{[(3S)-2-oxopyrrolidin-3-yl]methyl}propyl)amino]carbonyl}-3-methylbutyl)-4-methoxy-1H-indole-2-carboxamide protected the cells from the viral CPE at 39.7 µM and 88.9 µM, respectively ($EC_{50}$, Table 6). However, Vero cells express high levels of the efflux transporter P-gp (also known as MDR1 or ABCB1), of which N-((1S)-1-{[((1S)-3-hydroxy-2-oxo-1-{[(3S)-2-oxopyrrolidin-3-yl]methyl}propyl)amino]carbonyl}-3-methylbutyl)-4-methoxy-1H-indole-2-carboxamide is a known substrate. Therefore, the assays were repeated in the presence of a P-gp efflux inhibitor, CP-100356, 4-(3,4-Dihydro-6,7-dimethoxy-2(1H)-isoquinolinyl)-N-2[2-(3,4-dimethoxyphenyl)ethyl]-6,7-dimethoxy-2-quinazolinamine. N-((1S)-1-{[((1S)-3-hydroxy-2-oxo-1-{[(3S)-2-oxopyrrolidin-3-yl]methyl}propyl)amino]carbonyl}-3-methylbutyl)-4-methoxy-1H-indole-2-carboxamide exhibited a 117 to 173-fold increase in activity in the presence of 2 µM P-gp inhibitor, with $EC_{50}$ values of 0.23 µM in VeroE6-enACE2 cells and 0.76 µM in the VeroE6-EGFP cells (Table 6). The P-gp inhibitor alone had no antiviral or cytotoxic activity at these concentrations and did not cause cytotoxicity in the presence the protease inhibitor. There was a steep response to increasing doses of the parent compound N-((1S)-1-{[((1S)-3-hydroxy-2-oxo-1-{[(3S)-2-oxopyrrolidin-3-yl]methyl}propyl)amino]carbonyl}-3-methylbutyl)-4-methoxy-1H-indole-2-carboxamide, with a ~2-3 fold difference between ECK and ECK) in both cell types ($EC_{90}$=0.48 uM in VeroE6-enACE2 cells and EC90=1.6 uM in VeroE6-EGFP cells in the presence of the P-gp inhibitor). When lung cell lines were tested for antiviral potency in the presence and absence of P-gp inhibitor (A549-ACE2 and MRCS) no significant difference in antiviral potency was observed (Table 6). Additionally, the ECK and ECK) values in both veroE6 cell lines with 2 uM P-gp are similar to those obtained using different assay methods with different cell types, including by detecting viral protein in A549-ACE2 cells as well as using plaque assays in polarized human airway epithelial cells, where Pg-p expression is lower.

TABLE 5

In vitro antiviral activity, cytotoxicity and therapeutic index (TI) of (3S)-3-({N-[(4-methoxy-1H-indol-2-yl)carbonyl]-L-leucyl}amino)-2-oxo-4-[(3S)-2-oxopyrrolidin-3-yl]butyl dihydrogen phosphate

| Cells | Virus | Efflux Inhibitor | $EC_{50}$ µM GeoMean (95% CI) | $CC_{50}$ µM GeoMean (95% CI) | TI $CC_{50}/EC_{50}$ |
|---|---|---|---|---|---|
| Vero E6-enACE2 | SARS2 Washington1 | 0 | 86.7 (71, 106) n = 12 | >100 (ND) n = 6 | >1.0 |
|  |  | 0.5 µM | 26.6 (7.6, 93.6) n = 8 | >100 (ND) n = 6 | >4.82 |
|  |  | 2 µM | 3.8 (1.6, 8.8) n = 7 | >100 (ND) n = 6 | >22.5 |
| Vero E6-EGFP | SARS2 BetaCov GHB-03021/2020 | 0 | >50 (ND) n = 4 | >50 (ND) n = 4 | ND |
|  |  | 0.5 µM | 27 (6.3, 116) n = 4 | >50 (ND) n = 4 | >1.9 |
|  |  | 2 µM | 0.83 (0.50, 1.37) n = 4 | >50 (ND) n = 4 | >61.2 |

TABLE 5-continued

In vitro antiviral activity, cytotoxicity and therapeutic index (TI) of (3S)-3-({N-[(4-methoxy-1H-indol-2-yl)carbonyl]-L-leucyl}amino)-2-oxo-4-[(3S)-2-oxopyrrolidin-3-yl]butyl dihydrogen phosphate

| Cells | Virus | Efflux Inhibitor | $EC_{50}$ μM GeoMean (95% CI) | $CC_{50}$ μM GeoMean (95% CI) | TI $CC_{50}/EC_{50}$ |
|---|---|---|---|---|---|
| MRC-5 | HCoV-229E | 0 | 0.074 (0.013, 0.417) n = 3 | >100 n = 3 | >1500 |
|  |  | 0.5 μM | 0.058 (0.023, 0.15) n = 3 | >100 n = 3 | >1800 |

TABLE 6

In vitro antiviral activity, cytotoxicity and therapeutic index (TI) of the parent compound N-((1S)-1-{[((1S)-3-hydroxy-2-oxo-1-{[(3S)-2-oxopyrrolidin-3-yl]methyl}propyl)amino]carbonyl}-3-methylbutyl)-4-methoxy-1H-indole-2-carboxamide

| Cells | Virus | Efflux Inhibitor | $EC_{50}$ μM GeoMean (95% CI) | $CC_{50}$ μM GeoMean (95% CI) | TI $CC_{50}/EC_{50}$ |
|---|---|---|---|---|---|
| Vero E6-enACE2 | SARS2 Washington1 | 0 | 38.7 (29.8, 52.9) n = 12 | >100 (ND) n = 9 | >2.5 |
|  |  | 0.5 μM | 3.0 (1.13, 7.67) n = 7 | >100 (ND) n = 9 | >42 |
|  |  | 2 μM | 0.23 (0.13, 0.41) n = 6 | >100 (ND) n = 6 | >436 |
| Vero E6-EGFP | SARS2 BetaCov GHB-03021/2020 | 0 | 88.9 (76.8, 103) n = 10 | >100 (ND) n = 8 | >2.6 |
|  |  | 0.5 μM | 10.0 (3.93, 25.7) n = 10 | >100 (ND) n = 1 | >20.6 |
|  |  | 2 μM | 0.76 (0.45, 1.14) n = 4 | >50 (ND) n = 4 | >69 |
| MRC-5 | HCoV-229E | 0 | 0.069 (0.056, 0.085) n = 7 | >100 (ND) n = 5 | >510 |
|  |  | 0.5 μM | 0.080 (0.017, 0.37) n = 3 | >100 (ND) n = 3 | >770 |

The potency of the parent compound N-((1S)-1-{[(((1S)-3-hydroxy-2-oxo-1-{[(3S)-2-oxopyrrolidin-3-yl]methyl} propyl)amino]carbonyl}-3-methylbutyl)-4-methoxy-1H-indole-2-carboxamide in combination with either azithromycin or remdesivir for antiviral activity against SARS-CoV-2 in VeroE6 cells. In brief, VeroE6 cells that are enriched for hACE2 expression were batched innoculated with SARS-CoV-2 (USA_WA1/2020) at a multiplicity of infection of 0.002 in a BSL-3 lab. Virus innoculated cells are then added to assay ready compound plates at a density of 4,000 cells/well. Following a 3-day long incubation, a time at which virus-induced cytopathic effect is 95% in the untreated, infected control conditions, cell viability was evaluated using Cell Titer-Glo (Promega), according to the manufacturer's protocol, which quantitates ATP levels. Cytotoxicity of the compounds was assessed in parallel non-infected cells.

To examine whether combinatory treatments have synergistic or additive effects, each compound is tested at concentrations in a dose matrix. Chalice Analyzer was used to calculate the Loewe additivity and excess models. The Loewe excess is commonly used to indicate the excess percent inhibition; the excess percent inhibition is calculated by deducting the expected percent inhibition values of various combinations, assuming nonsynergy pairing in various models, from the experimental percent inhibition values. These data allowed calculation of the isobologram, synergy score, and best combination index (CI) for each pair. In general, synergy scores of >1 and CI of <1 indicate that a combination treatment has a synergistic effect; a synergy score of 1 and a CI of 1 indicate that a combination treatment has only an additive effect. *Antimicrob Agents Chemother.* 2015 April; 59(4): 2086-2093. doi: 10.1128/AAC.04779-14 To assess whether synergy could be achieved at high inhibition levels, the isobologram level was set at 0.9 to capture meaningful synergy with a 90% viral reduction (equivalent to a 1-$\log_{10}$ reduction).

The combination of the parent compound N-((1S)-1-{[((1S)-3-hydroxy-2-oxo-1-{[(3S)-2-oxopyrrolidin-3-yl]methyl} propyl)amino]carbonyl}-3-methylbutyl)-4-methoxy-1H-indole-2-carboxamide plus azithromycin generated synergy, with a synergy score of 3.76 and a CI of 0.4. The observed synergy was not due to cytotoxicity, as there was no significant cytotoxicity for all the combinations tested. The combination of N-((1S)-1-{[((1S)-3-hydroxy-2-oxo-1-{[(3S)-2-oxopyrrolidin-3-yl]methyl} propyl)amino]carbonyl}-3-methylbutyl)-4-methoxy-1H-indole-2-carboxamide and remdesivir demonstrated additivity, with a synergy score of 5.1 and a CI of 0.21. The observed synergy may potentially be used to reduce the doses and therefore to increase the safety margins of inhibitors to achieve a therapeutic window in vivo. Additionally, combination therapy could be utilized to minimize drug resistance.

Additional studies were carried out to further assess the potential for antiviral combination benefit of the parent compound N-((1S)-1-{[((1S)-3-hydroxy-2-oxo-1-{[(3S)-2- oxopyrrolidin-3-yl]methyl} propyl)amino] carbonyl}-3-methylbutyl)-4-methoxy-1H-indole-2-carboxamide in combination with remdesivir.

Combinations of antiviral agents, especially those targeting different steps in the virus replication cycle, are a frequently employed therapeutic strategy in treating viral diseases. As N-((1S)-1-{[((1S)-3-hydroxy-2-oxo-1-{[(3S)-2-oxopyrrolidin-3-yl]methyl} propyl)amino] carbonyl}-3-methylbutyl)-4-methoxy-1H-indole-2-carboxamide and remdesivir, a nucleoside RNA-dependent RNA polymerase inhibitor, target different steps in the viral replication cycle, the antiviral activity of the two compounds was evaluated alone and in combination using HeLa-ACE2 cells. Viral proteins were detected in this assay using convalescent human polyclonal sera from two different COVID-19 patients. N-((1S)-1-{[((1S)-3-hydroxy-2-oxo-1-{[(3S)-2-oxopyrrolidin-3-yl] methyl} propyl)amino] carbonyl}-3-methylbutyl)-4-methoxy-1H-indole-2-carboxamide (designated compound 1 in table 6) alone inhibited SARS-CoV-2 replication with an average $EC_{50}$ of 0.14 μM and $ECK$) of 0.40 μM; whereas remdesivir had an average $EC_{50}$ of 0.074 μM and $ECK$) of 0.17 μM (Table 7).

TABLE 7

In vitro activity of N-((1S)-1-{[((1S)-3-hydroxy-2-oxo-1-{[(3S)-2-oxopyrrolidin-3-yl]methyl}propyl)amino]carbonyl}-3-methylbutyl)-4-methoxy-1H-indole-2-carboxamide (compound 1) and remdesivir in HeLa-ACE2 cells

| Compound | $EC_{50}$ (μM) | $EC_{90}$ (μM) | n |
|---|---|---|---|
| compound 1 | 0.144 | 0.398 | 3 |
|  | (0.0738-0.280) | (0.143-1.11) |  |
| Remdesivir | 0.0739 | 0.168 | 4 |
|  | (0.629-0.0867) | (0.110-0.256) |  |

Combination studies were performed using a drug testing matrix and the data for the drug combination were analyzed using reference models (Loewe, Bliss, HSA) to classify the effects of the drug combination as either additive, synergistic or antagonistic (isobologram, synergy scores, and combination indices). In general, a synergy score of >1 and a combination index of <1 indicate that the combination treatment has a synergistic effect (Yeo et al, 2015). To assess whether synergy could be achieved at high inhibition levels, the isobologram level was set at 0.9 to capture meaningful synergy with a 90% viral reduction (equivalent to a 1 $log_{10}$ reduction).

Figure 5:
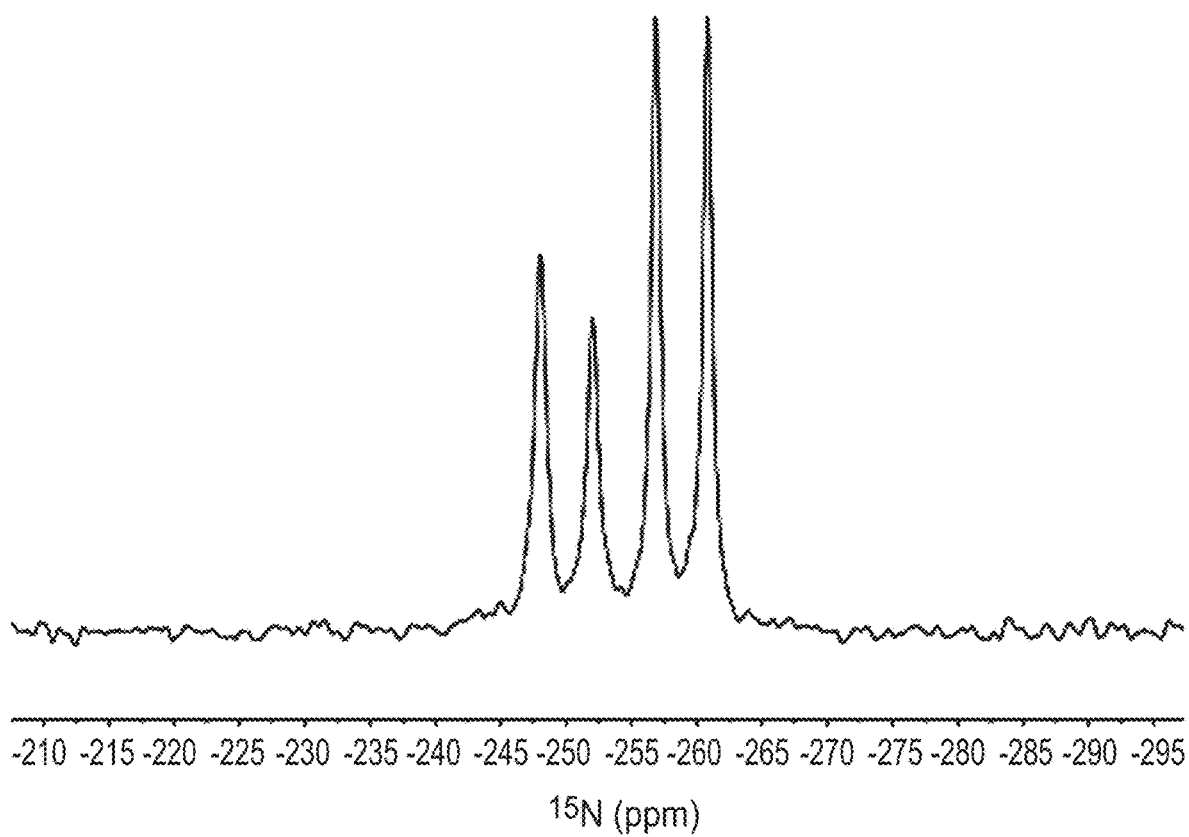
FIG. 5: $^{15}$N solid state NMR spectrum of Form 1 of (3S)-3-({N-[(4-methoxy-1H-indol-2-yl)carbonyl]-L-leucyl}amino)-2-oxo-4-[(3S)-2-oxopyrrolidin-3-yl]butyl dihydrogen phosphate hydrate.
Figure 6:
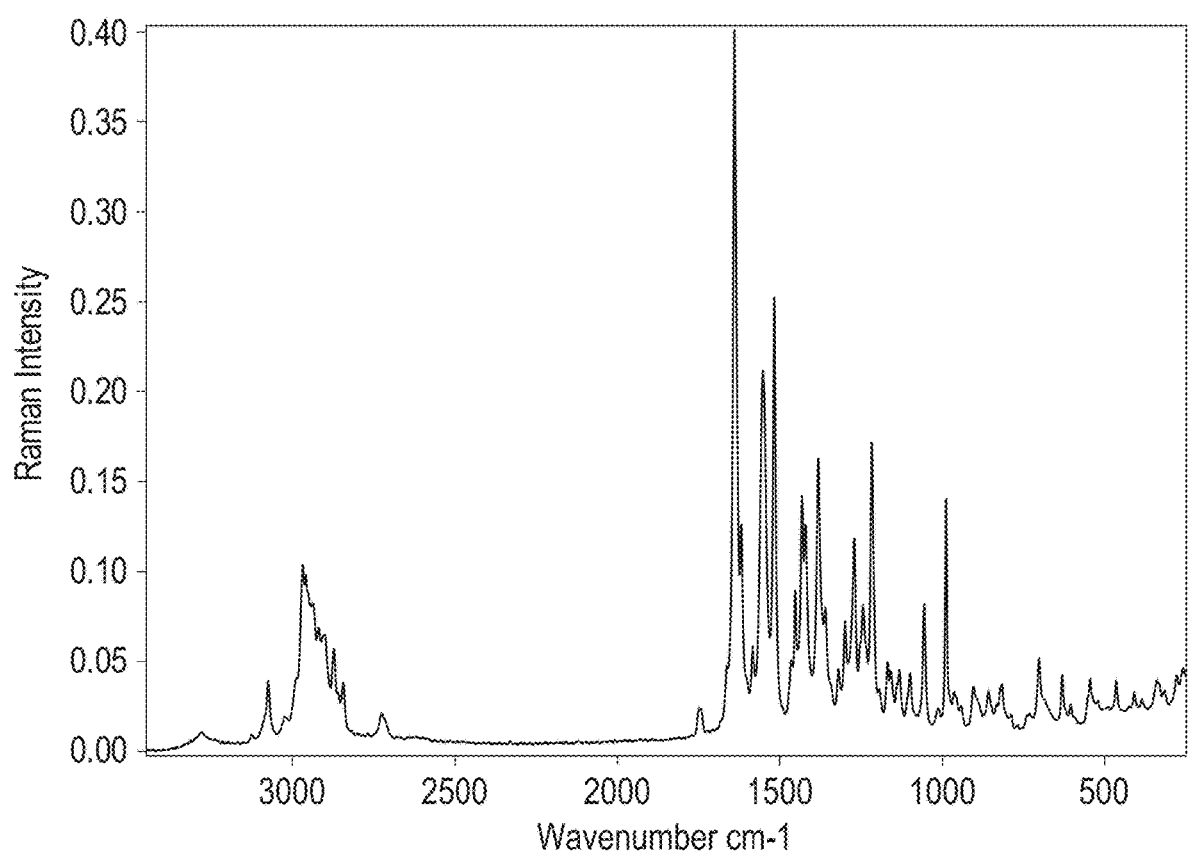
FIG. 6: Raman of Form 1 of (3S)-3-({N-[(4-methoxy-1H-indol-2-yl)carbonyl]-L-leucyl}amino)-2-oxo-4-[(3S)-2-oxopyrrolidin-3-yl]butyl dihydrogen phosphate hydrate.
Figure 8:
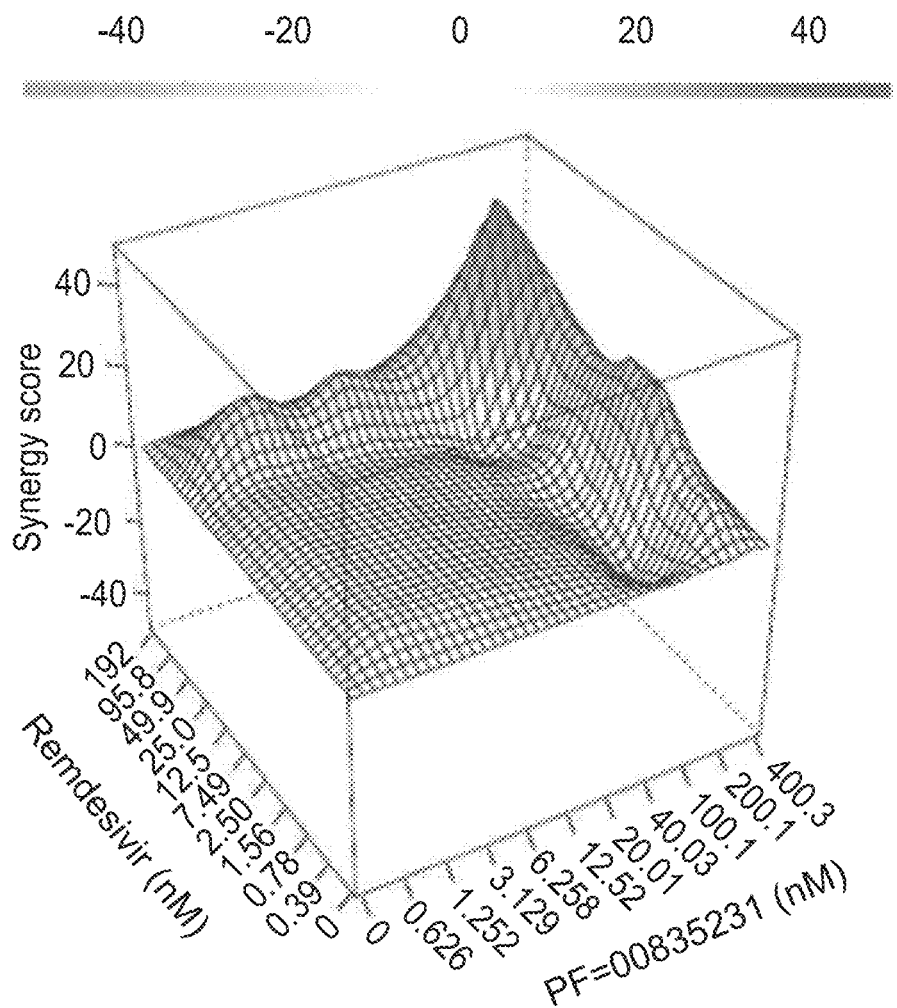
FIG. 8: Isobologram of antiviral activity of the parent compound N-((1S)-1-{[((1S)-3-hydroxy-2-oxo-1-{[(3S)-2-oxopyrrolidin-3-yl]methyl}propyl)amino]carbonyl}-3-methylbutyl)-4-methoxy-1H-indole-2-carboxamide in combination with remdesivir against SARS-CoV-2.

As summarized in Table 8, the combination of the parent compound N-((1S)-1-{[((1S)-3-hydroxy-2-oxo-1-{[(3S)-2-oxopyrrolidin-3-yl] methyl}propyl)amino]carbonyl}-3-methylbutyl)-4-methoxy-1H-indole-2-carboxamide and remdesivir exhibited synergy from patient #1 sera in 2 independent experiments and additivity in a single experiment with sera from patient #2 (Table 8). The different classification is most likely due to the different convalescent serum used as detection reagents. These same antiviral data were also analysed using Synergyfinder program, which also indicated that the 2 drugs were additive to synergistic, with a representative graph shown in FIG. 5. Antagonism was not demonstrated for the combination of N-((1S)-1-{[((1S)-3-hydroxy-2-oxo-1-{[(3S)-2-oxopyrrolidin-3-yl]methyl} propyl)amino]carbonyl}-3-methylbutyl)-4-methoxy-1H-indole-2-carboxamide and remdesivir in these studies. Serial dilutions of N-((1S)-1-{[((1S)-3-hydroxy-2-oxo-1-{[(3S)-2-oxopyrrolidin-3-yl] methyl}propyl)amino]carbonyl}-3-methylbutyl)-4-methoxy-1H-indole-2-carboxamide (designated PF-00835231 in FIG. 8) and remdesivir (concentrations are shown along axis in FIG. 8) were combined in a matrix format. A 3-dimensional drug interaction landscape plotting synergy scores analyzed using GeneData program across all concentrations tested (median scores of three replicates) are shown in FIG. 5. Area of the scores above the plain in the 3-dimensional graph indicates synergism, while under the plain indicates antagonism. The observed additivity/synergy was not due to cytotoxicity, as there was no noticeable cytotoxicity in virus infected host cells for all the combinations tested.

TABLE 8

Combination Synergy Score of parent compound N-((1S)-1-{[((1S)-3-hydroxy-2-oxo-1-{[(3S)-2-oxopyrrolidin-3-yl]methyl} propyl)amino] carbonyl}-3-methylbutyl)-4-methoxy-1H-indole-2-carboxamide with remdesivir.

| Patient Sera | Loewe Synergy Score | Bliss Synergy Score | HSA Synergy Score | Combination Index | n |
|---|---|---|---|---|---|
| 1 | 1.60 | 1.60 | 2.51 | 0.860 | 2 |
|  | (1.18; 2.02) | (1.59; 1.60) | (2.12; 2.89) | (0.837; 0.882) |  |
| 2 | (−0.0776) | (0.366) | (0.830) | (1.04) | 1 |

HSA = Highest single agent;
n = number of determinations;
Data shows average;
(individual values)

Favorable preclinical ADME and pharmacokinetic profile of N-(((1S)-1-{[((1S)-3-hydroxy-2-oxo-1-{[(3S)-2-oxopyrrolidin-3-yl]methyl} propyl)amino] carbonyl}-3-methylbutyl)-4-methoxy-1H-indole-2-carboxamide The metabolic stability of N-((1S)-1-{[((1S)-3-hydroxy-2-oxo-1-{[(3S)-2-oxopyrrolidin-3-yl]methyl}propyl)amino] carbonyl}-3-methylbutyl)-4-methoxy-1H-indole-2-carboxamide was evaluated in vitro using pooled human liver microsomes (HLM) and hepatocytes. The drug was shown to be metabolized by cytochrome P450 enzymes exhibiting an unbound $Cl_{int}$ 14 μl/min/mg. With the use of chemical inhibitors and recombinant heterologously expressed enzymes, CYP3A4 was identified as the major CYP involved in the metabolism of this compound. It was also noted that the polymorphically expressed CYP3A5 can also metabolize N-((1S)-1-{[((1S)-3-hydroxy-2-oxo-1-{[(3S)-2-oxopyrrolidin-3-yl]methyl} propyl)amino]carbonyl}-3-methylbutyl)-4-methoxy-1H-indole-2-carboxamide and that clearance may be slightly greater in CYP3A5 expressers. The potential for the compound to reversibly inhibit human cytochrome P450 enzymes (CYP1A2, 2B6, 2C8, 2C9, 2C19, 2D6, and 3A) was evaluated using probe substrates (supplemental) in pooled HLM and provided $IC_{50}$ values>200 μM and a weak signal for time dependent inhibition of CYP3A4/5 indicating N-((1S)-1-{[((1S)-3-hydroxy-2-oxo-1-{[(3S)-2-oxopyrrolidin-3-yl]methyl} propyl)amino] carbonyl}-3-methylbutyl)-4-methoxy-1H-indole-2-carboxamide provides a low risk of causing drug-drug interactions (DDI) on coadministration with other drugs. The potential for N-((1S)-1-{[((1S)-3-hydroxy-2-oxo-1-{[(3S)-2-oxopyrrolidin-3-yl]methyl} propyl)amino] carbonyl}-3-methylbutyl)-4-methoxy-1H-indole-2-carboxamide to inhibit a range of transporters (BCRP, Pgp, OATP1B1/1B3, OCT1/2, OAT1/3 and MATE1/2K) was evaluated using in vitro systems. The $IC_{50}$ values>20 μM indicating a low risk of causing DDI's due to transporter inhibition at the projected clinical exposure. The plasma protein binding of N-((1S)-1-{[((1S)-3-hydroxy-2-oxo-1-{[(3S)-2-oxopyrrolidin-3-yl] methyl}propyl)amino]carbonyl}-3-methylbutyl)-4-methoxy-1H-indole-2-carboxamide was measured across species using equilibrium dialysis showing moderate binding to plasma proteins with plasma free fractions of 0.26 to 0.46 across species.

N-((1S)-1-{[((1S)-3-hydroxy-2-oxo-1-{[(3S)-2-oxopyrrolidin-3-yl]methyl} propyl)amino] carbonyl}-3-methylbutyl)-4-methoxy-1H-indole-2-carboxamide was administered intravenously to rats, dogs and monkeys (1 or 2 mg/kg) and exhibited moderate plasma clearances (35-60% liver blood flow), low volumes of distribution (<1 L/Kg) and short half-lives (<1.5 h) across species in keeping with its neutral physiochemistry and lipophilicity (SFLogD$_{7.4}$=1.7). Following oral administration to rats (2 mg/kg) and monkeys (5 mg/kg) N-((1S)-1-{[((1S)-3-hydroxy-2-oxo-1-{[(3S)-2-oxopyrrolidin-3-yl]methyl}propyl)amino] carbonyl}-3-methylbutyl)-4-methoxy-1H-indole-2-carboxamide exhibited low bioavailability (<2%), likely due to a combination of low absorption because of its low permeability (apparent MDCK-LE permeability of 1.3×10$^{-6}$ cm/sec), low solubility, potential for active efflux in the gut by P-gp and BCRP, as well as the potential for amide hydrolysis by digestive enzymes in the gastrointestinal tract. In rat, dog and monkey approximately 10% of N-((1S)-1-{[((1S)-3-hydroxy-2-oxo-1-{[(3S)-2-oxopyrrolidin-3-yl]methyl} propyl)amino] carbonyl}-3-methylbutyl)-4-methoxy-1H-indole-2-carboxamide was eliminated unchanged in the urine indicating renal elimination may also play a minor role in the clearance of N-((1S)-1-{[((1S)-3-hydroxy-2-oxo-1-{[(3S)-2-oxopyrrolidin-3-yl]methyl}propyl)amino]carbonyl}-3-methylbutyl)-4-methoxy-1H-indole-2-carboxamide in humans.

Human pharmacokinetic predictions suitable for IV administration—taking into account the human in vitro metabolism data and in vivo pharmacokinetic (PK) data in rats, dogs and monkeys N-((1S)-1-{[((1S)-3-hydroxy-2-oxo-1-{[(3S)-2-oxopyrrolidin-3-yl]methyl} propyl)amino]carbonyl}-3-methylbutyl)-4-methoxy-1H-indole-2-carboxamide is predicted to exhibit a plasma clearance (CL$_p$) of ~6 ml/min/kg (major CYP, minor renal pathways) steady state volume of distribution (V$_{dss}$) of 1 L/kg and half-life of approximately 2 h in humans. Due to the limited oral bioavailability, short elimination half-life, and the likely need to maintain free systemic concentrations over time, a continuous intravenous (IV) infusion was proposed as the optimal dosing route and regimen.

Efficacious Target Concentration and Feasible Human Dose Projection to Achieve Target Ceff The inhibitory quotient (IQ) has been a useful metric for translating preclinical antiviral potencies to the clinic across a number of viral diseases. IQ is defined as the human C$_{min,u}$ unbound concentration divided by the in vitro unbound (serum adjusted) EC$_{50,u}$ value in the antiviral assay (equation 1).

$$IQ = \frac{C_{min,u}}{EC_{50,u}} \tag{1}$$

Some antiviral therapies have shown significant benefit with IQ close to 1; however, rapidly controlling viral replication frequently requires maintaining an exposure at least 10× higher than in vitro EC$_{50}$. Clinically approved protease inhibitors have effectively decreased viral loads when dosed at IQ values from 1-100, when protein binding and site of action exposure are taken into account. Importantly, antivirals in general and, specifically, protease inhibitors can potentially lead to increased mutations and additional drug resistance when dosed at an IQ less than 1.

How high an IQ value is required depends on the slope of the dose response curve. The Hill coefficient (m) and the EC$_{50}$ are related to the in vitro antiviral activity at a range of concentrations (C) by equation 2:

$$\text{in vitro antiviral acitivity} = 100 * \frac{C^m}{EC_{50}^m + C^m} \tag{2}$$

N-((1S)-1-{[((1S)-3-hydroxy-2-oxo-1-{[(3S)-2-oxopyrrolidin-3-yl]methyl} propyl)amino] carbonyl}-3-methylbutyl)-4-methoxy-1H-indole-2-carboxamide shows a high slope (m=3) across a range of in vitro antiviral assays, like those of clinical protease inhibitors targeting HIV and HCV. There is only a 2-to-3-fold difference between the antiviral EC$_{50}$ and EC$_{90}$ concentrations, rather than the typical 9-fold difference for antiviral agents with Hill coefficients of 1. Therefore, relatively small ratios of exposure to ECK values (3-10) are related to near complete viral suppression.

The projected minimally efficacious concentration (C$_{eff}$) was chosen to match the in vitro EC$_{90}$, consistent with the preclinical to clinical translation of approved protease inhibitors. Since N-((1S)-1-{[((1S)-3-hydroxy-2-oxo-1-{[(3S)-2-oxopyrrolidin-3-yl]methyl} propyl)amino]carbonyl}-3-methylbutyl)-4-methoxy-1H-indole-2-carboxamide was proposed to be administered by continuous infusion, the projected steady state exposure is equal to the C$_{min}$ maintained over the dosing interval. The dose response assay performed in the physiologically relevant cell type, human lung carcinoma, resulted in an average EC$_{90}$ value of 0.44 µM. This is consistent with additional antiviral data in Hela-ACE2 cells (EC$_{90}$=0.4 µM) and Vero-cell lines (EC$_{90}$=~0.48-1.6 µM) when a P-gp inhibitor was added to better reflect the lack of substantial P-gp transporter in the lung. Furthermore, the antiviral inhibition is supported by the antiviral time course experiment performed in a primary human airway epithelial model (preliminary data indicates an unbound EC$_{90}$<0.5 µM), indicating a consistent intrinsic anti-SARS-CoV-2 activity of N-((1S)-1-{[((1S)-3-hydroxy-2-oxo-1-{[(3S)-2-oxopyrrolidin-3-yl]methyl}propyl)amino] carbonyl}-3-methylbutyl)-4-methoxy-1H-indole-2-carboxamide across different cell types. Therefore, the proposed target C$_{eff}$ is ~0.5 µM.

Due to the rapid blood perfusion through the lungs and the continuous steady state intravenous infusion regimen, the free plasma and free lung concentrations are assumed to be in equilibrium and, therefore, the free plasma concentration provides a reasonable surrogate for the concentration at the main site of action of the disease. Based on the human PK predictions, the minimally efficacious dose of N-((1S)-1-{[((1S)-3-hydroxy-2-oxo-1-{[(3S)-2-oxopyrrolidin-3-yl] methyl} propyl)amino] carbonyl}-3-methylbutyl)-4-methoxy-1H-indole-2-carboxamide necessary to achieve this exposure is 320 mg/day administered as an intravenous continuous infusion. The required duration of dosing for efficacy remains uncertain and will need to be evaluated in humans. Based on clinical results from remdesivir a duration of up to 10 days of dosing may be required to provide improved patient outcomes.

The compound of Example 49, (3S)-3-({N-[(4-methoxy-1H-indol-2-yl)carbonyl]-L-leucyl}amino)-2-oxo-4-[(3S)-2-oxopyrrolidin-3-yl]butyl dihydrogen phosphate, has been found to have an advantageous aqueous solubility of greater than 200 mg/mL and can thus be formulated as an aqueous solution. For example, (3S)-3-({N-[(4-methoxy-1H-indol-2-yl)carbonyl]-L-leucyl}amino)-2-oxo-4-[(3S)-2-oxopyrrolidin-3-yl]butyl dihydrogen phosphate can be formulated as a solution in either a saline solution or dextrose solution which is suitable for intravenous administration. Intravenous administration of (3S)-3-({N-[(4-methoxy-1H-indol-2-yl)carbonyl]-L-leucyl}amino)-2-oxo-4-[(3S)-2-oxopyrrolidin-3-yl]butyl dihydrogen phosphate can be accomplished by administering a bolus of the compound or by continuous administration by infusion. A sterile frozen solution of (3S)-3-({N-[(4-methoxy-1H-indol-2-yl)carbonyl]-L-leucyl}amino)-2-oxo-4-[(3S)-2-oxopyrrolidin-3-yl]butyl dihydrogen phosphate can be thawed to yield a 25 mg/mL drug solution that can be dosed or can be diluted with 0.9% Sodium Chloride Injection, USP or 5% Dextrose Injection, USP. The dosage of (3S)-3-({N-[(4-methoxy-1H-indol-2-yl)carbonyl]-L-leucyl}amino)-2-oxo-4-[(3S)-2-oxopyrrolidin-3-yl]butyl dihydrogen phosphate administered to a patient could range from 100 mg to 10 g per day, from 250 mg to 7.5 g per day, from 0.5 g to 5 g per day, from 1 g to 4 g per day or from 2 g to 3 g per day. A dose of 500 mg/day of (3S)-3-({N-[(4-methoxy-1H-indol-2-yl)carbonyl]-L-leucyl}amino)-2-oxo-4-[(3S)-2-oxopyrrolidin-3-yl]butyl dihydrogen phosphate can readily be administered to a patient in view of the compound's solubility of 200 mg/mL or greater. This highly favorable solubility enables administration of (3S)-3-({N-[(4-methoxy-1H-indol-2-yl)carbonyl]-L-leucyl}amino)-2-oxo-4-[(3S)-2-oxopyrrolidin-3-yl]butyl dihydrogen phosphate in amounts that are 1×, 3×, 7× and 10× fold over the $EC_{90}$ for the compound and thus provides advantageous dosing flexibility in a clinical setting.

Single-Dose Pharmacokinetics of (3S)-3-({N-[(4-methoxy-1H-indol-2-yl)carbonyl]-L-leucyl}amino)-2-oxo-4-[(3S)-2-oxopyrrolidin-3-yl]butyl dihydrogen phosphate The pharmacokinetics of (3S)-3-({N-[(4-methoxy-1H-indol-2-yl)carbonyl]-L-leucyl}amino)-2-oxo-4-[(3S)-2-oxopyrrolidin-3-yl]butyl dihydrogen phosphate (compound of Example 49), the parent hydroxy compound N-((1S)-1-{[((1S)-3-hydroxy-2-oxo-1-{[(3S)-2-oxopyrrolidin-3-yl]methyl}propyl)amino]carbonyl}-3-methylbutyl)-4-methoxy-1H-indole-2-carboxamide and % conversion to N-((1S)-1-{[((1S)-3-hydroxy-2-oxo-1-{[(3S)-2-oxopyrrolidin-3-yl]methyl}propyl)amino]carbonyl}-3-methylbutyl)-4-methoxy-1H-indole-2-carboxamide (following IV dosing of (3S)-3-({N-[(4-methoxy-1H-indol-2-yl)carbonyl]-L-leucyl}amino)-2-oxo-4-[(3S)-2-oxopyrrolidin-3-yl]butyl dihydrogen phosphate) were characterized following single IV dosing in rats, dogs, and monkeys. 1.17 mg/kg of (3S)-3-({N-[(4-methoxy-1H-indol-2-yl)carbonyl]-L-leucyl}amino)-2-oxo-4-[(3S)-2-oxopyrrolidin-3-yl]butyl dihydrogen phosphate was administered to Rat (Wistar Han), Dog (Beagle) or Monkey (Cynomulgus). Clearance of (3S)-3-({N-[(4-methoxy-1H-indol-2-yl)carbonyl]-L-leucyl}amino)-2-oxo-4-[(3S)-2-oxopyrrolidin-3-yl]butyl dihydrogen phosphate was higher than hepatic blood flow and approximately 75% conversion to N-((1S)-1-{[((1S)-3-hydroxy-2-oxo-1-{[(3S)-2-oxopyrrolidin-3-yl]methyl}propyl)amino]carbonyl}-3-methylbutyl)-4-methoxy-1H-indole-2-carboxamide was observed in these species (68% in Rat, 81% in Dog and 76% in Monkey).

Metabolism studies of (3S)-3-({N-[(4-methoxy-1H-indol-2-yl)carbonyl]-L-leucyl}amino)-2-oxo-4-[(3S)-2-oxopyrrolidin-3-yl]butyl dihydrogen phosphate The in vitro metabolism contributing to the conversion of (3S)-3-({N-[(4-methoxy-1H-indol-2-yl)carbonyl]-L-leucyl}amino)-2-oxo-4-[(3S)-2-oxopyrrolidin-3-yl]butyl dihydrogen phosphate to N-((1S)-1-{[((1S)-3-hydroxy-2-oxo-1-{[(3S)-2-oxopyrrolidin-3-yl]methyl}propyl)amino]carbonyl}-3-methylbutyl)-4-methoxy-1H-indole-2-carboxamide was assessed in plasma and S9 fractions prepared from liver, kidney, and lung tissues of nonclinical species and humans. A high rate of metabolism of the phosphate compound to the hydroxy compound was observed in all the S9 fractions tested. In human liver microsomes (HLM) and human S9, both the depletion of (3S)-3-({N-[(4-methoxy-1H-indol-2-yl)carbonyl]-L-leucyl}amino)-2-oxo-4-[(3S)-2-oxopyrrolidin-3-yl]butyl dihydrogen phosphate and formation of N-((1S)-1-{[((1S)-3-hydroxy-2-oxo-1-{[(3S)-2-oxopyrrolidin-3-yl]methyl}propyl)amino]carbonyl}-3-methylbutyl)-4-methoxy-1H-indole-2-carboxamide were significantly increased during incubations prepared with Tris versus phosphate buffer, consistent with metabolic activity mediated by alkaline phosphatase.

A preliminary assessment of the in vitro metabolism of non-radiolabeled N-((1S)-1-{[((1S)-3-hydroxy-2-oxo-1-{[(3S)-2-oxopyrrolidin-3-yl]methyl}propyl)amino]carbonyly}-3-methylbutyl)-4-methoxy-1H-indole-2-carboxamide in liver microsomes and the in vivo metabolism in plasma from rats, dogs, and monkeys dosed with (3S)-3-({N-[(4-methoxy-1H-indol-2-yl)carbonyl]-L-leucyl}amino)-2-oxo-4-[(3S)-2-oxopyrrolidin-3-yl]butyl dihydrogen phosphate was conducted. In vivo, radiolabeled N-((1S)-1-{[((1S)-3-hydroxy-2-oxo-1-{[(3S)-2-oxopyrrolidin-3-yl]methyl}propyl)amino]carbonyl}-3-methylbutyl)-4-methoxy-1H-indole-2-carboxamide was the major drug related entity along with a possible epimer of that compound. All metabolites were formed via oxidative pathways and there were no unique human metabolites observed in vitro. The safety profile of (3S)-3-({N-[(4-methoxy-1H-indol-2-yl)carbonyl]-L-leucyl}amino)-2-oxo-4-[(3S)-2-oxopyrrolidin-3-yl]butyl dihydrogen phosphate and N-((1S)-1-{[((1S)-3-hydroxy-2-oxo-1-{[(3S)-2-oxopyrrolidin-3-yl]methyl}propyl)amino]carbonyl}-3-methylbutyl)-4-methoxy-1H-indole-2-carboxamide was assessed individually in a range of in vitro and in vivo safety studies in rats. In the in vitro studies, (3S)-3-({N-[(4-methoxy-1H-indol-2-yl)carbonyl]-L-leucyl}amino)-2-oxo-4-[(3S)-2-oxopyrrolidin-3-yl]butyl dihydrogen phosphate and N-((1S)-1-{[((1S)-3-hydroxy-2-oxo-1-{[(3S)-2-oxopyrrolidin-3-yl]methyl}propyl)amino]carbonyl}-3-methylbutyl)-4-methoxy-1H-indole-2-carboxamide were negative in the bacterial reverse mutation assay and did not induce micronuclei formation. Both the phosphate and parent compounds had minimal potential for secondary (off-target) pharmacology at clinically relevant exposures. Neither (3S)-3-({N-[(4-methoxy-1H-indol-2-yl)carbonyl]-L-leucyl}amino)-2-oxo-4-[(3S)-2-oxopyrrolidin-3-yl]butyl dihydrogen phosphate nor N-((1S)-1-{[((1S)-3-hydroxy-2-oxo-1-{[(3S)-2-oxopyrrolidin-3-yl]methyl}propyl)amino]carbonyl}-3-methylbutyl)-4-methoxy-1H-indole-2-carboxamide inhibited hERG current amplitude at up to 300 μM (1,770× and 600×, respectively, the projected unbound human $C_{max}$ of 0.17 and 0.50 μM, respectively, at the projected human efficacious dose) indicating a favorable cardiovascular safety profile. In human blood hemocompatibility assays, both compounds had no effect on hemolysis or flocculation/turbidity parameters, indicating compatibility with human blood and supporting intravenous administration.

(3S)-3-({N-[(4-methoxy-1H-indol-2-yl)carbonyl]-L-leucyl}amino)-2-oxo-4-[(3S)-2-oxopyrrolidin-3-yl]butyl dihydrogen phosphate was administered to rats via continuous IV infusion for 24 hours in a GLP study. There were no test article related findings and no target organ toxicity was identified. (3S)-3-({N-[(4-methoxy-1H-indol-2-yl)carbonyl]-L-leucyl}amino)-2-oxo-4-[(3S)-2-oxopyrrolidin-3-yl]butyl dihydrogen phosphate had no effects on neurological safety pharmacology parameters as assessed by functional observation battery in the 24 hour continuous IV infusion rat study. The no observed adverse effect level (NOAEL) was 1000 mg/kg. The parent compound N-((1S)-1-{[((1S)-3-hydroxy-2-oxo-1-{[(3S)-2-oxopyrrolidin-3-yl]methyl}propyl)amino]carbonyl}-3-methylbutyl)-4-methoxy-1H-indole-2-carboxamide was also administered to male rats via continuous IV infusion for 4 days in a non-GLP exploratory toxicity study and was tolerated at 246 mg/kg/day, the highest feasible dose tested. N-((1S)-1-{[((1S)-3-hydroxy-2-oxo-1-{[(3S)-2-oxopyrrolidin-3-yl]methyl}propyl)amino]carbonyl}-3-methylbutyl)-4-methoxy-1H-indole-2-carboxamide-related findings in this study were limited to minimal, non-adverse effects on clinical chemistry parameters including higher mean triglycerides, cholesterol, and phosphorus without any microscopic correlates or associated functional changes. No test article related adverse effects were seen in any study.

At the NOAEL from the 24 hour GLP continuous IV infusion study with (3S)-3-({N-[(4-methoxy-1H-indol-2-yl)carbonyl]-L-leucyl}amino)-2-oxo-4-[(3S)-2-oxopyrrolidin-3-yl]butyl dihydrogen phosphate (PF-07304814) in rats, the anticipated exposure margins for unbound $C_{max}$ and $AUC_{24}$ are 97× and 65× for (3S)-3-({N-[(4-methoxy-1H-indol-2-yl)carbonyl]-L-leucyl}amino)-2-oxo-4-[(3S)-2-oxopyrrolidin-3-yl]butyl dihydrogen phosphate and 25× and 21× for N-((1S)-1-{[((1S)-3-hydroxy-2-oxo-1-{[(3S)-2-oxopyrrolidin-3-yl]methyl}propyl)amino]carbonyl}-3-methylbutyl)-4-methoxy-1H-indole-2-carboxamide, at the projected minimum human efficacious dose of 0.5 g/day. This indicates the potential to safely evaluate multiples over ECK) in humans during clinical testing to understand exposure response relationship and to achieve high levels of inhibition, if required. Furthermore, no overlapping or additive toxicity with medications currently being used in standard of care COVID-19 treatment is expected with administration of (3S)-3-({N-[(4-methoxy-1H-indol-2-yl)carbonyl]-L-leucyl}amino)-2-oxo-4-[(3S)-2-oxopyrrolidin-3-yl]butyl dihydrogen phosphate in humans making this compound an attractive partner for combination therapy. Based on results from the set of safety studies conducted, (3S)-3-({N-[(4-methoxy-1H-indol-2-yl)carbonyl]-L-leucyl}amino)-2-oxo-4-[(3S)-2-oxopyrrolidin-3-yl]butyl dihydrogen phosphate exhibits an encouraging nonclinical safety profile. The predicted human pharmacokinetics of (3S)-3-({N-[(4-methoxy-1H-indol-2-yl)carbonyl]-L-leucyl}amino)-2-oxo-4-[(3S)-2-oxopyrrolidin-3-yl]butyl dihydrogen phosphate provide the ability to achieve systemic unbound concentrations of 0.5 µM (ECK) of the parent compound N-((1S)-1-{[((1S)-3-hydroxy-2-oxo-1-{[(3S)-2-oxopyrrolidin-3-yl]methyl}propyl)amino]carbonyl}-3-methylbutyl)-4-methoxy-1H-indole-2-carboxamide by delivering 500 mg of (3S)-3-({N-[(4-methoxy-1H-indol-2-yl)carbonyl]-L-leucyl}amino)-2-oxo-4-[(3S)-2-oxopyrrolidin-3-yl]butyl dihydrogen phosphate as a continuous infusion over 24 hours and infusion volumes<250 mL.

In Vivo Murine Infection Studies

Demonstration of drug efficacy in an animal model is important to establish a PK/PD relationship and provide supporting evidence for choice of clinical dosing parameters. The mouse-adapted (MA15) model of CoV-1 infection was used to evaluate the parent compound N-((1S)-1-{[((1S)-3-hydroxy-2-oxo-1-{[(3S)-2-oxopyrrolidin-3-yl]methyl}propyl)amino]carbonyl}-3-methylbutyl)-4-methoxy-1H-indole-2-carboxamide (active moiety formed following administration of the compound of Example 49); (See Deming RA., et al. A mouse-adapted SARS-coronavirus causes disease and mortality in BALB/c mice. PLoS Pathog. 2007; 3(1), e5 and Frieman M., et al. Molecular determinants of severe acute respiratory syndrome coronavirus pathogenesis and virulence in young and aged mouse models of human disease. J Virol. 2012; 86(2), 884-97). MA15-CoV-infected mice were treated with N-((1S)-1-{[((1S)-3-hydroxy-2-oxo-1-{[(3S)-2-oxopyrrolidin-3-yl]methyl}propyl)amino]carbonyl}-3-methylbutyl)-4-methoxy-1H-indole-2-carboxamide, 100 mg/kg, twice daily (BID) by the subcutaneous (s.c.) route. This dose was predicted to achieve a free drug exposure at $C_{min}$ of ≈500 nM or about 1×EC$_{90}$ (the concentration of compound required to reduce virus by 90% in in vitro assays of CoV-1 and CoV-2 replication), aligned with our potential minimal efficacious dose clinically. In one experiment, treatment was initiated at the time of infection (day 0) or delayed for 1- or 2-days post-infection. Lung viral titers on day 4 post-infection were reduced ≈2.0, 1.5 and 1.0 log 10 with treatment starting on days 0, 1, and 2 post infection, respectively. Weight loss and histopathologic signs of disease were decreased, particularly when dosing of N-((1S)-1-{[((1S)-3-hydroxy-2-oxo-1-{[(3S)-2-oxopyrrolidin-3-yl]methyl}propyl)amino]carbonyl}-3-methylbutyl)-4-methoxy-1H-indole-2-carboxamide was started on day 0. In a second experiment, treatment with N-((1S)-1-{[((1S)-3-hydroxy-2-oxo-1-{[(3S)-2-oxopyrrolidin-3-yl]methyl}propyl)amino]carbonyl}-3-methylbutyl)-4-methoxy-1H-indole-2-carboxamide was initiated on day 0 and the dose of drug was varied (30, 100, and 300 mg/kg, BID, s.c.). Lung viral titers from MA15 infected mice treated with N-((1S)-1-{[((1S)-3-hydroxy-2-oxo-1-{[(3S)-2-oxopyrrolidin-3-yl]methyl}propyl)amino]carbonyl}-3-methylbutyl)-4-methoxy-1H-indole-2-carboxamide or vehicle, were determined in a viral plaque assay on Vero cells and represented by plaque-forming units (PFU) per µg of lung tissue. The body weights of animals were determined each day and plotted as % starting weight, We observed a dose-dependent decline in day 4 lung viral titers for the three doses: ≈1.5 log 10 at 30 mg/kg; ≈3 log 10 at 100 mg/kg; and ≥3.5 log 10 at 300 mg/kg. The weight loss caused by the virus was reduced by treatment with the parent compound N-((1S)-1-{[((1S)-3-hydroxy-2-oxo-1-{[(3S)-2-oxopyrrolidin-3-yl]methyl}propyl)amino]carbonyl}-3-methylbutyl)-4-methoxy-1H-indole-2-carboxamide at all three doses. This data supports a prediction that 500 mg of (3S)-3-({N-[(4-methoxy-1H-indol-2-yl)carbonyl]-L-leucyl}amino)-2-oxo-4-[(3S)-2-oxopyrrolidin-3-yl]butyl dihydrogen phosphate administered as a continuous infusion over 24 hours can be an efficacious dose in humans for treatment of SARS-CoV-2.

All patents and publications described hereinabove are hereby incorporated by reference in their entirety. While the invention has been described in terms of various preferred embodiments and specific examples, the invention should be understood as not being limited by the foregoing detailed description, but as being defined by the appended claims and their equivalents.

What is claimed is:

1. Crystalline (3S)-3-({N-[(4-methoxy-1H-indol-2-yl)carbonyl]-L-leucyl}amino)-2-oxo-4-[(3S)-2-oxopyrrolidin-3-yl]butyl dihydrogen phosphate hydrate having one or more characteristics selected from the group consisting of a powder X-ray diffraction pattern, a $^{13}$C solid state NMR spectrum and a Raman spectrum;

wherein the powder X-ray diffraction pattern characteristic is selected from
a) a powder X-ray diffraction pattern comprising peaks at 4.1±0.2 and 7.2±0.2 degrees 2-Theta;
b) a powder X-ray diffraction pattern comprising peaks at 4.1±0.2, 7.2±0.2 and 10.4±0.2 degrees 2-Theta; and
c) a powder X-ray diffraction pattern comprising peaks at 4.1±0.2, 7.2±0.2, 10.4±0.2 and 14.5±0.2 degrees 2-Theta;

wherein the $^{13}$C solid state NMR spectrum characteristic is selected from
a) $^{13}$C solid state NMR spectrum comprising peaks at 21.7, 153.8 and 172.2 ppm; each peak±0.2 ppm;
b) a $^{13}$C solid state NMR spectrum comprising peaks at 21.7, 153.8, 172.2 and 118.6 ppm; each peak±0.2 ppm; and
c) a $^{13}$C solid state NMR spectrum comprising peaks at 21.7, 153.8, 172.2, 118.6 and 57.8 ppm; each peak±0.2 ppm; and wherein the Raman spectrum characteristic is selected from
a) a Raman spectrum comprising Raman peaks at 1271, 1421 and 1217 cm$^{-1}$, each peak±2 cm$^{-1}$,
b) a Raman spectrum comprising Raman peaks at 1271, 1421, 1217 and 1640 cm$^{-1}$; each peak±2 cm$^{-1}$ and c) a Raman spectrum comprising Raman peaks at 1271, 1421, 1217, 1640 and 3074 cm$^{-1}$; each peak±2 cm$^{-1}$.

2. The compound (3S)-3-({N-[(4-methoxy-1H-indol-2-yl)carbonyl]-L-leucyl}amino)-2-oxo-4-[(3S)-2-oxopyrrolidin-3-yl]butyl dihydrogen phosphate, methyl ethyl ketone solvate.

3. The compound of claim 2 which is a crystalline (3S)-3-({N-[(4-methoxy-1H-indol-2-yl)carbonyl]-L-leucyl}amino)-2-oxo-4-[(3S)-2-oxopyrrolidin-3-yl]butyl dihydrogen phosphate, methyl ethyl ketone solvate.

4. The compound of claim 3 which is crystalline (3S)-3-({N-[(4-methoxy-1H-indol-2-yl)carbonyl]-L-leucyl}amino)-2-oxo-4-[(3S)-2-oxopyrrolidin-3-yl]butyl dihydrogen phosphate, methyl ethyl ketone solvate having one or more characteristics selected from the group consisting of a powder X-ray diffraction pattern, a $^{13}$C NMR spectrum and a Raman spectrum;
wherein the powder X-ray diffraction pattern characteristic is selected from
a) a powder X-ray diffraction pattern comprising peaks at 7.7±0.2, 8.1±0.2 and 23.1±0.2 degrees 2-Theta;
b) a powder X-ray diffraction pattern comprising peaks at 7.7±0.2, 8.1±0.2, 23.1±0.2 and 17.0±0.2 degrees 2-Theta; and
c) a powder X-ray diffraction pattern comprising peaks at 7.7±0.2, 8.1±0.2, 23.1±0.2, 17.0±0.2 and 25.8±0.2 degrees 2-Theta;
wherein the $^{13}$C solid state NMR spectrum characteristic is selected from
a) a $^{13}$C solid state NMR spectrum comprising peaks at 7.2, 206.4 and 215.8 ppm; each ±0.2 ppm;
b) a $^{13}$C solid state NMR spectrum comprising peaks at 7.2, 206.4, 215.8 and 42.2 ppm; each ±0.2 ppm; and
c) a $^{13}$C solid state NMR spectrum comprising peaks at 7.2, 206.4, 215.8, 42.2 and 101.2 ppm; each ±0.2 ppm; and
wherein the Raman spectrum characteristic is selected from
a) a Raman spectrum comprising peaks at 1511, 1644 and 3081 cm$^{-1}$, each ±2 cm$^{-1}$,
b) a Raman spectrum comprising peaks at 1511, 1644, 3081 and 1265 cm$^{-1}$; each ±2 cm$^{-1}$; and
c) a Raman spectrum comprising peaks at 1511, 1644, 3081, 1265 and 446 cm$^{-1}$; each ±2 cm$^{-1}$.

5. The compound (3S)-3-({N-[(4-methoxy-1H-indol-2-yl)carbonyl]-L-leucyl}amino)-2-oxo-4-[(3S)-2-oxopyrrolidin-3-yl]butyl dihydrogen phosphate, dimethylsulfoxide solvate.

6. The compound of claim 5 which is crystalline (3S)-3-({N-[(4-methoxy-1H-indol-2-yl)carbonyl]-L-leucyl}amino)-2-oxo-4-[(3S)-2-oxopyrrolidin-3-yl]butyl dihydrogen phosphate, dimethylsulfoxide solvate.

7. The compound of claim 6 which is crystalline (3S)-3-({N-[(4-methoxy-1H-indol-2-yl)carbonyl]-L-leucyl}amino)-2-oxo-4-[(3S)-2-oxopyrrolidin-3-yl]butyl dihydrogen phosphate, dimethylsulfoxide solvate having one or more characteristics selected from the group consisting of a powder X-ray diffraction pattern, a $^{13}$C solid state NMR spectrum and a Raman spectrum;
wherein the powder X-ray diffraction pattern characteristic is selected from
a) a powder X-ray diffraction pattern comprising peaks at 7.4±0.2, 14.8±0.2 and 26.2±0.2 degrees 2-Theta;
b) a powder X-ray diffraction pattern comprising peaks at 7.4±0.2, 14.8±0.2, 26.2±0.2 and 10.8±0.2 degrees 2-Theta; and
c) a powder X-ray diffraction pattern comprising peaks at 7.4±0.2, 14.8±0.2, 26.2±0.2, 10.8±0.2 and 22.3±0.2 degrees 2-Theta;
wherein the $^{13}$C solid state NMR spectrum characteristic is selected from
a) a $^{13}$C solid state NMR spectrum comprising peaks at 173.4±0.2, 210.7±0.2 and 26.2±0.2 ppm;
b) a $^{13}$C solid state NMR spectrum comprising peaks at 173.4±0.2, 210.7±0.2, 26.2±0.2 and 22.8±0.2 ppm; and
c) a $^{13}$C solid state NMR spectrum comprising peaks at 173.4±0.2, 210.7±0.2, 26.2±0.2, 22.8±0.2 and 25.5±0.2 ppm; and
wherein the Raman spectrum characteristic is a Raman spectrum comprising peaks at 1717±2 and 675±2 cm$^{-1}$.

8. The compound (3S)-3-({N-[(4-methoxy-1H-indol-2-yl)carbonyl]-L-leucyl}amino)-2-oxo-4-[(3S)-2-oxopyrrolidin-3-yl]butyl dihydrogen phosphate, dimethylsulfoxide solvate hydrate.

9. The compound of claim 8 which is crystalline (3S)-3-({N-[(4-methoxy-1H-indol-2-yl)carbonyl]-L-leucyl}amino)-2-oxo-4-[(3S)-2-oxopyrrolidin-3-yl]butyl dihydrogen phosphate, dimethylsulfoxide solvate hydrate.

10. The compound of claim 6 which is crystalline (3S)-3-({N-[(4-methoxy-1H-indol-2-yl)carbonyl]-L-leucyl}amino)-2-oxo-4-[(3S)-2-oxopyrrolidin-3-yl]butyl dihydrogen phosphate, dimethylsulfoxide solvate hydrate having a powder X-ray diffraction pattern characteristic;
wherein the X-ray powder diffraction pattern characteristic is selected from
a) a powder X-ray diffraction pattern comprising peaks at 14.5±0.2, 25.6±0.2 and 26.6±0.2 degrees 2-Theta;
b) a powder X-ray diffraction pattern comprising peaks at 14.5±0.2, 25.6±0.2, 26.6±0.2 and 21.9±0.2 degrees 2-Theta; and
c) a powder X-ray diffraction pattern comprising peaks at 14.5±0.2, 25.6±0.2, 26.6±0.2, 21.9±0.2, 17.8±0.2 degrees 2-Theta.

11. A pharmaceutical composition comprising a therapeutically effective amount of (3S)-3-({N-[(4-methoxy-1H-indol-2-yl)carbonyl]-L-leucyl}amino)-2-oxo-4-[(3S)-2-oxopyrrolidin-3-yl]butyl dihydrogen phosphate, or a pharmaceutically acceptable salt, solvate or hydrate thereof, a pharmaceutically acceptable carrier and a buffering agent wherein:
a) the pharmaceutically acceptable salt is selected from the group consisting of benzathine, calcium, choline, diethylamine, diolamine, magnesium, meglumine, lysine, piperazine, potassium, tris(hydroxymethyl)aminomethane and sodium;
b) the molar ratio of the salt counterion to the (3S)-3-({N-[(4-methoxy-1H-indol-2-yl)carbonyl]-L-leucyl}amino)-2-oxo-4-[(3S)-2-oxopyrrolidin-3-yl]butyl dihydrogen phosphate in the pharmaceutically acceptable salt is approximately 0.5:1 to approximately 3:1; and
c) the buffering agent is selected from the group consisting of phosphoric acid, citric acid, maleic acid, tartaric acid, lactic acid and acetic acid.

12. The pharmaceutical composition of claim 11 wherein:
a) the pharmaceutically acceptable salt is sodium;
b) the molar ratio of the sodium counterion to the (3S)-3-({N-[(4-methoxy-1H-indol-2-yl)carbonyl]-L-leucyl}amino)-2-oxo-4-[(3S)-2-oxopyrrolidin-3-yl]

butyl dihydrogen phosphate in the pharmaceutically acceptable salt is approximately 0.5:1 to approximately 2:1;

c) the buffering agent is citric acid; and d) the molar ratio of (3S)-3-({N-[(4-methoxy-1H-indol-2-yl)carbonyl]-L-leucyl}amino)-2-oxo-4-[(3S)-2-oxopyrrolidin-3-yl]butyl dihydrogen phosphate to citric acid is approximately 2:1 to approximately 10:1.

13. The pharmaceutical composition of claim 11 wherein the composition is in the form of a powder or lyophile wherein the solution pH of the reconstituted formulation is in the range of 2 to 6.

14. The pharmaceutical composition of claim 13 wherein the solution pH of the reconstituted formulation is in the range of 3 to 5.

15. The pharmaceutical composition of claim 14 wherein the pharmaceutical composition further comprises one or more stabilizing agents.

16. The pharmaceutical composition of claim 15 wherein the one or more stabilizing agents are selected from the group consisting of polyethylene glycol 300, polyethylene glycol 400 and polyethylene glycol 3350.

17. The pharmaceutical composition of claim 14 wherein the pharmaceutical composition further comprises one or more solubilizing agents.

18. The pharmaceutical composition of claim 17 wherein the solubilizing agent is selected from the group consisting of polysorbate 20, polyethoxylated castor oil, polyethylene glycol (15)-hydroxystearate, hydroxypropyl-beta-cyclodextrin, sulfobutylether-beta cyclodextrin, gamma cyclodextrin, and polysorbate 80.

19. The pharmaceutical composition of claim 18 wherein the solubilizing agent is polysorbate 80 and the buffering agent is citric acid.

* * * * *

SEQUENCE LISTING

<160> NUMBER OF SEQ ID NOS: 2

<210> SEQ ID NO 1
<211> LENGTH: 306
<212> TYPE: PRT
<213> ORGANISM: Homo sapiens

<400> SEQUENCE: 1

```
Ser Gly Phe Arg Lys Met Ala Phe Pro Ser Gly Lys Val Glu Gly Cys
1               5                   10                  15

Met Val Gln Val Thr Cys Gly Thr Thr Thr Leu Asn Gly Leu Trp Leu
            20                  25                  30

Asp Asp Val Val Tyr Cys Pro Arg His Val Ile Cys Thr Ser Glu Asp
            35                  40                  45

Met Leu Asn Pro Asn Tyr Glu Asp Leu Leu Ile Arg Lys Ser Asn His
        50                  55                  60

Asn Phe Leu Val Gln Ala Gly Asn Val Gln Leu Arg Val Ile Gly His
65                  70                  75                  80

Ser Met Gln Asn Cys Val Leu Lys Leu Lys Val Asp Thr Ala Asn Pro
                85                  90                  95

Lys Thr Pro Lys Tyr Lys Phe Val Arg Ile Gln Pro Gly Gln Thr Phe
            100                 105                 110

Ser Val Leu Ala Cys Tyr Asn Gly Ser Pro Ser Gly Val Tyr Gln Cys
            115                 120                 125

Ala Met Arg Pro Asn Phe Thr Ile Lys Gly Ser Phe Leu Asn Gly Ser
        130                 135                 140

Cys Gly Ser Val Gly Phe Asn Ile Asp Tyr Asp Cys Val Ser Phe Cys
145                 150                 155                 160

Tyr Met His His Met Glu Leu Pro Thr Gly Val His Ala Gly Thr Asp
                165                 170                 175

Leu Glu Gly Asn Phe Tyr Gly Pro Phe Val Asp Arg Gln Thr Ala Gln
            180                 185                 190

Ala Ala Gly Thr Asp Thr Thr Ile Thr Val Asn Val Leu Ala Trp Leu
            195                 200                 205

Tyr Ala Ala Val Ile Asn Gly Asp Arg Trp Phe Leu Asn Arg Phe Thr
        210                 215                 220

Thr Thr Leu Asn Asp Phe Asn Leu Val Ala Met Lys Tyr Asn Tyr Glu
225                 230                 235                 240

Pro Leu Thr Gln Asp His Val Asp Ile Leu Gly Pro Leu Ser Ala Gln
                245                 250                 255

Thr Gly Ile Ala Val Leu Asp Met Cys Ala Ser Leu Lys Glu Leu Leu
            260                 265                 270

Gln Asn Gly Met Asn Gly Arg Thr Ile Leu Gly Ser Ala Leu Leu Glu
            275                 280                 285

Asp Glu Phe Thr Pro Phe Asp Val Val Arg Gln Cys Ser Gly Val Thr
        290                 295                 300

Phe Gln
305
```

<210> SEQ ID NO 2
<211> LENGTH: 306
<212> TYPE: PRT
<213> ORGANISM: Homo sapiens

<400> SEQUENCE: 2

```
Ser Gly Phe Arg Lys Met Ala Phe Pro Ser Gly Lys Val Glu Gly Cys
```

```
            1               5                   10                  15
        Met Val Gln Val Thr Cys Gly Thr Thr Thr Leu Asn Gly Leu Trp Leu
                        20                  25                  30

Asp Asp Val Val Tyr Cys Pro Arg His Val Ile Cys Thr Ser Glu Asp
                        35                  40                  45

Met Leu Asn Pro Asn Tyr Glu Asp Leu Leu Ile Arg Lys Ser Asn His
                50                  55                  60

Asn Phe Leu Val Gln Ala Gly Asn Val Gln Leu Arg Val Ile Gly His
        65                      70                  75                  80

Ser Met Gln Asn Cys Val Leu Lys Leu Lys Val Asp Thr Ala Asn Pro
                        85                  90                      95

Lys Thr Pro Lys Tyr Lys Phe Val Arg Ile Gln Pro Gly Gln Thr Phe
                        100                 105                 110

Ser Val Leu Ala Cys Tyr Asn Gly Ser Pro Ser Gly Val Tyr Gln Cys
                        115                 120                 125

Ala Met Arg Pro Asn Phe Thr Ile Lys Gly Ser Phe Leu Asn Gly Ser
                        130                 135                 140

Cys Gly Ser Val Gly Phe Asn Ile Asp Tyr Asp Cys Val Ser Phe Cys
        145                     150                 155                 160

Tyr Met His His Met Glu Leu Pro Thr Gly Val His Ala Gly Thr Asp
                        165                 170                 175

Leu Glu Gly Asn Phe Tyr Gly Pro Phe Val Asp Arg Gln Thr Ala Gln
                        180                 185                 190

Ala Ala Gly Thr Asp Thr Thr Ile Thr Val Asn Val Leu Ala Trp Leu
                        195                 200                 205

Tyr Ala Ala Val Ile Asn Gly Asp Arg Trp Phe Leu Asn Arg Phe Thr
        210                     215                 220

Thr Thr Leu Asn Asp Phe Asn Leu Val Ala Met Lys Tyr Asn Tyr Glu
        225                     230                 235                 240

Pro Leu Thr Gln Asp His Val Asp Ile Leu Gly Pro Leu Ser Ala Gln
                        245                 250                 255

Thr Gly Ile Ala Val Leu Asp Met Cys Ala Ser Leu Lys Glu Leu Leu
                        260                 265                 270

Gln Asn Gly Met Asn Gly Arg Thr Ile Leu Gly Ser Ala Leu Leu Glu
                        275                 280                 285

Asp Glu Phe Thr Pro Phe Asp Val Val Arg Gln Cys Ser Gly Val Thr
                        290                 295                 300

Phe Gln
        305
```